United States Patent
Castel et al.

(10) Patent No.: US 11,696,924 B2
(45) Date of Patent: Jul. 11, 2023

(54) COMBINATION THERAPY USING PDK1 AND PI3K INHIBITORS

(71) Applicant: MEMORIAL SLOAN-KETTERING CANCER CENTER, New York, NY (US)

(72) Inventors: Pau Castel, New York, NY (US); Jose Baselga, New York, NY (US); Maurizio Scaltriti, New Yok, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 116 days.

(21) Appl. No.: 15/873,324

(22) Filed: Jan. 17, 2018

(65) Prior Publication Data
US 2018/0147232 A1    May 31, 2018

Related U.S. Application Data

(63) Continuation of application No. PCT/US2016/042616, filed on Jul. 15, 2016.
(Continued)

(51) Int. Cl.
*A61K 31/713* (2006.01)
*A61K 31/506* (2006.01)
(Continued)

(52) U.S. Cl.
CPC ........ *A61K 31/713* (2013.01); *A61K 31/4439* (2013.01); *A61K 31/506* (2013.01);
(Continued)

(58) Field of Classification Search
CPC .............. A61K 31/4745; A61K 31/506; A61K 31/703; A61K 31/519; A61K 31/4439;
(Continued)

(56) References Cited

U.S. PATENT DOCUMENTS 7,105,563 B2    9/2006 Amaiz et al.
8,546,613 B2    10/2013 Fuchss et al.
(Continued)

FOREIGN PATENT DOCUMENTS

EP          1 486 488 A1    12/2004
WO     WO 2003/0643 97 A1    8/2003
(Continued)

OTHER PUBLICATIONS

Phosphoinositide 3-kinase class I. Downloaded from https://en.wikipedia.org/wiki/Phosphoinositide_3-kinase on Aug. 14, 2020.*
(Continued)

*Primary Examiner* — Terra C Gibbs
(74) *Attorney, Agent, or Firm* — Baker Botts L.L.P.

(57) ABSTRACT

The present invention relates to methods and compositions for inhibiting growth and proliferation of cancer cells resistant to PI3K inhibition using a combination of PDK1, SGK1 and PI3K inhibitors. The present invention is also directed to methods of treating cancer in a subject exhibiting cancer cells resistant to PI3K inhibition, comprising administering inhibitors of PI3K in combination with inhibitors of PDK1 and/or SGK1 to the subject.

9 Claims, 148 Drawing Sheets
Specification includes a Sequence Listing.

Related U.S. Application Data

(60) Provisional application No. 62/194,106, filed on Jul. 17, 2015.

(51) Int. Cl.

| | | |
|---|---|---|
| A61K 31/4439 | (2006.01) | |
| A61K 31/7105 | (2006.01) | |
| A61K 31/711 | (2006.01) | |
| A61K 45/06 | (2006.01) | |
| A61P 35/00 | (2006.01) | |

(52) U.S. Cl.
CPC ........ *A61K 31/711* (2013.01); *A61K 31/7105* (2013.01); *A61K 45/06* (2013.01); *A61P 35/00* (2018.01)

(58) Field of Classification Search
CPC . C07B 59/002; C12N 15/113; C12N 15/1138; C12N 15/11
See application file for complete search history.

(56) References Cited

U.S. PATENT DOCUMENTS

| | | |
|---|---|---|
| 2007/0135429 A1 | 6/2007 | Gopalsamy et al. |
| 2009/0111799 A1 | 4/2009 | Chen et al. |
| 2010/0035965 A1 | 2/2010 | Evers et al. |
| 2010/0144730 A1 | 6/2010 | Lind et al. |
| 2011/0269958 A1 | 11/2011 | Engelhardt et al. |
| 2012/0003668 A1 | 1/2012 | Hindie et al. |
| 2012/0208819 A1 | 8/2012 | Arndt et al. |
| 2012/0245355 A1 | 9/2012 | Viscomi et al. |
| 2012/0277229 A1 | 11/2012 | Bearss et al. |
| 2013/0053382 A1 | 2/2013 | Paliwal et al. |
| 2013/0165450 A1 | 6/2013 | Tsui et al. |
| 2013/0252950 A1 | 9/2013 | Blenis et al. |
| 2014/0017701 A1 | 1/2014 | Biondi et al. |

FOREIGN PATENT DOCUMENTS

| | | |
|---|---|---|
| WO | WO 2004/087707 A1 | 10/2004 |
| WO | WO 2005/041953 A1 | 5/2005 |
| WO | WO 2005/05423 8 A1 | 6/2005 |
| WO | WO 2006/015124 A2 | 2/2006 |
| WO | WO 2006/106326 A1 | 10/2006 |
| WO | WO 2008/005457 A2 | 1/2008 |
| WO | WO 2008/079988 A2 | 7/2008 |
| WO | WO 2008/107444 A1 | 9/2008 |
| WO | WO 2008/109599 A1 | 9/2008 |
| WO | WO 2008/109613 A1 | 9/2008 |
| WO | WO 2009/153313 A1 | 12/2009 |
| WO | WO 2010/007114 A2 | 1/2010 |
| WO | WO 2010/007116 A2 | 1/2010 |
| WO | WO 2010/017047 A1 | 2/2010 |
| WO | WO 2010/019637 A1 | 2/2010 |
| WO | WO 2010/065384 A1 | 6/2010 |
| WO | WO 2010/120854 A1 | 10/2010 |
| WO | WO 2010/127754 A1 | 11/2010 |
| WO | WO 2011/006567 A1 | 1/2011 |
| WO | WO 2011/044157 A1 | 4/2011 |
| WO | WO 2011/076327 A1 | 6/2011 |
| WO | WO 2011/137219 A1 | 11/2011 |
| WO | WO 2012/036974 A1 | 3/2012 |
| WO | WO 2012/058174 A1 | 5/2012 |
| WO | WO 2012/058176 A1 | 5/2012 |
| WO | WO 2012/072200 A1 | 6/2012 |
| WO | WO 2012/135799 A1 | 10/2012 |
| WO | WO 2014/046617 A1 | 3/2014 |
| WO | WO 2014/140065 A1 | 9/2014 |

OTHER PUBLICATIONS

Small molecule, Wikipedia. Downloaded from https://en.wikipedia.org/wiki/Small_molecule on Aug. 14, 2020.*

AdisInsight's definition of a small molecule:Nature Support downloaded from https://support.nature.com/en/support/solutions/articles/6000081256-adisinsight-s-definition-of-a-small-molecule on Aug. 14, 2020.*

Metabolomics, small molecules, downloaded from https://www.ebi.ac.uk/training-beta/online/courses/metabolomics-introduction/what-is/small-molecules/ on Aug. 14, 2020.*

Arizona Bioindustry Association, AZBio, small molecules, large biologies and the biosimilar debate downloaded from https://www.azbio.org/small-molecules-large-biologics-and-the-biosimilar-debate on Aug. 14, 2020.*

Halland et al. (ACS Med. Chem. Lett., 2015 vol. 6:73-78).*

Castel et al. (Cancer Cell, 2016 vol. 30:229-242).*

Najafov et al. (Biochemical Journal, 2011 vol. 433:357-369).*

Cancer Research Wales. No Two Cancers Are the Same. Downloaded from https://www.cancerresearchwales.co.uk/blog/no-two-cancers-are-the-same, downloaded on Sep. 29, 2021.*

Alessi et al., "Characterization of a 3-phosphoinositide-dependent protein kinase which phosphorylates and activates protein kinase Bα," Curr Biol. 7:261-269 (1997).

Alessi et al., "New Insights into mTOR Signaling: mTORC2 and Beyond," Sci Signal 2(67):pe27, 5 pages (2009).

Arencibia et al., "AGC protein kinases: From structural mechanism of regulation to allosteric drug development for the treatment of human diseases," Biochim Biophys Acta 1834:1302-1321 (2013).

Arteaga et al., "Multiple Translational Isoforms Give Functional Specificity to Serum-and Glucocorticoid-induced Kinase 1," Molecular Biology of the Cell 18:2072-2080 (2007).

Bhinder et al., "A simple method for analyzing actives in random RNAi screens: introducing the "H Score" for hit nomination & gene prioritization," Comb Chem High Throughput Screen 15(9):686-704 (2012).

Biondi et al., "The PIF-binding pocket in PDK1 is essential for activation of S6K and SGK, but not PKB," EMBO J 20(16):4380-4390 (2001).

Brunet et al., "Akt Promotes Cell Survival by Phosphorylating and Inhibiting a Forkhead Transcription Factor," Cell 96:857-868 (1999).

Brunet et al., "Protein Kinase SGK Mediates Survival Signals by Phosphorylating the Forkhead Transcription Factor FKHRL1 (FOXO3a)," Mol Cell Biol 21(3):952-965 (2001).

Castel et al., "Abstract 2107: PDK1 blockade overcomes intrinsic resistance to PI3Kα inhibition," Cancer Research, 76(14), 3 pages (2016).

Castel et al., "PDK1-SGK1 Signaling Sustains AKT-independent mTORC1 Activation and Confers Resistance to PI3Kα Inhibition," Cancer Cell 30:229-242 (2016).

Cerami et al., "The cBio Cancer Genomics Portal: An Open Platform for Exploring Multidimensional Cancer Genomics Data," Cancer Discov 2(5):401-404 (2012).

Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology," J Mol Diagn 17:251-264 (2015).

Ciriello et al., "Comprehensive Molecular Portraits of Invasive Lobular Breast Cancer," Cell 163:506-519 (2015).

Collins et al., "In vivo role of the PIF-binding docking site of PDK1 defined by knock-in mutation," EMBO J 22(16):4202-4211 (2003).

Costa et al. "Measurement of PIP3 Levels Reveals an Unexpected Role for p 110β in Early Adaptive Responses to p110α-Specific Inhibitors in Luminal Breast Cancer," Cancer Cell 27:97-108 (2015).

Currie et al., "Role of phosphatidylinositol 3,4,5-trisphosphate in regulating the activity and localization of 3-phosphoinositide-dependent protein kinase-1," The Biochem J 337:575-583 (1999).

Cybulski et al., "TOR complex 2: a signaling pathway of its own," Trends Biochem Sci 34(12):620-627 (2009).

D'Antona et al., "SI113, a Specific Inhibitor of the Sgk1 Kinase Activity that Counteracts Cancer Cell Proliferation," Cell Physiol Biochem 35:2006-2018 (2015).

Dibble et al., "TBC1D7 is a third subunit of the TSC1-TSC2 complex upstream of mTORC1," Mol. Cell 47(4):535-546 (2012).

(56) References Cited

OTHER PUBLICATIONS

Duan et al., "A Point-Charge Force Field for Molecular Mechanics Simulations of Proteins Based on Condensed-Phase Quantum Mechanical Calculations," Journal of Computational Chemistry 24:1999-2012 (2003).
Elkabets et al., "mTORCI Inhibition is Required for Sensitivity to PI3K p110α Inhibitors in PIK3CA-Mutant Breast Cancer," Sci Transl Med. 5(196):1-28 (2013).
Engelman, "Targeting PI3K signalling in cancer: opportunities, challenges and limitations," Nat Rev Cancer 9:550-562 (2009).
Ericson et al., "Genetic inactivation of AKT1, AKT2, and PDPK1 in human colorectal cancer cells clarifies their roles in tumor growth regulation," PNAS USA 107(6):2598-2603 (2010).
Erlanson et al., "Discovery of a potent and highly selective PDK1 inhibitor via fragment-based drug discovery," Biorg. Med. Chem. Lett. 21:3078-3083 (2011).
Fellmann et al., "An Optimized microRNA Backbone for Effective Single-Copy RNAi," Cell Reports 5:1704-1713 (2013).
Frias et al., "mSin1 is Necessary for Akt/PKB Phosphorylation, and Its Isoforms Define Three Distinct mTORC2s," Curr Biol 16:1865-1870 (2006).
Friesner et al., "Glide: A New Approach for Rapid, Accurate Docking and Scoring. 1. Method and Assessment of Docking Accuracy," Journal of Medicinal Chemistry 47:1739-1749 (2004).
Fritsch et al., "Characterization of the Novel and Specific PI3Ka Inhibitor NVP-BYL719 and Development of the Patient Stratification Strategy for Clinical Trials," Mol Cancer Ther. 13(5):1117-1129 (2014).
Fruman et al., "PI3K and Cancer: Lessons, Challenges and Opportunities," Nat Rev Drug Discov 13(2):140-156 (2014).
Gan et al., "Evidence for Direct Activation of mTORC2 Kinase Activity by Phosphatidylinositol 3,4,5-Trisphosphate," J Biol Chem 286(13):10998-11002 (2011).
Garcia-Martinez et al., "mTOR complex 2 (mTORC2) controls hydrophobic motif phosphorylation and activation of serum- and glucocorticoid-induced protein kinase 1 (SGK1)," Biochem J 416:375-385 (2008).
Gasser et al., "SGK3 mediates INPP4B-dependent PI 3-Kinase signaling in breast cancer," Mol Cell 56(4):595-607 (2014).
Guertin et al., "Ablation in Mice of the mTORC Components raptor, rictor, or mLST8 Reveals that mTORC2 is Required for Signaling to Akt-FOXO and PKCα, but Not S6K1," Dev Cell 11:859-871 (2006).
Halland et al., "Discovery of N-[4-(1H-Pyrazolo[3,4-b]pyrazin-6-yl)-phenyl]-sulfonamides as Highly Active and Selective SGK1 Inhibitors," ACS Med. Chem Lett 6:73-78 (2015).
Hayakawa et al., "Synthesis and biological evaluation of 4-morpholino-2-phenylquinazolines and related derivatives as novel PI3 kinase p110α inhibitors," Bioorg. Med. Chem. 14:6847-6858 (2006).
Hossen et al., "PDK1 disruptors and modulators: a patent review," Expert Op. Ther. Pat. 25(5):513-537 (2015).
Humphrey et al., "VMD: Visual Molecular Dynamics," Journal of Molecular Graphics 14:33-38 (1996).
Inoki et al., "Rheb GTPase is a direct target of TSC2 Gap activity and regulates mTOR signaling," Genes Dev 17:1829-1834 (2003).
Inoki et al., "TSC2 Integrates Wnt and Energy Signals via a Coordinated Phosphorylation by AMPK and GSK3 to Regulate Cell Growth," Cell 126:955-968 (2006).
Inoki et al., "TSC2 is phosphorylated and inhibited by Akt and suppresses mTOR signalling," Nat Cell Biol 4:648-657 (2002).
Inoki et al., "TSC2 Mediates Cellular Energy Response to Control Cell Growth and Survival," Cell 115:577-590 (2003).
International Search Report dated Oct. 6, 2016 in International Application No. PCT/US16/42616.
Jacinto et al., "SIN1/MTP1 Maintains rictor-mTOR Complex Integrity and Regulates Akt Phosphorylation and Substrate Specificity," Cell 127:125-137 (2006).
Juric et al., "Abstract CT-01: BYL719, a next generation PI3K alpha specific inhibitor: Preliminary safety, PK, and efficacy results from the first-in-human study," Cancer Research, 4 pages (2012).
Juric et al., "Abstract LB-64: GDC-0032, a beta isoform-sparing PI3K inhibitor: Results of a first-in-human phase Ia dose escalation study," Cancer Research, 4 pages (2013).
Juric et al., "Convergent loss of PTEN leads to clinical resistance to a PI3Kα inhibitor," Nature 518(7538):240-244 (2015).
Kannan et al., "Probing the Binding Mechanism of Mnk Inhibitors by Docking and Molecular Dynamics Simulations," Biochemistry 54:32-46 (2015).
Knight et al., "A Pharmacological Map of the PI3-K Family Defines a Role for p110α in Insulin Signaling," Cell 125:733-747 (2006).
Kobayashi et al., "Characterization of the structure and regulation of two novel isoforms of serum- and glucocorticoid-induced protein kinase," Biochem J 344:189-197 (1999).
Kobayashi et al., "Activation of serum- and glucocorticoid-regulated protein kinase by agonists that activate phosphatidylinositide 3-kinase is mediated by 3-phosphoinositide-dependent protein kinase-1 (PDK1) and PDK2," Biochem J 339:319-328 (1999).
Kondapaka et al., "Perifosine, a novel alkylphospholipid, inhibits protein kinase B activation," Mol Cancer Ther 2:1093-1103 (2003).
Li et al., "TSC2: filling the GAP in the mTOR signaling pathway," Trends Biochem Sci 29(1):32-38 (2004).
Liu et al., "PtdIns(3,4,5)P3-Dependent Activation of the mTORC2 Kinase Complex," Cancer Discov 5(11):1194-1209 (2015).
Ma et al., "Phosphorylation and Functional Inactivation of TSC2 by Erk: Implications for Tuberous Sclerosis and Cancer Pathogenesis," Cell 121:179-193 (2005).
Manning et al., "AKT/PKB Signaling: Navigating Downstream," Cell 129(7):1261-1274 (2007).
Manning et al., "Identification of the Tuberous Sclerosis Complex-2 Tumor Suppressor Gene Product Tuberin as a Target of the Phosphoinositide 3-Kinase/Akt Pathway," Mol Cell 10:151-162 (2002).
McManus et al., "The in vivo role of PtdIns(3,4,5)P3 binding to PDK1 PH domain defined by knockin mutation," EMBO J 23:2071-2082 (2004).
Medina, "Selective 3-Phosphoinositide-Dependent Kinase 1 (PDK1) Inhibitors: Dissecting the Function and Pharmacology of PDK1," J Med Chem. 56:2726-2737 (2013).
Menon et al., "Spatial Control of the TSC Complex Integrates Insulin and Nutrient Regulation of mTORC1 at the Lysosome," Cell 156(4):771-785 (2014).
Murray et al., "Exploitation of KESTREL to identify NDRG family members as physiological substrates for SGK1 and GSK3," Biochem J 384:477-488 (2004).
Nagashima et al., "Genetic and Pharmacological Inhibition of PDK1 in Cancer Cells Characterization of a Selective Allosteric Kinase Inhibitor," J Biol Chem. 286(8):6433-6448 (2011).
Najafov et al., "Akt is efficiently activated by PIF-pocket-and PtdIns(3,4,5)P3-dependent mechanisms leading to resistance to PDK1 inhibitors," Biochem J 448:285-295 (2012).
Najafov et al., "Characterization of GSK2334470, a novel and highly specific inhibitor of PDK1," Biochem J. 433:357-369 (2011).
Nittoli et al., "The identification of 8,9-dimethoxy-5-(2-aminoalkoxy-pyridin-3-yl)-benzo[c][2,7]naphthyridin-4-ylamines as potent inhibitors of 3-phosphoinositide-dependent kinase-1 (PDK-1)," Eur. J. Med. Chem. 45:1379-1386 (2010).
Pearce et al., "The nuts and bolts of AGC protein kinases," Nat Rev Mol Cell Biol 11:9-22 (2010).
Potter et al., "Akt regulates growth by directly phosphorylating Tsc2," Nat Cell Biol 4:658-665 (2002).
Reagan-Shaw et al., "Dose translation from animal to human studies revisited," The FASEB J., 22:659-661 (2007).
Rettenmaier et al., "A small-molecule mimic of a peptide docking motif inhibits the protein kinase PDK1," PNAS USA 111(52):18590-18595 (2014).
Rettenmaier et al., "Small-Molecule Allosteric Modulators of the Protein Kinase PDK1 from Structure-Based Docking," J. Med. Chem. 58(20):8285-8291 (2015).
Rodrik-Outmezguine et al., "mTOR kinase inhibition causes feedback-dependent biphasic regulation of AKT signaling," Cancer Discov 1(3):248-259 (2011).

(56) References Cited

OTHER PUBLICATIONS

Roux et al., "Tumor-promoting phorbol esters and activated Ras inactivate the tuberous sclerosis tumor suppressor complex via p90 ribosomal S6 kinase," PNAS USA 101(37):13489-13494 (2004).
Sali et al., "Comparative Protein Modelling by Satisfaction of Spatial Restraints," Journal of Molecular Biology 234:779-815 (1993).
Sancak et al., "PRAS40 is an Insulin-Regulated Inhibitor of the mTORC1 Protein Kinase," Mol Cell 25:903-915 (2007).
Sarbassov et al., "Phosphorylation and Regulation of Akt/PKB by the Rictor-mTOR Complex," Science 307:1098-1101 (2005).
Shevchenko et al., "In-gel digestion for mass spectrometric characterization of proteins and proteomes," Nature Protocols 1(6):2856-2860 (2006).
Silvera et al., "Translational control in cancer," Nat Rev Cancer 10:254-266 (2010).
Sommer et al., "Elevated SCK1 predicts resistance of breast cancer cells to Akt inhibitors," Biochem J. 452:499-508 (2013).
Supplementary European Search Report dated Jan. 21, 2019 in Application No. EP16828326.
Therasse et al., "New Guidelines to Evaluate the Response to Treatment in Solid Tumors," J Natl Cancer Inst 92:205-216 (2000).
Thorpe et al., "PI3K in cancer: divergent roles of isoforms, modes of activation and therapeutic targeting," Nat Rev Cancer 15:7-24 (2015).
Toska et al., "Repression of Transcription by WT1-BASP1 Requires the Myristoylation of BASP1 and the PIP2-Dependent Recruitment of Histone Deacetylase," Cell Reports 2(3):462-469 (2012).
Van Rheenen et al., "Correcting Confocal Acquisition to Optimize Imaging of Fluorescence Resonance Energy Transfer by Sensitized Emission," Biophysical Journal 86:2517-2529 (2004).
Vasudevan et al., "AKT-independent signaling downstream of oncogenic PIK3CA mutations in human cancer," Cancer Cell 16:21-32 (2009).
Wang et al., "Development and Testing of a General Amber Force Field," Journal of Computational Chemistry 25(9):1157-1174 (2004).
Webb et al., "FOXO transcription factors: key regulators of cellular quality control," Trends Biochem Sci 39(4):159-169 (2014).
Yang et al., "Crystal structure of an activated Akt/Protein Kinase B ternary complex with GSK3-peptide and AMP-PNP," Nature Structural Biology 9(12):940-944 (2002).
Yang et al., "Molecular Mechanism for the Regulation of Protein Kinase B/Akt by Hydrophobic Motif Phosphorylation," Molecular Cell 9:1227-1240 (2002).
Zhao et al., "Crystal structure of the kinase domain of serum and glucocorticoid-regulated kinase 1 in complex with AMP PNP," Protein Sci 16:2761-2769 (2007).
Zou et al., "A Novel Dual PI3Kα/mTOR inhibitor PI-103 with high antitumor activity in non-small cell lung cancer cells," Int J Mol Med. 24:97-101 (2009).

\* cited by examiner

HCC1954 CELL LINE

| GENE SYMBOL | RefSeq ID | GENE DESCRIPTION | H SCORE (DRUG) | VALIDATED VIABILITY | pS6 (S240/4) STAINING |
|---|---|---|---|---|---|
| AKAP8 | NM_005858 | A KINASE (PRKA) ANCHOR PROTEIN 8 | 67 | | |
| CAMKK2 | NM_006549 | CALCIUM/CALMODULIN-DEPENDENT PROTEIN KINASE KINASE 2, BETA | 67 | | |
| CHEK1 | NM_001274 | CHK1 CHECKPOINT HOMOLOG | 67 | | |
| DUSP10 | NM_007207 | DUAL SPECIFITY PHOSPHATE 10 | 67 | | |
| ERBB3 | NM_001005915 | v-erb-b2 ERYTHROBLASTIC LEUKEMIA VIRAL ONCOGENE HOMOLOG 3 | 67 | | |
| FBP1 | NM_000507 | FRUCTOSE-1,6-BISPHOSPHATASE 1 | 67 | | |
| FER | NM_005246 | fer (fps/fes RELATED) TYROSINE KINASE | 67 | | |
| PAPL | NM_001004318 | PURPLE ACID PHOSPHATASE LONG FORM | 67 | NO | NO |
| FLT1 | NM_002019 | fms-RELATED TYROSINE KINASE 1 (VASCULAR ENDOTHELIAL GROWTH FACTOR) | 67 | | |
| MTOR | NM_004958 | FK506 BINDING PROTEIN 12-RAPAMYCIN ASSOCIATED PROTEIN 1 | 67 | YES | YES |
| HDHD1A | NM_012080 | HALOACID DEHALOGENASE-LIKE HYDROLASE DOMAIN CONTAINING 1A | 67 | | |
| INPPL1 | NM_001567 | INOSITOL POLYPHOSPHATE PHOSPHATASE-LIKE 1 | 100 | | |
| IRAK4 | NM_016123 | INTERLEUKIN-1 RECEPTOR-ASSOCIATED KINASE 4 | 67 | | |
| JAK1 | NM_002227 | JANUS KINASE 1 | 67 | | |
| MAP2K3 | NM_002756 | MITOGEN-ACTIVATED PROTEIN KINASE KINASE 3 | 100 | | |
| MASTL | NM_032844 | MICROTUBULE ASSOCIATED SERINE/THREONINE KINASE-LIKE | 67 | | |
| MPP5 | NM_022474 | MEMBRANE PROTEIN, PALMITOYLATED 5 | 67 | | |
| MPP7 | NM_173496 | MEMBRANE PROTEIN, PALMITOYLATED 7 | 67 | | |
| MTMR1 | NM_003828 | MYOTUBULARIN RELATED PROTEIN 1 | 100 | | |
| MTMR3 | NM_021090 | MYOTUBULARIN RELATED PROTEIN 3 | 67 | | |
| MTMR6 | NM_004685 | MYOTUBULARIN RELATED PROTEIN 6 | 67 | | |
| MTMR8 | NM_017677 | MYOTUBULARIN RELATED PROTEIN 8 | 67 | | |

FIG. 1F

| | | | | | |
|---|---|---|---|---|---|
| NAP1L1 | NM_004537 | NUCLEOSOME ASSEMBLY PROTEIN 1-LIKE 1 | 100 | | |
| NAP1L4 | NM_005969 | NUCLEOSOME ASSEMBLY PROTEIN 1-LIKE 4 | 67 | | |
| NME4 | NM_005009 | NON-METASTATIC CELLS 4 | 67 | | |
| PDGFRA | NM_006206 | PLATELET-DERIVED GROWTH FACTOR RECEPTOR, ALPHA POLYPEPTIDE | 67 | | |
| PDPK1 | NM_002613 | 3-PHOSPHOINOSITIDE DEPENDENT PROTEIN KINASE-1 | 100 | YES | YES |
| PIK3CA | NM_006218 | PHOSPHOINOSITIDE-3-KINASE | 100 | NO | NO |
| PIP5KL1 | NM_173492 | PHOSPHATIDYLINOSITOL-4-PHOSPHATE 5-KINASE-LIKE 1 | 67 | | |
| PLK3 | NM_004073 | POLO-LIKE KINASE 3 | 100 | | |
| PPAP2B | NM_003713 | PHOSPHATIDIC ACID PHOSPHATASE TYPE 2B | 67 | | |
| PPP1R12A | NM_002480 | PROTEIN PHOSPHATASE 1, REGULATORY (INHIBITOR) SUBUNIT 12A | 67 | NO | NO |
| PPP1R12B | NM_032104 | PROTEIN PHOSPHATASE 1, REGULATORY (INHIBITOR) SUBUNIT 12B | 100 | | |
| PPP1R8 | NM_002713 | PROTEIN PHOSPHATASE 1, REGULATORY (INHIBITOR) SUBUNIT 8 | 67 | | |
| PPP6C | NM_002721 | PROTEIN PHOSPHATASE 6, CATALYTIC SUBUNIT | 67 | | |
| PTP4A1 | NM_003463 | PROTEIN TYROSINE PHOSPHATASE TYPE IVA | 67 | | |
| PTPN13 | NM_006264 | PROTEIN TYROSINE PHOSPHATASE, NON-RECEPTOR TYPE 13 | 67 | | |
| PXK | NM_017771 | PX DOMAIN CONTAINING SERINE/THERONINE KINASE | 67 | | |
| RBKS | NM_022128 | RIBOKINAS | 67 | | |
| SNRK | NM_017719 | SNF RELATED KINASE | 67 | | |
| TNK1 | NM_003985 | TYROSINE KINASE, NON-RECEPTOR | 67 | | |
| WNK2 | NM_006648 | WNK LYSINE DEFICIENT PROTEIN KINASE 2 | 67 | | |

FIG. 1F
CONTINUED

JIMT1 CELL LINE

| GENE SYMBOL | RefSeq ID | GENE DESCRIPTION | H SCORE (DRUG) | VALIDATED VIABILITY | pS6 (S240/4) STAINING |
|---|---|---|---|---|---|
| ACVRL1 | NM_000020 | ACTIVIN A RECEPTOR TYPE II-LIKE 1 | 67 | | |
| AKT1 | NM_001014431 | V-AKT MURINE THYMOMA VIRAL ONCOGENE HOMOLOG 1 | 67 | | |
| ALPI | NM_001631 | ALKALINE PHOSPHATASE, INTESTINAL | 67 | | |
| ALPL | NM_000478 | ALKALINE PHOSPHATASE, LIVER/BONE/KIDNEY | 67 | | |
| ARAF | NM_001654 | v-raf MURINE SARCOMA 3611 VIRAL ONCONGENE HOMOLOG | 67 | | |
| CDC42BPA | NM_003607 | CDC42 BINDING PROTEIN KINASE ALPHA | 67 | | |
| CDK2 | NM_001798 | CYCLIN-DEPENDENT KINASE 2 | 67 | | |
| CDK4 | NM_000075 | CYCLIN-DEPENDENT KINASE 4 | 100 | | |
| CDK9 | NM_001261 | CYCLIN-DEPENDENT KINASE 9 (CDK9), mRNA | 67 | | |
| CSNK1A1 | NM_001025105 | CASEIN KINASE 1, ALPHA 1 | 67 | | |
| CSNK1A1L | NM_0145203 | CASEIN KINASE 1, ALPHA 1-LIKE | 67 | | |
| CSNK1G2 | NM_001319 | CASEIN KINASE 1, GAMMA 2 | 67 | | |
| ENTPD2 | NM_001246 | ECTONUCLEOSIDE TRIPHOSPHATE DIPHOSPHOHYDROLASE 2 | 67 | | |
| EPHA3 | NM_005233 | EPH RECEPTOR A3 (EPHA3), TRANSCRIPT VARIANT 1, mRNA | 67 | | |
| EPHA5 | NM_004439 | EPH RECEPTOR A5 | 67 | | |
| EPHB2 | NM_004442 | EPH RECEPTOR B2 | 67 | | |
| PAPL | NM_001004318 | PURPLE ACID PHOSPHATASE LONG FORM | 67 | NO | NO |
| MTOR | NM_004958 | FK506 BINDING PROTEIN 12-RAPAMYCIN ASSOCIATED PROTEIN 1 | 67 | YES | YES |
| GK5 | NM_001039547 | GLYCEROL KINASE 5 | 67 | | |
| IGFN1 | NM_178275 | IMMUNOGLOBULIN-LIKE AND FIBRONECTIN TYPE III DOMAIN CONTAINING 1 | 67 | | |
| ITGB1BP3 | NM_170678 | INTEGRIN BETA 1 BINDING PROTEIN 3 | 67 | | |
| LRRK2 | NM_198578 | LEUCINE-RICH REPEAT KINASE 2 | 67 | | |
| LTK | NM_002344 | LEUKOCYTE RECEPTOR TYROSINE KINASE | 67 | | |

FIG. 1G

| | | | | | |
|---|---|---|---|---|---|
| *MAP2K2* | NM_030662 | MITOGEN-ACTIVATED PROTEIN KINASE KINASE | 67 | | |
| *MST1R* | NM_002447 | MACROPHAGE STIMULATING 1 RECEPTOR | 67 | | |
| *NEK3* | NM_002498 | NIMA (NEVER IN MITOSIS GENE A)-RELATED KINASE 3 | 67 | | |
| *NEK7* | NM_133494 | NIMA (NEVER IN MITOSIS GENE A)-RELATED KINASE 7 | 67 | | |
| *PDK2* | NM_002611 | PYRUVATE DEHYDROGENASE KINASE, ISOZYME 2 | 67 | | |
| *PDPK1* | NM_002613 | 3-PHOSPHOINOSITIDE DEPENDENT PROTEIN KINASE-1 | 67 | YES | YES |
| *PIK3CA* | NM_006218 | PHOSPHOINOSITIDE-3-KINASE, CATALYTIC, ALPHA POLYPEPTIDE | 67, 100 | NO | NO |
| *PPP1CA* | NM_001008709 | PROTEIN PHOSPHATASE 1, CATALYTIC SUBUNIT, ALPHA ISOFORM | 67 | | |
| *PPP1R12A* | NM_002480 | PROTEIN PHOSPHATASE 1, REGULATORY (INHIBITOR) SUBUNIT 12A | 67 | NO | NO |
| *PPP1R3F* | NM_033215 | PROTEIN PHOSPHATASE 1, REGULATORY (INHIBITOR) SUBUNIT 3F | 67 | | |
| *PPP2R5D* | NM_006245 | PROTEIN PHOSPHATASE 2, REGULATORY SUBUNIT B', DELTA ISOFORM | 67 | | |
| *PRKD2* | NM_001079880 | PROTEIN KINASE D2 | 67 | | |
| *PTPRF* | NM_002840 | PROTEIN TYROSINE PHOSPHATASE, RECEPTOR TYPE, F | 67 | | |
| *PTPRT* | NM_007050 | PROTEIN TYROSINE PHOSPHATASE, RECEPTOR TYPE, T | 67 | | |
| *TESK1* | NM_006285 | TESTIS-SPECIFIC KINASE 1 | 67 | | |
| *TRIB1* | NM_025195 | TRIBBLES HOMOLOG 1 | 67 | | |
| *WNK1* | NM_018979 | WNK LYSINE DEFICIENT PROTEIN KINASE 1 | 67 | | |

FIG. 1G
CONTINUED

| SGK1 mRNA | Median PFS (days) | POD |
|---|---|---|
| HIGH (n=3) | 56.0 | 3/3 |
| LOW (n=15) | 111.0 | 4/15 |

| pNDRG1 IHC | Median PFS (days) | POD |
|---|---|---|
| POSITIVE (n=5) | 56.0 | 5/5 |
| NEGATIVE (n=13) | 138.0 | 2/13 |

CAL-148:

Q298*
I253N

CAL51:

N323Kfs*2
V290*

| Species | | | | | | |
|---|---|---|---|---|---|---|
| | S939 | S981 | T993 | S1130–S1132 | T1462 | S1798 |
| H. sapiens | DSFRARSTSLNE | EAFRCRSISVSE | HVVRSRIQTSLT | RGARDRVRSMSGGH | SGLRPRGYTISD | VGQRKRLISSVE (SEQ ID NO: 8) |
| M. musculus | DSFRARSTSLNE | EAFRCRSISVSE | HVVRSRIQTSLT | RGARDRVRSMSGGH | SGLRPRGYTISD | TGQRKRLISSVD (SEQ ID NO: 9) |
| R. norvegicus | DSFRARSTSLNE | ------------ | ---SRIQTSLT | RGARDRVRSMSGGH | SGLRPRGYTISD | TGQRKRLISSVD (SEQ ID NO: 10) |
| B. taurus | DSFRARSTSLNE | DAFRCRSISVSE | HVVRSRIQTSLT | HGARDRVRSMSGGH | SGLRPRGYTISD | TGQRKRLISSVD (SEQ ID NO: 11) |
| G. gallus | DSFRARSTSLNE | DAFRCRSISVSE | HVVRSRIQTSIT | RSSRNRVRSMSGGH | SGHRPRGYTISD | TGQRKRLISSVD (SEQ ID NO: 12) |
| X. tropicalis | DSFRARSTSLNE | ------------ | ---SRMQTSVT | QTPHRVRSISGGH | TGHRPRGHTISD | TGQRTRLISAVD (SEQ ID NO: 13) |
| D. rerio | DSFRARSTSLNE | DAFRCRSISVSE | HAV-RRMQTSST | TNTRTRVRSISGGH | TGHRPRGHTISV | AGQRKRLVSTVD (SEQ ID NO: 14) |
| AGC consensus | RXRXXS (SEQ ID NO: 15) | RXRXXS (SEQ ID NO: 16) | RXRXXT (SEQ ID NO: 17) | RXRXXS (SEQ ID NO: 18) / RXRXXS (SEQ ID NO: 19) | RXRXXT (SEQ ID NO: 20) | RXRXXS (SEQ ID NO: 21) |

FIG. 14B

PDK1 amino acid sequence (GenBank Accession No. NP_001248745.1)

1 marttsqlyd avpiqssvvl cscpspsmvr tqtesstppg ipggsrqgpa mdgtaaeprp
61 gagslqhaqp ppqprkkrpe dfkfgkilge gsfstvvlar elatsreyai kilekrhiik
121 enkvpyvtre rdvmsrldhp ffvklyftfq ddeklyfgls yakngellky irkigsfdet
181 ctrfytaeiv saleylhgkg iihrdlkpen illnedmhiq itdfgtakvl speskqaran
241 sfvgtaqyvs pellteksac kssdlwalgc iiyqlvaglp pfragneyli fqkiikleyd
301 fpekffpkar dlvekllvld atkrlgceem egygplkahp ffesvtwenl hqqtppklta
361 ylpamsedde dcygnydnll sqfgcmqvss sssshslsas dtglpqrsgs nieqyihdld
421 snsfeldlqf sedekrllle kqaggnpclt grii  (SEQ ID NO: 22)

PDK1 amino acid sequence (GenBank Accession No. NP_002604.1)

1 marttsqlyd avpiqssvvl cscpspsmvr tqtesstppg ipggsrqgpa mdgtaaeprp
61 gagslqhaqp ppqprkkrpe dfkfgkilge gsfstvvlar elatsreyai kilekrhiik
121 enkvpyvtre rdvmsrldhp ffvklyftfq ddeklyfgls yakngellky irkigsfdet
181 ctrfytaeiv saleylhgkg iihrdlkpen illnedmhiq itdfgtakvl speskqaran
241 sfvgtaqyvs pellteksac kssdlwalgc iiyqlvaglp pfragneyli fqkiikleyd
301 fpekffpkar dlvekllvld atkrlgceem egygplkahp ffesvtwenl hqqtppklta
361 ylpamsedde dcygnydnll sqfgcmqvss sssshslsas dtglpqrsgs nieqyihdld
421 snsfeldlqf sedekrllle kqaggnpwhq fvennlilkm gpvdkrkglf arrrqlllte
481 gphlyyvdpv nkvlkgeipw sqelrpeakn fktffvhtpn rtyylmdpsg nahkwcrkiq
541 evwrqryqsh pdaavq (SEQ ID NO: 23)

PDK1 amino acid sequence (GenBank Accession No. NP_112558.2)

1 marttsqlyd avpiqssvvl cscpspsmvr tqtesstppg ipggsrqgpa mdgtaaeprp
61 gagslqhaqp ppqprkkrpe dfkfgkilge gsfstvvlar elatsreyat ransfvgtaq
121 yvspelltek sackssdlwa lgciiyqlva glppfragne ylifqkiikl eydfpekffp
181 kardlvekll vldatkrlgc eemegygplk ahpffesvtw enlhqqtppk ltaylpamse
241 ddedcygnyd nllsqfgcmq vssssshsl sasdtglpqr sgsnieqyih dldsnsfeld
301 lqfsedekrl llekqaggnp whqfvennli lkmgpvdkrk glfarrrqll ltegphlyyv

FIG. 16

361 dpvnkvlkge ipwsqelrpe aknfktffvh tpnrtyylmd psgnahkwcr kiqevwrqry 421 qshpdaavq (SEQ ID NO: 24)

FIG. 16
CONTINUED

SGK1 amino acid sequence (GenBank Accession No. NP_001137148.1)

1 mvnkdmngfp vkkcsafqff kkrvrrwiks pmvsvdkhqs pslkytgssm vhippgepdf
61 esslcqtclg ehafqrgvlp qenescswet qsgcevrepc nhaniltkpd prtfwtnddp
121 afmkqrrmgl ndfiqkiann syackhpevq silkisqpqe pelmnanpsp ppspsqqinl
181 gpssnphakp sdfhflkvig kgsfgkvlla rhkaeevfya vkvlqkkail kkkeekhims
241 ernvllknvk hpflvglhfs fqtadklyfv ldyinggelf yhlqrercfl eprarfyaae
301 iasalgylhs lnivyrdlkp enilldsqgh ivltdfglck eniehnstts tfcgtpeyla
361 pevlhkqpyd rtvdwwclga vlyemlyglp pfysrntaem ydnilnkplq lkpnitnsar
421 hllegllqkd rtkrlgakdd fmeikshvff slinwddlin kkitppfnpn vsgpndlrhf
481 dpefteepvp nsigkspdsv lvtasvkeaa eaflgfsyap ptdsfl (SEQ ID NO: 25)

SGK1 amino acid sequence (GenBank Accession No. NP_001137149.1)

1 mssqssslse acsreayssh nwalppasrs npqpaypwat rrmkeeaikp plkafmkqrr
61 mglndfiqki annsyackhp evqsilkisq pqepelmnan pspppspsqq inlgpssnph
121 akpsdfhflk vigkgsfgkv llarhkaeev fyavkvlqkk ailkkkeekh imsernvllk
181 nvkhpflvgl hfsfqtadkl yfvldyingg elfyhlqrer cfleprarfy aaeiasalgy
241 lhslnivyrd lkpenillds qghivltdfg lckeniehns ttstfcgtpe ylapevlhkq
301 pydrtvdwwc lgavlyemly glppfysrnt aemydnilnk plqlkpnitn sarhllegll
361 qkdrtkrlga kddfmeiksh vffslinwdd linkkitppf npnvsgpndl rhfdpeftee
421 pvpnsigksp dsvlvtasvk eaaeaflgfs yapptdsfl (SEQ ID NO: 26)

SGK1 amino acid sequence (GenBank Accession No. NP_001137150.1)

1 mgemqgalar arlesllrpr hkkraeaqkr sesfllsgla fmkqrrmgln dfiqkianns
61 yackhpevqs ilkisqpqep elmnanpspp pspsqqinlg pssnphakps dfhflkvigk
121 gsfgkvllar hkaeevfyav kvlqkkailk kkeekhimse rnvllknvkh pflvglhfsf
181 qtadklyfvl dyinggelfy hlqrercfle prarfyaaei asalgylhsl nivyrdlkpe
241 nilldsqghi vltdfglcke niehnsttst fcgtpeylap evlhkqpydr tvdwwclgav
301 lyemlyglpp fysrntaemy dnilnkplql kpnitnsarh llegllqkdr tkrlgakddf
361 meikshvffs linwddlink kitppfnpnv sgpndlrhfd pefteepvpn sigkspdsvl

FIG. 17

421 vtasvkeaae aflgfsyapp tdsfl (SEQ ID NO: 27)

SGK1 amino acid sequence (GenBank Accession No. NP_001278924.1)
1 mtvkteaakg tltysrmrgm vailiafmkq rrmglndfiq kiannsyack hpevqsilki
61 sqpqepelmn anpspppsps qqinlgpssn phakpsdfhf lkvigkgsfg kvllarhkae
121 evfyavkvlq kkailkkkel fyhlqrercf leprarfyaa eiasalgylh slnivyrdlk
181 penilldsqg hivltdfglc keniehnstt stfcgtpeyl apevlhkqpy drtvdwwclg
241 avlyemlygl ppfysrntae mydnilnkpl qlkpnitnsa rhllegllqk drtkrlgakd
301 dfmeikshvf fslinwddli nkkitppfnp nvsgpndlrh fdpefteepv pnsigkspds
361 vlvtasvkea aeaflgfsya pptdsfl (SEQ ID NO: 28)

SGK1 amino acid sequence (GenBank Accession No. NP_005618.2)
1 mtvkteaakg tltysrmrgm vailiafmkq rrmglndfiq kiannsyack hpevqsilki
61 sqpqepelmn anpspppsps qqinlgpssn phakpsdfhf lkvigkgsfg kvllarhkae
121 evfyavkvlq kkailkkkee khimsernvl lknvkhpflv glhfsfqtad klyfvldyin
181 ggelfyhlqr ercfleprar fyaaeiasal gylhslnivy rdlkpenill dsqghivltd
241 fglckenieh nsttstfcgt peylapevlh kqpydrtvdw wclgavlyem lyglppfysr
301 ntaemydnil nkplqlkpni tnsarhlleg llqkdrtkrl gakddfmeik shvffslinw
361 ddlinkkitp pfnpnvsgpn dlrhfdpeft eepvpnsigk spdsvlvtas vkeaaeaflg
421 fsyapptdsf l (SEQ ID NO: 29)

FIG. 17
CONTINUED p110α amino acid sequence (GenBank Accession No. NP_006209.2)

1 mpprpssgel wgihlmppri lvecllpngm ivtleclrea tlitikhelf kearkyplhq 61 llqdessyif vsvtqeaere effdetrrlc dlrlfqpflk viepvgnree kilnreigfa 121 igmpvcefdm vkdpevqdfr rnilnvckea vdlrdlnsph sramyvyppn vesspelpkh 181 iynkldkgqi ivviwvivsp nndkqkytlk inhdcvpeqv iaeairkktr smllsseqlk 241 lcvleyqgky ilkvcgcdey flekyplsqy kyirscimlg rmpnlmlmak eslysqlpmd 301 cftmpsysrr istatpymng etstkslwvi nsalrikilc atyvnvnird idkiyvrtgi 361 yhggeplcdn vntqrvpcsn prwnewlnyd iyipdlpraa rlclsicsvk grkgakeehc 421 plawgninlf dytdtlvsgk malnlwpvph gledllnpig vtgsnpnket pclelefdwf 481 ssvvkfpdms vieehanwsv sreagfsysh aglsnrlard nelrendkeq lkaistrdpl 541 seiteqekdf lwshrhycvt ipeilpklll svkwnsrdev aqmyclvkdw ppikpeqame 601 lldcnypdpm vrgfavrcle kyltddklsq yliqlvqvlk yeqyldnllv rfllkkaltn 661 qrighfffwh lksemhnktv sqrfgllles ycracgmylk hlnrqveame klinltdilk 721 qekkdetqkv qmkflveqmr rpdfmdalqg flsplnpahq lgnlrleecr imssakrplw 781 lnwenpdims ellfqnneii fkngddlrqd mltlqiirim eniwqnqgld lrmlpygcls 841 igdcvgliev vrnshtimqi qckgglkgal qfnshtlhqw lkdknkgeiy daaidlftrs 901 cagycvatfi lgigdrhnsn imvkddgqlf hidfghfldh kkkkfgykre rvpfvltqdf 961 liviskgaqe ctktrefer qemcykayla irqhanlfin lfsmmlgsgm pelqsfddia 1021 yirktlaldk teqealeyfm kqmndahhgg wttkmdwifh tikqhaln (SEQ ID NO: 30)

FIG. 18

PDK1 nucleic acid sequence (GenBank Accession No. NM_001261816)

1 gcggcgccgg gggcgggggg cggcgggcga cggggcgggc gcaggatgag ggcggccatt
61 gctggggctc cgcttcgggg aggaggacgc tgaggaggcg ccgagccgcg cagcgctgcg
121 ggggaggcgc ccgcgccgac gcggggccca tggccaggac caccagccag ctgtatgacg
181 ccgtgcccat ccagtccagc gtggtgttat gttcctgccc atccccatca atggtgagga
241 cccagactga gtccagcacg cccccctgga ttcctggtgg cagcaggcag ggccccgcca
301 tggacggcac tgcagccgag cctcggcccg gcgccggctc cctgcagcat gcccagcctc
361 cgccgcagcc tcggaagaag cggcctgagg acttcaagtt tgggaaaatc cttggggaag
421 gctctttttc cacggttgtc ctggctcgag aactggcaac ctccagagaa tatgcgatta
481 aaattctgga gaagcgacat atcataaaag agaacaaggt cccctatgta accagagagc
541 gggatgtcat gtcgcgcctg gatcacccct ctttgttaa gctttacttc acatttcagg
601 acgacgagaa gctgtatttc ggccttagtt atgccaaaaa tggagaacta cttaaatata
661 ttcgcaaaat cggttcattc gatgagacct gtacccgatt ttacacggct gagattgtgt
721 ctgctttaga gtacttgcac ggcaagggca tcattcacag ggaccttaaa ccggaaaaca
781 ttttgttaaa tgaagatatg cacatccaga tcacagattt tggaacagca aaagtcttat
841 ccccagagag caaacaagcc agggccaact cattcgtggg aacagcgcag tacgtttctc
901 cagagctgct cacggagaag tccgcctgta agagttcaga cctttgggct cttggatgca
961 taatatacca gcttgtggca ggactcccac cattccgagc tggaaacgag tatcttatat
1021 ttcagaagat cattaagttg gaatatgact ttccagaaaa attcttccct aaggcaagag
1081 acctcgtgga gaaacttttg gttttagatg ccacaaagcg gttaggctgt gaggaaatgg
1141 aaggatacgg acctcttaaa gcacacccgt tcttcgagtc cgtcacgtgg gagaacctgc
1201 accagcagac gcctccgaag ctcaccgctt acctgccggc tatgtcggaa gacgacgagg
1261 actgctatgg caattatgac aatctcctga gccagtttgg ctgcatgcag gtgtcttcgt
1321 cctcctcctc acactccctg tcagcctccg acacgggcct gccccagagg tcaggcagca
1381 acatagagca gtacattcac gatctggact cgaactcctt tgaactggac ttacagtttt
1441 ccgaagatga aagaggttg ttgttggaga agcaggctgg cggaaaccct tgcctaacag
1501 gacgtattat ctgatggacc ccagcgggaa cgcacacaag tggtgcagga agatccagga
1561 ggtttggagg cagcgatacc agagccaccc ggacgccgct gtgcagtgac gtggcctgcg
1621 gccgggctgc ccttcgctgc caggacacct gccccagcgc ggcttggccg ccatccggga
1681 cgcttccaga ccacctgcca gccatcacaa ggggaacgca gaggcggaaa ccttgcagca

FIG. 19

```
1741 tttttattta aaagaaaaga agaaaaaaaa cacccaacca cacaaagaac aaaaccagta
1801 acaaacacaa aggaattcag ggtcgctttg cttgctctct gtgctccgtg gaggcctccg
1861 tgtgccctcg ttgccgtggg gacccagctc catgcacgtc aacccagtcc cgcccagact
1921 agtggacaga cctggtgtca ccagttttc ctagcatcag tccgaaccat gcgcccgccc
1981 tgccccaact gtgtgctggt cctgctgtgg ccgaggggac cgggtgtgtt tggctcttta
2041 tgcccctccc gctgtggtcc tggaactctt caccagggag ggagccctgc gggggccgca
2101 gctttgtgga gggagccgcc gtgcttctgt cacctgctcc ctttcttgcg tctccctgtg
2161 atgggccctt aggcctggct gggcccatta catatccctg tggtggctct ggtggcagct
2221 ttctgtggcc cctgctgtgt tggcaggcag gtttgcgtgg tgaggagcgg gaggggttgg
2281 agtggtgcgg gagcaggctg ccgagtggag ggtgccatcg agggctccgg atcccttatc
2341 ctacttagca gtgttggtct ctggggctgg aagccgagcg catgctggga gcggtactgt
2401 cagaagtgag cccagttagt accccgctgg ctcactgcac gagagagtcc tgccccgagc
2461 cctaggtggg gccaggaggt gccttggaga agccagccag agcagagagg gctgctgact
2521 tccgtgtgga gcagagaggc ctgagggcct cctaaaaggt ttaaatgtcc acgcctctcc
2581 agttgctgaa gtagggtctg agagaaccct ggcatcagca gacccagggt gcttctgtct
2641 cctgcagacc acgccaggga gtgcagacac caccgtcaca cacgccccctt ttgtgttttg
2701 gttcaagttt ctcagagccc ctcagagctt ctacatctgt gcatcagaaa tctcacagcc
2761 ttctcatgct gccggctcat ctgggcccat agagtgggct ttgccagttg ctgttgcaca
2821 ggaggcgaga acagcacact tcaaccccag cttgctggtc ggctttcctc tagagagagc
2881 cggttttggg gccatttccc tttgatgctt tggtggcctt gccccgctct gcagcacaga
2941 caggccagat gcatttgtcc tttgcctagc tactccccag gtagagagtg ctcctggtgg
3001 cctggcaggt ctgggccctt ctctccctgc ccaggttgtc cctggagggc agccctcact
3061 cctttgggg gagaggcaga cattgctgcc cacagacctg cctctgactc aactgtgtcc
3121 accctccctg gtccctaccc ccaagtcaca ggtgactcag cagtgaccct gtgtgccagg
3181 ccagatccaa actgagaggg aaggtgtcgt ttttacactg ctaatgacga gagtggctct
3241 ttttagctag gcgagtacag acggggcctg ggagggggca gagatgttcc ccaggccctg
3301 cctgtggttc ctgcctgggc cttggctgct gctgtgtgag agctgcatgt gagcctgtga
3361 ccgtgagctg gggtgagctg ggccgcacct accctggggc cccagggagc aggacgctcc
3421 ggggcccagc acgttgccct gggcctgtgg ccggagtcgg agtcctctct cctcctcctg
```

FIG. 19
CONTINUED 3481 gcttttggaa aggcttggct gtgttgggga gtctctctta gcccttcag gaatttctgt 3541 tcaggcttcc tcctcctcat cagctatttt acccatctca gaacgtcctg tgtctccatg 3601 taggagagtg gctctctcag atctctcagg gcgtctggtt atagggaaac aagtggagca 3661 gggacgtggc tttaattgga gcactcggct gggctgcttg gggagactct tccgtgcgtt 3721 cttcctctgg atagaaccac cacctcctgg gcgtcactga caagctccat cttaacctcc 3781 aaagccacag aactaggggc tcagagccag agctggcagc cgccagccaa aatgatgcca 3841 ttgcctgagc tgacagccaa gcccttctgt gggtcacctt tctcctcacc cagccccttg 3901 ctcttccctt ttgaaaggcc cgtgtgtttt ctttccttac cctgtgcttg ctcatgtcta 3961 ctccggtttt ctctaccaca tccttagagc catcacctgg cacgcaggcg ccttacattc 4021 tacggtagaa cgtggggtac tgtgtgtgca catagacaca cttacgtgga attacagttg 4081 tgggtttatc caagatgagg aagatttcac ctgctgttta atagacttgg ggccatgtgc 4141 ctccccacac atgggcaagg acaggtggaa tgtcgggacc acactgtgcg gcttctcggc 4201 acaaagcgga gggaggctgt ggtcgctgcc ggcctaggtg tcccaggtgc cccgcctttc 4261 tctgggacac agttgggggc tggcttctga gggattcctt tctcccctct ttgtgtggcc 4321 ccagccaggg cggtgggcag tcctggtgta gagcacaagc ctctccaccc tagagaaatg 4381 cctctgtacc acggctacca tgtggaacct taacttgcag aaggcttgtt aacaattgtt 4441 ttgagagaga tggctggtca tgccacagct gctggggact ccgcctactc cagccctctt 4501 gggacacact gtgggatttg tggcccttcc ccagaggaat tgtggagact gtcccatgga 4561 acaaaccctc aggcaccagc acagggctct gggtgactca gtaaaactaa cgtttgtctc 4621 tgacaagatc agctgtaggc tcaccggcca gagaagacca ctgtgagcat tttgccgtat 4681 atcctgccct gccatttgtt cactttttaa actaaaatag gaacatccga cacacaccgt 4741 ttgcatcgtc ttctcccttg atattttaag cattttccca tgtcatgagt ttctcagaaa 4801 catgttttta acaattgtac tatttagtca ttgtccattt actataattt atctgaccat 4861 ttccctactg taaaatactt aagacggttt ctgatttttc cactatttaa ataatgctgt 4921 gatgaatatc tttaaaatct tctgatttct tactttttc ccccttagat gcctggaagt 4981 ggtattttga ggtgaaagag tttgttcatt ttgaagatat ttctgtctct ctctcgacct 5041 gatgtgtaga cgctcacttc cagtagcaga accaccttag ttgtgtctta cagattctga 5101 acaaatcggt ttctgataag ccatgtgttc caaagaatgt ctgaataaga ccgctcttta 5161 tttaaatgct aagaggatgt cactactgca atccatctgt ggccgatttt ttccaagagc 5221 caatttcctt gttttggttg caagaacctg gctctgcctg catgtcagct ctctgccctc

FIG. 19
CONTINUED 5281 cctgctgccg tggctttcaa gcgcttggca gaatcttgta cttcgtgtcc acaatggtac 5341 tgaatttgca tctgcacagt cagcagagat aacaagtgtt gaactgacct tgccacatgc 5401 ttagtgagtg atttgtaatt aagtttatag actcagaagg tatattagga catttggaat 5461 cagtagcaga gcaaagcctc tttgaaaaaa accacgtagc tgattgggtt ttacaagagt 5521 gcatttgtct ccccttcca cccgtggggc cccaccttca ggtcttagtg gttcacaaga 5581 gcccagcagc caggctggct ttttcattgt agggcgtggt tgtcccagct ggtgtagatt 5641 tcaggccgcc ccccccaact ccctgcccac agtgttgcag attgcctggc tggcagcaag 5701 tccagaccac ccaaatttgg ttggattctt catttctcca ctgtagttgg ggtccattga 5761 ttgtgcaggg aacgtgcag gaggttttc taggcaccgt gttcagtgct gcttcactct 5821 accagagatt atggccaaat tgcacggaat tggtttctt gccctctgaa gcctgagggc 5881 ccccccttgc ctggctggtt gacagacccg gggtggtcac tgctgagact tcagagatcg 5941 cagctgctgt gagaatacgg tgaaggtact ttgttctgga agatgttgtc atacactttt 6001 ccccagttat tttcaaactt gacatgagcc tatgttgact cactgggtgg gggtcccttc 6061 ttacgcagca cacgtggcaa gtgcctgaat cggggctgga ggcacttcag agcctctgag 6121 gggccaccac ttctggccca aaattgcagg gttgtagatg aggctgcctg tggagaactg 6181 gtgtgaggag gaagctgttt ccaacaaaga gcactttcat ctgttgagat ggctgtggtg 6241 agcaactgaa cgagcctacg tgtgtacctg aattttcccc gtaactcatt tcttccatat 6301 gaagaaacac caaactatgt acagagaact ttttacaaaa ggcagacctt ttttaagctg 6361 tgtaacccac atagcctaac cacctggcag aatgactacg aataggggtc attgtgctgg 6421 taaaagcctc tattacgact gtaagtaagt tggatgttgg caaaattaaa ttgttacagt 6481 atttagagct gctgtagctg ttccttcaca acataaaata ggataaatga ctagtacgtc 6541 tttcaggtgg gtggcaagca gaacatgcgt aatattctct acctggtctg tagctgtaac 6601 tgtgatgtac agacaaagca aaaattaaaa gaacttatga aaacaaatgc aatgatacta 6661 ggatatacac ttttgtattt ttattcttat ataaggttat ttgctggcta ttgttggcct 6721 ctagttcagt ctgtgttatt taaattctaa tatatgaatt atttgaattg aattcatgtt 6781 cggggccacg ttgttgtatg tattgatgta cagccttgaa tgtgaataat tattgtaaac 6841 tatattttac aacttttttt ctggctttat tatataaatt ttctattggg tcagtgattt 6901 aatcatataa tttaatgaat ctgtttatcc tttttttttt tccaaatact tgtgctttag 6961 gtgtagttac cagatgatga attttcctcg tatggtcagt agtcttgtaa taaaaagcat 7021 gtagagtgta ga (SEQ ID NO: 31)

FIG. 19
CONTINUED

PDK1 nucleic acid sequence (GenBank Accession No. NM_002613)

```
1    gcggcgccgg gggcggggggg cggcgggcga cggggcgggc gcaggatgag ggcggccatt
61   gctggggctc cgcttcgggg aggaggacgc tgaggaggcg ccgagccgcg cagcgctgcg
121  ggggaggcgc ccgcgccgac gcggggccca tggccaggac caccagccag ctgtatgacg
181  ccgtgcccat ccagtccagc gtggtgttat gttcctgccc atccccatca atggtgagga
241  cccagactga gtccagcacg cccccctggca ttcctggtgg cagcaggcag ggccccgcca
301  tggacggcac tgcagccgag cctcggcccg gcgccggctc cctgcagcat gcccagcctc
361  cgccgcagcc tcggaagaag cggcctgagg acttcaagtt tgggaaaatc cttggggaag
421  gctctttttc cacggttgtc ctggctcgag aactggcaac ctccagagaa tatgcgatta
481  aaattctgga gaagcgacat atcataaaag agaacaaggt cccctatgta accagagagc
541  gggatgtcat gtcgcgcctg gatcacccct tctttgttaa gctttacttc acatttcagg
601  acgacgagaa gctgtatttc ggccttagtt atgccaaaaa tggagaacta cttaaatata
661  ttcgcaaaat cggttcattc gatgagacct gtacccgatt ttacacggct gagattgtgt
721  ctgctttaga gtacttgcac ggcaagggca tcattcacag ggaccttaaa ccggaaaaca
781  ttttgttaaa tgaagatatg cacatccaga tcacagattt tggaacagca aaagtcttat
841  ccccagagag caaacaagcc agggccaact cattcgtggg aacagcgcag tacgtttctc
901  cagagctgct cacggagaag tccgcctgta agagttcaga cctttgggct cttggatgca
961  taatatacca gcttgtggca ggactcccac cattccgagc tggaaacgag tatcttatat
1021 ttcagaagat cattaagttg gaatatgact ttccagaaaa attcttccct aaggcaagag
1081 acctcgtgga gaaacttttg gttttagatg ccacaaagcg gttaggctgt gaggaaatgg
1141 aaggatacgg acctcttaaa gcacacccgt tcttcgagtc cgtcacgtgg gagaacctgc
1201 accagcagac gcctccgaag ctcaccgctt acctgccggc tatgtcggaa gacgacgagg
1261 actgctatgg caattatgac aatctcctga gccagtttgg ctgcatgcag gtgtcttcgt
1321 cctcctcctc acactccctg tcagcctccg acacgggcct gccccagagg tcaggcagca
1381 acatagagca gtacattcac gatctggact cgaactcctt tgaactggac ttacagtttt
1441 ccgaagatga aagaggttg ttgttggaga agcaggctgg cggaaaccct tggcaccagt
1501 ttgtagaaaa taatttaata ctaaagatgg gcccagtgga taagcggaag ggtttatttg
1561 caagacgacg acagctgttg ctcacagaag gaccacattt atattatgtg gatcctgtca
1621 acaaagttct gaaaggtgaa attccttggt cacaagaact tcgaccagag gccaagaatt
1681 ttaaaacttt ctttgtccac acgcctaaca ggacgtatta tctgatggac cccagcggga
```

FIG. 19
CONTINUED 1741 acgcacacaa gtggtgcagg aagatccagg aggtttggag gcagcgatac cagagccacc 1801 cggacgccgc tgtgcagtga cgtggcctgc ggccgggctg cccttcgctg ccaggacacc 1861 tgccccagcg cggcttggcc gccatccggg acgcttccag accacctgcc agccatcaca 1921 aggggaacgc agaggcggaa accttgcagc attttatttt aaaagaaaag aagaaaaaaa 1981 acacccaacc acacaaagaa caaaaccagt aacaaacaca aaggaattca gggtcgcttt 2041 gcttgctctc tgtgctccgt ggaggcctcc gtgtgccctc gttgccgtgg ggacccagct 2101 ccatgcacgt caacccagtc ccgcccagac tagtggacag acctggtgtc accagttttt 2161 cctagcatca gtccgaacca tgcgcccgcc ctgccccaac tgtgtgctgg tcctgctgtg 2221 gccgagggga ccgggtgtgt ttggctcttt atgcccctcc cgctgtggtc ctggaactct 2281 tcaccaggga gggagccctg cgggggccgc agctttgtgg agggagccgc cgtgcttctg 2341 tcacctgctc cctttcttgc gtctccctgt gatgggccct taggcctggc tgggcccatt 2401 acatatccct gtggtggctc tggtggcagc tttctgtggc ccctgctgtg ttggcaggca 2461 ggtttgcgtg gtgaggagcg ggaggggttg gagtggtgcg ggagcaggct gccgagtgga 2521 gggtgccatc gagggctccg gatcccttat cctacttagc agtgttggtc tctggggctg 2581 gaagccgagc gcatgctggg agcggtactg tcagaagtga gcccagttag taccccgctg 2641 gctcactgca cgagagagtc ctgccccgag ccctaggtgg ggccaggagg tgccttggag 2701 aagccagcca gagcagagag ggctgctgac ttccgtgtgg agcagagagg cctgagggcc 2761 tcctaaaagg tttaaatgtc cacgcctctc cagttgctga agtagggtct gagagaaccc 2821 tggcatcagc agacccaggg tgcttctgtc tcctgcagac cacgccaggg agtgcagaca 2881 ccaccgtcac acacgcccct tttgtgtttt ggttcaagtt tctcagagcc cctcagagct 2941 tctacatctg tgcatcagaa atctcacagc cttctcatgc tgccggctca tctgggccca 3001 tagagtgggc tttgccagtt gctgttgcac aggaggcgag aacagcacac ttcaaccccca 3061 gcttgctggt cggctttcct ctagagagag ccggttttgg ggccatttcc ctttgatgct 3121 ttggtggcct tgccccgctc tgcagcacag acaggccaga tgcatttgtc ctttgcctag 3181 ctactcccca ggtagagagt gctcctggtg gcctggcagg tctgggccct tctctccctg 3241 cccaggttgt ccctggaggg cagccctcac tcccttggg ggagaggcag acattgctgc 3301 ccacagacct gcctctgact caactgtgtc caccctccct ggtccctacc cccaagtcac 3361 aggtgactca gcagtgaccc tgtgtgccag gccagatcca aactgagagg gaaggtgtcg 3421 tttttacact gctaatgacg agagtggctc tttttagcta ggcgagtaca gacggggcct 3481 gggaggggggc agagatgttc cccaggccct gcctgtggtt cctgcctggg ccttggctgc

FIG. 19
CONTINUED

```
3541 tgctgtgtga gagctgcatg tgagcctgtg accgtgagct ggggtgagct gggccgcacc
3601 taccctgggg ccccagggag caggacgctc cggggcccag cacgttgccc tgggcctgtg
3661 gccggagtcg gagtcctctc tcctcctcct ggcttttgga aaggcttggc tgtgttggggg
3721 agtctctctt agccctttca ggaatttctg ttcaggcttc ctcctcctca tcagctattt
3781 tacccatctc agaacgtcct gtgtctccat gtaggagagt ggctctctca gatctctcag
3841 ggcgtctggt tatagggaaa caagtggagc agggacgtgg ctttaattgg agcactcggc
3901 tgggctgctt ggggagactc ttccgtgcgt tcttcctctg gatagaacca ccacctcctg
3961 ggcgtcactg acaagctcca tcttaacctc caaagccaca gaactagggg ctcagagcca
4021 gagctggcag ccgccagcca aaatgatgcc attgcctgag ctgacagcca agcccttctg
4081 tgggtcacct ttctcctcac ccagccccct gctcttccct tttgaaaggc ccgtgtgttt
4141 tctttcctta ccctgtgctt gctcatgtct actccggttt tctctaccac atccttagag
4201 ccatcacctg gcacgcaggc gccttacatt ctacggtaga acgtggggta ctgtgtgtgc
4261 acatagacac acttacgtgg aattacagtt gtgggtttat ccaagatgag gaagatttca
4321 cctgctgttt aatagacttg gggccatgtg cctccccaca catgggcaag gacaggtgga
4381 atgtcgggac cacactgtgc ggcttctcgg cacaaagcgg agggaggctg tggtcgctgc
4441 cggcctaggt gtcccaggtg ccccgccttt ctctgggaca cagttgggggg ctggcttctg
4501 agggattcct ttctcccctc tttgtgtggc cccagccagg gcggtgggca gtcctggtgt
4561 agagcacaag cctctccacc ctagagaaat gcctctgtac cacggctacc atgtggaacc
4621 ttaacttgca gaaggcttgt taacaattgt tttgagagag atggctggtc atgccacagc
4681 tgctggggac tccgcctact ccagccctct tgggacacac tgtgggattt gtggcccttc
4741 cccagaggaa ttgtggagac tgtcccatgg aacaaaccct caggcaccag cacagggctc
4801 tgggtgactc agtaaaacta acgtttgtct ctgacaagat cagctgtagg ctcaccggcc
4861 agagaagacc actgtgagca ttttgccgta tatcctgccc tgccatttgt tcacttttta
4921 aactaaaata ggaacatccg acacacaccg tttgcatcgt cttctccctt gatattttaa
4981 gcattttccc atgtcatgag tttctcagaa acatgttttt aacaattgta ctatttagtc
5041 attgtccatt tactataatt tatctgacca tttccctact gtaaaatact taagacggtt
5101 tctgattttt ccactattta aataatgctg tgatgaatat ctttaaaatc ttctgatttc
5161 ttactttttt ccccctaga tgcctggaag tggtattttg aggtgaaaga gtttgttcat
5221 tttgaagata tttctgtctc tctctcgacc tgatgtgtag acgctcactt ccagtagcag
5281 aaccaccta gttgtgtctt acagattctg aacaaatcgg tttctgataa gccatgtgtt
```

FIG. 19
CONTINUED 5341 ccaaagaatg tctgaataag accgctcttt atttaaatgc taagaggatg tcactactgc 5401 aatccatctg tggccgattt tttccaagag ccaatttcct tgttttggtt gcaagaacct 5461 ggctctgcct gcatgtcagc tctctgccct ccctgctgcc gtggctttca agcgcttggc 5521 agaatcttgt acttcgtgtc cacaatggta ctgaatttgc atctgcacag tcagcagaga 5581 taacaagtgt tgaactgacc ttgccacatg cttagtgagt gatttgtaat taagtttata 5641 gactcagaag gtatattagg acatttggaa tcagtagcag agcaaagcct ctttgaaaaa 5701 aaccacgtag ctgattgggt tttacaagag tgcatttgtc tcccccttcc acccgtgggg 5761 ccccaccttc aggtcttagt ggttcacaag agcccagcag ccaggctggc tttttcattg 5821 tagggcgtgg ttgtcccagc tggtgtagat ttcaggccgc ccccccaac tccctgccca 5881 cagtgttgca gattgcctgg ctggcagcaa gtccagacca cccaaatttg gttggattct 5941 tcatttctcc actgtagttg gggtccattg attgtgcagg ggaacgtgca ggaggttttt 6001 ctaggcaccg tgttcagtgc tgcttcactc taccagagat tatggccaaa ttgcacggaa 6061 tttggtttct tgccctctga agcctgaggg ccccccttg cctggctggt tgacagaccc 6121 ggggtggtca ctgctgagac ttcagagatc gcagctgctg tgagaatacg gtgaaggtac 6181 tttgttctgg aagatgttgt catacacttt tccccagtta ttttcaaact tgacatgagc 6241 ctatgttgac tcactgggtg ggggtccctt cttacgcagc acacgtggca agtgcctgaa 6301 tcggggctgg aggcacttca gagcctctga ggggccacca cttctggccc aaaattgcag 6361 ggttgtagat gaggctgcct gtggagaact ggtgtgagga ggaagctgtt tccaacaaag 6421 agcactttca tctgttgaga tggctgtggt gagcaactga acgagcctac gtgtgtacct 6481 gaattttccc cgtaactcat ttcttccata tgaagaaaca ccaaactatg tacagagaac 6541 tttttacaaa aggcagacct tttttaagct gtgtaaccca catagcctaa ccacctggca 6601 gaatgactac gaatagggt cattgtgctg gtaaaagcct ctattacgac tgtaagtaag 6661 ttggatgttg gcaaaattaa attgttacag tatttagagc tgctgtagct gttccttcac 6721 aacataaaat aggataaatg actagtacgt ctttcaggtg ggtggcaagc agaacatgcg 6781 taatattctc tacctggtct gtagctgtaa ctgtgatgta cagacaaagc aaaaattaaa 6841 agaacttatg aaaacaaatg caatgatact aggatataca cttttgtatt tttattctta 6901 tataaggtta tttgctggct attgttggcc tctagttcag tctgtgttat ttaaattcta 6961 atatatgaat tatttgaatt gaattcatgt tcggggccac gttgttgtat gtattgatgt 7021 acagccttga atgtgaataa ttattgtaaa ctatatttta caactttttt tctggcttta 7081 ttatataaat tttctattgg gtcagtgatt taatcatata atttaatgaa tctgtttatc

FIG. 19
CONTINUED 7141 cttttttttt ttccaaatac ttgtgcttta ggtgtagtta ccagatgatg aattttcctc 7201 gtatggtcag tagtcttgta ataaaaagca tgtagagtgt aga (SEQ ID NO: 32)

PDK1 nucleic acid sequence (GenBank Accession No. NM_031268)

1 gcggcgccgg gggcgggggg cggcgggcga cggggcgggc gcaggatgag ggcggccatt 61 gctggggctc cgcttcgggg aggaggacgc tgaggaggcg ccgagccgcg cagcgctgcg 121 ggggaggcgc ccgcgccgac gcggggccca tggccaggac caccagccag ctgtatgacg 181 ccgtgcccat ccagtccagc gtggtgttat gttcctgccc atccccatca atggtgagga 241 cccagactga gtccagcacg cccctggca ttcctggtgg cagcaggcag ggccccgcca 301 tggacggcac tgcagccgag cctcggcccg cgccggctc cctgcagcat gcccagcctc 361 cgccgcagcc tcggaagaag cggcctgagg acttcaagtt tgggaaaatc cttggggaag 421 gctctttttc cacggttgtc ctggctcgag aactggcaac ctccagaaa tatgcgacca 481 gggccaactc attcgtggga acagcgcagt acgtttctcc agagctgctc acggagaagt 541 ccgcctgtaa gagttcagac ctttgggctc ttggatgcat aatataccag cttgtggcag 601 gactcccacc attccgagct ggaaacgagt atcttatatt tcagaagatc attaagttgg 661 aatatgactt tccagaaaaa ttcttccta aggcaagaga cctcgtggag aaactttgg 721 ttttagatgc cacaaagcgg ttaggctgtg aggaaatgga aggatacgga cctcttaaag 781 cacacccgtt cttcgagtcc gtcacgtggg agaacctgca ccagcagacg cctccgaagc 841 tcaccgctta cctgccggct atgtcggaag acgacgagga ctgctatggc aattatgaca 901 atctcctgag ccagtttggc tgcatgcagg tgtcttcgtc ctcctcctca cactccctgt 961 cagcctccga cacgggcctg ccccagaggt caggcagcaa catagagcag tacattcacg 1021 atctggactc gaactccttt gaactggact acagttttc cgaagatgag aagaggttgt 1081 tgttggagaa gcaggctggc ggaaaccctt ggcaccagtt tgtagaaaat aatttaatac 1141 taaagatggg cccagtggat aagcggaagg gtttatttgc aagacgacga cagctgttgc 1201 tcacagaagg accacattta tattatgtgg atcctgtcaa caaagttctg aaaggtgaaa 1261 ttccttggtc acaagaactt cgaccagagg ccaagaattt taaaactttc tttgtccaca 1321 cgcctaacag gacgtattat ctgatggacc ccagcgggaa cgcacacaag tggtgcagga 1381 agatccagga ggtttggagg cagcgatacc agagccaccc ggacgccgct gtgcagtgac 1441 gtggcctgcg gccgggctgc ccttcgctgc caggacacct gccccagcgc ggcttggccg 1501 ccatccggga cgcttccaga ccacctgcca gccatcacaa ggggaacgca gaggcggaaa

FIG. 19
CONTINUED

```
1561 ccttgcagca tttttattta aaagaaaaga agaaaaaaaa cacccaacca cacaaagaac
1621 aaaaccagta acaaacacaa aggaattcag ggtcgctttg cttgctctct gtgctccgtg
1681 gaggcctccg tgtgccctcg ttgccgtggg gacccagctc catgcacgtc aacccagtcc
1741 cgcccagact agtggacaga cctggtgtca ccagtttttc ctagcatcag tccgaaccat
1801 gcgcccgccc tgcccaact gtgtgctggt cctgctgtgg ccgaggggac cgggtgtgtt
1861 tggctcttta tgcccctccc gctgtggtcc tggaactctt caccagggag ggagccctgc
1921 ggggggccgca gctttgtgga gggagccgcc gtgcttctgt cacctgctcc ctttcttgcg
1981 tctccctgtg atgggcccctt aggcctggct gggcccatta catatccctg tggtggctct
2041 ggtggcagct ttctgtggcc cctgctgtgt tggcaggcag gtttgcgtgg tgaggagcgg
2101 gaggggttgg agtggtgcgg gagcaggctg ccgagtggag ggtgccatcg agggctccgg
2161 atcccttatc ctacttagca gtgttggtct ctggggctgg aagccgagcg catgctggga
2221 gcggtactgt cagaagtgag cccagttagt accccgctgg ctcactgcac gagagagtcc
2281 tgccccgagc cctaggtggg gccaggaggt gccttggaga agccagccag agcagagagg
2341 gctgctgact tccgtgtgga gcagagaggc ctgagggcct cctaaaaggt ttaaatgtcc
2401 acgcctctcc agttgctgaa gtagggtctg agagaaccct ggcatcagca gacccagggt
2461 gcttctgtct cctgcagacc acgccaggga gtgcagacac caccgtcaca cacgccccctt
2521 ttgtgttttg gttcaagttt ctcagagccc ctcagagctt ctacatctgt gcatcagaaa
2581 tctcacagcc ttctcatgct gccggctcat ctgggcccat agagtgggct ttgccagttg
2641 ctgttgcaca ggaggcgaga acagcacact tcaacccag cttgctggtc ggcttttcctc
2701 tagagagagc cggtttttggg gccattttccc tttgatgctt tggtggcctt gccccgctct
2761 gcagcacaga caggccagat gcatttgtcc tttgcctagc tactccccag gtagagagtg
2821 ctcctggtgg cctggcaggt ctgggcccctt ctctccctgc ccaggttgtc cctggagggc
2881 agccctcact ccctttgggg gagaggcaga cattgctgcc cacagacctg cctctgactc
2941 aactgtgtcc accctccctg gtccctaccc ccaagtcaca ggtgactcag cagtgaccct
3001 gtgtgccagg ccagatccaa actgagaggg aaggtgtcgt ttttacactg ctaatgacga
3061 gagtggctct ttttagctag gcgagtacag acggggcctg ggaggggggca gagatgttcc
3121 ccaggccctg cctgtggttc ctgcctgggc cttggctgct gctgtgtgag agctgcatgt
3181 gagcctgtga ccgtgagctg gggtgagctg ggccgcacct accctggggc cccagggagc
3241 aggacgctcc ggggcccagc acgttgccct gggcctgtgg ccggagtcgg agtcctctct
3301 cctcctcctg gcttttggaa aggcttggct gtgttgggga gtctctctta gcccttttcag
```

FIG. 19
CONTINUED 3361 gaatttctgt tcaggcttcc tcctcctcat cagctatttt acccatctca gaacgtcctg 3421 tgtctccatg taggagagtg gctctctcag atctctcagg gcgtctggtt atagggaaac 3481 aagtggagca gggacgtggc tttaattgga gcactcggct gggctgcttg gggagactct 3541 tccgtgcgtt cttcctctgg atagaaccac cacctcctgg gcgtcactga caagctccat 3601 cttaacctcc aaagccacag aactaggggc tcagagccag agctggcagc cgccagccaa 3661 aatgatgcca ttgcctgagc tgacagccaa gcccttctgt gggtcacctt tctcctcacc 3721 cagccccttg ctcttccctt ttgaaaggcc cgtgtgtttt ctttccttac cctgtgcttg 3781 ctcatgtcta ctccggtttt ctctaccaca tccttagagc catcacctgg cacgcaggcg 3841 ccttacattc tacggtagaa cgtggggtac tgtgtgtgca catagacaca cttacgtgga 3901 attacagttg tgggtttatc caagatgagg aagatttcac ctgctgttta atagacttgg 3961 ggccatgtgc ctccccacac atgggcaagg acaggtggaa tgtcgggacc acactgtgcg 4021 gcttctcggc acaaagcgga gggaggctgt ggtcgctgcc ggcctaggtg tcccaggtgc 4081 cccgcctttc tctgggacac agttgggggc tggcttctga gggattcctt tctcccctct 4141 ttgtgtggcc ccagccaggg cggtgggcag tcctggtgta gagcacaagc ctctccaccc 4201 tagagaaatg cctctgtacc acggctacca tgtggaacct taacttgcag aaggcttgtt 4261 aacaattgtt ttgagagaga tggctggtca tgccacagct gctggggact ccgcctactc 4321 cagccctctt gggacacact gtgggatttg tggcccttcc ccagaggaat tgtggagact 4381 gtcccatgga acaaaccctc aggcaccagc acagggctct gggtgactca gtaaaactaa 4441 cgtttgtctc tgacaagatc agctgtaggc tcaccggcca gagaagacca ctgtgagcat 4501 tttgccgtat atcctgccct gccatttgtt cacttttaa actaaaatag gaacatccga 4561 cacacaccgt ttgcatcgtc ttctcccttg atattttaag cattttccca tgtcatgagt 4621 ttctcagaaa catgttttta acaattgtac tatttagtca ttgtccattt actataattt 4681 atctgaccat ttccctactg taaaatactt aagacggttt ctgattttc cactatttaa 4741 ataatgctgt gatgaatatc tttaaaatct tctgatttct tacttttttc cccttagat 4801 gcctggaagt ggtattttga ggtgaaagag tttgttcatt ttgaagatat ttctgtctct 4861 ctctcgacct gatgtgtaga cgctcacttc cagtagcaga accaccttag ttgtgtctta 4921 cagattctga acaaatcggt ttctgataag ccatgtgttc caaagaatgt ctgaataaga 4981 ccgctcttta tttaaatgct aagaggatgt cactactgca atccatctgt ggccgatttt 5041 ttccaagagc caatttcctt gttttggttg caagaacctg gctctgcctg catgtcagct 5101 ctctgccctc cctgctgccg tggctttcaa gcgcttggca gaatcttgta cttcgtgtcc

FIG. 19
CONTINUED 5161 acaatggtac tgaatttgca tctgcacagt cagcagagat aacaagtgtt gaactgacct 5221 tgccacatgc ttagtgagtg atttgtaatt aagtttatag actcagaagg tatattagga 5281 catttggaat cagtagcaga gcaaagcctc tttgaaaaaa accacgtagc tgattgggtt 5341 ttacaagagt gcatttgtct cccccttcca cccgtggggc cccaccttca ggtcttagtg 5401 gttcacaaga gcccagcagc caggctggct ttttcattgt agggcgtggt tgtcccagct 5461 ggtgtagatt tcaggccgcc ccccccaact ccctgcccac agtgttgcag attgcctggc 5521 tggcagcaag tccagaccac ccaaatttgg ttggattctt catttctcca ctgtagttgg 5581 ggtccattga ttgtgcaggg gaacgtgcag gaggttttc taggcaccgt gttcagtgct 5641 gcttcactct accagagatt atggccaaat tgcacggaat ttggtttctt gccctctgaa 5701 gcctgagggc ccccccttgc ctggctggtt gacagacccg gggtggtcac tgctgagact 5761 tcagagatcg cagctgctgt gagaatacgg tgaaggtact ttgttctgga agatgttgtc 5821 atacactttt ccccagttat tttcaaactt gacatgagcc tatgttgact cactgggtgg 5881 gggtcccttc ttacgcagca cacgtggcaa gtgcctgaat cggggctgga ggcacttcag 5941 agcctctgag gggccaccac ttctggccca aaattgcagg gttgtagatg aggctgcctg 6001 tggagaactg gtgtgaggag gaagctgttt ccaacaaaga gcactttcat ctgttgagat 6061 ggctgtggtg agcaactgaa cgagcctacg tgtgtacctg aatttccccc gtaactcatt 6121 tcttccatat gaagaaacac caaactatgt acagagaact ttttacaaaa ggcagacctt 6181 ttttaagctg tgtaacccac atagcctaac cacctggcag aatgactacg aatagggggtc 6241 attgtgctgg taaaagcctc tattacgact gtaagtaagt tggatgttgg caaaattaaa 6301 ttgttacagt atttagagct gctgtagctg ttccttcaca acataaaata ggataaatga 6361 ctagtacgtc tttcaggtgg gtggcaagca gaacatgcgt aatattctct acctggtctg 6421 tagctgtaac tgtgatgtac agacaaagca aaattaaaa gaacttatga aaacaaatgc 6481 aatgatacta ggatatacac ttttgtattt ttattcttat ataaggttat ttgctggcta 6541 ttgttggcct ctagttcagt ctgtgttatt taaattctaa tatatgaatt atttgaattg 6601 aattcatgtt cggggccacg ttgttgtatg tattgatgta cagccttgaa tgtgaataat 6661 tattgtaaac tatattttac aactttttt ctggctttat tatataaatt ttctattggg 6721 tcagtgattt aatcatataa tttaatgaat ctgtttatcc ttttttttt tccaaatact 6781 tgtgctttag gtgtagttac cagatgatga attttcctcg tatggtcagt agtcttgtaa 6841 taaaaagcat gtagagtgta ga (SEQ ID NO: 33)

FIG. 19
CONTINUED

SGK1 nucleic acid sequence (GenBank Accession No. NM_001143676)

```
   1 agatattcat gaaccgttgc ttcttccagc ctcgccttct cgctccctct gcctttctgg
  61 cgctgttctc cctccctccc tctggcttct gctctttctt actccttctc tcagctgctt
 121 aactacagct cccactggaa cttgcacaat caaaaacaac tctcctctct caagccgcct
 181 ccaggagcgc atcacctgga gaagagcgac tcgctccccg cgccggccgc ggaagagcag
 241 ccaggtagct gggggcgggg aggcgtaccc ttctcccgct cggtaagagc cacagcatct
 301 ccccggagat tggccgtatc ccaccgtccg gcccccaggg tcctgcagcg gtgatgcata
 361 tgtttcggag caatgatgga aggagaaaag ccgctgtcgg tggcaactga aagtggggag
 421 aggttgctgc agtagctggt gctgcagaat gcgcgagtga agaactgagc cccgctagat
 481 tctccatccc gctcagtctt cattaactgt ctgcaggagg taaaccgggg aaacagatat
 541 gcactaacca ggcgggtgcc aacctggatc tataactgtg aattccccac ggtggaaaat
 601 ggtaaacaaa gacatgaatg gattcccagt caagaaatgc tcagccttcc aatttttttaa
 661 gaagcgggta cgaaggtgga tcaagagccc aatggtcagt gtggacaagc atcagagtcc
 721 cagcctgaag tacaccggct cctccatggt gcacatccct ccaggggagc cagacttcga
 781 gtcttccttg tgtcaaacat gcctgggtga acatgctttc caaagagggg ttctccctca
 841 ggagaacgag tcatgttcat gggaaactca atctgggtgt gaagtgagag agccatgtaa
 901 tcatgccaac atcctgacca agcccgatcc aagaaccttc tggactaatg atgatccagc
 961 tttcatgaag cagaggagga tgggtctgaa cgactttatt cagaagattg ccaataactc
1021 ctatgcatgc aaacaccctg aagttcagtc catcttgaag atctcccaac ctcaggagcc
1081 tgagcttatg aatgccaacc cttctcctcc accaagtcct tctcagcaaa tcaaccttgg
1141 cccgtcgtcc aatcctcatg ctaaaccatc tgactttcac ttcttgaaag tgatcggaaa
1201 gggcagtttt ggaaaggttc ttcagcaag acacaaggca gaagaagtgt ctatgcagt
1261 caaagtttta cagaagaaag caatcctgaa aaagaaagag gagaagcata ttatgtcgga
1321 gcggaatgtt ctgttgaaga atgtgaagca cccttttcctg gtgggccttc acttctcttt
1381 ccagactgct gacaaattgt actttgtcct agactacatt aatggtggag agttgttcta
1441 ccatctccag agggaacgct gcttcctgga accacgggct cgtttctatg ctgctgaaat
1501 agccagtgcc ttgggctacc tgcattcact gaacatcgtt tatagagact aaaaccaga
1561 gaatattttg ctagattcac agggacacat tgtccttact gacttcggac tctgcaagga
1621 gaacattgaa cacaacagca caacatccac cttctgtggc acgccggagt atctcgcacc
1681 tgaggtgctt cataagcagc cttatgacag gactgtggac tggtggtgcc tgggagctgt
```

FIG. 20

1741 cttgtatgag atgctgtatg gcctgccgcc tttttatagc cgaaacacag ctgaaatgta 1801 cgacaacatt ctgaacaagc ctctccagct gaaaccaaat attacaaatt ccgcaagaca 1861 cctcctggag ggcctcctgc agaaggacag gacaaagcgg ctcggggcca aggatgactt 1921 catggagatt aagagtcatg tcttcttctc cttaattaac tgggatgatc tcattaataa 1981 gaagattact cccccttta acccaaatgt gagtgggccc aacgacctac ggcactttga 2041 ccccgagttt accgaagagc ctgtccccaa ctccattggc aagtcccctg acagcgtcct 2101 cgtcacagcc agcgtcaagg aagctgccga ggctttccta ggcttttcct atgcgcctcc 2161 cacggactct ttcctctgaa ccctgttagg gcttggtttt aaaggatttt atgtgtgttt 2221 ccgaatgttt tagttagcct tttggtggag ccgccagctg acaggacatc ttacaagaga 2281 atttgcacat ctctggaagc ttagcaatct tattgcacac tgttcgctgg aagcttttg 2341 aagagcacat tctcctcagt gagctcatga ggttttcatt tttattcttc cttccaacgt 2401 ggtgctatct ctgaaacgag cgttagagtg ccgccttaga cggaggcagg agtttcgtta 2461 gaaagcggac gctgttctaa aaaaggtctc ctgcagatct gtctgggctg tgatgacgaa 2521 tattatgaaa tgtgcctttt ctgaagagat tgtgttagct ccaaagcttt tcctatcgca 2581 gtgtttcagt tctttatttt cccttgtgga tatgctgtgt gaaccgtcgt gtgagtgtgg 2641 tatgcctgat cacagatgga ttttgttata agcatcaatg tgacacttgc aggacactac 2701 aacgtgggac attgtttgtt tcttccatat ttggaagata aatttatgtg tagacttttt 2761 tgtaagatac ggttaataac taaaatttat tgaaatggtc ttgcaatgac tcgtattcag 2821 atgcttaaag aaagcattgc tgctacaaat atttctattt ttagaaaggg tttttatgga 2881 ccaatgcccc agttgtcagt cagagccgtt ggtgttttc attgtttaaa atgtcacctg 2941 taaaatgggc attatttatg ttttttttt tgcattcctg ataattgtat gtattgtata 3001 aagaacgtct gtacattggg ttataacact agtatatta aacttacagg cttatttgta 3061 atgtaaacca ccattttaat gtactgtaat taacatggtt ataatacgta caatccttcc 3121 ctcatcccat cacacaactt tttttgtgtg tgataaactg attttggttt gcaataaaac 3181 cttgaaaaat atttacatat aaaaaaaa (SEQ ID NO: 34)

SGK1 nucleic acid sequence (GenBank Accession No. NM_001143677)

1 aagtggggtt cataacagaa cagggatagc cgtctctggc tcgtgctctc atgtcatctc 61 agagttccag cttatcagag gcatgtagca gggaggctta ttccagccat aactgggctc

FIG. 20
CONTINUED

```
121 tacctccagc ctccagaagt aatccccaac ctgcatatcc ttgggcaacc cgaagaatga
181 aagaagaagc tataaaaccc cctttgaaag ctttcatgaa gcagaggagg atgggtctga
241 acgactttat tcagaagatt gccaataact cctatgcatg caaacaccct gaagttcagt
301 ccatcttgaa gatctcccaa cctcaggagc ctgagcttat gaatgccaac ccttctcctc
361 caccaagtcc ttctcagcaa atcaaccttg gcccgtcgtc caatcctcat gctaaaccat
421 ctgactttca cttcttgaaa gtgatcggaa agggcagttt tggaaaggtt cttctagcaa
481 gacacaaggc agaagaagtg ttctatgcag tcaaagtttt acagaagaaa gcaatcctga
541 aaaagaaaga ggagaagcat attatgtcgg agcggaatgt tctgttgaag aatgtgaagc
601 acccttttcct ggtgggcctt cacttctctt tccagactgc tgacaaattg tactttgtcc
661 tagactacat taatggtgga gagttgttct accatctcca gagggaacgc tgcttcctgg
721 aaccacgggc tcgtttctat gctgctgaaa tagccagtgc cttgggctac ctgcattcac
781 tgaacatcgt ttatagagac ttaaaaccag agaatatttt gctagattca cagggacaca
841 ttgtccttac tgacttcgga ctctgcaagg agaacattga acacaacagc acaacatcca
901 ccttctgtgg cacgccggag tatctcgcac ctgaggtgct tcataagcag ccttatgaca
961 ggactgtgga ctggtggtgc ctgggagctg tcttgtatga gatgctgtat ggcctgccgc
1021 cttttatag ccgaaacaca gctgaaatgt acgacaacat tctgaacaag cctctccagc
1081 tgaaaccaaa tattacaaat tccgcaagac acctcctgga gggcctcctg cagaaggaca
1141 ggacaaagcg gctcgggggcc aaggatgact tcatggagat taagagtcat gtcttcttct
1201 ccttaattaa ctgggatgat ctcattaata agaagattac tcccccttt aacccaaatg
1261 tgagtgggcc caacgaccta cggcactttg accccgagtt taccgaagag cctgtccca
1321 actccattgg caagtccccct gacagcgtcc tcgtcacagc cagcgtcaag gaagctgccg
1381 aggctttcct aggcttttcc tatgcgcctc ccacggactc tttcctctga accctgttag
1441 ggcttggttt taaaggattt tatgtgtgtt tccgaatgtt ttagttagcc ttttggtgga
1501 gccgccagct gacaggacat cttacaagag aatttgcaca tctctggaag cttagcaatc
1561 ttattgcaca ctgttcgctg gaagcttttt gaagagcaca ttctcctcag tgagctcatg
1621 aggttttcat ttttattctt ccttccaacg tggtgctatc tctgaaacga gcgttagagt
1681 gccgccttag acggaggcag gagtttcgtt agaaagcgga cgctgttcta aaaaaggtct
1741 cctgcagatc tgtctgggct gtgatgacga atattatgaa atgtgccttt tctgaagaga
```

FIG. 20
CONTINUED 1801 ttgtgttagc tccaaagctt ttcctatcgc agtgtttcag ttctttattt tcccttgtgg 1861 atatgctgtg tgaaccgtcg tgtgagtgtg gtatgcctga tcacagatgg attttgttat 1921 aagcatcaat gtgacacttg caggacacta caacgtggga cattgtttgt ttcttccata 1981 tttggaagat aaatttatgt gtagactttt ttgtaagata cggttaataa ctaaaattta 2041 ttgaaatggt cttgcaatga ctcgtattca gatgcttaaa gaaagcattg ctgctacaaa 2101 tatttctatt tttagaaagg gtttttatgg accaatgccc cagttgtcag tcagagccgt 2161 tggtgttttt cattgtttaa aatgtcacct gtaaaatggg cattatttat gtttttttt 2221 ttgcattcct gataattgta tgtattgtat aaagaacgtc tgtacattgg gttataacac 2281 tagtatattt aaacttacag gcttatttgt aatgtaaacc accattttaa tgtactgtaa 2341 ttaacatggt tataatacgt acaatccttc cctcatccca tcacacaact ttttttgtgt 2401 gtgataaact gattttggtt tgcaataaaa ccttgaaaaa tatttacata taaaaaaaa (SEQ ID NO: 35)

SGK1 nucleic acid sequence (GenBank Accession No. NM_001143678)

1 acattcctga cctctccctc cccctttcc ctctttcttt ccttccttcc tcctcttcca 61 agttctggga ttttttcagcc ttgcttggtt ttggccaaaa gcacaaaaaa ggcgttttcg 121 gaagcgaccc gaccgtgcac aagggccatt tgtttgtttt gggactcggg gcaggaaatc 181 ttgcccggcc tgagtcacgg cggctccttc aaggaaacgt cagtgctcgc cggtcgctct 241 cgtctgccgc gcgccccgcc gcccgctgcc catggggag atgcagggcg cgctggccag 301 agcccggctc gagtccctgc tgcggccccg ccacaaaaag agggccgagg cgcagaaaag 361 gagcgagtcc ttcctgctga gcggactggc tttcatgaag cagaggagga tgggtctgaa 421 cgactttatt cagaagattg ccaataactc ctatgcatgc aaacaccctg aagttcagtc 481 catcttgaag atctcccaac ctcaggagcc tgagcttatg aatgccaacc cttctcctcc 541 accaagtcct tctcagcaaa tcaaccttgg cccgtcgtcc aatcctcatg ctaaaccatc 601 tgactttcac ttcttgaaag tgatcggaaa gggcagtttt ggaaaggttc ttctagcaag 661 acacaaggca gaagaagtgt tctatgcagt caaagtttta cagaagaaag caatcctgaa 721 aaagaaagag gagaagcata ttatgtcgga gcggaatgtt ctgttgaaga atgtgaagca 781 cccctttcctg gtgggccttc acttctcttt ccagactgct gacaaattgt actttgtcct 841 agactacatt aatggtggag agttgttcta ccatctccag agggaacgct gcttcctgga 901 accacgggct cgtttctatg ctgctgaaat agccagtgcc ttgggctacc tgcattcact

FIG. 20
CONTINUED 961 gaacatcgtt tatagagact taaaaccaga gaatattttg ctagattcac agggacacat 1021 tgtccttact gacttcggac tctgcaagga gaacattgaa cacaacagca caacatccac 1081 cttctgtggc acgccggagt atctcgcacc tgaggtgctt cataagcagc cttatgacag 1141 gactgtggac tggtggtgcc tgggagctgt cttgtatgag atgctgtatg gcctgccgcc 1201 tttttatagc cgaaacacag ctgaaatgta cgacaacatt ctgaacaagc ctctccagct 1261 gaaaccaaat attacaaatt ccgcaagaca cctcctggag ggcctcctgc agaaggacag 1321 gacaaagcgg ctcggggcca aggatgactt catggagatt aagagtcatg tcttcttctc 1381 cttaattaac tgggatgatc tcattaataa gaagattact cccccttttt acccaaatgt 1441 gagtgggccc aacgacctac ggcactttga ccccgagttt accgaagagc ctgtccccaa 1501 ctccattggc aagtcccctg acagcgtcct cgtcacagcc agcgtcaagg aagctgccga 1561 ggctttccta ggcttttcct atgcgcctcc cacggactct ttcctctgaa ccctgttagg 1621 gcttggtttt aaaggatttt atgtgtgttt ccgaatgttt tagttagcct tttggtggag 1681 ccgccagctg acaggacatc ttacaagaga atttgcacat ctctggaagc ttagcaatct 1741 tattgcacac tgttcgctgg aagcttttg aagagcacat tctcctcagt gagctcatga 1801 ggttttcatt tttattcttc cttccaacgt ggtgctatct ctgaaacgag cgttagagtg 1861 ccgccttaga cggaggcagg agtttcgtta gaaagcggac gctgttctaa aaaaggtctc 1921 ctgcagatct gtctgggctg tgatgacgaa tattatgaaa tgtgcctttt ctgaagagat 1981 tgtgttagct ccaaagcttt tcctatcgca gtgtttcagt tctttatttt cccttgtgga 2041 tatgctgtgt gaaccgtcgt gtgagtgtgg tatgcctgat cacagatgga ttttgttata 2101 agcatcaatg tgacacttgc aggacactac aacgtgggac attgtttgtt tcttccatat 2161 ttggaagata aatttatgtg tagacttttt tgtaagatac ggttaataac taaaatttat 2221 tgaaatggtc ttgcaatgac tcgtattcag atgcttaaag aaagcattgc tgctacaaat 2281 atttctattt ttagaaaggg ttttttatgga ccaatgcccc agttgtcagt cagagccgtt 2341 ggtgtttttc attgtttaaa atgtcacctg taaaatgggc attatttatg tttttttttt 2401 tgcattcctg ataattgtat gtattgtata aagaacgtct gtacattggg ttataacact 2461 agtatattta aacttacagg cttatttgta atgtaaacca ccattttaat gtactgtaat 2521 taacatggtt ataatacgta caatccttcc ctcatcccat cacacaactt tttttgtgtg 2581 tgataaactg attttggttt gcaataaaac cttgaaaaat atttacatat aaaaaaaa (SEQ ID NO: 36)

FIG. 20
CONTINUED

SGK1 nucleic acid sequence (GenBank Accession No. NM_001291995)

1 tttttataa ggccgagcgc gcggcctggc gcagcatacg ccgagccggt ctttgagcgc 61 taacgtcttt ctgtctcccc gcggtggtga tgacggtgaa aactgaggct gctaagggca 121 ccctcactta ctccaggatg aggggcatgg tggcaattct catcgctttc atgaagcaga 181 ggaggatggg tctgaacgac tttattcaga agattgccaa taactcctat gcatgcaaac 241 accctgaagt tcagtccatc ttgaagatct cccaacctca ggagcctgag cttatgaatg 301 ccaacccttc tcctccacca agtccttctc agcaaatcaa ccttggcccg tcgtccaatc 361 ctcatgctaa accatctgac tttcacttct gaaagtgat cggaaagggc agttttggaa 421 aggttcttct agcaagacac aaggcagaag aagtgttcta tgcagtcaaa gttttacaga 481 agaaagcaat cctgaaaaag aaagagttgt tctaccatct ccagagggaa cgctgcttcc 541 tggaaccacg ggctcgtttc tatgctgctg aaatagccag tgccttgggc tacctgcatt 601 cactgaacat cgtttataga gacttaaaac cagagaatat tttgctagat tcacagggac 661 acattgtcct tactgacttc ggactctgca aggagaacat tgaacacaac agcacaacat 721 ccaccttctg tggcacgccg gagtatctcg cacctgaggt gcttcataag cagccttatg 781 acaggactgt ggactggtgg tgcctgggag ctgtcttgta tgagatgctg tatggcctgc 841 cgccttttta tagccgaaac acagctgaaa tgtacgacaa cattctgaac aagcctctcc 901 agctgaaacc aaatattaca aattccgcaa gacacctcct ggagggcctc ctgcagaagg 961 acaggacaaa gcggctcggg gccaaggatg acttcatgga gattaagagt catgtcttct 1021 tctccttaat taactgggat gatctcatta ataagaagat tactccccct tttaacccaa 1081 atgtgagtgg gcccaacgac ctacggcact tgacccccga gtttaccgaa gagcctgtcc 1141 ccaactccat tggcaagtcc cctgacagcg tcctcgtcac agccagcgtc aaggaagctg 1201 ccgaggcttt cctaggcttt tcctatgcgc ctcccacgga ctctttcctc tgaaccctgt 1261 tagggcttgg ttttaaagga ttttatgtgt gtttccgaat gttttagtta gccttttggt 1321 ggagccgcca gctgacagga catcttacaa gagaatttgc acatctctgg aagcttagca 1381 atcttattgc acactgttcg ctggaagctt tttgaagagc acattctcct cagtgagctc 1441 atgaggtttt cattttattt cttccttcca acgtggtgct atctctgaaa cgagcgttag 1501 agtgccgcct tagacggagg caggagtttc gttagaaagc ggacgctgtt ctaaaaaagg 1561 tctcctgcag atctgtctgg gctgtgatga cgaatattat gaaatgtgcc ttttctgaag 1621 agattgtgtt agctccaaag ctttcctat cgcagtgttt cagttcttta ttttcccttg 1681 tggatatgct gtgtgaaccg tcgtgtgagt gtggtatgcc tgatcacaga tggattttgt

FIG. 20
CONTINUED 1741 tataagcatc aatgtgacac ttgcaggaca ctacaacgtg ggacattgtt tgtttcttcc
1801 atatttggaa gataaattta tgtgtagact tttttgtaag atacggttaa taactaaaat
1861 ttattgaaat ggtcttgcaa tgactcgtat tcagatgctt aaagaaagca ttgctgctac
1921 aaatatttct atttttagaa agggttttta tggaccaatg ccccagttgt cagtcagagc
1981 cgttggtgtt tttcattgtt taaaatgtca cctgtaaaat gggcattatt tatgtttttt
2041 tttttgcatt cctgataatt gtatgtattg tataaagaac gtctgtacat tgggttataa
2101 cactagtata tttaaactta caggcttatt tgtaatgtaa accaccattt taatgtactg
2161 taattaacat ggttataata cgtacaatcc ttccctcatc ccatcacaca acttttttg
2221 tgtgtgataa actgattttg gtttgcaata aaaccttgaa aaatatttac atataaaaaa
2281 aa (SEQ ID NO: 37)

SGK1 nucleic acid sequence (GenBank Accession No. NM_005627)
1 tttttttataa ggccgagcgc gcggcctggc gcagcatacg ccgagccggt ctttgagcgc
61 taacgtcttt ctgtctcccc gcggtggtga tgacggtgaa aactgaggct gctaagggca
121 ccctcactta ctccaggatg aggggcatgg tggcaattct catcgctttc atgaagcaga
181 ggaggatggg tctgaacgac tttattcaga agattgccaa taactcctat gcatgcaaac
241 accctgaagt tcagtccatc ttgaagatct cccaacctca ggagcctgag cttatgaatg
301 ccaacccttc tcctccacca agtccttctc agcaaatcaa ccttggcccg tcgtccaatc
361 ctcatgctaa accatctgac tttcacttct tgaaagtgat cggaaagggc agttttggaa
421 aggttcttct agcaagacac aaggcagaag aagtgttcta tgcagtcaaa gtttacagag
481 agaaagcaat cctgaaaaag aaagaggaga agcatattat gtcggagcgg aatgttctgt
541 tgaagaatgt gaagcaccct ttcctggtgg gccttcactt ctctttccag actgctgaca
601 aattgtactt tgtcctagac tacattaatg gtggagagtt gttctaccat ctccagaggg
661 aacgctgctt cctggaacca cgggctcgtt tctatgctgc tgaaatagcc agtgccttgg
721 gctacctgca ttcactgaac atcgttttata gagacttaaa accagagaat attttgctag
781 attcacaggg acacattgtc cttactgact tcggactctg caaggagaac attgaacaca
841 acagcacaac atccaccttc tgtggcacgc cggagtatct cgcacctgag gtgcttcata
901 agcagcctta tgacaggact gtggactggt ggtgcctggg agctgtcttg tatgagatgc
961 tgtatggcct gccgccttt tatagccgaa acacagctga aatgtacgac aacattctga 1021 acaagcctct ccagctgaaa ccaaatatta caaattccgc aagacacctc ctggagggcc 1081 tcctgcagaa ggacaggaca aagcggctcg gggccaagga tgacttcatg gagattaaga 1141 gtcatgtctt cttctcctta attaactggg atgatctcat taataagaag attactcccc 1201 cttttaaccc aaatgtgagt gggcccaacg acctacggca ctttgacccc gagtttaccg 1261 aagagcctgt ccccaactcc attggcaagt cccctgacag cgtcctcgtc acagccagcg 1321 tcaaggaagc tgccgaggct ttcctaggct tttcctatgc gcctcccacg gactctttcc 1381 tctgaacccct gttagggctt ggttttaaag gattttatgt gtgtttccga atgttttagt 1441 tagccttttg gtggagccgc cagctgacag gacatcttac aagagaattt gcacatctct 1501 ggaagcttag caatcttatt gcacactgtt cgctggaagc ttttgaaga gcacattctc 1561 ctcagtgagc tcatgaggtt ttcatttta ttcttccttc caacgtggtg ctatctctga 1621 aacgagcgtt agagtgccgc cttagacgga ggcaggagtt tcgttagaaa gcggacgctg 1681 ttctaaaaaa ggtctcctgc agatctgtct gggctgtgat gacgaatatt atgaaatgtg 1741 ccttttctga agagattgtg ttagctccaa agctttttcct atcgcagtgt ttcagttctt 1801 tattttcccct tgtggatatg ctgtgtgaac cgtcgtgtga gtgtggtatg cctgatcaca 1861 gatggatttt gttataagca tcaatgtgac acttgcagga cactacaacg tgggacattg 1921 tttgtttctt ccatatttgg aagataaatt tatgtgtaga ctttttttgta agatacggtt 1981 aataactaaa atttattgaa atggtcttgc aatgactcgt attcagatgc ttaaagaaag 2041 cattgctgct acaaatattt ctattttag aaagggtttt tatggaccaa tgccccagtt 2101 gtcagtcaga gccgttggtg ttttttcattg tttaaaatgt cacctgtaaa atgggcatta 2161 tttatgtttt ttttttttgca ttcctgataa ttgtatgtat tgtataaaga acgtctgtac 2221 attgggttat aacactagta tatttaaact tacaggctta tttgtaatgt aaaccaccat 2281 tttaatgtac tgtaattaac atggttataa tacgtacaat ccttccctca tcccatcaca 2341 caactttttt tgtgtgtgat aaactgattt tggtttgcaa taaaaccttg aaaaatattt 2401 acatataaaa aaaa (SEQ ID NO: 38)

FIG. 20
CONTINUED p110α nucleic acid sequence (GenBank Accession No. NM_006218)

1 tctccctcgg cgccgccgcc gccgcccgcg gggctgggac ccgatgcggt tagagccgcg
61 gagcctggaa gagccccgag cgtttctgct ttgggacaac catacatcta attccttaaa
121 gtagttttat atgtaaaact tgcaaagaat cagaacaatg cctccacgac catcatcagg
181 tgaactgtgg ggcatccact tgatgccccc aagaatccta gtagaatgtt tactaccaaa
241 tggaatgata gtgactttag aatgcctccg tgaggctaca ttaataacca taaagcatga
301 actatttaaa gaagcaagaa atacccccct ccatcaactt cttcaagatg aatcttctta
361 cattttcgta agtgttactc aagaagcaga aagggaagaa ttttttgatg aaacaagacg
421 actttgtgac cttcggcttt ttcaacccct tttaaaagta attgaaccag taggcaaccg
481 tgaagaaaag atcctcaatc gagaaattgg ttttgctatc ggcatgccag tgtgtgaatt
541 tgatatggtt aaagatccag aagtacagga cttccgaaga aatattctga cgtttgtaa
601 agaagctgtg gatcttaggg acctcaattc acctcatagt agagcaatgt atgtctatcc
661 tccaaatgta gaatcttcac cagaattgcc aaagcacata tataataaat tagataaagg
721 gcaaataata gtggtgatct gggtaatagt ttctccaaat aatgacaagc agaagtatac
781 tctgaaaatc aaccatgact gtgtaccaga acaagtaatt gctgaagcaa tcaggaaaaa
841 aactcgaagt atgttgctat cctctgaaca actaaaactc tgtgttttag aatatcaggg
901 caagtatatt ttaaaagtgt gtggatgtga tgaatacttc ctagaaaaat atcctctgag
961 tcagtataag tatataagaa gctgtataat gcttgggagg atgcccaatt tgatgttgat
1021 ggctaaagaa agcctttatt ctcaactgcc aatggactgt tttacaatgc catcttattc
1081 cagacgcatt tccacagcta caccatatat gaatggagaa acatctacaa aatcccttg
1141 ggttataaat agtgcactca gaataaaaat tctttgtgca acctacgtga atgtaaatat
1201 tcgagacatt gataagatct atgttcgaac aggtatctac catggaggag aacccttatg
1261 tgacaatgtg aacactcaaa gagtaccttg ttccaatccc aggtggaatg aatggctgaa
1321 ttatgatata tacattcctg atcttcctcg tgctgctcga ctttgccttt ccatttgctc
1381 tgttaaaggc cgaaagggtg ctaaagagga acactgtcca ttggcatggg gaaatataaa
1441 cttgtttgat tacacagaca ctctagtatc tggaaaaatg gctttgaatc tttggccagt
1501 acctcatgga ttagaagatt tgctgaaccc tattggtgtt actggatcaa atccaaataa
1561 agaaactcca tgcttagagt tggagtttga ctggttcagc agtgtggtaa agttcccaga

FIG. 21

1621 tatgtcagtg attgaagagc atgccaattg gtctgtatcc cgagaagcag gatttagcta 1681 ttcccacgca ggactgagta acagactagc tagagacaat gaattaaggg aaaatgacaa 1741 agaacagctc aaagcaattt ctacacgaga tcctctctct gaaatcactg agcaggagaa 1801 agattttcta tggagtcaca gacactattg tgtaactatc cccgaaattc tacccaaatt 1861 gcttctgtct gttaaatgga attctagaga tgaagtagcc cagatgtatt gcttggtaaa 1921 agattggcct ccaatcaaac ctgaacaggc tatggaactt ctggactgta attacccaga 1981 tcctatggtt cgaggttttg ctgttcggtg cttggaaaaa tatttaacag atgacaaact 2041 ttctcagtat ttaattcagc tagtacaggt cctaaaatat gaacaatatt tggataactt 2101 gcttgtgaga tttttactga agaaagcatt gactaatcaa aggattgggc acttttctt 2161 ttggcattta aaatctgaga tgcacaataa aacagttagc cagaggtttg gcctgctttt 2221 ggagtcctat tgtcgtgcat gtgggatgta tttgaagcac ctgaataggc aagtcgaggc 2281 aatggaaaag ctcattaact taactgacat tctcaaacag gagaagaagg atgaaacaca 2341 aaaggtacag atgaagtttt tagttgagca aatgaggcga ccagatttca tggatgctct 2401 acagggcttt ctgtctcctc taaaccctgc tcatcaacta ggaaacctca ggcttgaaga 2461 gtgtcgaatt atgtcctctg caaaaaggcc actgtggttg aattgggaga acccagacat 2521 catgtcagag ttactgtttc agaacaatga gatcatcttt aaaaatgggg atgatttacg 2581 gcaagatatg ctaacacttc aaattattcg tattatggaa aatatctggc aaaatcaagg 2641 tcttgatctt cgaatgttac cttatggttg tctgtcaatc ggtgactgtg tgggacttat 2701 tgaggtggtg cgaaattctc acactattat gcaaattcag tgcaaaggcg gcttgaaagg 2761 tgcactgcag ttcaacagcc acacactaca tcagtggctc aaagacaaga acaaaggaga 2821 aatatatgat gcagccattg acctgtttac acgttcatgt gctggatact gtgtagctac 2881 cttcattttg ggaattggag atcgtcacaa tagtaacatc atggtgaaag acgatggaca 2941 actgtttcat atagattttg gacacttttt ggatcacaag aagaaaaaat ttggttataa 3001 acgagaacgt gtgccatttg ttttgacaca ggatttctta atagtgatta gtaaaggagc 3061 ccaagaatgc acaaagacaa gagaatttga gaggtttcag gagatgtgtt acaaggctta 3121 tctagctatt cgacagcatg ccaatctctt cataaatctt ttctcaatga tgcttggctc 3181 tggaatgcca gaactacaat cttttgatga cattgcatac attcgaaaga ccctagcctt 3241 agataaaact gagcaagagg ctttggagta tttcatgaaa caaatgaatg atgcacatca

FIG. 21
CONTINUED 3301 tggtggctgg acaacaaaaa tggattggat cttccacaca attaaacagc atgcattgaa 3361 ctgaaaagat aactgagaaa atgaaagctc actctggatt ccacactgca ctgttaataa 3421 ctctcagcag gcaaagaccg attgcatagg aattgcacaa tccatgaaca gcattagaat 3481 ttacagcaag aacagaaata aaatactata taatttaaat aatgtaaacg caaacagggt 3541 tgatagcac ttaaactagt tcatttcaaa attaagcttt agaataatgc gcaatttcat 3601 gttatgcctt aagtccaaaa aggtaaactt tgaagattgt ttgtatcttt ttttaaaaaa 3661 caaaacaaaa caaaaatccc caaaatatat agaaatgatg gagaaggaaa aagtgatggt 3721 ttttttttgtc ttgcaaatgt tctatgtttt gaaatgtgga cacaacaaag gctgttattg 3781 cattaggtgt aagtaaactg gagtttatgt taaattacat tgattggaaa agaatgaaaa 3841 tttcttattt ttccattgct gttcaattta tagtttgaag tgggtttttg actgcttgtt 3901 taatgaagaa aaatgcttgg ggtggaaggg actcttgaga tttcaccaga gactttttct 3961 ttttaataaa tcaaaccttt tgatgatttg aggttttatc tgcagttttg gaagcagtca 4021 caaatgagac ctgttataag gtggtatttt ttttttttctt ctggacagta tttaaaggat 4081 cttattctta tttcccaggg aaattctggg ctcccacaaa gtaaaaaaaa aaaaaaatca 4141 tagaaaaaga atgagcagga atagttctta ttccagaatt gtacagtatt caccttaagt 4201 tgattttttt tctccttctg caattgaact gaatacattt ttcatgcatg ttttccagaa 4261 aatagaagta ttaatgttat taaaaagatt attttttttta ttaaaggcta tttatattat 4321 agaaactatc attaatatat attctttatt tacatgatct gtcccatagt catgcattgt 4381 tttgcaccccc aaattttttta ttgttcatag cagcatggtc agctttcttc ttgatctata 4441 gatgaggctc aggcactatc ccatttatac caataaccag tgtataacta cttaaggaaa 4501 acataaaaac ttcatcttct ttccttttat ttcttatgtg aatctcccgt cttccattct 4561 cttttataat tgagaatgtc tcaatcatat gaaattagtt accagaatta acacaattta 4621 gactatcttc ctgattcctt aaacccctttt actgaagtat actcatgaat aatactttaa 4681 aatatggggg aatagaaacc atgaactttt taccttttta aactatttat ccatatctcc 4741 aaagtagaac attaaaccat tttaagatat gtctcattcc caagtagtca gagctcactc 4801 tccaacttta ttaaatacta tttgagcaca ggacacattc ttaaacatttt tgaaaaacat 4861 taacccaaga tgtagaggct actgctagtc gtcattctag aatctgatat tttactctgt 4921 atttgaaatg aatgattaat gtcctaggaa attagcttta gcagatgtcc aggtgccaca

FIG. 21
CONTINUED 4981 tcaaaaaagt gcaataatta ttgacagttt tttagattag gcatattatt ggaaaacaac 5041 tttataaaga gtgaacattg tatactctag taaaacagca tcactttaaa aatattcatt 5101 tatgaaatct gttacctata gttgaagtct tgagtagtga acaagggact ctaataccaa 5161 tactcttaat atctggctat tttagatccc ttaaagggca taattattgg aaatttaggt 5221 atttcactaa agcatgtata taatattgcc aacaagaaaa gtaaatttga agattaaggg 5281 aacttacttc tgcaaactgt cttgcgatag ttaagcagaa tttaaactct gttttaagca 5341 ggaaaccaga aagattattt tgcagttgta gaagatttca taacttatta aaacttatta 5401 acattttgtg ttgtttagat ataggcagtt gatacatact aacatcccag ccttttcaat 5461 atcagggtta aattatagga aaactcagta aaatggtaca aatctgaaag tttgatggta 5521 gaaactgaag atttaacaga gaactgtgtt ttacccgagt gccaaaaatg ctgtgagcct 5581 ccttgcacaa aatttatacc acttttgcat ttttatctat cagtccagat agttgtctcc 5641 cctccttctc ccaggacctc tccaccatta aaatgcacaa accacatggc cgatttcacc 5701 atttacattt attttcaaaa gttactacaa ccaaattaat tctattagaa gaaatgtaga 5761 caaattctat aaagactata gattgtgacc taagaaagaa atgaggcaaa gaaccaaaca 5821 ttgaattaaa tgctacatgg gtgactaaga tctgtttcaa gtcagtgata atatagccac 5881 ttctgggtac ttcagtatca gagatcagtt ctcgtggttt agacagttcc tatctatagc 5941 tgactatcct tgtccttgaa tatggtgtaa ctgactattg gctctacagt tttattgggc 6001 cacttaagaa atatttcctt gaataattat tttgagaaaa agtctaaaag taataaaaat 6061 aattttaaac acactgtagt aagaaatgac tgttggaaaa ttatgctttc actttctacc 6121 atattctcag ctatacaaaa ccatttattt tgaagatttt tagactactg ttaatttgaa 6181 atctgttact cttattgtgg aatttgtttt tttaaaaaag atgtttctaa ttggattttt 6241 aaaagaagaa tggaatttgg ttgctatttt acaatagaac ctaagctttt tgtggttctt 6301 agtgtcctat gtaaaactta gtgtcaaagt aatcaacttt gagattttcc cttctattct 6361 gctttatatt aaaagcccat tagaaaatgg gaacctggtg aatatataat gaattgtaaa 6421 atattttaat gtgtaacttt ttcaactgtg aaactgactt gatttttga tgaaaacagc 6481 tgctgataaa gtattttgtg taaagtgtag ttcttattaa tcaggaaaat gatgacttga 6541 ttagactgta tatgccctct tggatttat tttaaatgga ttggtgactt tcacataggt 6601 aaaacacagt ccatctgtat tctttttcc atcaaaaatc gagtgatttg gaattataaa

FIG. 21
CONTINUED 6661 aaaattgtga gcagcctatt tgaaaggcat catggaaatt tcacagcaca ataacacgga 6721 tttgtttttt cttaatgatg taaatccgtt taattcatac tttgatcaat agcccatgct 6781 tgccaactct gaagaaattt aatttccagc agtattttaa agctagcctg ttaactttt 6841 ctgaatattt aaagttcctc tttttctat gtctgcacaa actgcagacc tgggctggac 6901 ccacatactc aagagtccac cttaagaaat tattttgatg tccaagacat cactaaaata 6961 tttaagttta aagataatat gtggtgttaa tagattgtgg tgcttttact atttaaagac 7021 aactttcata cttcagatgt ttttgagaag aggggaatgt gaggggaggg ggcagaacag 7081 ggaggagttg tttgaatgaa ttacattctt tatatccatc ctgctcattt ggggcatgtc 7141 tttaagagaa ggctgaaagt tgtgagagta tattgtatac cgtaagagaa tcaactcttc 7201 atcatggatg ggattgtgaa ggctgaacta taaaattcag cattgacagc atcctcaatt 7261 aataattctt ggtgacagaa taatacagct gggctgtttt ttaaaatata aacaatacca 7321 tttttaatta ttacattaaa aattgtaaat atatctatgt gccatggcct gggaagcctg 7381 ctttcttttt tcataaaaat tattttact gtatgaaaag atcatggggt ttagctcaaa 7441 atatctgtgg tcctgataaa attggattgg taactctacc tcagaaggaa aatgggaaaa 7501 aaaaatagat gagtcacaat tcaatacttc aagctcagaa actgtgcaga tcactgaatt 7561 ttagatttat aaagtcagag ttggcatgcc ttgtttttaa tgatatggaa gaccttaaga 7621 aaaaaacttg gctgaagttt aatcgttggt ccagccattt gaaaaaggca atagtttgag 7681 gaggttcccg aattcggcat ttgaaattca ttttgttctc tcttcttcat tattagtgca 7741 tttggtgtgt gtatacttgc acacaattct gtttgtgtac acactgcttg cttagcccta 7801 gtcaagaggc atcttttata aaaggtgtaa agaaatatca aggttctaaa attcggaaga 7861 gtttagaatt tattaggagt ttcccaagtt gggatgttag tctttaaata aacttcatgc 7921 acctattcca cttaaggttt tgcacctcct ttttattagt gcagtgccat ttcttctgct 7981 tgattttagg tatgttaata ttccagcctt gctagttagc ataaagtgac aggtgtgagc 8041 catgaggaaa ttttctgact taatttgtac acaactacat ataagagttt tagtggagga 8101 aaaaaattag tcccttgtgc gtatacagta gttaggtaaa tgattttct accaacagta 8161 tactccattc ctcatgtagg taagtacaga aaaggttttt aaatgtattt ttttagccag 8221 ttaaagtcta tgaatctatc tgcaacctta tttaatctgt cactataata attttgtggt 8281 tatgctaaga accatgtata cttttaggta ttcttatttt tgtcaatttt tctaggttgg

FIG. 21
CONTINUED

```
8341 caaggaggca gaaaaccttc attgtttcat attaaaatat aattagacta aacttaattc
8401 tagtatgaat ttccaaaatc attatctatt tatttcattt ttatttaatt ttgtttttat
8461 ttcattttta aaagtcccct gttcaattta acttatgttc ctaagagagg ttggagaact
8521 tggccttcat ctgatttcaa aaatgttttg agtttcaaat gaagttaatg gtttcagtgt
8581 gattcagtcc tcagacctaa ttgggttgaa taaaatctaa aagaatatac ccttttggag
8641 cataacattt taataccttg gggaatgtgg cactaccaaa agaagactac taacacgtca
8701 gatgttcacc tggaagcttt atcaagaaat tcgaaccacc cttttggccc cattaattgt
8761 agcaagttta tttctctata ttttgtcatt cagtgaattg aagtcctgtg gtatactgca
8821 ttcattagaa gaaaaacgtt tttaatgtcc ttttaatgat ggcccagaaa gcatttgaca
8881 cagcaagatg catgtgttac tatattgaga atatagaata ataacagtat cactaaattt
8941 aagacctctt cccagtcttg ctgttcctag caagaagttt ggcctgtgac tgcacttact
9001 gtttatgctc atcagaaact gtcaatgtct gcttttcttt aactctgcag tctgtaacat
9061 cacgctgttt attaaaaaaa aaaagaaaaa ttaaaaaaaa aaaa (SEQ ID NO: 39)
```

FIG. 21
CONTINUED

SEQUENCE LISTING

```
<160> NUMBER OF SEQ ID NOS: 72

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (6)..(6)
<223> OTHER INFORMATION: Ser or Thr

<400> SEQUENCE: 1

Arg Xaa Arg Xaa Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Arg Ser Thr Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Cys Arg Ser Ile Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Asp Arg Val Arg Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Val Arg Ser Met Ser
1               5

<210> SEQ ID NO 6
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 6

Arg Pro Arg Gly Tyr Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Lys Arg Leu Ile Ser
1               5

<210> SEQ ID NO 8
<211> LENGTH: 74
<212> TYPE: PRT
<213> ORGANISM: Homo sapiens

<400> SEQUENCE: 8

Asp Ser Phe Arg Ala Arg Ser Thr Ser Leu Asn Glu Glu Ala Phe Arg
1               5                   10                  15

Cys Arg Ser Ile Ser Val Ser Glu His Val Val Arg Ser Arg Ile Gln
                20                  25                  30

Thr Ser Leu Thr Arg Gly Ala Arg Asp Arg Val Arg Ser Met Ser Gly
            35                  40                  45

Gly His Ser Gly Leu Arg Pro Arg Gly Tyr Thr Ile Ser Asp Val Gly
    50                  55                  60

Gln Arg Lys Arg Leu Ile Ser Ser Val Glu
65                  70

<210> SEQ ID NO 9
<211> LENGTH: 74
<212> TYPE: PRT
<213> ORGANISM: Mus musculus

<400> SEQUENCE: 9

Asp Ser Phe Arg Ala Arg Ser Thr Ser Leu Asn Glu Glu Ala Phe Arg
1               5                   10                  15

Cys Arg Ser Ile Ser Val Ser Glu His Val Val Arg Ser Arg Ile Gln
                20                  25                  30

Thr Ser Leu Thr Arg Gly Ala Arg Asp Arg Val Arg Ser Met Ser Gly
            35                  40                  45

Gly His Ser Gly Leu Arg Pro Arg Gly Tyr Thr Ile Ser Asp Thr Gly
    50                  55                  60

Gln Arg Lys Arg Leu Ile Ser Ser Val Asp
65                  70

<210> SEQ ID NO 10
<211> LENGTH: 58
<212> TYPE: PRT
<213> ORGANISM: Rattus norvegicus

<400> SEQUENCE: 10

Asp Ser Phe Arg Ala Arg Ser Thr Ser Leu Asn Glu Ser Arg Ile Gln
```

```
                1               5                   10                  15
            Thr Ser Leu Thr Arg Gly Ala Arg Asp Arg Val Arg Ser Met Ser Gly
                            20                  25                  30

Gly His Ser Gly Leu Arg Pro Arg Gly Tyr Thr Ile Ser Asp Thr Gly
                        35                  40                  45

Gln Arg Lys Arg Leu Ile Ser Ser Val Asp
                50                  55

<210> SEQ ID NO 11
<211> LENGTH: 74
<212> TYPE: PRT
<213> ORGANISM: Bos taurus

<400> SEQUENCE: 11

Asp Ser Phe Arg Ala Arg Ser Thr Ser Leu Asn Glu Asp Ala Phe Arg
1               5                   10                  15

Cys Arg Ser Ile Ser Val Ser Glu His Val Val Arg Ser Arg Ile Gln
            20                  25                  30

Thr Ser Leu Thr His Gly Ala Arg Asp Arg Val Arg Ser Met Ser Gly
        35                  40                  45

Gly His Ser Gly Leu Arg Pro Arg Gly Tyr Thr Ile Ser Asp Thr Gly
    50                  55                  60

Gln Arg Lys Arg Leu Val Ser Ser Val Asp
65                  70

<210> SEQ ID NO 12
<211> LENGTH: 74
<212> TYPE: PRT
<213> ORGANISM: Gallus gallus domesticus

<400> SEQUENCE: 12

Asp Ser Phe Arg Ala Arg Ser Thr Ser Leu Asn Glu Asp Ala Phe Arg
1               5                   10                  15

Ser Arg Ser Ile Ser Val Ser Glu His Val Val Arg Ser Arg Ile Gln
            20                  25                  30

Thr Ser Ile Thr Arg Ser Ser Arg Asn Arg Val Arg Ser Met Ser Gly
        35                  40                  45

Gly His Ser Gly His Arg Pro Arg Gly Tyr Thr Ile Ser Asp Thr Gly
    50                  55                  60

Gln Arg Lys Arg Leu Ile Ser Ser Val Asp
65                  70

<210> SEQ ID NO 13
<211> LENGTH: 58
<212> TYPE: PRT
<213> ORGANISM: Xenopus tropicalis

<400> SEQUENCE: 13

Asp Ser Phe Arg Ala Arg Ser Thr Ser Leu Asn Glu Ser Arg Met Gln
1               5                   10                  15

Thr Ser Val Thr Gln Thr Pro Arg His Arg Val Arg Ser Met Ser Gly
            20                  25                  30

Gly Thr Thr Gly His Arg Pro Arg Gly His Thr Ile Ser Asp Thr Gly
        35                  40                  45

Gln Arg Thr Arg Leu Ile Ser Ala Val Asp
    50                  55

<210> SEQ ID NO 14
```

-continued

```
<211> LENGTH: 73
<212> TYPE: PRT
<213> ORGANISM: Danio rerio

<400> SEQUENCE: 14

Asp Ser Phe Arg Ala Arg Ser Thr Ser Leu Asn Glu Asp Ala Phe Arg
1               5                   10                  15

Ser Arg Ser Ile Ser Val Ser Glu His Ala Val Arg Arg Met Gln Thr
            20                  25                  30

Ser Ser Thr Thr Asn Thr Arg Thr Arg Val Arg Ser Ile Ser Gly Gly
        35                  40                  45

His Thr Gly His Arg Pro Arg Gly His Thr Ile Ser Val Ala Gly Gln
    50                  55                  60

Arg Lys Arg Leu Val Ser Thr Val Asp
65                  70

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 15

Arg Xaa Arg Xaa Xaa Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 16

Arg Xaa Arg Xaa Xaa Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
```

```
<222> LOCATION: (4)..(5)
<223> OTHER INFORMATION: Any amino acid

<400> SEQUENCE: 17

Arg Xaa Arg Xaa Xaa Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 18

Arg Xaa Arg Xaa Xaa Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 19

Arg Xaa Arg Xaa Xaa Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 20

Arg Xaa Arg Xaa Xaa Thr
1               5

<210> SEQ ID NO 21
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 21

Arg Xaa Arg Xaa Xaa Ser
1               5

<210> SEQ ID NO 22
<211> LENGTH: 454
<212> TYPE: PRT
<213> ORGANISM: Homo sapiens

<400> SEQUENCE: 22

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Gln Pro Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
        115                 120                 125

Arg Glu Arg Asp Val Met Ser Arg Leu Asp His Pro Phe Phe Val Lys
    130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285
```

```
Leu Ile Phe Gln Lys Ile Ile Lys Leu Glu Tyr Asp Phe Pro Glu Lys
            290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
                355                 360                 365

Asp Glu Asp Cys Tyr Gly Asn Tyr Asp Asn Leu Leu Ser Gln Phe Gly
            370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                    405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Cys
                435                 440                 445

Leu Thr Gly Arg Ile Ile
            450

<210> SEQ ID NO 23
<211> LENGTH: 556
<212> TYPE: PRT
<213> ORGANISM: Homo sapiens

<400> SEQUENCE: 23

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
            195                 200                 205
```

```
Glu Asn Ile Leu Leu Asn Glu Asp Met His Ile Gln Ile Thr Asp Phe
        210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
                260                 265                 270

Tyr Gln Leu Val Ala Gly Leu Pro Pro Phe Arg Ala Gly Asn Glu Tyr
            275                 280                 285

Leu Ile Phe Gln Lys Ile Ile Lys Leu Glu Tyr Asp Phe Pro Glu Lys
        290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
        435                 440                 445

His Gln Phe Val Glu Asn Asn Leu Ile Leu Lys Met Gly Pro Val Asp
    450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
                500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
        530                 535                 540

Gln Arg Tyr Gln Ser His Pro Asp Ala Ala Val Gln
545                 550                 555

<210> SEQ ID NO 24
<211> LENGTH: 429
<212> TYPE: PRT
<213> ORGANISM: Homo sapiens

<400> SEQUENCE: 24

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
```

```
                20                  25                  30
Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Thr Arg Ala
            100                 105                 110

Asn Ser Phe Val Gly Thr Ala Gln Tyr Val Ser Pro Glu Leu Leu Thr
        115                 120                 125

Glu Lys Ser Ala Cys Lys Ser Ser Asp Leu Trp Ala Leu Gly Cys Ile
    130                 135                 140

Ile Tyr Gln Leu Val Ala Gly Leu Pro Pro Phe Arg Ala Gly Asn Glu
145                 150                 155                 160

Tyr Leu Ile Phe Gln Lys Ile Ile Lys Leu Glu Tyr Asp Phe Pro Glu
                165                 170                 175

Lys Phe Phe Pro Lys Ala Arg Asp Leu Val Glu Lys Leu Leu Val Leu
            180                 185                 190

Asp Ala Thr Lys Arg Leu Gly Cys Glu Glu Met Glu Gly Tyr Gly Pro
        195                 200                 205

Leu Lys Ala His Pro Phe Phe Glu Ser Val Thr Trp Glu Asn Leu His
    210                 215                 220

Gln Gln Thr Pro Pro Lys Leu Thr Ala Tyr Leu Pro Ala Met Ser Glu
225                 230                 235                 240

Asp Asp Glu Asp Cys Tyr Gly Asn Tyr Asp Asn Leu Leu Ser Gln Phe
                245                 250                 255

Gly Cys Met Gln Val Ser Ser Ser Ser Ser His Ser Leu Ser Ala
            260                 265                 270

Ser Asp Thr Gly Leu Pro Gln Arg Ser Gly Ser Asn Ile Glu Gln Tyr
        275                 280                 285

Ile His Asp Leu Asp Ser Asn Ser Phe Glu Leu Asp Leu Gln Phe Ser
    290                 295                 300

Glu Asp Glu Lys Arg Leu Leu Leu Glu Lys Gln Ala Gly Gly Asn Pro
305                 310                 315                 320

Trp His Gln Phe Val Glu Asn Asn Leu Ile Leu Lys Met Gly Pro Val
                325                 330                 335

Asp Lys Arg Lys Gly Leu Phe Ala Arg Arg Arg Gln Leu Leu Leu Thr
            340                 345                 350

Glu Gly Pro His Leu Tyr Tyr Val Asp Pro Val Asn Lys Val Leu Lys
        355                 360                 365

Gly Glu Ile Pro Trp Ser Gln Glu Leu Arg Pro Glu Ala Lys Asn Phe
    370                 375                 380

Lys Thr Phe Phe Val His Thr Pro Asn Arg Thr Tyr Tyr Leu Met Asp
385                 390                 395                 400

Pro Ser Gly Asn Ala His Lys Trp Cys Arg Lys Ile Gln Glu Val Trp
                405                 410                 415

Arg Gln Arg Tyr Gln Ser His Pro Asp Ala Ala Val Gln
            420                 425
```

<210> SEQ ID NO 25

```
<211> LENGTH: 526
<212> TYPE: PRT
<213> ORGANISM: Homo sapiens

<400> SEQUENCE: 25
```

| | | | | | | | | | | | | | | |
|---|---|---|---|---|---|---|---|---|---|---|---|---|---|---|
| Met | Val | Asn | Lys | Asp | Met | Asn | Gly | Phe | Pro | Val | Lys | Lys | Cys | Ser | Ala |
| 1 | | | | 5 | | | | | 10 | | | | | 15 | |
| Phe | Gln | Phe | Phe | Lys | Lys | Arg | Val | Arg | Arg | Trp | Ile | Lys | Ser | Pro | Met |
| | | | 20 | | | | | 25 | | | | | 30 | | |
| Val | Ser | Val | Asp | Lys | His | Gln | Ser | Pro | Ser | Leu | Lys | Tyr | Thr | Gly | Ser |
| | | 35 | | | | | 40 | | | | | 45 | | | |
| Ser | Met | Val | His | Ile | Pro | Pro | Gly | Glu | Pro | Asp | Phe | Glu | Ser | Ser | Leu |
| | 50 | | | | | 55 | | | | | 60 | | | | |
| Cys | Gln | Thr | Cys | Leu | Gly | Glu | His | Ala | Phe | Gln | Arg | Gly | Val | Leu | Pro |
| 65 | | | | | 70 | | | | | 75 | | | | | 80 |
| Gln | Glu | Asn | Glu | Ser | Cys | Ser | Trp | Glu | Thr | Gln | Ser | Gly | Cys | Glu | Val |
| | | | | 85 | | | | | 90 | | | | | 95 | |
| Arg | Glu | Pro | Cys | Asn | His | Ala | Asn | Ile | Leu | Thr | Lys | Pro | Asp | Pro | Arg |
| | | | 100 | | | | | 105 | | | | | 110 | | |
| Thr | Phe | Trp | Thr | Asn | Asp | Asp | Pro | Ala | Phe | Met | Lys | Gln | Arg | Arg | Met |
| | | | 115 | | | | | 120 | | | | | 125 | | |
| Gly | Leu | Asn | Asp | Phe | Ile | Gln | Lys | Ile | Ala | Asn | Asn | Ser | Tyr | Ala | Cys |
| | 130 | | | | | 135 | | | | | 140 | | | | |
| Lys | His | Pro | Glu | Val | Gln | Ser | Ile | Leu | Lys | Ile | Ser | Gln | Pro | Gln | Glu |
| 145 | | | | | 150 | | | | | 155 | | | | | 160 |
| Pro | Glu | Leu | Met | Asn | Ala | Asn | Pro | Ser | Pro | Pro | Pro | Ser | Pro | Ser | Gln |
| | | | | 165 | | | | | 170 | | | | | 175 | |
| Gln | Ile | Asn | Leu | Gly | Pro | Ser | Ser | Asn | Pro | His | Ala | Lys | Pro | Ser | Asp |
| | | | 180 | | | | | 185 | | | | | 190 | | |
| Phe | His | Phe | Leu | Lys | Val | Ile | Gly | Lys | Gly | Ser | Phe | Gly | Lys | Val | Leu |
| | | | 195 | | | | | 200 | | | | | 205 | | |
| Leu | Ala | Arg | His | Lys | Ala | Glu | Glu | Val | Phe | Tyr | Ala | Val | Lys | Val | Leu |
| | 210 | | | | | 215 | | | | | 220 | | | | |
| Gln | Lys | Lys | Ala | Ile | Leu | Lys | Lys | Lys | Glu | Glu | Lys | His | Ile | Met | Ser |
| 225 | | | | | 230 | | | | | 235 | | | | | 240 |
| Glu | Arg | Asn | Val | Leu | Leu | Lys | Asn | Val | Lys | His | Pro | Phe | Leu | Val | Gly |
| | | | | 245 | | | | | 250 | | | | | 255 | |
| Leu | His | Phe | Ser | Phe | Gln | Thr | Ala | Asp | Lys | Leu | Tyr | Phe | Val | Leu | Asp |
| | | | 260 | | | | | 265 | | | | | 270 | | |
| Tyr | Ile | Asn | Gly | Gly | Glu | Leu | Phe | Tyr | His | Leu | Gln | Arg | Glu | Arg | Cys |
| | | | 275 | | | | | 280 | | | | | 285 | | |
| Phe | Leu | Glu | Pro | Arg | Ala | Arg | Phe | Tyr | Ala | Ala | Glu | Ile | Ala | Ser | Ala |
| | 290 | | | | | 295 | | | | | 300 | | | | |
| Leu | Gly | Tyr | Leu | His | Ser | Leu | Asn | Ile | Val | Tyr | Arg | Asp | Leu | Lys | Pro |
| 305 | | | | | 310 | | | | | 315 | | | | | 320 |
| Glu | Asn | Ile | Leu | Leu | Asp | Ser | Gln | Gly | His | Ile | Val | Leu | Thr | Asp | Phe |
| | | | | 325 | | | | | 330 | | | | | 335 | |
| Gly | Leu | Cys | Lys | Glu | Asn | Ile | Glu | His | Asn | Ser | Thr | Thr | Ser | Thr | Phe |
| | | | 340 | | | | | 345 | | | | | 350 | | |
| Cys | Gly | Thr | Pro | Glu | Tyr | Leu | Ala | Pro | Glu | Val | Leu | His | Lys | Gln | Pro |
| | | | 355 | | | | | 360 | | | | | 365 | | |
| Tyr | Asp | Arg | Thr | Val | Asp | Trp | Trp | Cys | Leu | Gly | Ala | Val | Leu | Tyr | Glu |
| | 370 | | | | | 375 | | | | | 380 | | | | |
| Met | Leu | Tyr | Gly | Leu | Pro | Pro | Phe | Tyr | Ser | Arg | Asn | Thr | Ala | Glu | Met |

```
                385                 390                 395                 400
Tyr Asp Asn Ile Leu Asn Lys Pro Leu Gln Leu Lys Pro Asn Ile Thr
                    405                 410                 415

Asn Ser Ala Arg His Leu Leu Glu Gly Leu Leu Gln Lys Asp Arg Thr
                    420                 425                 430

Lys Arg Leu Gly Ala Lys Asp Phe Met Glu Ile Lys Ser His Val
                    435                 440                 445

Phe Phe Ser Leu Ile Asn Trp Asp Asp Leu Ile Asn Lys Lys Ile Thr
450                 455                 460

Pro Pro Phe Asn Pro Asn Val Ser Gly Pro Asn Asp Leu Arg His Phe
465                 470                 475                 480

Asp Pro Glu Phe Thr Glu Pro Val Pro Asn Ser Ile Gly Lys Ser
                    485                 490                 495

Pro Asp Ser Val Leu Val Thr Ala Ser Val Lys Glu Ala Ala Glu Ala
                500                 505                 510

Phe Leu Gly Phe Ser Tyr Ala Pro Pro Thr Asp Ser Phe Leu
                515                 520                 525

<210> SEQ ID NO 26
<211> LENGTH: 459
<212> TYPE: PRT
<213> ORGANISM: Homo sapiens

<400> SEQUENCE: 26

Met Ser Ser Gln Ser Ser Leu Ser Glu Ala Cys Ser Arg Glu Ala
1               5                   10                  15

Tyr Ser Ser His Asn Trp Ala Leu Pro Ala Ser Arg Ser Asn Pro
                20                  25                  30

Gln Pro Ala Tyr Pro Trp Ala Thr Arg Arg Met Lys Glu Glu Ala Ile
                35                  40                  45

Lys Pro Pro Leu Lys Ala Phe Met Lys Gln Arg Arg Met Gly Leu Asn
50                  55                  60

Asp Phe Ile Gln Lys Ile Ala Asn Asn Ser Tyr Ala Cys Lys His Pro
65                  70                  75                  80

Glu Val Gln Ser Ile Leu Lys Ile Ser Gln Pro Gln Glu Pro Glu Leu
                85                  90                  95

Met Asn Ala Asn Pro Ser Pro Pro Ser Pro Ser Gln Gln Ile Asn
                100                 105                 110

Leu Gly Pro Ser Ser Asn Pro His Ala Lys Pro Ser Asp Phe His Phe
        115                 120                 125

Leu Lys Val Ile Gly Lys Gly Ser Phe Gly Lys Val Leu Leu Ala Arg
        130                 135                 140

His Lys Ala Glu Glu Val Phe Tyr Ala Val Lys Val Leu Gln Lys Lys
145                 150                 155                 160

Ala Ile Leu Lys Lys Lys Glu Glu Lys His Ile Met Ser Glu Arg Asn
                165                 170                 175

Val Leu Leu Lys Asn Val Lys His Pro Phe Leu Val Gly Leu His Phe
                180                 185                 190

Ser Phe Gln Thr Ala Asp Lys Leu Tyr Phe Val Leu Asp Tyr Ile Asn
                195                 200                 205

Gly Gly Glu Leu Phe Tyr His Leu Gln Arg Glu Arg Cys Phe Leu Glu
        210                 215                 220

Pro Arg Ala Arg Phe Tyr Ala Ala Glu Ile Ala Ser Ala Leu Gly Tyr
225                 230                 235                 240
```

Leu His Ser Leu Asn Ile Val Tyr Arg Asp Leu Lys Pro Glu Asn Ile
            245                 250                 255

Leu Leu Asp Ser Gln Gly His Ile Val Leu Thr Asp Phe Gly Leu Cys
            260                 265                 270

Lys Glu Asn Ile Glu His Asn Ser Thr Thr Ser Thr Phe Cys Gly Thr
            275                 280                 285

Pro Glu Tyr Leu Ala Pro Glu Val Leu His Lys Gln Pro Tyr Asp Arg
            290                 295                 300

Thr Val Asp Trp Trp Cys Leu Gly Ala Val Leu Tyr Glu Met Leu Tyr
305                 310                 315                 320

Gly Leu Pro Pro Phe Tyr Ser Arg Asn Thr Ala Glu Met Tyr Asp Asn
            325                 330                 335

Ile Leu Asn Lys Pro Leu Gln Leu Lys Pro Asn Ile Thr Asn Ser Ala
            340                 345                 350

Arg His Leu Leu Glu Gly Leu Leu Gln Lys Asp Arg Thr Lys Arg Leu
            355                 360                 365

Gly Ala Lys Asp Asp Phe Met Glu Ile Lys Ser His Val Phe Phe Ser
            370                 375                 380

Leu Ile Asn Trp Asp Asp Leu Ile Asn Lys Lys Ile Thr Pro Pro Phe
385                 390                 395                 400

Asn Pro Asn Val Ser Gly Pro Asn Asp Leu Arg His Phe Asp Pro Glu
            405                 410                 415

Phe Thr Glu Glu Pro Val Pro Asn Ser Ile Gly Lys Ser Pro Asp Ser
            420                 425                 430

Val Leu Val Thr Ala Ser Val Lys Glu Ala Ala Glu Ala Phe Leu Gly
            435                 440                 445

Phe Ser Tyr Ala Pro Pro Thr Asp Ser Phe Leu
450                 455

<210> SEQ ID NO 27
<211> LENGTH: 445
<212> TYPE: PRT
<213> ORGANISM: Homo sapiens

<400> SEQUENCE: 27

Met Gly Glu Met Gln Gly Ala Leu Ala Arg Ala Arg Leu Glu Ser Leu
1               5                   10                  15

Leu Arg Pro Arg His Lys Lys Arg Ala Glu Ala Gln Lys Arg Ser Glu
            20                  25                  30

Ser Phe Leu Leu Ser Gly Leu Ala Phe Met Lys Gln Arg Arg Met Gly
            35                  40                  45

Leu Asn Asp Phe Ile Gln Lys Ile Ala Asn Asn Ser Tyr Ala Cys Lys
    50                  55                  60

His Pro Glu Val Gln Ser Ile Leu Lys Ile Ser Gln Pro Gln Glu Pro
65                  70                  75                  80

Glu Leu Met Asn Ala Asn Pro Ser Pro Pro Ser Pro Ser Gln Gln
            85                  90                  95

Ile Asn Leu Gly Pro Ser Ser Asn Pro His Ala Lys Pro Ser Asp Phe
            100                 105                 110

His Phe Leu Lys Val Ile Gly Lys Gly Ser Phe Gly Lys Val Leu Leu
            115                 120                 125

Ala Arg His Lys Ala Glu Glu Val Phe Tyr Ala Val Lys Val Leu Gln
            130                 135                 140

Lys Lys Ala Ile Leu Lys Lys Lys Glu Glu Lys His Ile Met Ser Glu
145                 150                 155                 160

```
Arg Asn Val Leu Leu Lys Asn Val Lys His Pro Phe Leu Val Gly Leu
                165                 170                 175

His Phe Ser Phe Gln Thr Ala Asp Lys Leu Tyr Phe Val Leu Asp Tyr
            180                 185                 190

Ile Asn Gly Gly Glu Leu Phe Tyr His Leu Gln Arg Glu Arg Cys Phe
        195                 200                 205

Leu Glu Pro Arg Ala Arg Phe Tyr Ala Ala Glu Ile Ala Ser Ala Leu
    210                 215                 220

Gly Tyr Leu His Ser Leu Asn Ile Val Tyr Arg Asp Leu Lys Pro Glu
225                 230                 235                 240

Asn Ile Leu Leu Asp Ser Gln Gly His Ile Val Leu Thr Asp Phe Gly
                245                 250                 255

Leu Cys Lys Glu Asn Ile Glu His Asn Ser Thr Thr Ser Thr Phe Cys
            260                 265                 270

Gly Thr Pro Glu Tyr Leu Ala Pro Glu Val Leu His Lys Gln Pro Tyr
        275                 280                 285

Asp Arg Thr Val Asp Trp Trp Cys Leu Gly Ala Val Leu Tyr Glu Met
    290                 295                 300

Leu Tyr Gly Leu Pro Pro Phe Tyr Ser Arg Asn Thr Ala Glu Met Tyr
305                 310                 315                 320

Asp Asn Ile Leu Asn Lys Pro Leu Gln Leu Lys Pro Asn Ile Thr Asn
                325                 330                 335

Ser Ala Arg His Leu Leu Glu Gly Leu Leu Gln Lys Asp Arg Thr Lys
            340                 345                 350

Arg Leu Gly Ala Lys Asp Asp Phe Met Glu Ile Lys Ser His Val Phe
        355                 360                 365

Phe Ser Leu Ile Asn Trp Asp Asp Leu Ile Asn Lys Lys Ile Thr Pro
    370                 375                 380

Pro Phe Asn Pro Asn Val Ser Gly Pro Asn Asp Leu Arg His Phe Asp
385                 390                 395                 400

Pro Glu Phe Thr Glu Glu Pro Val Pro Asn Ser Ile Gly Lys Ser Pro
                405                 410                 415

Asp Ser Val Leu Val Thr Ala Ser Val Lys Glu Ala Ala Glu Ala Phe
            420                 425                 430

Leu Gly Phe Ser Tyr Ala Pro Pro Thr Asp Ser Phe Leu
        435                 440                 445

<210> SEQ ID NO 28
<211> LENGTH: 387
<212> TYPE: PRT
<213> ORGANISM: Homo sapiens

<400> SEQUENCE: 28

Met Thr Val Lys Thr Glu Ala Ala Lys Gly Thr Leu Thr Tyr Ser Arg
1               5                   10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
        35                  40                  45

Cys Lys His Pro Glu Val Gln Ser Ile Leu Lys Ile Ser Gln Pro Gln
    50                  55                  60

Glu Pro Glu Leu Met Asn Ala Asn Pro Ser Pro Pro Ser Pro Ser
65                  70                  75                  80

Gln Gln Ile Asn Leu Gly Pro Ser Ser Asn Pro His Ala Lys Pro Ser
```

```
                85                  90                  95
Asp Phe His Phe Leu Lys Val Ile Gly Lys Gly Ser Phe Gly Lys Val
                100                 105                 110

Leu Leu Ala Arg His Lys Ala Glu Glu Val Phe Tyr Ala Val Lys Val
            115                 120                 125

Leu Gln Lys Lys Ala Ile Leu Lys Lys Lys Glu Leu Phe Tyr His Leu
        130                 135                 140

Gln Arg Glu Arg Cys Phe Leu Glu Pro Arg Ala Arg Phe Tyr Ala Ala
145                 150                 155                 160

Glu Ile Ala Ser Ala Leu Gly Tyr Leu His Ser Leu Asn Ile Val Tyr
                165                 170                 175

Arg Asp Leu Lys Pro Glu Asn Ile Leu Leu Asp Ser Gln Gly His Ile
            180                 185                 190

Val Leu Thr Asp Phe Gly Leu Cys Lys Glu Asn Ile Glu His Asn Ser
        195                 200                 205

Thr Thr Ser Thr Phe Cys Gly Thr Pro Glu Tyr Leu Ala Pro Glu Val
210                 215                 220

Leu His Lys Gln Pro Tyr Asp Arg Thr Val Asp Trp Trp Cys Leu Gly
225                 230                 235                 240

Ala Val Leu Tyr Glu Met Leu Tyr Gly Leu Pro Pro Phe Tyr Ser Arg
                245                 250                 255

Asn Thr Ala Glu Met Tyr Asp Asn Ile Leu Asn Lys Pro Leu Gln Leu
            260                 265                 270

Lys Pro Asn Ile Thr Asn Ser Ala Arg His Leu Leu Glu Gly Leu Leu
        275                 280                 285

Gln Lys Asp Arg Thr Lys Arg Leu Gly Ala Lys Asp Asp Phe Met Glu
290                 295                 300

Ile Lys Ser His Val Phe Phe Ser Leu Ile Asn Trp Asp Asp Leu Ile
305                 310                 315                 320

Asn Lys Lys Ile Thr Pro Pro Phe Asn Pro Asn Val Ser Gly Pro Asn
                325                 330                 335

Asp Leu Arg His Phe Asp Pro Glu Phe Thr Glu Glu Pro Val Pro Asn
            340                 345                 350

Ser Ile Gly Lys Ser Pro Asp Ser Val Leu Val Thr Ala Ser Val Lys
        355                 360                 365

Glu Ala Ala Glu Ala Phe Leu Gly Phe Ser Tyr Ala Pro Pro Thr Asp
370                 375                 380

Ser Phe Leu
385

<210> SEQ ID NO 29
<211> LENGTH: 431
<212> TYPE: PRT
<213> ORGANISM: Homo sapiens

<400> SEQUENCE: 29

Met Thr Val Lys Thr Glu Ala Ala Lys Gly Thr Leu Thr Tyr Ser Arg
1               5                   10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
        35                  40                  45

Cys Lys His Pro Glu Val Gln Ser Ile Leu Lys Ile Ser Gln Pro Gln
    50                  55                  60
```

-continued

Glu Pro Glu Leu Met Asn Ala Asn Pro Ser Pro Pro Ser Pro Ser
 65                  70                  75                  80

Gln Gln Ile Asn Leu Gly Pro Ser Ser Asn Pro His Ala Lys Pro Ser
             85                  90                  95

Asp Phe His Phe Leu Lys Val Ile Gly Lys Gly Ser Phe Gly Lys Val
            100                 105                 110

Leu Leu Ala Arg His Lys Ala Glu Glu Val Phe Tyr Ala Val Lys Val
        115                 120                 125

Leu Gln Lys Lys Ala Ile Leu Lys Lys Lys Glu Glu Lys His Ile Met
    130                 135                 140

Ser Glu Arg Asn Val Leu Leu Lys Asn Val Lys His Pro Phe Leu Val
145                 150                 155                 160

Gly Leu His Phe Ser Phe Gln Thr Ala Asp Lys Leu Tyr Phe Val Leu
                165                 170                 175

Asp Tyr Ile Asn Gly Gly Glu Leu Phe Tyr His Leu Gln Arg Glu Arg
            180                 185                 190

Cys Phe Leu Glu Pro Arg Ala Arg Phe Tyr Ala Ala Glu Ile Ala Ser
        195                 200                 205

Ala Leu Gly Tyr Leu His Ser Leu Asn Ile Val Tyr Arg Asp Leu Lys
    210                 215                 220

Pro Glu Asn Ile Leu Leu Asp Ser Gln Gly His Ile Val Leu Thr Asp
225                 230                 235                 240

Phe Gly Leu Cys Lys Glu Asn Ile Glu His Asn Ser Thr Thr Ser Thr
                245                 250                 255

Phe Cys Gly Thr Pro Glu Tyr Leu Ala Pro Glu Val Leu His Lys Gln
            260                 265                 270

Pro Tyr Asp Arg Thr Val Asp Trp Trp Cys Leu Gly Ala Val Leu Tyr
        275                 280                 285

Glu Met Leu Tyr Gly Leu Pro Pro Phe Tyr Ser Arg Asn Thr Ala Glu
    290                 295                 300

Met Tyr Asp Asn Ile Leu Asn Lys Pro Leu Gln Leu Lys Pro Asn Ile
305                 310                 315                 320

Thr Asn Ser Ala Arg His Leu Leu Glu Gly Leu Leu Gln Lys Asp Arg
                325                 330                 335

Thr Lys Arg Leu Gly Ala Lys Asp Asp Phe Met Glu Ile Lys Ser His
            340                 345                 350

Val Phe Phe Ser Leu Ile Asn Trp Asp Asp Leu Ile Asn Lys Lys Ile
        355                 360                 365

Thr Pro Pro Phe Asn Pro Asn Val Ser Gly Pro Asn Asp Leu Arg His
    370                 375                 380

Phe Asp Pro Glu Phe Thr Glu Glu Pro Val Pro Asn Ser Ile Gly Lys
385                 390                 395                 400

Ser Pro Asp Ser Val Leu Val Thr Ala Ser Val Lys Glu Ala Ala Glu
                405                 410                 415

Ala Phe Leu Gly Phe Ser Tyr Ala Pro Pro Thr Asp Ser Phe Leu
            420                 425                 430

<210> SEQ ID NO 30
<211> LENGTH: 1068
<212> TYPE: PRT
<213> ORGANISM: Homo sapiens

<400> SEQUENCE: 30

Met Pro Pro Arg Pro Ser Ser Gly Glu Leu Trp Gly Ile His Leu Met
1               5                   10                  15

-continued

```
Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
 50                  55                  60

Glu Ser Ser Tyr Ile Phe Val Ser Val Thr Gln Glu Ala Glu Arg Glu
 65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430
```

-continued

```
Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
```

```
                 850               855                 860
Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
                915                 920                 925

Leu Phe His Ile Asp Phe Gly His Phe Leu Asp His Lys Lys Lys Lys
            930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn  Leu Phe Ser Met Met  Leu Gly Ser
                995                1000                1005

Gly Met  Pro Glu Leu Gln Ser  Phe Asp Asp Ile Ala  Tyr Ile Arg
            1010                1015                1020

Lys Thr  Leu Ala Leu Asp Lys  Thr Glu Gln Glu Ala  Leu Glu Tyr
            1025                1030                1035

Phe Met  Lys Gln Met Asn Asp  Ala His His Gly Gly  Trp Thr Thr
            1040                1045                1050

Lys Met  Asp Trp Ile Phe His  Thr Ile Lys Gln His  Ala Leu Asn
            1055                1060                1065

<210> SEQ ID NO 31
<211> LENGTH: 7032
<212> TYPE: DNA
<213> ORGANISM: Homo sapiens

<400> SEQUENCE: 31
gcggcgccgg gggcgggggg cggcgggcga cggggcgggc gcaggatgag ggcggccatt    60 gctgggggctc cgcttcgggg aggaggacgc tgaggaggcg ccgagccgcg cagcgctgcg   120
ggggaggcgc ccgcgccgac gcggggccca tggccaggac caccagccag ctgtatgacg   180
ccgtgcccat ccagtccagc gtggtgttat gttcctgccc atccccatca atggtgagga   240
cccagactga gtccagcacg ccccctggca ttcctggtgg cagcaggcag ggccccgcca   300
tggacggcac tgcagccgag cctcggcccg gcgccggctc cctgcagcat gcccagcctc   360
cgccgcagcc tcggaagaag cggcctgagg acttcaagtt tgggaaaatc cttgggaag    420 gctctttttc cacggttgtc ctggctcgag aactggcaac ctccagagaa tatgcgatta   480
aaattctgga agcgacat atcataaaag agaacaaggt cccctatgta accagagagc    540
gggatgtcat gtcgcgcctg atcacccct tctttgttaa gctttacttc acatttcagg    600
acgacgagaa gctgtatttc ggccttagtt atgccaaaaa tggagaacta cttaaatata    660
ttcgcaaaat cggttcattc gatgagacct gtacccgatt ttacacggct gagattgtgt    720
ctgctttaga gtacttgcac ggcaagggca tcattcacag ggaccttaaa ccggaaaaca    780
ttttgttaaa tgaagatatg cacatccaga tcacagattt tggaacagca aaagtcttat    840
ccccagagag caaacaagcc agggccaact cattcgtggg aacagcgcag tacgtttctc    900
```

```
cagagctgct cacggagaag tccgcctgta agagttcaga cctttgggct cttggatgca    960
taatatacca gcttgtggca ggactcccac cattccgagc tggaaacgag tatcttatat   1020
ttcagaagat cattaagttg aatatgact ttccagaaaa attcttccct aaggcaagag   1080
acctcgtgga gaaacttttg gttttagatg ccacaaagcg gttaggctgt gaggaaatgg   1140
aaggatacgg acctcttaaa gcacacccgt tcttcgagtc cgtcacgtgg gagaacctgc   1200
accagcagac gcctccgaag ctcaccgctt acctgccggc tatgtcggaa gacgacgagg   1260
actgctatgg caattatgac aatctcctga gccagtttgg ctgcatgcag gtgtcttcgt   1320
cctcctcctc acactccctg tcagcctccg acacgggcct gccccagagg tcaggcagca   1380
acatagagca gtacattcac gatctggact cgaactcctt tgaactggac ttacagtttt   1440
ccgaagatga gaagaggttg ttgttggaga agcaggctgg cggaaaccct tgcctaacag   1500
gacgtattat ctgatggacc ccagcgggaa cgcacacaag tggtgcagga agatccagga   1560
ggtttggagg cagcgatacc agagccaccc ggacgccgct gtgcagtgac gtggcctgcg   1620
gccgggctgc ccttcgctgc caggacacct gccccagcgc ggcttggccg ccatccggga   1680
cgcttccaga ccacctgcca gccatcacaa ggggaacgca gaggcggaaa ccttgcagca   1740 ttttttattta aagaaaaga agaaaaaaaa cacccaacca cacaagaac aaaaccagta   1800 acaaacacaa aggaattcag ggtcgctttg cttgctctct gtgctccgtg gaggcctccg   1860
tgtgccctcg ttgccgtggg gacccagctc catgcacgtc aacccagtcc cgcccagact   1920
agtggacaga cctggtgtca ccagtttttc ctagcatcag tccgaaccat gcgcccgccc   1980
tgccccaact gtgtgctggt cctgctgtgg ccgaggggac cgggtgtgtt tggctcttta   2040
tgcccctccc gctgtggtcc tggaactctt caccagggag ggagccctgc ggggggccgca   2100 gctttgtgga gggagccgcc gtgcttctgt cacctgctcc cttctcttgcg tctccctgtg   2160 atgggccctt aggcctggct gggcccatta catatccctg tggtggctct ggtggcagct   2220
ttctgtggcc cctgctgtgt tggcaggcag gtttgcgtgg tgaggagcgg gaggggttgg   2280
agtggtgcgg gagcaggctg ccgagtggag ggtgccatcg agggctccgg atcccttatc   2340
ctacttagca gtgttggtct ctggggctgg aagccgagcg catgctggga gcggtactgt   2400
cagaagtgag cccagttagt accccgctgg ctcactgcac gagagagtcc tgccccgagc   2460
cctaggtggg gccaggaggt gccttggaga agccagccag agcagagagg gctgctgact   2520
tccgtgtgga gcagagaggc ctgagggcct cctaaaaggt ttaaatgtcc acgcctctcc   2580
agttgctgaa gtagggtctg agagaaccct ggcatcagca gacccagggt gcttctgtct   2640
cctgcagacc acgccaggga gtgcagacac caccgtcaca cacgcccctt ttgtgttttg   2700
gttcaagttt ctcagagccc ctcagagctt ctacatctgt gcatcagaaa tctcacagcc   2760
ttctcatgct gccggctcat ctgggcccat agagtgggct ttgccagttg ctgttgcaca   2820
ggaggcgaga acagcacact tcaaccccag cttgctggtc ggctttcctc tagagagagc   2880
cggttttggg gccatttccc tttgatgctt tggtggcctt gccccgctct gcagcacaga   2940
caggccagat gcatttgtcc tttgcctagc tactccccag gtagagagtg ctcctggtgg   3000
cctggcaggt ctgggccctt ctctccctgc ccaggttgtc cctggagggc agccctcact   3060
ccctttgggg gagaggcaga cattgctgcc cacagacctg cctctgactc aactgtgtcc   3120
accctccctg gtccctaccc ccaagtcaca ggtgactcag cagtgaccct gtgtgccagg   3180
ccagatccaa actgagaggg aaggtgtcgt ttttacactg ctaatgacga gagtggctct   3240
ttttagctag gcgagtacag acggggcctg ggaggggca gagatgttcc ccaggccctg   3300
```

```
cctgtggttc ctgcctgggc cttggctgct gctgtgtgag agctgcatgt gagcctgtga   3360
ccgtgagctg gggtgagctg ggccgcacct accctggggc cccagggagc aggacgctcc   3420
ggggcccagc acgttgccct gggcctgtgg ccggagtcgg agtcctctct cctcctcctg   3480
gcttttggaa aggcttggct gtgttgggga gtctctctta gcccttttcag gaatttctgt   3540 tcaggcttcc tcctcctcat cagctatttt acccatctca gaacgtcctg tgtctccatg   3600
taggagagtg gctctctcag atctctcagg gcgtctggtt atagggaaac aagtggagca   3660
gggacgtggc tttaattgga gcactcggct gggctgcttg gggagactct tccgtgcgtt   3720
cttcctctgg atagaaccac cacctcctgg gcgtcactga caagctccat cttaacctcc   3780
aaagccacag aactaggggc tcagagccag agctggcagc cgccagccaa aatgatgcca   3840
ttgcctgagc tgacagccaa gcccttctgt gggtcacctt tctcctcacc cagcccttg    3900 ctcttccctt ttgaaaggcc cgtgtgtttt ctttccttac cctgtgcttg ctcatgtcta   3960
ctccggtttt ctctaccaca tccttagagc catcacctgg cacgcaggcg ccttacattc   4020
tacggtagaa cgtggggtac tgtgtgtgca catagacaca cttacgtgga attacagttg   4080
tgggtttatc caagatgagg aagatttcac ctgctgttta atagacttgg ggccatgtgc   4140
ctccccacac atgggcaagg acaggtggaa tgtcgggacc acactgtgcg gcttctcggc   4200
acaaagcgga gggaggctgt ggtcgctgcc ggcctaggtg tcccaggtgc cccgcctttc   4260
tctgggacac agttggggc tggcttctga gggattcctt tctccctct ttgtgtggcc     4320 ccagccaggg cggtgggcag tcctggtgta gagcacaagc ctctccaccc tagagaaatg   4380
cctctgtacc acggctacca tgtggaacct taacttgcag aaggcttgtt aacaattgtt   4440
ttgagagaga tggctggtca tgccacagct gctggggact ccgcctactc cagccctctt   4500
gggacacact gtgggatttg tggcccttcc ccagaggaat tgtggagact gtcccatgga   4560
acaaaccctc aggcaccagc acagggctct gggtgactca gtaaaactaa cgtttgtctc   4620
tgacaagatc agctgtaggc tcaccggcca gagaagacca ctgtgagcat tttgccgtat   4680
atcctgccct gccatttgtt cacttttttaa actaaaatag gaacatccga cacacaccgt   4740
ttgcatcgtc ttctcccttg atattttaag cattttccca tgtcatgagt ttctcagaaa   4800
catgttttta acaattgtac tatttagtca ttgtccattt actataattt atctgaccat   4860
ttccctactg taaaatactt aagacggttt ctgattttc cactatttaa ataatgctgt    4920
gatgaatatc tttaaaatct tctgattct tactttttc cccttagat gcctggaagt       4980 ggtattttga ggtgaaagag tttgttcatt ttgaagatat ttctgtctct ctctcgacct   5040
gatgtgtaga cgctcacttc cagtagcaga accaccttag ttgtgtctta cagattctga   5100
acaaatcggt ttctgataag ccatgtgttc caaagaatgt ctgaataaga ccgctctta    5160 tttaaatgct aagaggatgt cactactgca atccatctgt ggccgatttt ttccaagagc   5220
caatttcctt gttttggttg caagaacctg gctctgcctg catgtcagct ctctgccctc   5280
cctgctgccg tggctttcaa gcgcttggca gaatcttgta cttcgtgtcc acaatggtac   5340
tgaatttgca tctgcacagt cagcagagat aacaagtgtt gaactgacct tgccacatgc   5400
ttagtgagtg atttgtaatt aagttttatag actcagaagg tatattagga catttggaat   5460
cagtagcaga gcaaagcctc tttgaaaaaa accacgtagc tgattgggtt ttacaagagt   5520
gcatttgtct ccccccttcca cccgtggggc cccaccttca ggtcttagtg gttcacaaga   5580
gcccagcagc caggctggct ttttcattgt agggcgtggt tgtcccagct ggtgtagatt   5640
```

```
tcaggccgcc ccccccaact ccctgcccac agtgttgcag attgcctggc tggcagcaag   5700
tccagaccac ccaaatttgg ttggattctt catttctcca ctgtagttgg ggtccattga   5760
ttgtgcaggg aacgtgcag gaggttttc taggcaccgt gttcagtgct gcttcactct    5820
accagagatt atggccaaat tgcacggaat ttggtttctt gccctctgaa gcctgagggc   5880
ccccccttgc ctggctggtt gacagacccg gggtggtcac tgctgagact tcagagatcg   5940
cagctgctgt gagaatacgg tgaaggtact ttgttctgga agatgttgtc atacactttt   6000
ccccagttat tttcaaactt gacatgagcc tatgttgact cactgggtgg gggtcccttc   6060
ttacgcagca cacgtggcaa gtgcctgaat cggggctgga ggcacttcag agcctctgag   6120
gggccaccac ttctggccca aaattgcagg gttgtagatg aggctgcctg tggagaactg   6180
gtgtgaggag gaagctgttt ccaacaaaga gcactttcat ctgttgagat ggctgtggtg   6240
agcaactgaa cgagcctacg tgtgtacctg aattttcccc gtaactcatt tcttccatat   6300
gaagaaacac caaactatgt acagagaact ttttacaaaa ggcagacctt ttttaagctg   6360
tgtaacccac atagcctaac cacctggcag aatgactacg aataggggtc attgtgctgg   6420
taaaagcctc tattacgact gtaagtaagt tggatgttgg caaaattaaa ttgttacagt   6480
atttagagct gctgtagctg ttccttcaca acataaaata ggataaatga ctagtacgtc   6540
tttcaggtgg gtggcaagca gaacatgcgt aatattctct acctggtctg tagctgtaac   6600
tgtgatgtac agacaaagca aaattaaaa gaacttatga aaacaaatgc aatgatacta   6660
ggatatacac ttttgtattt ttattcttat ataaggttat ttgctggcta ttgttggcct   6720
ctagttcagt ctgtgttatt taaattctaa tatatgaatt atttgaattg aattcatgtt   6780
cggggccacg ttgttgtatg tattgatgta cagccttgaa tgtgaataat tattgtaaac   6840 tatatttac aacttttttt ctggctttat tatataaatt ttctattggg tcagtgattt    6900
aatcatataa tttaatgaat ctgtttatcc tttttttttt tccaaatact tgtgctttag   6960
gtgtagttac cagatgatga attttcctcg tatggtcagt agtcttgtaa taaaaagcat   7020
gtagagtgta ga                                                     7032
```

<210> SEQ ID NO 32
<211> LENGTH: 7243
<212> TYPE: DNA
<213> ORGANISM: Homo sapiens

<400> SEQUENCE: 32

```
gcggcgccgg gggcgggggg cggcgggcga cggggcgggc gcaggatgag ggcggccatt     60 gctgggctc cgcttcgggg aggaggacgc tgaggaggcg ccgagccgcg cagcgctgcg    120
ggggaggcgc ccgcgccgac gcggggccca tggccaggac caccagccag ctgtatgacg    180
ccgtgcccat ccagtccagc gtggtgttat gttcctgccc atccccatca atggtgagga    240
cccagactga gtccagcacg ccccctggca ttcctggtgg cagcaggcag ggccccgcca    300
tggacggcac tgcagccgag cctcggcccg gcgccggctc cctgcagcat gcccagcctc    360
cgccgcagcc tcggaagaag cggcctgagg acttcaagtt tgggaaaatc cttggggaag    420
gctctttttc cacggttgtc ctggctcgag aactggcaac ctccagagaa tatgcgatta    480
aaattctgga gaagcgacat atcataaaag agaacaaggt cccctatgta accagagagc    540
gggatgtcat gtcgcgcctg gatcacccct tctttgttaa gctttacttc acatttcagg    600
acgacgagaa gctgtatttc ggccttagtt atgccaaaaa tggagaacta cttaaatata    660
ttcgcaaaat cggttcattc gatgagacct gtacccgatt ttacacggct gagattgtgt    720
```

```
ctgctttaga gtacttgcac ggcaagggca tcattcacag ggaccttaaa ccggaaaaca    780
ttttgttaaa tgaagatatg cacatccaga tcacagattt tggaacagca aaagtcttat    840
ccccagagag caaacaagcc agggccaact cattcgtggg aacagcgcag tacgtttctc    900
cagagctgct cacggagaag tccgcctgta agagttcaga cctttgggct cttggatgca    960
taatatacca gcttgtggca ggactcccac cattccgagc tggaaacgag tatcttatat   1020
ttcagaagat cattaagttg gaatatgact ttccagaaaa attcttccct aaggcaagag   1080
acctcgtgga gaaacttttg gttttagatg ccacaaagcg gttaggctgt gaggaaatgg   1140
aaggatacgg acctcttaaa gcacacccgt tcttcgagtc cgtcacgtgg gagaacctgc   1200
accagcagac gcctccgaag ctcaccgctt acctgccggc tatgtcggaa gacgacgagg   1260
actgctatgg caattatgac aatctcctga gccagtttgg ctgcatgcag gtgtcttcgt   1320
cctcctcctc acactccctg tcagcctccg acacgggcct gccccagagg tcaggcagca   1380
acatagagca gtacattcac gatctggact cgaactcctt tgaactggac ttacagtttt   1440
ccgaagatga gaagaggttg ttgttggaga agcaggctgg cggaaaccct tggcaccagt   1500
ttgtagaaaa taatttaata ctaaagatgg gcccagtgga taagcggaag ggtttatttg   1560
caagacgacg acagctgttg ctcacagaag gaccacattt atattatgtg gatcctgtca   1620
acaaagttct gaaaggtgaa attccttggt cacaagaact tcgaccagag gccaagaatt   1680
ttaaaacttt ctttgtccac acgcctaaca ggacgtatta tctgatggac cccagcggga   1740
acgcacacaa gtggtgcagg aagatccagg aggtttggag gcagcgatac cagagccacc   1800
cggacgccgc tgtgcagtga cgtggcctgc ggccgggctg cccttcgctg ccaggacacc   1860
tgccccagcg cggcttggcc gccatccggg acgcttccag accacctgcc agccatcaca   1920
aggggaacgc agaggcggaa accttgcagc atttttattt aaaagaaaag aagaaaaaaa   1980
acacccaacc acacaaagaa caaaaccagt aacaaacaca aaggaattca gggtcgcttt   2040
gcttgctctc tgtgctccgt ggaggcctcc gtgtgccctc gttgccgtgg ggacccagct   2100
ccatgcacgt caacccagtc ccgcccagac tagtggacag acctggtgtc accagttttt   2160
cctagcatca gtccgaacca tgcgcccgcc ctgcccaaac tgtgtgctgg tcctgctgtg   2220
gccgagggga ccgggtgtgt ttggctcttt atgcccctcc cgctgtggtc ctggaactct   2280
tcaccaggga gggagccctg cggggccgc agctttgtgg agggagccgc cgtgcttctg   2340
tcacctgctc cctttcttgc gtctccctgt gatgggccct taggcctggc tgggcccatt   2400
acatatccct gtggtggctc tggtggcagc tttctgtggc ccctgctgtg ttggcaggca   2460
ggtttgcgtg gtgaggagcg ggaggggttg gagtggtgcg ggagcaggct gccgagtgga   2520
gggtgccatc gagggctccg gatcccttat cctacttagc agtgttggtc tctgggctg    2580
gaagccgagc gcatgctggg agcggtactg tcagaagtga gcccagttag taccccgctg   2640
gctcactgca cgagagagtc ctgccccgag ccctaggtgg ggccaggagg tgccttggag   2700
aagccagcca gagcagagag ggctgctgac ttccgtgtgg agcagagagg cctgagggcc   2760
tcctaaaagg tttaaatgtc cacgcctctc cagttgctga gtagggtct gagagaaccc    2820
tggcatcagc agacccaggg tgcttctgtc tcctgcagac cacgccaggg agtgcagaca   2880
ccaccgtcac acacgcccct tttgtgtttt ggttcaagtt tctcagagcc cctcagagct   2940
tctacatctg tgcatcagaa atctcacagc cttctcatgc tgccggctca tctgggccca   3000
tagagtgggc tttgccagtt gctgttgcac aggaggcgag aacagcacac ttcaacccca   3060
```

```
gcttgctggt cggctttcct ctagagagag ccggttttgg ggccatttcc ctttgatgct    3120
ttggtggcct tgccccgctc tgcagcacag acaggccaga tgcatttgtc ctttgcctag    3180
ctactcccca ggtagagagt gctcctggtg gcctggcagg tctgggccct tctctccctg    3240
cccaggttgt ccctggaggg cagccctcac tcccttgggg ggagaggcag acattgctgc    3300
ccacagacct gcctctgact caactgtgtc caccctccct ggtccctacc cccaagtcac    3360
aggtgactca gcagtgaccc tgtgtgccag gccagatcca aactgagagg gaaggtgtcg    3420 ttttacact gctaatgacg agagtggctc tttttagcta ggcgagtaca gacggggcct    3480 gggaggggc agagatgttc cccaggcct gcctgtggtt cctgcctggg ccttggctgc    3540
tgctgtgtga gagctgcatg tgagcctgtg accgtgagct ggggtgagct gggccgcacc    3600
taccctgggg ccccagggag caggacgctc cggggcccag cacgttgccc tgggcctgtg    3660
gccggagtcg gagtcctctc tcctcctcct ggcttttgga aaggcttggc tgtgttgggg    3720
agtctctctt agccctttca ggaatttctg ttcaggcttc ctcctcctca tcagctattt    3780
tacccatctc agaacgtcct gtgtctccat gtaggagagt ggctctctca gatctctcag    3840
ggcgtctggt tatagggaaa caagtggagc agggacgtgg ctttaattgg agcactcggc    3900
tgggctgctt ggggagactc ttccgtgcgt tcttcctctg gatagaacca ccacctcctg    3960
ggcgtcactg acaagctcca tcttaacctc caaagccaca gaactagggg ctcagagcca    4020
gagctggcag ccgccagcca aaatgatgcc attgcctgag ctgacagcca agcccttctg    4080
tgggtcacct ttctcctcac ccagccccctt gctcttccct tttgaaaggc ccgtgtgttt    4140 tctttccctta ccctgtgctt gctcatgtct actccggttt tctctaccac atccttagag    4200
ccatcacctg gcacgcaggc gccttacatt ctacggtaga acgtggggta ctgtgtgtgc    4260
acatagacac acttacgtgg aattacagtt gtgggtttat ccaagatgag gaagatttca    4320
cctgctgttt aatagacttg gggccatgtg cctccccaca catgggcaag acaggtgga    4380 atgtcgggac cacactgtgc ggcttctcgg cacaaagcgg agggaggctg tggtcgctgc    4440
cggcctaggt gtcccaggtg ccccgccttt ctctgggaca cagttggggg ctggcttctg    4500
agggattcct ttctccccctc tttgtgtggc cccagccagg gcggtgggca gtcctggtgt    4560
agagcacaag cctctccacc ctagagaaat gcctctgtac cacggctacc atgtggaacc    4620
ttaacttgca gaaggcttgt taacaattgt tttgagagag atggctggtc atgccacagc    4680
tgctggggac tccgcctact ccagccctct tgggacacac tgtgggattt gtggcccttc    4740
cccagaggaa ttgtggagac tgtcccatgg aacaaaccct caggcaccag cacagggctc    4800
tgggtgactc agtaaaacta acgtttgtct ctgacaagat cagctgtagg ctcaccggcc    4860
agagaagacc actgtgagca ttttgccgta tatcctgccc tgccatttgt tcactttta    4920 aactaaaata ggaacatccg acacacaccg tttgcatcgt cttctcccctt gatatttaa    4980 gcattttccc atgtcatgag tttctcagaa acatgttttt aacaattgta ctatttagtc    5040
attgtccatt tactataatt tatctgacca tttccctact gtaaaatact taagacggtt    5100
tctgattttt ccactattta aataatgctg tgatgaatat cttaaaatc ttctgatttc    5160 ttactttttt ccccctttaga tgcctggaag tggtattttg aggtgaaaga gtttgttcat    5220
tttgaagata tttctgtctc tctctcgacc tgatgtgtag acgctcactt ccagtagcag    5280
aaccacctta gttgtgtctt acagattctg aacaaatcgg tttctgataa gccatgtgtt    5340
ccaaagaatg tctgaataag accgctcttt atttaaatgc taagaggatg tcactactgc    5400
aatccatctg tggccgattt tttccaagag ccaatttcct tgttttggtt gcaagaacct    5460
```

```
ggctctgcct gcatgtcagc tctctgccct ccctgctgcc gtggcttttca agcgcttggc    5520 agaatcttgt acttcgtgtc cacaatggta ctgaatttgc atctgcacag tcagcagaga    5580
taacaagtgt tgaactgacc ttgccacatg cttagtgagt gatttgtaat taagtttata    5640
gactcagaag gtatattagg acatttggaa tcagtagcag agcaaagcct ctttgaaaaa    5700
aaccacgtag ctgattgggt tttacaagag tgcatttgtc tccccttcc acccgtgggg     5760 ccccaccttc aggtcttagt ggttcacaag agcccagcag ccaggctggc tttttcattg    5820
tagggcgtgg ttgtcccagc tggtgtagat ttcaggccgc ccccccaac tccctgccca     5880 cagtgttgca gattgcctgg ctgcagcaa gtccagacca cccaaatttg gttggattct     5940
tcatttctcc actgtagttg gggtccattg attgtgcagg gaacgtgca ggaggttttt     6000 ctaggcaccg tgttcagtgc tgcttcactc taccagagat tatggccaaa ttgcacggaa    6060
tttggtttct tgccctctga agcctgaggg ccccccttg cctggctggt tgacagaccc     6120 gggtggtca ctgctgagac ttcagagatc gcagctgctg tgagaatacg gtgaaggtac     6180
tttgttctgg aagatgttgt catacacttt tccccagtta ttttcaaact tgacatgagc    6240
ctatgttgac tcactgggtg ggggtcccctt cttacgcagc acacgtggca agtgcctgaa    6300
tcggggctgg aggcacttca gagcctctga ggggccacca cttctggccc aaaattgcag    6360
ggttgtagat gaggctgcct gtggagaact ggtgtgagga ggaagctgtt tccaacaaag    6420
agcactttca tctgttgaga tggctgtggt gagcaactga acgagcctac gtgtgtacct    6480 gaatttttccc cgtaactcat tcttccata tgaagaaaca ccaaactatg tacagagaac    6540 ttttttacaaa aggcagacct tttttaagct gtgtaaccca catagcctaa ccacctggca    6600
gaatgactac gaataggggt cattgtgctg gtaaaagcct ctattacgac tgtaagtaag    6660
ttggatgttg gcaaaattaa attgttacag tatttagagc tgctgtagct gttccttcac    6720
aacataaaat aggataaatg actagtacgt ctttcaggtg ggtggcaagc agaacatgcg    6780
taatattctc tacctggtct gtagctgtaa ctgtgatgta cagacaaagc aaaaattaaa    6840
agaacttatg aaaacaaatg caatgatact aggatataca cttttgtatt tttattctta    6900
tataaggtta tttgctggct attgttggcc tctagttcag tctgtgttat ttaaattcta    6960
atatatgaat tatttgaatt gaattcatgt tcggggccac gttgttgtat gtattgatgt    7020
acagccttga atgtgaataa ttattgtaaa ctatatttta caactttttt tctggcttta    7080
ttatataaat tttctattgg gtcagtgatt taatcatata atttaatgaa tctgtttatc    7140
cttttttttt ttccaaatac ttgtgcttta ggtgtagtta ccagatgatg aattttcctc    7200
gtatggtcag tagtcttgta ataaaaagca tgtagagtgt aga                      7243
```

<210> SEQ ID NO 33
<211> LENGTH: 6862
<212> TYPE: DNA
<213> ORGANISM: Homo sapiens

<400> SEQUENCE: 33

```
gcggcgccgg gggcgggggg cggcgggcga cggggcgggc gcaggatgag ggcggccatt      60 gctgggctc cgcttcgggg aggaggacgc tgaggaggcg ccgagccgcg cagcgctgcg     120
ggggaggcgc ccgcgccgac gcggggccca tggccaggac caccagccag ctgtatgacg    180
ccgtgcccat ccagtccagc gtggtgttat gttcctgccc atccccatca atggtgagga    240
cccagactga gtccagcacg cccctggca ttcctggtgg cagcaggcag ggccccgcca     300
```

```
tggacggcac tgcagccgag cctcggcccg gcgccggctc cctgcagcat gcccagcctc    360
cgccgcagcc tcggaagaag cggcctgagg acttcaagtt tgggaaaatc cttggggaag    420 gctcttttc cacggttgtc ctggctcgag aactggcaac ctccagagaa tatgcgacca     480
gggccaactc attcgtggga acagcgcagt acgtttctcc agagctgctc acggagaagt    540
ccgcctgtaa gagttcagac cttttgggctc ttggatgcat aatataccag cttgtggcag   600
gactcccacc attccgagct ggaaacgagt atcttatatt tcagaagatc attaagttgg    660
aatatgactt tccagaaaaa ttcttcccta aggcaagaga cctcgtggag aaacttttgg    720
ttttagatgc cacaaagcgg ttaggctgtg aggaaatgga aggatacgga cctcttaaag    780
cacacccgtt cttcgagtcc gtcacgtggg agaacctgca ccagcagacg cctccgaagc    840
tcaccgctta cctgccggct atgtcggaag acgacgagga ctgctatggc aattatgaca    900
atctcctgag ccagtttggc tgcatgcagg tgtcttcgtc ctcctcctca cactccctgt    960
cagcctccga cacgggcctg ccccagaggt caggcagcaa catagagcag tacattcacg   1020
atctggactc gaactccttt gaactggact acagttttc cgaagatgag aagaggttgt    1080
tgttggagaa gcaggctggc ggaaaccctt ggcaccagtt tgtagaaaat aatttaatac   1140
taaagatggg cccagtggat aagcggaagg gtttatttgc aagacgacga cagctgttgc   1200
tcacagaagg accacattta tattatgtgg atcctgtcaa caaagttctg aaaggtgaaa   1260
ttccttggtc acaagaactt cgaccagagg ccaagaattt taaaactttc tttgtccaca   1320
cgcctaacag gacgtattat ctgatggacc ccagcgggaa cgcacacaag tggtgcagga   1380
agatccagga ggtttggagg cagcgatacc agagccaccc ggacgccgct gtgcagtgac   1440
gtggcctgcg gccgggctgc ccttcgctgc caggacacct gccccagcgc ggcttggccg   1500
ccatccggga cgcttccaga ccacctgcca gccatcacaa ggggaacgca gaggcggaaa   1560
ccttgcagca tttttattta aagaaaaga agaaaaaaaa cacccaacca cacaaagaac   1620
aaaaccagta acaaacacaa aggaattcag ggtcgctttg cttgctctct gtgctccgtg   1680
gaggcctccg tgtgccctcg ttgccgtggg acccagctc catgcacgtc aacccagtcc    1740
cgcccagact agtggacaga cctggtgtca ccagttttc ctagcatcag tccgaaccat    1800
gcgcccgccc tgcccaact gtgtgctggt cctgctgtgg ccgagggac cgggtgtgtt     1860 tggctctta tgcccctccc gctgtggtcc tggaactctt caccagggag ggagccctgc    1920
gggggccgca gctttgtgga gggagccgcc gtgcttctgt cacctgctcc ctttcttgcg   1980
tctccctgtg atgggccctt aggcctggct gggcccatta catatccctg tggtggctct   2040
ggtggcagct ttctgtggcc cctgctgtgt tggcaggcag gtttgcgtgg tgaggagcgg   2100 gagggggttgg agtggtgcgg gagcaggctg ccgagtggag ggtgccatcg agggctccgg   2160
atcccttatc ctacttagca gtgttggtct ctggggctgg aagccgagcg catgctggga   2220
gcggtactgt cagaagtgag cccagttagt accccgctgg ctcactgcac gagagagtcc   2280
tgccccgagc cctaggtggg gccaggaggt gccttggaga agccagccag agcagagagg   2340
gctgctgact ccgtgtgga gcagagaggc ctgagggcct cctaaaaggt ttaaatgtcc    2400
acgcctctcc agttgctgaa gtagggtctg agagaaccct ggcatcagca gacccagggt   2460
gcttctgtct cctgcagacc acgccaggga gtgcagacac caccgtcaca cacgcccctt   2520
ttgtgttttg gttcaagttt ctcagagccc ctcagagctt ctacatctgt gcatcagaaa   2580
tctcacagcc ttctcatgct gccggctcat ctgggcccat agagtgggct ttgccagttg   2640
ctgttgcaca ggaggcgaga acagcacact tcaaccccag cttgctggtc ggctttcctc   2700
```

```
tagagagagc cggttttggg gccatttccc tttgatgctt tggtggcctt gccccgctct   2760
gcagcacaga caggccagat gcatttgtcc tttgcctagc tactcccag gtagagagtg    2820 ctcctggtgg cctggcaggt ctgggccctt ctctccctgc ccaggttgtc cctggagggc   2880
agccctcact ccctttgggg gagaggcaga cattgctgcc cacagacctg cctctgactc   2940
aactgtgtcc accctccctg gtccctaccc ccaagtcaca ggtgactcag cagtgaccct   3000
gtgtgccagg ccagatccaa actgagaggg aaggtgtcgt ttttacactg ctaatgacga   3060
gagtggctct ttttagctag gcgagtacag acggggcctg ggaggggca gagatgttcc    3120 ccaggccctg cctgtggttc ctgcctgggc cttggctgct gctgtgtgag agctgcatgt   3180
gagcctgtga ccgtgagctg gggtgagctg ggccgcacct accctggggc cccagggagc   3240
aggacgctcc ggggcccagc acgttgccct gggcctgtgg ccggagtcgg agtcctctct   3300
cctcctcctg gcttttggaa aggcttggct gtgttgggga gtctctctta gccctttcag   3360
gaatttctgt tcaggcttcc tcctcctcat cagctatttt acccatctca gaacgtcctg   3420
tgtctccatg taggagagtg gctctctcag atctctcagg gcgtctggtt atagggaaac   3480
aagtggagca gggacgtggc tttaattgga gcactcggct gggctgcttg ggagactct    3540 tccgtgcgtt cttcctctgg atagaaccac cacctcctgg gcgtcactga caagctccat   3600
cttaacctcc aaagccacag aactaggggc tcagagccag agctggcagc cgccagccaa   3660
aatgatgcca ttgcctgagc tgacagccaa gcccttctgt gggtcacctt tctcctcacc   3720
cagccccttg ctcttccctt ttgaaaggcc cgtgtgtttt ctttccttac cctgtgcttg   3780
ctcatgtcta ctccggtttt ctctaccaca tccttagagc catcacctgg cacgcaggcg   3840
ccttacattc tacggtagaa cgtggggtac tgtgtgtgca catagacaca cttacgtgga   3900
attacagttg tgggtttatc caagatgagg aagatttcac ctgctgttta atagacttgg   3960
ggccatgtgc ctccccacac atgggcaagg acaggtggaa tgtcgggacc acactgtgcg   4020
gcttctcggc acaaagcgga gggaggctgt ggtcgctgcc ggcctaggtg tcccaggtgc   4080
cccgcctttc tctgggacac agttgggggc tggcttctga gggattcctt tctccctct    4140 ttgtgtggcc ccagccaggg cggtgggcag tcctggtgta gagcacaagc ctctccaccc   4200
tagagaaatg cctctgtacc acggctacca tgtggaacct taacttgcag aaggcttgtt   4260
aacaattgtt ttgagagaga tggctggtca tgccacagct gctggggact ccgcctactc   4320
cagccctctt gggacacact gtgggatttg tggcccttcc ccagaggaat tgtggagact   4380
gtcccatgga acaaaccctc aggcaccagc acagggctct gggtgactca gtaaaactaa   4440
cgtttgtctc tgacaagatc agctgtaggc tcaccggcca gagaagacca ctgtgagcat   4500
tttgccgtat atcctgccct gccatttgtt cactttttaa actaaaatag gaacatccga   4560
cacacaccgt ttgcatcgtc ttctcccttg atattttaag cattttccca tgtcatgagt   4620
ttctcagaaa catgttttta acaattgtac tatttagtca ttgtccattt actataattt   4680
atctgaccat ttccctactg taaaatactt aagacggttt ctgattttc cactatttaa    4740 ataatgctgt gatgaatatc tttaaaatct tctgatttct tacttttttc ccccttagat   4800
gcctggaagt ggtattttga ggtgaaagag tttgttcatt ttgaagatat ttctgtctct   4860
ctctcgacct gatgtgtaga cgctcacttc cagtagcaga accaccttag ttgtgtctta   4920
cagattctga acaaatcggt ttctgataag ccatgtgttc caaagaatgt ctgaataaga   4980
ccgctcttta tttaaatgct aagaggatgt cactactgca atccatctgt ggccgatttt   5040
```

```
ttccaagagc caatttcctt gttttggttg caagaacctg gctctgcctg catgtcagct    5100
ctctgccctc cctgctgccg tggctttcaa gcgcttggca gaatcttgta cttcgtgtcc    5160
acaatggtac tgaatttgca tctgcacagt cagcagagat aacaagtgtt gaactgacct    5220
tgccacatgc ttagtgagtg atttgtaatt aagtttatag actcagaagg tatattagga    5280
catttggaat cagtagcaga gcaaagcctc tttgaaaaaa accacgtagc tgattgggtt    5340
ttacaagagt gcatttgtct ccccctteca cccgtgggge cccaccttea ggtcttagtg    5400
gttcacaaga gcccagcagc caggctggct ttttcattgt agggcgtggt tgtcccagct    5460
ggtgtagatt tcaggccgcc ccccccaact ccctgcccac agtgttgcag attgcctggc    5520
tggcagcaag tccagaccac ccaaatttgg ttggattctt catttctcca ctgtagttgg    5580
ggtccattga ttgtgcaggg gaacgtgcag gaggttttc taggcaccgt gttcagtgct    5640
gcttcactct accagagatt atggccaaat tgcacggaat ttggtttctt gccctctgaa    5700
gcctgagggc cccccttgc ctggctggtt gacagacccg gggtggtcac tgctgagact    5760
tcagagatcg cagctgctgt gagaatacgg tgaaggtact ttgttctgga agatgttgtc    5820
atacactttt ccccagttat tttcaaactt gacatgagcc tatgttgact cactgggtgg    5880
gggtcccttc ttacgcagca cacgtggcaa gtgcctgaat cggggctgga ggcacttcag    5940
agcctctgag gggccaccac ttctggccca aaattgcagg gttgtagatg aggctgcctg    6000
tggagaactg gtgtgaggag gaagctgttt ccaacaaaga gcactttcat ctgttgagat    6060
ggctgtggtg agcaactgaa cgagcctacg tgtgtacctg aattttcccc gtaactcatt    6120
tcttccatat gaagaaacac caaactatgt acagagaact ttttacaaaa ggcagacctt    6180
ttttaagctg tgtaacccac atagcctaac cacctggcag aatgactacg aataggggtc    6240
attgtgctgg taaaagcctc tattacgact gtaagtaagt tggatgttgg caaaattaaa    6300
ttgttacagt atttagagct gctgtagctg ttccttcaca acataaaata ggataaatga    6360
ctagtacgtc tttcaggtgg gtggcaagca gaacatgcgt aatattctct acctggtctg    6420
tagctgtaac tgtgatgtac agacaaagca aaaattaaaa gaacttatga aaacaaatgc    6480
aatgatacta ggatatacac ttttgtattt ttattcttat ataaggttat ttgctggcta    6540
ttgttggcct ctagttcagt ctgtgttatt taaattctaa tatatgaatt atttgaattg    6600
aattcatgtt cggggccacg ttgttgtatg tattgatgta cagccttgaa tgtgaataat    6660
tattgtaaac tatatttac aacttttttt ctggctttat tatataaatt ttctattggg    6720
tcagtgattt aatcatataa tttaatgaat ctgtttatcc ttttttttt tccaaatact    6780
tgtgctttag gtgtagttac cagatgatga attttcctcg tatggtcagt agtcttgtaa    6840
taaaaagcat gtagagtgta ga                                            6862
```

<210> SEQ ID NO 34
<211> LENGTH: 3208
<212> TYPE: DNA
<213> ORGANISM: Homo sapiens

<400> SEQUENCE: 34

```
agatattcat gaaccgttgc ttcttccagc ctcgccttct cgctccctct gcctttctgg     60
cgctgttctc cctccctccc tctggcttct gctctttctt actccttctc tcagctgctt    120
aactacagct cccactggaa cttgcacaat caaaaacaac tctcctctct caagccgcct    180
ccaggagcgc atcacctgga gaagagcgac tcgctccccg cgccggccgc ggaagagcag    240
ccaggtagct gggggcgggg aggcgtaccc ttctcccgct cggtaagagc cacagcatct    300
```

```
ccccggagat tggccgtatc ccaccgtccg gcccccaggg tcctgcagcg gtgatgcata    360
tgtttcggag caatgatgga aggagaaaag ccgctgtcgg tggcaactga aagtggggag    420
aggttgctgc agtagctggt gctgcagaat gcgcgagtga agaactgagc cccgctagat    480
tctccatccc gctcagtctt cattaactgt ctgcaggagg taaaccgggg aaacagatat    540
gcactaacca ggcgggtgcc aacctggatc tataactgtg aattccccac ggtggaaaat    600
ggtaaacaaa gacatgaatg gattcccagt caagaaatgc tcagccttcc aattttttaa    660
gaagcgggta cgaaggtgga tcaagagccc aatggtcagt gtggacaagc atcagagtcc    720
cagcctgaag tacaccggct cctccatggt gcacatccct caggggagc cagacttcga     780 gtcttccttg tgtcaaacat gcctgggtga acatgctttc caaagagggg ttctccctca    840
ggagaacgag tcatgttcat gggaaactca atctgggtgt gaagtgagag agccatgtaa    900
tcatgccaac atcctgacca agcccgatcc aagaaccttc tggactaatg atgatccagc    960
tttcatgaag cagaggagga tgggtctgaa cgactttatt cagaagattg ccataactc    1020 ctatgcatgc aaacaccctg aagttcagtc catcttgaag atctcccaac ctcaggagcc   1080 tgagcttat aatgccaacc cttctcctcc accaagtcct tctcagcaaa tcaaccttgg    1140
cccgtcgtcc aatcctcatg ctaaaccatc tgactttcac ttcttgaaag tgatcggaaa   1200
gggcagtttt ggaaaggttc ttctagcaag acacaaggca gaagaagtgt tctatgcagt   1260
caaagtttta cagaagaaag caatcctgaa aaagaaagag gagaagcata ttatgtcgga   1320
gcggaatgtt ctgttgaaga atgtgaagca cccttttcctg gtgggccttc acttctcttt   1380
ccagactgct gacaaattgt actttgtcct agactacatt aatggtggag agttgttcta   1440
ccatctccag agggaacgct gcttcctgga accacgggct cgtttctatg ctgctgaaat   1500
agccagtgcc ttgggctacc tgcattcact gaacatcgtt tatagagact aaaaccaga    1560 gaatattttg ctagattcac agggacacat tgtccttact gacttcggac tctgcaagga   1620
gaacattgaa cacaacagca caacatccac cttctgtggc acgccggagt atctcgcacc   1680
tgaggtgctt cataagcagc cttatgacag gactgtggac tggtggtgcc tgggagctgt   1740
cttgtatgag atgctgtatg gcctgccgcc tttttatagc cgaaacacag ctgaaatgta   1800
cgacaacatt ctgaacaagc ctctccagct gaaaccaaat attacaaatt ccgcaagaca   1860
cctcctggag ggcctcctgc agaaggacag gacaaagcgg ctcggggcca aggatgactt   1920
catggagatt aagagtcatg tcttcttctc cttaattaac tgggatgatc tcattaataa   1980
gaagattact ccccctttta acccaaatgt gagtgggccc aacgacctac ggcactttga   2040
ccccgagttt accgaagagc ctgtccccaa ctccattggc aagtcccctg acagcgtcct   2100
cgtcacagcc agcgtcaagg aagctgccga ggctttccta ggcttttcct atgcgcctcc   2160
cacggactct ttcctctgaa ccctgttagg gcttggtttt aaaggatttt atgtgtgttt   2220
ccgaatgttt tagttagcct tttggtggag ccgccagctg acaggacatc ttacaagaga   2280
atttgcacat ctctggaagc ttagcaatct tattgcacac tgttcgctgg aagcttttg    2340 aagagcacat tctcctcagt gagctcatga ggttttcatt tttattcttc cttccaacgt   2400
ggtgctatct ctgaaacgag cgttagagtg ccgccttaga cggaggcagg agtttcgtta   2460
gaaagcggac gctgttctaa aaaaggtctc ctgcagatct gtctgggctg tgatgacgaa   2520
tattatgaaa tgtgcctttt ctgaagagat tgtgttagct ccaaagcttt tcctatcgca   2580
gtgtttcagt tctttatttt cccttgtgga tatgctgtgt gaaccgtcgt gtgagtgtgg   2640
```

| | |
|---|---:|
| tatgcctgat cacagatgga ttttgttata agcatcaatg tgacacttgc aggacactac | 2700 |
| aacgtgggac attgtttgtt tcttccatat ttggaagata aatttatgtg tagacttttt | 2760 |
| tgtaagatac ggttaataac taaaatttat tgaaatggtc ttgcaatgac tcgtattcag | 2820 |
| atgcttaaag aaagcattgc tgctacaaat atttctattt ttagaaaggg ttttatgga | 2880 |
| ccaatgcccc agttgtcagt cagagccgtt ggtgttttc attgtttaaa atgtcacctg | 2940 |
| taaaatgggc attatttatg ttttttttt tgcattcctg ataattgtat gtattgtata | 3000 |
| aagaacgtct gtacattggg ttataacact agtatattta aacttacagg cttatttgta | 3060 |
| atgtaaacca ccattttaat gtactgtaat taacatggtt ataatacgta caatccttcc | 3120 |
| ctcatcccat cacacaactt tttttgtgtg tgataaactg attttggttt gcaataaaac | 3180 |
| cttgaaaaat atttacatat aaaaaaaa | 3208 |

<210> SEQ ID NO 35
<211> LENGTH: 2459
<212> TYPE: DNA
<213> ORGANISM: Homo sapiens

<400> SEQUENCE: 35

| | |
|---|---:|
| aagtggggtt cataacagaa cagggatagc cgtctctggc tcgtgctctc atgtcatctc | 60 |
| agagttccag cttatcagag gcatgtagca gggaggctta ttccagccat aactgggctc | 120 |
| tacctccagc ctccagaagt aatccccaac ctgcatatcc ttgggcaacc cgaagaatga | 180 |
| aagaagaagc tataaaaccc cctttgaaag cttcatgaa gcagaggagg atgggtctga | 240 |
| acgactttat tcagaagatt gccataact cctatgcatg caaacaccct gaagttcagt | 300 |
| ccatcttgaa gatctcccaa cctcaggagc ctgagcttat gaatgccaac ccttctcctc | 360 |
| caccaagtcc ttctcagcaa atcaaccttg gcccgtcgtc caatcctcat gctaaaccat | 420 |
| ctgactttca cttcttgaaa gtgatcggaa agggcagttt tggaaaggtt cttctagcaa | 480 |
| gacacaaggc agaagaagtg ttctatgcag tcaaagtttt acagaagaaa gcaatcctga | 540 |
| aaagaaaga ggagaagcat attatgtcgg agcggaatgt tctgttgaag aatgtgaagc | 600 |
| accctttcct ggtgggcctt cacttctctt tccagactgc tgacaaattg tactttgtcc | 660 |
| tagactacat taatggtgga gagttgttct accatctcca gagggaacgc tgcttcctgg | 720 |
| aaccacgggc tcgtttctat gctgctgaaa tagccagtgc cttgggctac ctgcattcac | 780 |
| tgaacatcgt ttatagagac ttaaaaccag agaatatttt gctagattca cagggacaca | 840 |
| ttgtccttac tgacttcgga ctctgcaagg agaacattga acacaacagc acaacatcca | 900 |
| ccttctgtgg cacgccggag tatctcgcac ctgaggtgct tcataagcag ccttatgaca | 960 |
| ggactgtgga ctggtggtgc ctgggagctg tcttgtatga gatgctgtat ggcctgccgc | 1020 |
| ctttttatag ccgaaacaca gctgaaatgt acgacaacat tctgaacaag cctctccagc | 1080 |
| tgaaaccaaa tattcaaat tccgcaagac acctcctgga gggcctcctg cagaaggaca | 1140 |
| ggacaaagcg gctcgggcc aaggatgact tcatggagat taagagtcat gtcttcttct | 1200 |
| ccttaattaa ctgggatgat ctcattaata agaagattac tccccttttt aacccaaatg | 1260 |
| tgagtgggcc caacgaccta cggcactttg accccgagtt taccgaagag cctgtcccca | 1320 |
| actccattgg caagtcccct gacagcgtcc tcgtcacagc cagcgtcaag gaagctgccg | 1380 |
| aggctttcct aggcttttcc tatgcgcctc ccacggactc tttcctctga accctgttag | 1440 |
| ggcttggttt taaaggattt tatgtgtgtt tccgaatgtt ttagttagcc ttttggtgga | 1500 |
| gccgccagct gacaggacat cttacaagag aatttgcaca tctctggaag cttagcaatc | 1560 |

-continued

```
ttattgcaca ctgttcgctg gaagcttttt gaagagcaca ttctcctcag tgagctcatg      1620
aggttttcat tttattcttc ccttccaacg tggtgctatc tctgaaacga gcgttagagt      1680
gccgccttag acggaggcag gagtttcgtt agaaagcgga cgctgttcta aaaaaggtct      1740
cctgcagatc tgtctgggct gtgatgacga atattatgaa atgtgccttt tctgaagaga      1800
ttgtgttagc tccaaagctt ttcctatcgc agtgtttcag ttctttattt tcccttgtgg      1860
atatgctgtg tgaaccgtcg tgtgagtgtg gtatgcctga tcacagatgg attttgttat      1920
aagcatcaat gtgacacttg caggacacta caacgtggga cattgtttgt ttcttccata      1980
tttggaagat aaatttatgt gtagactttt ttgtaagata cggttaataa ctaaaattta      2040
ttgaaatggt cttgcaatga ctcgtattca gatgcttaaa gaaagcattg ctgctacaaa      2100
tatttctatt tttagaaagg gtttttatgg accaatgccc cagttgtcag tcagagccgt      2160
tggtgttttt cattgtttaa aatgtcacct gtaaatgggg cattatttat gttttttttt      2220
ttgcattcct gataattgta tgtattgtat aaagaacgtc tgtacattgg gttataacac      2280
tagtatattt aaacttacag gcttatttgt aatgtaaacc accattttaa tgtactgtaa      2340
ttaacatggt tataatacgt acaatccttc cctcatccca tcacacaact tttttgtgt       2400 gtgataaact gattttggtt tgcaataaaa ccttgaaaaa tatttacata taaaaaaaa      2459
```

<210> SEQ ID NO 36
<211> LENGTH: 2638
<212> TYPE: DNA
<213> ORGANISM: Homo sapiens

<400> SEQUENCE: 36

```
acattcctga cctctccctc ccccttttcc ctctttcttt ccttccttcc tcctcttcca        60
agttctggga tttttcagcc ttgcttggtt ttggccaaaa gcacaaaaaa ggcgttttcg       120
gaagcgaccc gaccgtgcac aagggccatt tgtttgtttt gggactcggg gcaggaaatc       180
ttgcccggcc tgagtcacgg cggctccttc aaggaaacgt cagtgctcgc cggtcgctct       240
cgtctgccgc gcgccccgcc gcccgctgcc catgggggag atgcagggcg cgctggccag       300
agcccggctc gagtccctgc tgcggccccg ccacaaaaag agggccgagg cgcagaaaag       360
gagcgagtcc ttcctgctga gcggactggc tttcatgaag cagaggagga tgggtctgaa       420
cgactttatt cagaagattg ccaataactc ctatgcatgc aaacaccctg aagttcagtc       480
catcttgaag atctcccaac ctcaggagcc tgagcttatg aatgccaacc cttctcctcc       540
accaagtcct tctcagcaaa tcaaccttgg cccgtcgtcc aatcctcatg ctaaaccatc       600
tgactttcac ttcttgaaag tgatcggaaa gggcagtttt ggaaaggttc ttctagcaag       660
acacaaggca gaagaagtgt tctatgcagt caaagtttta cagaagaaag caatcctgaa       720
aaagaaagag gagaagcata ttatgtcgga gcggaatgtt ctgttgaaga atgtgaagca       780
ccctttcctg gtgggccttc acttctcttt ccagactgct gacaaattgt actttgtcct       840
agactacatt aatggtggag agttgttcta ccatctccag agggaacgct gcttcctgga       900
accacgggct cgtttctatg ctgctgaaat agccagtgcc ttgggctacc tgcattcact       960
gaacatcgtt tatagagact aaaaccagag aatattttg ctagattcac agggacacat      1020
tgtccttact gacttcggac tctgcaagga gaacattgaa cacaacagca caacatccac      1080
cttctgtggc acgccggagt atctcgcacc tgaggtgctt cataagcagc ttatgacag       1140 gactgtggac tggtggtgcc tgggagctgt cttgtatgag atgctgtatg gcctgccgcc      1200
```

| | |
|---|---|
| tttttatagc cgaaacacag ctgaaatgta cgacaacatt ctgaacaagc ctctccagct | 1260 |
| gaaaccaaat attacaaatt ccgcaagaca cctcctggag ggcctcctgc agaaggacag | 1320 |
| gacaaagcgg ctcggggcca aggatgactt catggagatt aagagtcatg tcttcttctc | 1380 |
| cttaattaac tgggatgatc tcattaataa gaagattact cccccttta acccaaatgt | 1440 |
| gagtgggccc aacgacctac ggcactttga ccccgagttt accgaagagc ctgtccccaa | 1500 |
| ctccattggc aagtcccctg acagcgtcct cgtcacagcc agcgtcaagg aagctgccga | 1560 |
| ggctttccta ggcttttcct atgcgcctcc cacggactct ttcctctgaa ccctgttagg | 1620 |
| gcttggtttt aaaggatttt atgtgtgttt ccgaatgttt tagttagcct tttggtggag | 1680 |
| ccgccagctg acaggacatc ttacaagaga atttgcacat ctctggaagc ttagcaatct | 1740 |
| tattgcacac tgttcgctgg aagcttttg aagagcacat tctcctcagt gagctcatga | 1800 |
| ggttttcatt tttattcttc cttccaacgt ggtgctatct ctgaaacgag cgttagagtg | 1860 |
| ccgccttaga cggaggcagg agtttcgtta gaaagcggac gctgttctaa aaaaggtctc | 1920 |
| ctgcagatct gtctgggctg tgatgacgaa tattatgaaa tgtgccttt ctgaagagat | 1980 |
| tgtgttagct ccaaagcttt tcctatcgca gtgtttcagt tctttatttt cccttgtgga | 2040 |
| tatgctgtgt gaaccgtcgt gtgagtgtgg tatgcctgat cacagatgga ttttgttata | 2100 |
| agcatcaatg tgacacttgc aggacactac aacgtgggac attgtttgtt tcttccatat | 2160 |
| ttggaagata aatttatgtg tagactttt tgtaagatac ggttaataac taaaattat | 2220 |
| tgaaatggtc ttgcaatgac tcgtattcag atgcttaaag aaagcattgc tgctacaaat | 2280 |
| atttctattt ttagaaaggg ttttatgga ccaatgcccc agttgtcagt cagagccgtt | 2340 |
| ggtgttttc attgtttaaa atgtcacctg taaaatgggc attatttatg tttttttt | 2400 |
| tgcattcctg ataattgtat gtattgtata agaacgtct gtacattggg ttataacact | 2460 |
| agtatattta aacttacagg cttatttgta atgtaaacca ccattttaat gtactgtaat | 2520 |
| taacatggtt ataatacgta caatccttcc ctcatcccat cacacaactt tttttgtgtg | 2580 |
| tgataaactg attttggttt gcaataaaac cttgaaaaat atttacatat aaaaaaaa | 2638 |

```
<210> SEQ ID NO 37
<211> LENGTH: 2282
<212> TYPE: DNA
<213> ORGANISM: Homo sapiens

<400> SEQUENCE: 37
```

| | |
|---|---|
| tttttttataa ggccgagcgc gcggcctggc gcagcatacg ccgagccggt ctttgagcgc | 60 |
| taacgtctttt ctgtctcccc gcggtggtga tgacggtgaa aactgaggct gctaagggca | 120 |
| ccctcactta ctccaggatg aggggcatgg tggcaattct catcgctttc atgaagcaga | 180 |
| ggaggatggg tctgaacgac tttattcaga agattgccaa taactcctat gcatgcaaac | 240 |
| accctgaagt tcagtccatc ttgaagatct cccaacctca ggagcctgag cttatgaatg | 300 |
| ccaacccttc tcctccacca agtccttctc agcaaatcaa ccttggcccg tcgtccaatc | 360 |
| ctcatgctaa accatctgac tttcacttct tgaaagtgat cggaaagggc agttttggaa | 420 |
| aggttcttct agcaagacac aaggcagaag aagtgttcta tgcagtcaaa gttttacaga | 480 |
| agaaagcaat cctgaaaaag aaagagttgt tctaccatct ccagagggaa cgctgcttcc | 540 |
| tggaaccacg ggctcgtttc tatgctgctg aaatagccag tgccttgggc tacctgcatt | 600 |
| cactgaacat cgtttataga gacttaaaac cagagaatat tttgctagat tcacagggac | 660 |
| acattgtcct tactgacttc ggactctgca aggagaacat tgaacacaac agcacaacat | 720 |

```
ccaccttctg tggcacgccg gagtatctcg cacctgaggt gcttcataag cagccttatg      780
acaggactgt ggactggtgg tgcctgggag ctgtcttgta tgagatgctg tatggcctgc      840
cgccttttta tagccgaaac acagctgaaa tgtacgacaa cattctgaac aagcctctcc      900
agctgaaacc aaatattaca aattccgcaa gacacctcct ggagggcctc ctgcagaagg      960
acaggacaaa gcggctcggg gccaaggatg acttcatgga gattaagagt catgtcttct     1020
tctccttaat taactgggat gatctcatta ataagaagat tactccccct tttaacccaa     1080
atgtgagtgg gcccaacgac ctacggcact tgaccccga gtttaccgaa gagcctgtcc      1140
ccaactccat tggcaagtcc cctgacagcg tcctcgtcac agccagcgtc aaggaagctg     1200
ccgaggcttt cctaggcttt tcctatgcgc ctcccacgga ctctttcctc tgaaccctgt     1260
tagggcttgg ttttaaagga ttttatgtgt gtttccgaat gttttagtta gccttttggt     1320
ggagccgcca gctgacagga catcttacaa gagaatttgc acatctctgg aagcttagca     1380
atcttattgc acactgttcg ctggaagctt tttgaagagc acattctcct cagtgagctc     1440
atgaggtttt cattttttatt cttccttcca acgtggtgct atctctgaaa cgagcgttag     1500
agtgccgcct tagacggagg caggagtttc gttagaaagc ggacgctgtt ctaaaaaagg     1560
tctcctgcag atctgtctgg gctgtgatga cgaatattat gaaatgtgcc ttttctgaag     1620
agattgtgtt agctccaaag cttttcctat cgcagtgttt cagttcttta ttttcccttg     1680
tggatatgct gtgtgaaccg tcgtgtgagt gtggtatgcc tgatcacaga tggattttgt     1740
tataagcatc aatgtgacac ttgcaggaca ctacaacgtg ggacattgtt tgtttcttcc     1800
atatttggaa gataaattta tgtgtagact tttttgtaag atacggttaa taactaaaat     1860
ttattgaaat ggtcttgcaa tgactcgtat tcagatgctt aaagaaagca ttgctgctac     1920
aaatatttct attttttagaa agggttttta tggaccaatg ccccagttgt cagtcagagc     1980
cgttggtgtt tttcattgtt taaaatgtca cctgtaaaat gggcattatt tatgtttttt     2040
tttttgcatt cctgataatt gtatgtattg tataaagaac gtctgtacat tgggttataa     2100
cactagtata tttaaactta caggcttatt tgtaatgtaa accaccattt taatgtactg     2160
taattaacat ggttataata cgtacaatcc ttccctcatc ccatcacaca acttttttttg    2220 tgtgtgataa actgattttg gtttgcaata aaaccttgaa aaatatttac atataaaaaa     2280
aa                                                                    2282
```

<210> SEQ ID NO 38
<211> LENGTH: 2414
<212> TYPE: DNA
<213> ORGANISM: Homo sapiens

<400> SEQUENCE: 38

```
tttttttataa ggccgagcgc gcggcctggc gcagcatacg ccgagccggt ctttgagcgc      60
taacgtcttt ctgtctcccc gcggtggtga tgacggtgaa aactgaggct gctaagggca      120
ccctcactta ctccaggatg aggggcatgg tggcaattct catcgctttc atgaagcaga      180
ggaggatggg tctgaacgac tttattcaga agattgccaa taactccat gcatgcaaac      240 accctgaagt tcagtccatc ttgaagatct cccaacctca ggagcctgag cttatgaatg      300
ccaacccttc tcctccacca agtccttctc agcaaatcaa ccttggcccg tcgtccaatc      360
ctcatgctaa accatctgac tttcacttct tgaaagtgat cggaaagggc agttttggaa      420
aggttcttct agcaagacac aaggcagaag aagtgttcta tgcagtcaaa gttttacaga     480
```

| | | |
|---|---|---|
| agaaagcaat cctgaaaaag aaagaggaga agcatattat gtcggagcgg aatgttctgt | 540 |
| tgaagaatgt gaagcaccct ttcctggtgg gccttcactt ctctttccag actgctgaca | 600 |
| aattgtactt tgtcctagac tacattaatg gtggagagtt gttctaccat ctccagaggg | 660 |
| aacgctgctt cctggaacca cgggctcgtt tctatgctgc tgaaatagcc agtgccttgg | 720 |
| gctacctgca ttcactgaac atcgtttata gagacttaaa accagagaat attttgctag | 780 |
| attcacaggg acacattgtc cttactgact tcggactctg caaggagaac attgaacaca | 840 |
| acagcacaac atccaccttc tgtggcacgc cggagtatct cgcacctgag gtgcttcata | 900 |
| agcagcctta tgacaggact gtggactggt ggtgcctggg agctgtcttg tatgagatgc | 960 |
| tgtatggcct gccgcctttt tatagccgaa acacagctga aatgtacgac aacattctga | 1020 |
| acaagcctct ccagctgaaa ccaaatatta caaattccgc aagacacctc ctggagggcc | 1080 |
| tcctgcagaa ggacaggaca aagcggctcg gggccaagga tgacttcatg gagattaaga | 1140 |
| gtcatgtctt cttctcctta ttaactggg atgatctcat taataagaag attactcccc | 1200 |
| ctttaaccc aaatgtgagt gggcccaacg acctacggca ctttgacccc gagtttaccg | 1260 |
| aagagcctgt ccccaactcc attggcaagt cccctgacag cgtcctcgtc acagccagcg | 1320 |
| tcaaggaagc tgccgaggct ttcctaggct tttcctatgc gcctcccacg gactctttcc | 1380 |
| tctgaacccct gttagggctt ggttttaaag gattttatgt gtgtttccga atgttttagt | 1440 |
| tagccttttg gtggagccgc cagctgacag gacatcttac aagagaattt gcacatctct | 1500 |
| ggaagcttag caatcttatt gcacactgtt cgctggaagc ttttgaaga gcacattctc | 1560 |
| ctcagtgagc tcatgaggtt ttcatttta ttcttccttc caacgtggtg ctatctctga | 1620 |
| aacgagcgtt agagtgccgc cttagacgga ggcaggagtt tcgttagaaa gcggacgctg | 1680 |
| ttctaaaaaa ggtctcctgc agatctgtct gggctgtgat gacgaatatt atgaaatgtg | 1740 |
| cctttctga agagattgtg ttagctccaa agcttttcct atcgcagtgt ttcagttctt | 1800 |
| tattttccct tgtggatatg ctgtgtgaac cgtcgtgtga gtgtggtatg cctgatcaca | 1860 |
| gatggatttt gttataagca tcaatgtgac acttgcagga cactacaacg tgggacattg | 1920 |
| tttgtttctt ccatatttgg aagataaatt tatgtgtaga ctttttttgta agatacggtt | 1980 |
| aataactaaa atttattgaa atggtcttgc aatgactcgt attcagatgc ttaaagaaag | 2040 |
| cattgctgct acaaatatttt ctatttttag aaagggtttt tatggaccaa tgccccagtt | 2100 |
| gtcagtcaga gccgttggtg tttttcattg tttaaaatgt cacctgtaaa atgggcatta | 2160 |
| tttatgtttt ttttttttgca ttcctgataa ttgtatgtat tgtataaaga acgtctgtac | 2220 |
| attgggttat aacactagta tatttaaact tacaggctta tttgtaatgt aaaccaccat | 2280 |
| tttaatgtac tgtaattaac atggttataa tacgtacaat ccttccctca tcccatcaca | 2340 |
| caactttttt tgtgtgtgat aaactgattt tggtttgcaa taaaaccttg aaaaatatttt | 2400 |
| acatataaaa aaaa | 2414 |

<210> SEQ ID NO 39
<211> LENGTH: 9104
<212> TYPE: DNA
<213> ORGANISM: Homo sapiens

<400> SEQUENCE: 39

| | | |
|---|---|---|
| tctccctcgg cgccgccgcc gccgcccgcg gggctgggac ccgatgcggt tagagccgcg | 60 |
| gagcctggaa gagcccccgag cgtttctgct ttgggacaac catacatcta attccttaaa | 120 |
| gtagttttat atgtaaaact tgcaaagaat cagaacaatg cctccacgac catcatcagg | 180 |

```
tgaactgtgg ggcatccact tgatgccccc aagaatccta gtagaatgtt tactaccaaa    240
tggaatgata gtgactttag aatgcctccg tgaggctaca ttaataacca taaagcatga    300
actatttaaa gaagcaagaa atacccccct ccatcaactt cttcaagatg aatcttctta    360
cattttcgta agtgttactc aagaagcaga aagggaagaa tttttttgatg aaacaagacg   420 actttgtgac cttcggcttt ttcaacccctt tttaaaagta attgaaccag taggcaaccg    480
tgaagaaaag atcctcaatc gagaaattgg ttttgctatc ggcatgccag tgtgtgaatt    540
tgatatggtt aaagatccag aagtacagga cttccgaaga atattctga cgtttgtaa     600 agaagctgtg atcttaggg acctcaattc acctcatagt agagcaatgt atgtctatcc     660
tccaaatgta gaatcttcac cagaattgcc aaagcacata taataaat tagataaagg      720 gcaaataata gtggtgatct gggtaatagt ttctccaaat aatgacaagc agaagtatac    780
tctgaaaatc aaccatgact gtgtaccaga caagtaatt gctgaagcaa tcaggaaaaa      840
aactcgaagt atgttgctat cctctgaaca actaaaactc tgtgttttag aatatcaggg    900
caagtatatt ttaaaagtgt gtggatgtga tgaatacttc ctagaaaaat atcctctgag    960
tcagtataag tatataagaa gctgtataat gcttgggagg atgcccaatt tgatgttgat   1020
ggctaaagaa agcctttatt ctcaactgcc aatggactgt tttacaatgc catcttattc   1080
cagacgcatt tccacagcta caccatatat gaatggagaa acatctacaa aatcccttg    1140 ggttataaat agtgcactca gaataaaaat tctttgtgca acctacgtga atgtaaatat   1200
tcgagacatt gataagatct atgttcgaac aggtatctac catggaggag aacccttatg   1260
tgacaatgtg aacactcaaa gagtaccttg ttccaatccc aggtggaatg aatggctgaa   1320
ttatgatata tacattcctg atcttcctcg tgctgctcga ctttgccttt ccatttgctc   1380
tgttaaaggc cgaaagggtg ctaaagagga acactgtcca ttggcatggg gaaatataaa   1440
cttgtttgat tacacagaca ctctagtatc tggaaaaatg gctttgaatc tttggccagt   1500
acctcatgga ttagaagatt tgctgaaccc tattggtgtt actggatcaa atccaaataa   1560
agaaactcca tgcttagagt tggagtttga ctggttcagc agtgtggtaa agttcccaga   1620
tatgtcagtg attgaagagc atgccaattg gtctgtatcc cgagaagcag gatttagcta   1680
ttcccacgca ggactgagta acagactagc tagagacaat gaattaaggg aaaatgacaa   1740
agaacagctc aaagcaattt ctacacgaga tcctctctct gaaatcactg agcaggagaa   1800
agattttcta tggagtcaca gacactattg tgtaactatc cccgaaattc tacccaaatt   1860
gcttctgtct gttaaatgga attctagaga tgaagtagcc cagatgtatt gcttggtaaa   1920
agattggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc acttttctt    2160 ttggcattta aaatctgaga tgcacaataa aacagttagc cagaggtttg gcctgcttt    2220 ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
acagggcttt ctgtctcctc taaacccctgc tcatcaacta ggaaacctca ggcttgaaga   2460
gtgtcgaatt atgtcctctg caaaaaggcc actgtggttg aattgggaga acccagacat   2520
```

```
catgtcagag ttactgtttc agaacaatga gatcatcttt aaaaatgggg atgatttacg    2580
gcaagatatg ctaacacttc aaattattcg tattatggaa atatctggc aaaatcaagg     2640
tcttgatctt cgaatgttac cttatggttg tctgtcaatc ggtgactgtg tgggacttat    2700
tgaggtggtg cgaaattctc acactattat gcaaattcag tgcaaaggcg gcttgaaagg    2760
tgcactgcag ttcaacagcc acacactaca tcagtggctc aaagacaaga acaaaggaga    2820
aatatatgat gcagccattg acctgtttac acgttcatgt gctggatact gtgtagctac    2880
cttcattttg ggaattggag atcgtcacaa tagtaacatc atggtgaaag acgatggaca    2940
actgtttcat atagattttg gacactttt ggatcacaag aagaaaaaat ttggttataa     3000
acgagaacgt gtgccatttg ttttgacaca ggatttctta atagtgatta gtaaaggagc    3060
ccaagaatgc acaaagacaa gagaatttga gaggtttcag gagatgtgtt acaaggctta    3120
tctagctatt cgacagcatg ccaatctctt cataaatctt ttctcaatga tgcttggctc    3180
tggaatgcca gaactacaat cttttgatga cattgcatac attcgaaaga ccctagcctt    3240
agataaaact gagcaagagg ctttggagta tttcatgaaa caaatgaatg atgcacatca    3300
tggtggctgg acaacaaaaa tggattggat cttccacaca attaaacagc atgcattgaa    3360
ctgaaaagat aactgagaaa atgaaagctc actctggatt ccacactgca ctgttaataa    3420
ctctcagcag gcaagaccg attgcatagg aattgcacaa tccatgaaca gcattagaat    3480
ttacagcaag aacagaaata aaatactata aatttaaat aatgtaaacg caaacagggt     3540
ttgatagcac ttaaactagt tcatttcaaa attaagcttt agaataatgc gcaatttcat    3600
gttatgcctt aagtccaaaa aggtaaactt tgaagattgt ttgtatcttt ttttaaaaaa    3660
caaaacaaaa caaaaatccc caaaatatat agaaatgatg gagaaggaaa aagtgatggt    3720
tttttttgtc ttgcaaatgt tctatgtttt gaaatgtgga cacaacaaag gctgttattg    3780
cattaggtgt aagtaaactg gagtttatgt taaattacat tgattggaaa agaatgaaaa    3840
tttcttattt ttccattgct gttcaattta tagtttgaag tgggttttg actgcttgtt     3900
taatgaagaa aaatgcttgg ggtggaaggg actcttgaga tttcaccaga gacttttct    3960
ttttaataaa tcaaaccttt tgatgatttg aggtttatc tgcagttttg gaagcagtca     4020
caaatgagac ctgttataag gtggtatttt ttttttttctt ctggacagta tttaaaggat   4080
cttattctta tttcccaggg aaattctggg ctcccacaaa gtaaaaaaaa aaaaaatca    4140
tagaaaaaga atgagcagga atagttctta ttccagaatt gtacagtatt caccttaagt    4200
tgattttttt tctccttctg caattgaact gaatacattt ttcatgcatg ttttccagaa    4260
aatagaagta ttaatgttat taaaaagatt attttttta ttaaaggcta tttatattat     4320
agaaactatc attaatatat attctttatt tacatgatct gtcccatagt catgcattgt    4380
tttgcacccc aaatttttta ttgttcatag cagcatggtc agctttcttc ttgatctata    4440
gatgaggctc aggcactatc ccatttatac caataaccag tgtataacta cttaaggaaa    4500
acataaaaac ttcatcttct ttccttttat ttcttatgtg aatctcccgt cttccattct    4560
ctttttataat tgagaatgtc tcaatcatat gaaattagtt accagaatta acacaattta    4620
gactatcttc ctgattcctt aaaccccttt actgaagtat actcatgaat aatactttaa    4680
aatatggggg aatagaaacc atgaactttt tacctttta aactatttat ccatatctcc     4740
aaagtagaac attaaaccat tttaagatat gtctcattcc caagtagtca gagctcactc    4800
tccaacttta ttaaatacta tttgagcaca ggacacattc ttaaacatttt tgaaaaacat   4860
taacccaaga tgtagaggct actgctagtc gtcattctag aatctgatat tttactctgt    4920
```

```
atttgaaatg aatgattaat gtcctaggaa attagcttta gcagatgtcc aggtgccaca    4980
tcaaaaaagt gcaataatta ttgacagttt tttagattag gcatattatt ggaaaacaac    5040
tttataaaga gtgaacattg tatactctag taaaacagca tcactttaaa aatattcatt    5100
tatgaaatct gttacctata gttgaagtct tgagtagtga acaagggact ctaataccaa    5160
tactcttaat atctggctat tttagatccc ttaagggca taattattgg aaatttaggt    5220
atttcactaa agcatgtata taatattgcc aacaagaaaa gtaaatttga agattaaggg    5280
aacttacttc tgcaaactgt cttgcgatag ttaagcagaa tttaaactct gttttaagca    5340
ggaaaccaga aagattattt tgcagttgta gaagatttca taacttatta aaacttatta    5400
acattttgtg ttgtttagat ataggcagtt gatacatact aacatcccag cctttttcaat   5460 atcagggtta aattatagga aaactcagta aaatggtaca aatctgaaag tttgatggta    5520
gaaactgaag atttaacaga gaactgtgtt ttacccgagt gccaaaaatg ctgtgagcct    5580
ccttgcacaa aatttatacc acttttgcat ttttatctat cagtccagat agttgtctcc    5640
cctccttctc ccaggacctc tccaccatta aaatgcacaa accacatggc cgatttcacc    5700
atttacattt attttcaaaa gttactacaa ccaaattaat tctattagaa gaaatgtaga    5760
caaattctat aaagactata gattgtgacc taagaaagaa atgaggcaaa gaaccaaaca    5820
ttgaattaaa tgctacatgg gtgactaaga tctgtttcaa gtcagtgata atatagccac    5880
ttctgggtac ttcagtatca gagatcagtt ctcgtggttt agacagttcc tatctatagc    5940
tgactatcct tgtccttgaa tatggtgtaa ctgactattg gctctacagt tttattgggc    6000
cacttaagaa atatttcctt gaataattat tttgagaaaa agtctaaaag taataaaaat    6060
aattttaaac acactgtagt aagaaatgac tgttggaaaa ttatgctttc actttctacc    6120
atattctcag ctatacaaaa ccatttattt tgaagatttt tagactactg ttaatttgaa    6180
atctgttact cttattgtgg aatttgtttt tttaaaaaag atgtttctaa ttggattttt    6240
aaaagaagaa tggaatttgg ttgctatttt acaatagaac ctaagctttt tgtggttctt    6300
agtgtcctat gtaaaactta gtgtcaaagt aatcaacttt gagatttttcc cttctattct    6360 gctttatatt aaaagcccat tagaaaatgg gaacctggtg aatatataat gaattgtaaa    6420 atatttaat gtgtaacttt ttcaactgtg aaactgactt gatttttttga tgaaaacagc    6480 tgctgataaa gtattttgtg taaagtgtag ttcttattaa tcaggaaaat gatgacttga    6540
ttagactgta tatgccctct tggattttat tttaaatgga ttggtgactt tcacataggt    6600
aaaacacagt ccatctgtat tcttttttcc atcaaaaatc gagtgatttg gaattataaa    6660
aaaattgtga gcagcctatt tgaaaggcat catggaaatt tcacagcaca ataacacgga    6720
tttgtttttt cttaatgatg taaatccgtt taattcatac tttgatcaat agcccatgct    6780
tgccaactct gaagaaattt aatttccagc agtattttaa agctagcctg ttaactttt    6840 ctgaatattt aaagttcctc tttttctat gtctgcacaa actgcagacc tgggctggac    6900
ccacatactc aagagtccac cttaagaaat tattttgatg tccaagacat cactaaaata    6960
tttaagttta aagataatat gtggtgttaa tagattgtgg tgcttttact atttaaagac    7020
aactttcata cttcagatgt ttttgagaag aggggaatgt gaggggaggg ggcagaacag    7080
ggaggagttg tttgaatgaa ttacattctt tatatccatc ctgctcattt ggggcatgtc    7140
tttaagagaa ggctgaaagt tgtgagagta tattgtatac cgtaagagaa tcaactcttc    7200
atcatggatg ggattgtgaa ggctgaacta taaaattcag cattgacagc atcctcaatt    7260
```

-continued

```
aataattctt ggtgacagaa taatacagct gggctgtttt ttaaaatata acaatacca      7320 tttttaatta ttacattaaa aattgtaaat atatctatgt gccatggcct gggaagcctg      7380
cttctttttt tcataaaaat tattttact gtatgaaaag atcatggggt ttagctcaaa      7440
atatctgtgg tcctgataaa attggattgg taactctacc tcagaaggaa aatgggaaaa      7500
aaaaatagat gagtcacaat tcaatacttc aagctcagaa actgtgcaga tcactgaatt      7560
ttagatttat aaagtcagag ttggcatgcc ttgtttttaa tgatatggaa gaccttaaga      7620
aaaaaacttg gctgaagttt aatcgttggt ccagccattt gaaaaaggca atagtttgag      7680
gaggttcccg aattcggcat ttgaaattca ttttgttctc tcttcttcat tattagtgca      7740
tttggtgtgt gtatacttgc acacaattct gtttgtgtac acactgcttg cttagcccta      7800
gtcaagaggc atcttttata aaggtgtaa agaaatatca aggttctaaa attcggaaga      7860
gtttagaatt tattaggagt ttcccaagtt gggatgttag tctttaaata aacttcatgc      7920
acctattcca cttaaggttt tgcacctcct ttttattagt gcagtgccat ttcttctgct      7980
tgattttagg tatgttaata ttccagcctt gctagttagc ataaagtgac aggtgtgagc      8040
catgaggaaa ttttctgact taatttgtac acaactacat ataagagttt tagtggagga      8100
aaaaaattag tcccttgtgc gtatacagta gttaggtaaa tgattttct accaacagta      8160 tactccattc ctcatgtagg taagtacaga aaaggttttt aaatgtattt ttttagccag      8220
ttaaagtcta tgaatctatc tgcaacctta tttaatctgt cactataata attttgtggt      8280
tatgctaaga accatgtata ctttaggta ttcttatttt tgtcaattt tctaggttgg      8340 caaggaggca gaaaaccttc attgtttcat attaaaatat aattagacta aacttaattc      8400
tagtatgaat ttccaaaatc attatctatt tatttcattt ttatttaatt ttgttttat      8460 ttcattttta aaagtcccctt gttcaattta acttatgttc ctaagagagg ttggagaact      8520
tggccttcat ctgatttcaa aaatgttttg agtttcaaat gaagttaatg gtttcagtgt      8580
gattcagtcc tcagacctaa ttgggttgaa taaaatctaa aagaatatac ccttttggag      8640
cataacattt taataccttg gggaatgtgg cactaccaaa agaagactac taacacgtca      8700
gatgttcacc tggaagcttt atcaagaaat tcgaaccacc cttttggccc cattaattgt      8760
agcaagttta tttctctata ttttgtcatt cagtgaattg aagtcctgtg gtatactgca      8820
ttcattagaa gaaaaacgtt tttaatgtcc tttaatgat ggcccagaaa gcatttgaca      8880
cagcaagatg catgtgttac tatattgaga atatagaata ataacagtat cactaaattt      8940
aagacctctt cccagtcttg ctgttcctag caagaagttt ggcctgtgac tgcacttact      9000
gtttatgctc atcagaaact gtcaatgtct gcttttcttt aactctgcag tctgtaacat      9060
cacgctgttt attaaaaaaa aaagaaaaa ttaaaaaaaa aaaa                       9104
```

<210> SEQ ID NO 40
<211> LENGTH: 97
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 40

```
tgctgttgac agtgagcgca ggaattataa tgcttatcta tagtgaagcc acagatgtat      60
agataagcat tataattcct atgcctactg cctcgga                              97
```

<210> SEQ ID NO 41

<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgctgttgac agtgagcgca gaagtgttct atgcagtcaa tagtgaagcc acagatgtat    60
tgactgcata gaacacttct ttgcctactg cctcgga                            97

<210> SEQ ID NO 42
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgctgttgac agtgagcgag gagcggaatg ttctgttgaa tagtgaagcc acagatgtat    60
tcaacagaac attccgctcc gtgcctactg cctcgga                            97

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Pro Arg Thr Ser Ser Phe Ala Glu Gly Lys Lys
1               5                   10

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctgatcaccg gcctcaat                                                 18

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggaagacatt gagcttctct gg                                            22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
ttcttgtccc accacttgaa                                                    20
```

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
ctgacatgtg acatcctggt g                                                  21
```

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
cctcagagag tagcagctca ca                                                 22
```

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
cagagccttt tcattcttgg a                                                  21
```

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
ctgcagatgg agcatgttgt                                                    20
```

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
tcttcacgag gaggcttgat                                                    20
```

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
cgtcttcccc tccatcgt                                                      18
```

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaaggtgtgg tgccagattt                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagctcagtg ctgttggtgg                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
accatccaac cctggagatc                                                    20

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gacaatcaaa gtccttccca aa                                                 22

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctttTgacc tgtgctgttg t                                                  21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaagaaaatc cctcccctct t                                                  21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cactcacctc aagcccattt                                           20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gggagggaga ggtcaggaat                                           20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tcgcttgtta cctcctcacg                                           20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aattttagaa tttggaagag ga                                        22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acaaccttaa attaaaccca aa                                        22

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gagggagagg ttaggaatgt                                           20

```
<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccctcccttc rcttattacc tcctcac                                          27

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ttttgaagta atttttgaga atatt                                            25

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gacaggactg tggactggtg                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tttcagctgt gtttcggcta                                                  20

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Lys Arg Asn Arg Thr Leu Thr Lys
1               5

<210> SEQ ID NO 70
<211> LENGTH: 15
<212> TYPE: PRT
<213> ORGANISM: Homo sapiens

<400> SEQUENCE: 70

Arg Pro His Phe Pro Gln Phe Ser Tyr Ser Ala Ser Gly Thr Ala
1               5                   10                  15

<210> SEQ ID NO 71
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtccgttccg cat                                                      13

<210> SEQ ID NO 72
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72 acacgtga                                                             8
```

COMBINATION THERAPY USING PDK1 AND PI3K INHIBITORS

CROSS REFERENCE TO RELATED APPLICATIONS

This application is a Continuation of International Patent Application No. PCT/US16/42616 filed Jul. 15, 2016, which claims priority to U.S. Provisional Application No. 62/194,106 filed Jul. 17, 2015, the contents of each of which are incorporated by reference in their entirety, and to each of which priority is claimed.

GRANT INFORMATION

This invention was made with government support under CA190642 awarded by the National Institutes of Health. The government has certain rights in the invention.

SEQUENCE LISTING

The specification further incorporates by reference the Sequence Listing submitted herewith via EFS on Jan. 17, 2018. Pursuant to 37 C.F.R. § 1.52(e)(5), the Sequence Listing text file, identified as 0727340657SEQ.txt, is 114,725 bytes and was created on Jan. 17, 2018. The Sequence Listing electronically filed herewith, does not extend beyond the scope of the specification and thus does not contain new matter.

1. INTRODUCTION

The present invention relates to methods and compositions for inhibiting growth and proliferation of cancer cells resistant to PI3K inhibition using a combination of PDK1, SGK1 and PI3K inhibitors.

2. BACKGROUND OF THE INVENTION

The PI3K pathway integrates many extracellular stimuli, triggering the phosphorylation of key downstream effectors such as AKT and the mammalian Target of Rapamycin Complex 1 and 2 (mTORC1 and 2). This signaling cascade is essential for regulating cell size, proliferation, survival, and metabolism. Activation of PI3K results in the synthesis of the second messenger phosphatidylinositol-(3,4,5)-triphosphate ($PIP_3$) at the plasma membrane, which in turn promotes the recruitment of the pleckstrin homology (PH) domain-containing proteins PDK1 and AKT. The physical proximity at the plasma membrane allows PDK1, a constitutively active kinase, to phosphorylate AKT at the activation loop (T308). A second phosphorylation in the hydrophobic motif (S473) is then carried out by mTORC2 to fully activate AKT. Once active, AKT is able to phosphorylate a variety of substrates including antiapoptotic and cell cycle related proteins or transcription factors. Moreover, AKT predominantly mediates the crosstalk between the PI3K pathway and mTORC1.

PIK3CA, the gene encoding the alpha isoform of PI3K (PI3Kα, p110α), is frequently mutated in breast cancer, resulting in increased levels of active PI3K, and increased levels of active mTORC1, a downstream target of PI3K. Accordingly, the development of inhibitors that selectively target this isoform may be therapeutically beneficial. However, a proportion of PIK3CA-mutant patients remain insensitive to PI3Kα blockade.

3. SUMMARY OF THE INVENTION

The present invention relates to methods of inhibiting growth and proliferation of cancer cells resistant to PI3K inhibition using a combination of PDK1 and PI3K inhibitors, or SGK1 and PI3K inhibitors. It is based, at least in part, on the discoveries that (i) in cells that are resistant to PI3K inhibition (i.e., the cells express active mTORC1 in the presence of PI3K and AKT inactivation), PDK1 activates mTORC1 through a PI3K independent pathway involving SGK1; (ii) combined inhibition of PI3K and PDK1, or PI3K and SGK1, in cells resistant to PIK3 inhibitor monotherapy resensitizes the cells to the PI3K inhibitor and reduces mTORC1 activity and (iii) combination therapy with PI3K and PDK1 inhibition, or PI3K and SGK1 inhibition, reduced tumor size in vivo in xenografts of PI3K resistant cells.

In certain non-limiting embodiments, the present invention provides for methods of treating and/or inhibiting the progression of cancer and/or tumor growth, in a subject in need thereof by administering an agent in an amount effective to decrease activity of mTORC1, for example, a decrease in translation of cellular mTORC1 target proteins. Activity of mTORC1 can be determined, for example, by measuring the level of phosphorylated S6 protein, wherein a decrease in the level of phosphorylated S6 protein indicates a decrease in mTORC1 activity.

In certain non-limiting embodiments, the cancer and/or tumor cells present in the subject express a mutant form of the PIK3CA gene which encodes the alpha isoform of PI3K, p110α.

In certain non-limiting embodiments, the agent comprises an inhibitor of PI3K (phosphoinositide 3-kinase; Phosphatidylinositol-4,5-bisphosphate 3-kinase) and an inhibitor of PDK1 (3-phosphoinositide dependent protein kinase-1) and/or SGK1 (serine/threonine-protein kinase).

In one non-limiting embodiment, the inhibitor of PI3K is an inhibitor of the p110α isoform of PI3K.

In certain non-limiting embodiments, mTORC1 (mammalian Target of Rapamycin Complex 1) can comprise, for example, a complex of mTOR (mechanistic target of rapamycin), Raptor (regulatory-associated protein of mTOR), mLST8 (mammalian lethal with SEC13 protein 8), PRAS (Proline-rich AKT1 substrate 1), and DEPTOR (DEP domain-containing mTOR-interacting protein).

The present invention also provides for methods of reducing or inhibiting cancer cell growth, and/or tumor cell growth, for example, growth of a cancer cell and/or tumor cell expressing a mutant PI3K, for example, a mutant p110α, by contacting an agent described herein to a cancer and/or tumor cell in an amount effective to inhibit or reduce cell growth. In certain embodiments, the agent is contacted to the cell in an amount effective to decrease the size of the tumor or the number of cancer cells. In certain embodiments, the agent is contacted to the cell in an amount effective to inhibit activity of mTORC1. In other embodiments, the agent is contacted to the cell in an amount effective to inhibit or reduce PI3K activity and PDK1 and/or SGK1 activity, for example, a decrease in the ability of PI3K and PDK1 and/or SGK1 to phosphorylate target proteins.

In certain non-limiting embodiments, the present invention provides for a method of treating cancer in a subject comprising administering, to the subject, an effective amount of an agent that inhibits the PI3K/AKT pathway and an effective amount of an agent that inhibits PDK1 activity, the SGK1 pathway, or a combination thereof.

In certain non-limiting embodiments, the present invention provides for a method of treating cancer in a subject according to the foregoing method, wherein the cancer cells of the patient are resistant to PI3K/ATK inhibitor monotherapy.

In certain non-limiting embodiments, the method comprises administering an effective amount of an agent that inhibits the PI3K/AKT pathway and an effective amount of an agent that inhibits PDK1 activity.

In certain non-limiting embodiments, the method comprises administering an effective amount of an agent that inhibits the PI3K/AKT pathway and an effective amount of an agent that inhibits the SGK1 pathway.

In certain non-limiting embodiments, the agent that inhibits the PI3K/AKT pathway is an agent that selectively acts at the alpha isoform (p110α) of PI3K.

In certain non-limiting embodiments, the agent that inhibits PI3K comprises a nucleic acid that specifically binds to a PI3K nucleic acid, for example, a p110α nucleic acid, and reduces PI3K activity and/or expression. In certain non-limiting embodiments, the agent comprises micro RNA (miRNA), interfering RNA (RNAi) molecule, shRNA molecule, antisense RNA, catalytic RNA, and/or catalytic DNA.

In certain non-limiting embodiments, the agent that inhibits PI3K is an agent that selectively inhibits the alpha isoform (p110α) of PI3K, for example, BYL719 (Apelisib), BAY80-6946 (Copanlisib), CH5132799, GDC-0941 (Pictilisib), A66, PIK 90, HS-173, MLN1117, GDC-0032, and combinations thereof.

In certain non-limiting embodiments, the agent that inhibits the PI3K/AKT pathway is selected from the group consisting of GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, MK2206 and combinations thereof.

In certain non-limiting embodiments, the agent that inhibits PDK1 activity is selected from the group consisting of GSK2334470, BX-912, BX-795, BAG 956, OSU 03012, PHT-427, and combinations thereof.

In certain non-limiting embodiments, the agent comprises a nucleic acid that specifically binds to a PDK1 nucleic acid, for example, a PDPK1 nucleic acid, and reduces PDK1 activity and/or expression. In certain embodiments, the agent comprises micro RNA (miRNA), interfering RNA (RNAi) molecule, shRNA molecule, antisense RNA, catalytic RNA, and/or catalytic DNA.

In certain non-limiting embodiments, the agent that inhibits the SGK1 pathway is selected from the group consisting of GSK650394, SI113, and combinations thereof.

In certain non-limiting embodiments, the agent comprises a nucleic acid that specifically binds to a SGK1 nucleic acid, for example, a SGK1 nucleic acid, and reduces SGK1 activity and/or expression. In certain non-limiting embodiments, the agent comprises micro RNA (miRNA), interfering RNA (RNAi) molecule, shRNA molecule, antisense RNA, catalytic RNA, and/or catalytic DNA.

In certain non-limiting embodiments, the present invention provides for a method of treating cancer in a subject, wherein the subject has a gain-of-function mutation in the PI3K/AKT pathway.

In certain non-limiting embodiments, the gain-of-function mutation in the PI3K/AKT pathway is an activating mutation in PIK3CA.

In certain embodiments, the gain-of-function mutation in the PI3K/AKT pathway is an activating mutation in PIK3CA, for example, a mutation at amino acid 88, 143, 345, 420, 542, 545, and/or 1047 of the PIK3CA amino acid sequence.

In certain embodiments, the activating mutation is selected from the group consisting of R88Q, N345K, E542K, E545K, E545Q, H1047L, H1047Q, H1047R, C420R, and/or I143V, or combinations thereof.

In certain non-limiting embodiments, the present invention provides for a method of treating cancer in a subject, wherein the cancer is breast cancer.

In certain non-limiting embodiments, the present invention provides for a method of treating cancer in a subject comprising (i) determining whether the subject expresses cancer cells that are resistant to treatment with a PI3K/AKT pathway inhibitor, wherein the resistant cells treated with the inhibitor sustain mTORC1 activity; and (ii) where the subject expresses cancer cells that are resistant to treatment with a PI3K/AKT pathway inhibitor, treating the subject with an agent that inhibits the PI3K/AKT pathway and an agent that inhibits PDK1 activity, SGK1 pathway, or a combination thereof.

In certain-non limiting embodiments, the method comprises administering an effective amount of an agent that inhibits the PI3K/AKT pathway and an effective amount of an agent that inhibits PDK1 activity.

In certain non-limiting embodiments, the method comprises administering an effective amount of an agent that inhibits the PI3K/AKT pathway and an effective amount of an agent that inhibits the SGK1 pathway.

In certain embodiments, the present invention provides for pharmaceutical compositions which include an agent that inhibits PI3K, PDK1 and/or SGK1, as described herein, alone or in combination with at least one other agent, such as a stabilizing compound or additional therapeutic agent, and can be administered in any sterile, biocompatible pharmaceutical carrier, including, but not limited to, saline, buffered saline, dextrose, and water.

In certain non-limiting embodiments, the compositions can be administered to the patient intravenously in a pharmaceutically acceptable carrier such as physiological saline. In certain non-limiting embodiments, standard methods for intracellular delivery can be used. In certain non-limiting embodiments, the formulations of the present invention are useful for parenteral administration, such as intravenous, subcutaneous, intramuscular, and intraperitoneal administration.

In certain non-limiting embodiments, the present invention further provides for kits comprising one or more agent that can (i) decrease the activity of mTORC1; (ii) decrease the activity PI3K and decrease the activity of PDK1 and/or SGK1; and/or (iii) reduce or inhibit cancer cell and/or tumor cell growth. In certain non-limiting embodiments, the present invention provides for a kit comprising an agent that inhibits the PI3K/AKT pathway and an agent that inhibits PDK1 activity, SGK1 pathway, or a combination thereof.

4. BRIEF DESCRIPTION OF THE FIGURES

FIG. 1A-G Shows that RNAi screening reveals PDK1 as a target for BYL719-resistant cells. A) Overview of the large screening carried out in this work. B) Venn diagram indicating the number of genes found to sensitize to BYL719 in each cell line and in common. The table contains the gene name and NCBI mRNA accession number targeted by the siRNA found to sensitize both cell lines to BYL719. C) Representative images of pS6 (S240/4) staining in JIMT1 cells treated with BYL719 (1 μM), everolimus (50 nM), or IGF-1 (20 ng×mL$^{-1}$) for 4 hours (h), and quantification of pS6 (S240/4) staining in cells treated with everolimus or IGF-1. D) Quantification of pS6 (S240/4) staining in the siCTR, siMTOR, and siPDPK1 transfected cells in the presence of DMSO or BYL719 (1 µM) in JIMT1 cells. Quantification of the whole well green fluorescence is indicated as a fold change of the control untreated cells. E) Screening representative images of pS6 (S240/4) staining in JIMT1 cells transfected with siCTR, siMTOR, and siPDPK1 in the presence or absence of BYL719 (1 µM). F) Genes identified in the siRNA screening using the HCC1954 cell line. G) Genes identified in the siRNA screening using the JIMT1 cell line.

FIG. 2A-N Shows that PDK1 inhibition sensitizes resistant cells to BYL719. A) Dose-response curves from HCC1954 or JIMT1 shGFP and shPDK1 cells treated with BYL719 for 6 days. B) Western blot comparing HCC1954 shGFP and shPDK1 cells treated with BYL719 (1 µM) for 4 h; and a Western blot comparing JIMT1 shGFP and shPDK1 cells treated with BYL719 (1 µM) for 4 h. C) $m^7$GTP pull down assay for HCC1954 shGFP and shPDK1 cells treated with BYL719 (1 µM) for 4 h; and a western blot of PARP comparing HCC1954 shGFP and shPDK1 cells treated with BYL719 (1 µM) for 24 h. Quantification of the $m^7$GTP-precipitated proteins is indicated in fold change. AZD8055 is used as a control at 1 D) Caspase DEVDase activity of HCC1954 shGFP and shPDK1 cells treated with BYL719 (1 µM) for 12 h in the presence or absence of caspase inhibitor zVAD-fmk (20 µM). Staurosporine is used as a positive control (1 µM; 4 h). E) HCC1954 shGFP and shPDK1 in vivo xenograft treated with Vehicle or BYL719 (n=10/arm). F) IHC analysis of tumors from E collected at the end of the experiment. G) Western blot analysis of phosphorylated RSK2 (S227) in HCC1954 and JIMT1 cells treated with increasing concentrations of GSK2334470 for 8 hr; Dose-response curves from HCC1954 and JIMT1 resistant cell lines treated with GSK2334470 for 6 days; Dose-response curves from HCC1954, JIMT1 and BT20 cells treated with BYL719 in the presence or absence of GSK2334470 (1 µM) during 6 days. H) Western blot comparing HCC1954 cells treated with BYL719 (1 µM), GSK2334470 (1 µM), or the combination of both agents for 4 h. I) Western blot of PARP HCC1954 cells treated with BYL719 (1 µM), GSK2334470 (1 µM), or the combination of both agents for 24 h. J) Caspase DEVDase activity of lysates from HCC1954 cells treated with BYL719 (1 µM), GSK2334470 (1 µM), or the combination of both agents for 12 h in the presence or absence of caspase inhibitor zVAD-fmk (20 µM). Staurosporine is used as a positive control (1 µM, 4 h). K) HCC1954 in vivo xenograft treated with Vehicle, BYL719 (25 mg/kg p.o., daily), GSK2334470 (100 mg/kg, i.p., 3 times/week), or the combination of both agents (n=10/arm). L) IHC analysis of tumors from K collected at the end of the experiment. M, N) JIMT1 in vivo xenograft tested as described in (K) and (L) for HCC1954 in vivo xenograft. P values are calculated using Student's t-test. Error bars are ±SEM.

FIG. 3A-H Shows FOXO activation upon PDK1 and PI3Kα inhibition. A) Heat map showing changes in the top differentially expressed genes in both HCC1954 and JIMT1 cells treated with DMSO, BYL719 (1 µM), GSK2334470 (1 µM), or the combination of both agents for 4 h. B) Enrichment plot for the FOXO3 signature in HCC1954 cells. C) Heat map showing changes in previously described FOXO3 targets. D) ERBB3, TNFSF10, BCL6, and IRS2 mRNA expression in HCC1954 cells treated with DMSO, BYL719 (1 µM), GSK2334470 (1 µM), or the combination of both agents for 4 h.
E) FOXO3A immunofluorescence in HCC1954 cells treated with DMSO, BYL719 (1 µM), GSK2334470 (1 µM), or the combination of both agents for 4h. F) Western blot analysis of FOXO1/3 phosphorylation (T24/T32) in HCC1954 and JIMT1cells treated with DMSO, BYL719 (1 µM), GSK2334470 (1 µM), or the combination of both agents for 4 h. G) Luciferase reporter assay in HCC1954 cells stably transduced with the FOXO consensus motif reporter construct treated as indicated for 12 h (RLU, Relative light units). H) ChIP-qPCR assay of FOXO3A binding at TNFSF10A and IRS2 promoters in HCC1954 cells treated as indicated in F. P values are calculated using Student's t-test. Error bars are ±SEM.

FIG. 4A-I Shows SGK1 up-regulation in BYL719-resistant cell lines. A) SGK1 mRNA levels in breast cancer cell lines sensitive or resistant to BYL719 (n=27). B) SGK1 mRNA levels in PIK3CA-mutant breast cancer cell lines sensitive or resistant to BYL719. C) Western blot of SGK1, SGK2, SGK3 and phosphorylated NDRG1 in a panel of PIK3CA—mutant breast cancer cell lines sensitive or resistant to BYL719. D) Western blot for NDRG1 and phosphorylated NDRG1 (T346) in BYL719-sensitive and -resistant breast cancer cell lines treated with BYL719 (1 µM) for 4 h. E) Western blot of phosphorylated NDRG1 (T346) in the indicated cell lines treated with DMSO, BYL719 (1 µM), GSK2334470 (1 µM), or the combination of both agents for 4 h. F) SGK1 activity in the presence of BYL719, GSK2334470, or both; and Akt activity in the presence of BYL719, GSK2334470, or both. G) Representative images of phosphorylated NDRG1 (T346) IHC in breast cancers tumors and quantification of the stainings observed in a cohort of 273 breast cancers cases. H) Summary of the median number of days of progression free survival (PFS) and the number of patients experiencing progression of disease (POD) as best response according to RECIST criteria in association with SGK1 mRNA levels and positivity to pNDRG1 staining by IHC. I) Waterfall plot showing changes in tumor size of the patients included in the study. Heat map represents the SGK1 mRNA levels for each tumor sample. P values are calculated using Student's t-test. Error bars are ±SEM.

FIG. 5A-M Shows a novel SGK1 inhibitor sensitizes resistant cells to BYL719. A) Dose-response curves from MDA-MB-361 cells transduced with pLenti7.3-LacZ or pLenti7.3-SGK1 (Δ60, S422D) treated with increasing concentrations of BYL719 for 6 days. B) Western blot analysis of LacZ and SGK1 MDA-MB-361 cells treated with BYL719 (1 µM) for 4 h. C) Chemical structure of SGK1-inh and in vitro SGK1 kinase activity assay in the presence of increasing concentrations of SGK1-inh. IC50 was 4.8 nM. D) In vitro SGK2 kinase activity assay in the presence of increasing concentrations of SGK1-inh. IC50 was 2.8 nM. E) In vitro SGK3 kinase activity assay in the presence of increasing concentrations of SGK1-inh. IC50 was 590 nM. F) Docking overview of SGK1-inh in the DFG-out conformation of SGK1. The DFG motif amino acids are indicated (D240, F241, G242). G) Detailed residues that mediate the interaction between SGK1-inh and the inactive conformation of SGK1. Hydrogen bonds are shown as dotted lines. H) Western blot quantification of NDRG1 phosphorylation (T346) in HCC1954 cells treated with increasing concentrations of SGK1-inh for 4 hours in the absence or presence of BYL719 (1 µM). I) Western blot analysis HCC1954 cells treated with BYL719 (1 µM), SGK1-inh (10 or the combination of both agents for 4 hours. J) Dose-response curves from HCC1954 cells treated with BYL719 for 6 days in the absence or presence of SGK1-inh (2 µM). K) HCC1954 in vivo xenograft treated with Vehicle, BYL719, SGK1-inh, or the combination of both agents (n=10/arm). L) IHC analysis of tumors from K collected at the end of the experiment. M) Top panel: growth curves of HCC1954 cells stably expressing doxycycline-inducible control (REN) or SGK1 knockdown treated with increasing concentrations of BYL719 for 6 days. Bottom panel: Western blot analysis of GFP-sorted control (REN) and SGK1 shRNA cells treated with BYL719 (1 μM) for 4 h. P values are calculated using Student's t-test. Error bars are ±SEM.

FIG. 6A-I Shows that SGK1 interacts with and phosphorylates TSC2. A) Flag co-immunoprecipitation assay in 293T cells transfected with the indicated plasmids. B) Representative efficiency images from the FRET experiment performed in HeLa cells with the constructs indicated (above) Scale bar: 5 μm. Quantification of FRET efficiency dots is indicated. C) (Upper panel) Schematic cartoon of the different truncation mutants used in co-immunoprecipitation assays. Domains are indicated: LZ (leucine zipper); CC (coiled coil); GAP (GTP-ase activation protein) (Lower panel) Co-immunoprecipitation assay in 293T cells between Flag-SGK1 and different truncation mutants of HA-TSC2. Asterisk indicates an unspecific band for the heavy chain of IgG. D) In vitro kinase assay using recombinant His-SGK1 and immunoprecipitated Flag-TSC2 from 293T cells as a substrate. Cells were pretreated with MK2206 (2 μM, 1 h) to deplete endogenous phosphorylation of TSC2. E) Schematic view and amino acid sequence of the predicted SGK1 phosphorylation sites in TSC2. (Left panel) Quantification of the phosphorylated sites identified using LC-MS/MS in the absence or presence of recombinant SGK1 are indicated. F) In vitro kinase assay using recombinant His-SGK1 and immunoprecipitated Flag-TSC2 (WT) or (6A) as a substrate. G) Western blot of phosphorylated TSC2 (S939) in HCC1954 cells treated with DMSO, BYL719 (1 μM), GSK2334470 (1 μM), or the combination of both agents for 4 h. H) Co-immunoprecipitation of endogenous SGK1 and TSC2 in JIMT1 cells. I) Western blot of phosphorylated TSC2 (S939) in HCC1954 and JIMT1 cells treated with DMSO, BYL719 (1 μM), GSK2334470 (1 μM), SGK1-inh (10 μM), or the combination of both agents for 4 hr. P values are calculated using Student's t-test. Error bars are ±SEM FIG. 7 Shows SGK1 expression in breast cancer patients. Representative images for Low, Intermediate and High pNDRG1 (T346) expression in breast cancer patients.

FIG. 8A-C Shows A) Western blot of HCT116 PDPK1$^{+/+}$ and PDPK1$^{-/-}$ isogenic cell lines treated with increasing concentrations of BYL719. B) Western blot of HCT116 PDPK1$^{-/-}$ cells transfected with different pCCL-PDK1 mutants. EV (empty vector), WT (wild type), KD (kinase death; K111N), KE (PIP3-binding deficient; K465E), LE (PIF-binding pocket deficient; L155E). C) Schematic representation of the effects of the PIP3-binding and PIF-binding pocket deficient mutants used in (FIG. 8B). Small black circles indicate phosphate groups and small white circles indicate hydrophilic-charged amino acid E. Arrows indicate electric charge repulsion.

FIG. 9A-D Shows A) Western blot comparing JIMT1 cells treated with BYL719 (1 μM), GSK2334470 (1 μM), or the combination of both agents for 4 h. B) Same as A using BT20 TNBC cells. C) S-phase quantification in JIMT1 cells treated with BYL719 (1 GSK2334470 (1 μM), or the combination of both agents for 24 h and stained with Propidium iodide for cell cycle analysis. D) m$^7$GTP pull down assay for HCC1954 cells treated with BYL719 (1 μM), GSK2334470 (1 μM), or the combination of both agents for 4 h. Quantification of the m$^7$GTP-precipitated proteins is indicated in fold change. AZD8055 is used as a control at 1 μM. P values are calculated using Student's t-test. Error bars are ±SEM.

FIG. 10A-E Shows A) Differentially expressed genes in JIMT1 (left) and HCC1954 (right) cells treated with BYL719 (1 μM), GSK2334470 (1 μM), or the combination of both agents for 4 h. B) Enrichment plot for the FOXO3 signature in JIMT1 cells. C) ERBB3, TNFSF 10, BCL6, and IRS2 mRNA expression in JIMT1 cells treated with DMSO, BYL719 (1 μM), GSK2334470 (1 μM), or the combination of both agents for 4 h.

D) FOXO3A immunofluorescence in JIMT1 cells treated with DMSO, BYL719 (1 μM), GSK2334470 (1 μM), or the combination of both agents for 4 h. E) ChIP assay for TNFSF 10A and IRS2 in JIMT1 cells treated as indicated in A. P values are calculated using Student's t-test. Error bars are ±SEM.

FIG. 11A-L Shows A) Cell viability of breast cancer cell lines treated with BYL719 and classified according to the SGK1 mRNA expression in high (>median expression) and low (<median expression) (n=27). B) SGK2 and SGK3 mRNA levels in breast cancer cell lines sensitive or resistant to BYL719 (n=27). C) Quantification of pNDRG1 (T346) basal levels in PIK3CA-mutant breast cancer cell lines classified according to their sensitivity to BYL719. D) Western blot of HCC1954 cells treated with increasing concentrations of the mTOR catalytic inhibitor AZD8055 in the presence or absence of GSK2334470 (1 μM). E) Dose-response curves from HCC1954 and JIMT1 cells treated with increasing concentrations of GSK2334470 in the presence or absence of the mTOR catalytic inhibitor AZD8055 (1 μM) for 6 days. F) Western blot of JIMT1 shGFP and shRICTOR cells treated with increasing concentrations of GSK2334470. G) pAKT (S473) Western blot in CAL-148 and CAL51 cells treated with BYL719 (1 μM) and AZD6482 (1 μM) during 4 h. Mutations identified in PTEN are shown below. H) Bisulfite sequencing of the promoter region of SGK1 in a cohort of eight breast cancer cell lines classified according to their sensitivity to BYL719. In the box, the three CpG sites identified to be differentially methylated. TSS: Transcription Start Site. I) Schematic representation of the three CpG sites (bold) identified to be differentially methylated in the promoter of SGK1. Below, pyrosequencing quantification of the methylated CpG sites in eleven breast cancer cell lines classified according to their sensitivity to BYL719. Box indicates the median and the interquartile range, while whiskers represent minimum and maximum. J) Correlation between the SGK1 mRNA levels and the percentage of CpG promoter methylation in the cells indicated in FIG. 11I. R indicates the R-square goodness of fit, and all correlations had a significant p value <0.05. K) ChIP-qPCR assay of RNA Polymerase II (Pol II) and the phosphorylated S5 of RNA Polymerase II (Pol II pS5) for SGK1 promoter in unmethylated (resistant) and methylated (sensitive) cell lines. Primers for the SGK1 promoter were design in order to amplify the region containing the three CpG islands identified in this study. CTD: C-terminal domain. L) RT-qPCR analysis of SGK1 mRNA levels in methylated sensitive cell lines treated for 72 h with the demethylating agent 5-aza-2'-deoxycytidine (5 μM) and the histone deacetylase inhibitor panobinostat (LBH) (50 nM). P values are calculated using Student's t-test. Error bars are ±SEM.

FIG. 12A-K Shows A) SGK1-inh IC50 determination in an ATP competition assay using increasing concentration of ATP. B) In vitro mTOR kinase assay using recombinant 4EBP1 as a substrate in the presence of increasing concentrations of SGK1-inh. IC50 value is >5000 nM. C) Selectivity screening results of SGK1-inh at 1 μM against a library containing 140 representative kinases. Values are available at the Kinase Inhibitor Database of the MRC Protein Phosphorylation and Ubiquitylation Unit of the University of Dundee. D) Western blot comparing JIMT1 cells treated with BYL719 (1 µM), SGK1-inh (10 µM), or the combination of both agents for 4 h. E) Dose-response curves from JIMT1 cells treated with increasing concentrations of BYL719 in the presence or absence of SGK1-inh (14 g; 2 µM) for 6 days. F) Same as E using BT20 TNBC cells. G) In vitro S6K1 kinase assay using recombinant KKRNRTLTK peptide as a substrate in the presence of increasing concentrations of SGK1-inh. IC50 value is indicated. H) In vitro S6K1 kinase assay using constitutively active S6K kinase immunoprecipitated from 293T cells expressing HA-S6K (ΔCT T389E) and treated with increasing concentrations of SGK1-inh. Recombinant GST-S6 was used as a substrate and phosphorylated S6 (S235/6) antibody was used for the detection of phosphorylated substrate by Western blot. IC50 value is indicated. I) Western blot analysis of S6K targets in TSC2 knockout mouse embryonic fibroblasts (MEF) and fibroblasts derived from a TSC2-null Lymphangioleiomyomatosis (LAM) patient treated with increasing concentrations of SGK1-inh for 4 h. Everolimus was used as a positive control at 200 nM. Error bars are ±SEM. J) m$^7$GTP pull down assay for HCC1954 cells treated with BYL719 (1 µM), SGK1-inh (10 µM), or the combination of both agents for 4 hr. Quantification of the m$^7$GTP-precipitated proteins is indicated in fold change. AZD8055 is used as a control at 1 µM). K) p4EBP1 (T37/46) IHC from tumors. Scale bar: 100 µM. Error bars are ±SEM.

FIG. 13A-D Shows A) Molecular docking snapshot of SGK1-inh and the active conformation of SGK1 complex. B) Docking prediction between the active conformation of SGK1 and ATP. Hydrogen bonds are shown as dotted lines and Mg$^{+2}$ as a grey sphere. C) Distribution of energies (ΔG) of conformations sampled during MD simulations of SGK1 bound to SGK1-inh or ATP. Distribution of van der Waals' interactions and electrostatic solvation contribution for the total binding energy are shown. D) Decomposition of binding free energy on per residue basis for SGK1 (DFG-out) and SGK1-inh complex. Alanine scanning results for the selected residues are also shown (bottom panel).

FIG. 14A-I Shows A) Co-immunoprecipitation assay using Flag-mTOR (left) or Flag-TSC2 (right) and HA-SGK1 in 293T cells. B) Alignment of the sequence of TSC2 comprising the AGC phosphorylation motifs RXRXX(S/T) (SEQ ID NO:1). R-1 and R-3 are highlighted in bold and phosphorylatable S or T in bold and underlined. Alignment was performed with ClustalW2 using the protein sequence from mouse (*Mus musculus*), rat (*Rattus norvegicus*), cattle (*Bos taurus*), chicken (*Gallus gallus domesticus*), frog (*Xenopus tropicalis*), and zebrafish (*Danio rerio*). C) Dose-response curves from T47D shGFP and shTSC2 cells treated with increasing concentrations of BYL719 for 6 days. D) Western blot from T47D shGFP and shTSC2 cells treated with BYL719 (1 µM) for 4 h. E) Western blot analysis of sucrose gradient fractions collected upon ultracentrifugation. Columns were packed in densities ranging from 0.4 to 1 M of sucrose, and a small aliquot of each fraction was analyzed by Western blot. Densitometry quantification of the sucrose gradient results are represented and dotted lines indicate the fractions in which the TSC complex is highly enriched, as assessed by the immunodetection of the three components TSC1, TSC2, and TBC1D7. F) Representative signaling integration of other kinases involved in the phosphorylation of TSC2. Residues previously identified to be phosphorylated by the indicated kinases are shown. Domains are indicated: LZ (leucine zipper); CC (coiled coil); GAP (GTP-ase activation protein). G) Western blot analysis of HCC1954 cells treated with the MEK inhibitors PD0325901 (1 µM) and GSK1120212 (50 nM) in the presence or absence of BYL719 (1 µM) for 4 h. H) Western blot analysis of HCC1954 cells treated with the AMPK inductors 2-deoxyglucose (50 mM) and A769662 (300 µM) in the presence or absence of BYL719 (1 µM) for 4 h. Phosphorylation of the previously described substrate Acetyl-CoA Carboxylase (ACC) S79 is shown as control for AMPK activation. I) Western blot analysis of HCC1954 cells treated with increasing concentrations of the WNT antagonist Dickkopf WNT signaling pathway inhibitor 1 (DKK-1) for 30 min in the presence or absence of BYL719 (1 µM) for 4 h. Phosphorylation of the previously described substrate β-catenin S33/7 is shown as control for GSK3β activation. Error bars are ±SEM.

FIG. 15 Shows a proposed model of PI3Kα resistance in SGK1 expressing cells. PIK3CA-mutant breast tumors depend on the PI3K pathway, which mainly signals through AKT. AKT phosphorylates and inhibits FOXO3 and TSC2, promoting mTORC1 activity and tumor progression (left panel). In the presence of PI3Kα inhibitors, PIP3 levels in the plasma membrane are negligible and AKT cannot be activated. High SGK1 cells become resistant to PI3Kα inhibitors, as SGK1 is not fully inhibited in the presence of these therapies, supporting FOXO3 and TSC2 phosphorylation, which promotes mTORC1 activity and tumor progression (middle panel). When SGK1 expressing cells are treated with PI3Kα and PDK1 inhibitors, both AKT and SGK1 are inhibited, inducing tumor regression as a result of FOXO3 activation and mTORC1 inhibition.

FIG. 16 Shows amino acid sequences of PDK1.

FIG. 17 Shows amino acid sequences of SGK1.

FIG. 18 Shows amino acid sequences of p110α isoform of PI3K.

FIG. 19 Shows nucleic acid sequences encoding PDK1.

FIG. 20 Shows nucleic acid sequences encoding SGK1.

FIG. 21 Shows nucleic acid sequences encoding the p110α isoform of PI3K.

5. DETAILED DESCRIPTION OF THE INVENTION

Figure 1A:
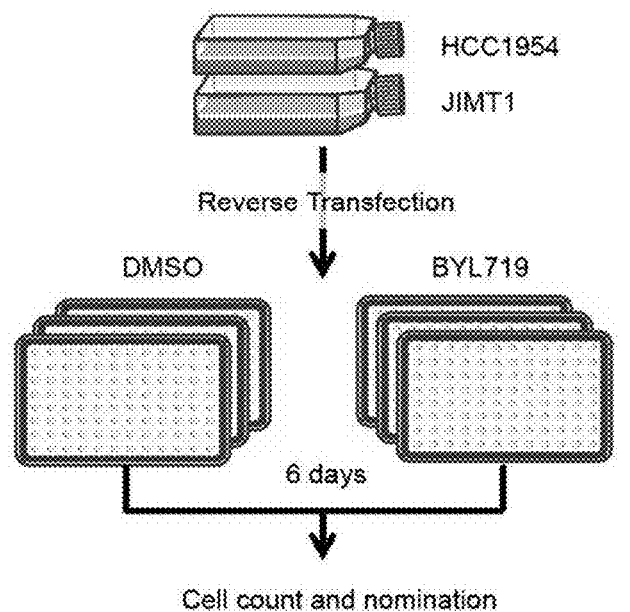

The present invention relates to methods and compositions for inhibiting growth and proliferation of cancer cells resistant to PI3K inhibition using a combination of PDK1 and PI3K inhibitors. It is based, at least in part, on the discovery that inhibition of PDK1 is able to sensitize cancer cells to PI3K inhibitors in cellular and in vivo models. Without being bound to any theory, PDK1 activates different kinases of the AGC kinase family via phosphorylation. In one non-limiting example, PI3K inhibitors do not exhibit an antitumoral effect in breast cancer cells that express high levels of SGK1. In such cells, SGK1 can activate mTORC1, which confers resistance to PI3K inhibitors. By inhibiting PDK1 in these tumors, the activity of SGK1 is subsequently inhibited, and the cells are sensitized to PI3K inhibitors, which can inhibit tumor cell growth and survival.

Accordingly, in a non-limiting embodiment of the present invention, there is an interaction between a PI3K pathway and a PDK1/SGK1 pathway to activate mTORC1 in cells resistant to PI3K inhibitor activity (i.e., cells that express active mTORC1 in the presence of PI3K inhibition), whereby inhibiting both PI3K activity and PDK1 and/or SGK1 activity reduces tumor cell growth and survival.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

For clarity of description and not by way of limitation, the detailed description of the invention is divided into the following subsections:
  (i) PI3K, PDK1 and SGK1;
  (ii) PI3K, PDK1 and SGK1 inhibitors;
  (iii) pharmaceutical compositions;
  (iv) methods of treatment; and
  (v) kits.

The following are terms relevant to the present invention:

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

An "effective amount" of a substance as that term is used herein is that amount sufficient to effect beneficial or desired results, including clinical results, and, as such, an "effective amount" depends upon the context in which it is being applied. In the context of administering a composition to treat and/or reduce the severity of cancer cell growth in a subject, an effective amount of a composition described herein is an amount sufficient to treat and/or ameliorate cancer cell growth, as well as decrease the severity and/or reduce the likelihood of cancer cell growth. The decrease can be a 10%, 20%, 30%, 40%, 50%, 60%, 70%, 80%, 90%, 95%, 98% or 99% decrease in severity of cancer cell growth, or likelihood of developing cancer. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

5.1 PI3K, PDK1 and SGK1

In certain non-limiting embodiments, the invention provides for a method of treating and/or inhibiting the progression of cancer in a subject, and also a method of inhibiting cancer cell and/or tumor cell growth and proliferation, comprising inhibiting or reducing PI3K activity (for example, by inhibiting the p110α isoform of PI3K) and PDK1 and/or SGK1 activity.

In certain non-limiting embodiments, human PDK1 is a protein having an amino acid sequence as set forth in NCBI Accession No. NP_001248745 (SEQ ID NO: 22), NP_002604 (SEQ ID NO: 23), NP_112558 (SEQ ID NO: 24), or a sequence at least 80, 85, 90, or 95 percent homologous thereto or at least 99 percent homologous thereto (homology, as that term is used herein, may be measured using standard software such as BLAST or FASTA), and is encoded, for example, by PDPK1 gene comprising a nucleic acid having a sequence as set forth in NCBI Accession No. NM_001261816 (SEQ ID NO: 31), NM_002613 (SEQ ID NO: 32), NM_031268 (SEQ ID NO: 33) or a sequence at least 80, 85, 90, or 95 percent homologous thereto or at least 99 percent homologous thereto (homology, as that term is used herein, may be measured using standard software such as BLAST or FASTA).

In certain non-limiting embodiments, human SGK1 is a protein having an amino acid sequence as set forth in NCBI Accession No. NP_001137148 (SEQ ID NO: 25), NP_001137149 (SEQ ID NO: 26), NP_001137150 (SEQ ID NO: 27), NP_001278924 (SEQ ID NO: 28), NP_005618 (SEQ ID NO: 29), or a sequence at least 80, 85, 90, or 95 percent homologous thereto or at least 99 percent homologous thereto (homology, as that term is used herein, may be measured using standard software such as BLAST or FASTA), and is encoded, for example, by a SGK1 gene comprising a nucleic acid having a sequence as set forth in NCBI Accession No. NM_001143676 (SEQ ID NO: 34), NM_001143677 (SEQ ID NO: 35), NM_001143678 (SEQ ID NO: 36), NM_001291995 (SEQ ID NO: 37), NM_005627 (SEQ ID NO: 38), or a sequence at least 80, 85, 90, or 95 percent homologous thereto or at least 99 percent homologous thereto (homology, as that term is used herein, may be measured using standard software such as BLAST or FASTA).

In certain non-limiting embodiments, the human p110α isoform of PI3K is a protein having an amino acid sequence as set forth in NCBI Accession No. NP_006209 (SEQ ID NO: 30), or a sequence at least 80, 85, 90, or 95 percent homologous thereto or at least 99 percent homologous thereto (homology, as that term is used herein, may be measured using standard software such as BLAST or FASTA), and is encoded, for example, by an PIK3CA gene comprising a nucleic acid having a sequence as set forth in NCBI Accession No. NM_006218 (SEQ ID NO: 39), or a sequence at least 80, 85, 90, or 95 percent homologous thereto or at least 99 percent homologous thereto (homology, as that term is used herein, may be measured using standard software such as BLAST or FASTA).

In certain embodiments, the p110α is a mutant p110α, wherein the mutation is a gain-of-function mutation activating p110α. The mutation can be, for example, a mutation at amino acid position 88, 143, 345, 420, 542, 545, and/or 1047 of the p110α protein sequence. In certain embodiments, the activating mutation is selected from the group consisting of R88Q, N345K, E542K, E545K, E545Q, H1047L, H1047Q, H1047R, C420R, and/or I143V, and combinations thereof.

5.2 PI3K, PDK1 and SGK1 Inhibitors

The present invention provides for agents that decrease the activity or expression level of PI3K, PDK1 and/or SGK1. In certain embodiments, the agent inhibits the ability of PI3K, PDK1 and/or SGK1 to phosphorylate a target protein. In certain embodiments, the agent inhibits the PI3K/AKT pathway, PDK1 activity and/or SGK1 pathway.

PI3K inhibitors that may be used according to the invention include inhibitors that are highly specific for PI3K or, alternatively, are PI3K selective. Inhibitors of the PI3K/AKT pathway may also be used according to certain embodiments of the invention, for example, but not limited to, inhibitors specific or selective for Akt1, Akt2, Akt3 or IRS2.

In certain embodiments, the agent comprises a PI3K inhibitor. In certain embodiments, the inhibitor selectively acts at the p110α isoform of PI3K. In one non-limiting embodiment, the PI3K inhibitor is selected from the group consisting of BYL719 (Apelisib; Fritsch et al., 1 Cancer Ther. 2014 May; 13(5):1117-29; doi: 10.1158/1535-7163), BAY80-6946 (Copanlisib; 2-Amino-N-[7-methoxy-8-(3-morpholin-4-ylpropoxy)-2,3-dihydroimidazo[1,2-c]quinazolin-5-yl]pyrimidine-5-carboxamide), CH5132799, GDC-0941 (Pictilisib), A66, PIK 90, HS-173, MLN1117, GDC-0032, and combinations thereof.

In certain embodiments, the agent comprises a PI3K inhibitor, wherein the agent inhibits the PI3K/AKT pathway. In one non-limiting embodiment, the PI3K inhibitor is selected from the group consisting of GDC-0032, BKM-120, BEZ235, GNE-317, PI-103 (Zou et al., Int J Mol Med. 2009 July; 24(1):97-1010), PIK-75, BGT226, GSK1059615, PF-04691502, CNIO-PI3Ki, GSK2126558, XL147, PKI-402, GDC0980, perifosine (Kondapaka et al., Mol Cancer Ther Nov. 2003 2; 1093), 2-methyl-5-nitro-2-[(6-bromoimidazo[1,2-a]pyridin-3-yl)methylene]-1-methylhydrazide-benzenesulfonic acid, monohydrochloride (Fan et al., Cell 125 733-747 (2006)), CAS 371943-05-4 (Hayakawa, M., et al. 2006. Bioorg. Med. Chem. 14: 6847-6858), MK2206 (8-[4-(1-aminocyclobutyl)phenyl]-9-phenyl-1,2,4-triazolo[3,4-f][1,6]naphthyridin-3(2H)-one, dihydrochloride), and combinations thereof.

In other embodiments, the agent comprises a nucleic acid that specifically binds to a PI3K nucleic acid, for example, a p110α nucleic acid, and reduces PI3K activity and/or expression. In certain embodiments, the agent comprises micro RNA (miRNA), interfering RNA (RNAi) molecule, shRNA molecule, antisense RNA, catalytic RNA, and/or catalytic DNA.

PDK1 inhibitors that may be used according to the invention include inhibitors that are highly specific for PDK1 or, alternatively, are PDK1 selective. Inhibitors of the PDK1/SGK1 pathway may also be used according to certain embodiments of the invention. In one non-limiting embodiment, the PDK1 inhibitor is selected from the group consisting of GSK2334470, BX-912, BX-795, BAG 956, OSU 03012, PHT-427, and combinations thereof. Additional PDK1 inhibitors are described by Medina, J Med Chem. 2013 Apr. 11; 56(7):2726-37; Nagashima et al., J Biol Chem. 2011 Feb. 25; 286(8):6433-48; U.S. Publication No. 2010/0144730; Rettenmaier et al., 2014, Proc. Natl. Acad. Sci. U.S.A. 111(52):18590-18595; Rettenmaier et al., 2015, J. Med. Chem. 58(20):8285-8291; Hossen et al., 2015, Expert Op. Ther. Pat. 25(5):513-537; International Publication No. WO 2005/041953; International Publication No. WO 2006/106326; U.S. Pat. No. 7,105,563; International Publication No. WO 2008/005457; International Publication No. WO2005054238; International Publication No. WO 2006/015124; International Publication No. WO 2004/087707; International Publication No. WO 2003/064397; U.S. Publication No. 2007/0135429; E.P. Patent No. 1486488; International Publication No. WO 2011/076327; International Publication No. WO 2011/006567; International Publication No. WO 2010/017047; Erlanson et al., 2011, Biorg. Med. Chem. Lett. 21:3078-83; Nagashim et al., 2011, J. Biol. Chem. 286:6433-48; International Publication No. WO 2010/065384; International Publication No. WO 2010/127754; International Publication No. WO 2008/107444; International Publication No. WO 2010/007114; International Publication No. WO 2010/007116; International Publication No. WO 2010/019637; International Publication No. WO 2010/120854; International Publication No. WO 2009/153313; International Publication No. WO 2008/079988; International Publication No. WO 2011/044157; International Publication No. WO 2008/109599; International Publication No. WO 2008/109613; Nittoli et al., 2010, Eur. J. Med. Chem. 45:1379-86; U.S. Publication No. 2009/0111799; U.S. Publication No. 2012/0208819; U.S. Publication No. 2014/0017701; U.S. Publication No. 2011/0269958; U.S. Publication No. 2012/0245355; International Publication No. WO 2012/072200; International Publication No. WO 2012/036974; International Publication No. WO 2012/058174; U.S. Publication No. 2013/0165450; International Publication No. WO 2012/058176; International Publication No. WO 2011/137219; U.S. Publication No. 2013/0053382; U.S. Publication No. 2012/0277229; International Publication No. WO 2012/135799; and U.S. Publication No. 2012/0003668. (Each of which is incorporated by reference in its entirety herein).

In other embodiments, the agent comprises a nucleic acid that specifically binds to a PDK1 nucleic acid, for example, a PDPK1 nucleic acid, and reduces PDK1 activity and/or expression. In certain embodiments, the agent comprises micro RNA (miRNA), interfering RNA (RNAi) molecule, shRNA molecule, antisense RNA, catalytic RNA, and/or catalytic DNA.

SGK1 inhibitors that may be used according to the invention include inhibitors that are highly specific for SGK1 or, alternatively, are SGK1 selective. In one non-limiting embodiment, the SGK1 inhibitor is selected from the group consisting of GSK650394, SI113, and combinations thereof. Additional SGK1 inhibitors are described by Halland et al. ACS Med Chem Lett. 2014 Oct. 23; 6(1):73-8; U.S. Pat. No. 8,546,613; and International Publication No. WO 2014/140065 A1 (each of which is incorporated by reference in its entirety herein).

In other embodiments, the agent comprises a nucleic acid that specifically binds to a SGK1 nucleic acid, for example, a SGK1 nucleic acid, and reduces SGK1 activity and/or expression. In certain embodiments, the agent comprises micro RNA (miRNA), interfering RNA (RNAi) molecule, shRNA molecule, antisense RNA, catalytic RNA, and/or catalytic DNA.

5.3 Pharmaceutical Compositions

In certain embodiments, the present invention provides for pharmaceutical compositions which include an agent that inhibits PI3K, PDK1 and/or SGK1, as described herein, alone or in combination with at least one other agent, such as a stabilizing compound or additional therapeutic agent, and can be administered in any sterile, biocompatible pharmaceutical carrier, including, but not limited to, saline, buffered saline, dextrose, and water.

As used herein, the term "pharmaceutically acceptable carrier" refers to any and all solvents, dispersion media, coatings, binders, antibacterial and antifungal agents, isotonic and absorption delaying agents, and the like, compatible with pharmaceutical administration. The use of such media and agents for pharmaceutically active substances is well known in the art. Pharmaceutically acceptable carriers are generally nontoxic to recipients at the dosages and concentrations employed, and include, but are not limited to, buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, a suitable pharmaceutically acceptable carrier can include one or more of water, saline, phosphate buffered saline, dextrose, glycerol, ethanol or combinations thereof.

The composition can be in a liquid or lyophilized form and include a diluent (Tris, citrate, acetate or phosphate buffers) having various pH values and ionic strengths, solubilizer such as Tween or Polysorbate, carriers such as human serum albumin or gelatin, preservatives such as thimerosal, parabens, benzylalconium chloride or benzyl alcohol, antioxidants such as ascrobic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain embodiments, the methods and compositions of the present invention find use in reducing, inhibiting or reversing cancer and/or tumor growth. The compositions can be administered to the patient intravenously in a pharmaceutically acceptable carrier such as physiological saline. Standard methods for intracellular delivery can be used (e.g., delivery via liposome). Such methods are well known to those of ordinary skill in the art. The formulations of the present invention are useful for parenteral administration, such as intravenous, subcutaneous, intramuscular, and intraperitoneal administration. Therapeutic administration of a compound intracellularly can also be accomplished using gene therapy. The route of administration eventually chosen will depend upon a number of factors and can be ascertained by one skilled in the art.

In certain embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include, in certain embodiments, compositions where the active ingredients are contained in an effective amount to achieve the intended purpose. The amount will vary from one individual to another and will depend upon a number of factors, including the overall physical condition of the patient, e.g., severity and the underlying cause of the motor neuron disease.

In certain embodiments, the formulations of the present invention can be administered for prophylactic and/or therapeutic treatments. For example, in alternative embodiments, pharmaceutical compositions of the present invention are administered in an amount sufficient to treat, prevent and/or ameliorate a disease, e.g., cancer. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain embodiments, the compositions described herein can be administered to a patient alone, or in combination with one or more other drugs, nucleotide sequences, lifestyle changes, etc. used in the treatment or prevention of disease, e.g., cancer, or symptoms thereof or in pharmaceutical compositions where it is mixed with excipient(s) or other pharmaceutically acceptable carriers.

In certain embodiments, the pharmaceutically acceptable carrier is pharmaceutically inert. In certain embodiments of the present invention, the compositions described herein can be administered alone to a subject suffering from a disease, e.g., cancer. The dosage regimen also takes into consideration pharmacokinetic parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the present invention are correct and appropriate.

Single or multiple administrations of formulations can be given depending on the dosage and frequency as required and tolerated by the patient. In certain embodiments, the formulations should provide a sufficient quantity of active agent to effectively treat, prevent or ameliorate the disease to be treated, e.g., cancer, or symptoms or complications thereof as described herein.

In certain embodiments, the compositions of the present invention are administered once, twice, or three times per day; or once, twice, or three times per week, by intravenous (IV) or subcutaneous (SC) injection to reach a suggested target therapeutic endpoint. Once the target has been achieved, a maintenance dosing schedule is established which will vary depending upon the patient.

In certain embodiments, the pharmaceutical formulation can be suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In certain embodiments, the present invention provides a parenteral formulation comprising an inhibitor of the PI3K/Akt pathway, and an inhibitor of PDK1 and/or SGK1.

5.4. Methods of Treatment

The present invention relates to methods and compositions for inhibiting growth and proliferation of cancer cells resistant to PI3K inhibition using a combination of PDK1 and PI3K inhibitors.

In certain non-limiting embodiments, the present invention provides for a method of treating and/or reducing the severity of cancer or the presence of a tumor, by administering to a subject in need thereof, a composition comprising an inhibitor of PI3K activity and an inhibitor of PDK1 and/or SGK1 activity, as described herein.

As used herein "treating" refers to achieving a reduction in the growth and/or proliferation of cancer cells or tumor tisue, or reducing the risk of occurrence or recurrence of cancer cells or tumor tissue in a subject in need of such treatment, such as, but not limited to, a subject that has been diagnosed with cancer, is at risk for having cancer, or has a family history of cancer. Non-limiting examples of a reduction in the growth and/or proliferation of cancer cells or tumor tissue, include maintenance of size, reduction in size, maintenance of volume, reduction in volume, maintenance of structural integrity, and/or reduction in risk of rupture and/or hemorrhage.

Subjects in need of such treatment or compositions include subjects who have been diagnosed with, or are at risk for developing, cancer. In certain embodiments, the cancer is breast cancer. In other non-limiting embodiments, the cancer comprises cells comprising a mutated PI3K or subunit thereof, for example but not limited to, a mutated PIK3CA and/or a mutated p85.

In certain embodiments, a subject who is at risk for developing cancer is a subject who has or had family members diagnosed with cancer.

In certain non-limiting embodiments, the cancer cells present in the subject are resistant to PI3K inhibition (i.e., the cells express active mTORC1 in the presence of PI3K and AKT inactivation).

In other non-limiting embodiments, the cancer cells of the subject express a mutant form of the PIK3CA gene which encodes the alpha isoform of PI3K, p110α. In one non-limiting embodiment, the mutation is a gain-of-function mutation activating p110α. The mutation can be, for example, a mutation at amino acid position 88, 143, 345, 420, 542, 545, and/or 1047 of the p110α protein sequence. In certain embodiments, the activating mutation is selected from the group consisting of R88Q, N345K, E542K, E545K, E545Q, H1047L, H1047Q, H1047R, C420R, and/or I143 V, and combinations thereof.

The present invention provides for a method of treating a subject suffering from cancer, comprising administering, to the subject, an effective amount of an agent comprising a PI3K inhibitor and an inhibitor of PDK1 and/or SGK1, wherein the agent is administered in an amount effective to inhibit or reduced the activity of PI3K, PDK1 and/or SGK1 to phosphorylate a target.

In certain non-limiting embodiments, the methods of the present invention comprise administering, to the subject, an effective amount of an agent comprising a PI3K inhibitor and an inhibitor of PDK1 and/or SGK1, wherein inhibition of PI3K and PDK1 and/or SGK1 results in the reduced activity or expression of mTORC1, for example, a decrease in translation of cellular mTORC1 target proteins. Activity of mTORC1 can be determined, for example, by measuring the level of phosphorylated S6K, S6, and/or 4EBP1 protein, wherein a decrease in the level of phosphorylated S6K, S6 and/or 4EBP1protein indicates a decrease in mTORC1 activity.

In certain non-limiting embodiments, the agent is administered in an amount effective to increase cell death of cancer cells and/or tumor cells in a treated subject, lengthen subject survival, or a combination thereof.

In certain non-limiting embodiments, an effective amount of an agent described herein is an amount which treats or reduces the severity of cancer in a subject. For example, treating or reducing the severity of cancer refers to an amelioration in the clinical symptoms or signs of cancer, for example, but not by way of limitation, reduction in tumor volume, and/or reduction in cells expressing cancer markers such as, for example but not limited to, HER2, EGFR, ER, Ki67, PCNA, or other proliferative markers known in the art. In other non-limiting embodiments, the effective amount of the agent is an amount that increases the number of apoptotic cancer cells in the subject, for example, as evidenced by an increase in cleaved caspase 3 and/or 7, cleaved PARP, and/or TUNEL.

The present invention also provides for methods comprising contacting an agent as described herein to a cell, wherein the agent is contacted to the cell in an amount effective to inhibit activity and/or expression of PI3K as well as the activity and/or expression of PDK1 and/or SGK1 in the cell, for example, in an amount effective to inhibit or reduced the activity of PI3K, PDK1 and/or SGK1 to phosphorylate a target. In other non-limiting embodiments, the agent is contacted to the cell in an amount effective to inhibit or reduce the activity and/or expression of mTORC1.

In certain non-limiting embodiments, the cell is resistant to PI3K inhibition (i.e., the cell expresses active mTORC1 in the presence of PI3K and AKT inactivation).

In other non-limiting embodiments, the cell expresses a mutant form of the PIK3CA gene which encodes the alpha isoform of PI3K, p110α. In one non-limiting embodiment, the mutation is a gain-of-function mutation activating p110α. The mutation can be, for example, a mutation at amino acid position 88, 143, 345, 420, 542, 545, and/or 1047 of the p110α protein sequence. In certain embodiments, the activating mutation is selected from the group consisting of R88Q, N345K, E542K, E545K, E545Q, H1047L, H1047Q, H1047R, C420R, and/or I143V,and combinations thereof.

In certain non-limiting embodiments, the cell is a cancer cell and/or tumor cell, and the agent is contacted to the cell in an amount effective to inhibit cell growth and proliferation.

In other non-limiting embodiments, the agent is contacted to the cell in an amount effective to increase the activity of FoxO transcription factors, and/or increase the expression level FoxO transcription factor targets, for example, but not limited to, one or more of CCNG2, ERBB3, TNFSF10, BCL6, and IRS2.

In another non-limiting embodiment, the agent is contacted to the cell in an amount effective to increase the activity of FoxO transcription factors, and decrease the expression level of FoxO transcription factor targets, for example, but not limited to, CCND1.

In yet other non-limiting embodiments, the agent is contacted to the cell in an amount effective to increase activity of FoxO1/3, for example, by decreasing phosphorylation of FoxO1/3, for example, at its T32 and/or T24 residue, respectively. In other embodiments, the agent is contacted to the cell in an amount effective to increase nuclear translocation of FoxO1/3.

In certain embodiments, an agent of the present invention, e.g., an inhibitor of the PI3K/Akt pathway (e.g., a PI3K inhibitor) can be administered to a subject at an amount of about 0.01 mg/kg to about 10 mg/kg (see Reagan-Shaw et al., The FASEB J., Vol. 22: 659-661 (2008)). For example, and not by way of limitation, an inhibitor can be administered at an amount of about 0.01 mg/kg to about 9.5 mg/kg, about 0.01 mg/kg to about 9 mg/kg, about 0.01 mg/kg to about 8.5 mg/kg, about 0.01 mg/kg to about 8 mg/kg, about 0.01 mg/kg to about 7.5 mg/kg, about 0.01 mg/kg to about 7 mg/kg, about 0.01 mg/kg to about 6.5 mg/kg, about 0.01 mg/kg to about 6 mg/kg, about 0.01 mg/kg to about 5.5 mg/kg, about 0.01 mg/kg to about 5 mg/kg, about 0.01 mg/kg to about 4.5 mg/kg, about 0.01 mg/kg to about 4 mg/kg, about 0.01 mg/kg to about 3.5 mg/kg, about 0.01 mg/kg to about 3 mg/kg, about 0.01 mg/kg to about 2.5 mg/kg, about 0.01 mg/kg to about 2 mg/kg, about 0.01 mg/kg to about 1.5 mg/kg, about 0.01 mg/kg to about 1 mg/kg, about 0.01 mg/kg to about 0.5 mg/kg, about 0.01 mg/kg to about 0.1 mg/kg, about 0.1 mg/kg to about 10 mg/kg, about 0.5 mg/kg to about 10 mg/kg, about 1 mg/kg to about 10 mg/kg, about 1.5 mg/kg to about 10 mg/kg, about 2 mg/kg to about 10 mg/kg, about 2.5 mg/kg to about 10 mg/kg, about 3 mg/kg to about 10 mg/kg, about 3.5 mg/kg to about 10 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg, e.g., by one or more separate administrations, or by continuous infusion. In certain embodiments, an inhibitor of the present invention can be administered at an amount of about 0.5 mg/kg to about 5 mg/kg, or about 1 mg/kg to about 3 mg/kg, e.g., about 2 mg/kg.

In certain embodiments, an agent of the present invention, e.g., an inhibitor of PDK1 activity (e.g., a PDK1 inhibitor) can be administered to a subject at an amount of about 1 mg/kg to about 20 mg/kg (see Reagan-Shaw et al., The FASEB J., Vol. 22: 659-661 (2008)). For example, and not by way of limitation, an inhibitor can be administered at an amount of about 1 mg/kg to about 19 mg/kg, about 1 mg/kg to about 18 mg/kg, about 1 mg/kg to about 17 mg/kg, about 1 mg/kg to about 16 mg/kg, about 1 mg/kg to about 15 mg/kg, about 1 mg/kg to about 14 mg/kg, about 1 mg/kg to about 13 mg/kg, about 1 mg/kg to about 12 mg/kg, about 1 mg/kg to about 11 mg/kg, about 1 mg/kg to about 10 mg/kg, about 1 mg/kg to about 9.5 mg/kg, about 1 mg/kg to about 9 mg/kg, about 1 mg/kg to about 8.5 mg/kg, about 1 mg/kg to about 8 mg/kg, about 1 mg/kg to about 7.5 mg/kg, about 1 mg/kg to about 7 mg/kg, about 1 mg/kg to about 6.5 mg/kg, about 1 mg/kg to about 6 mg/kg, about 1 mg/kg to about 5.5 mg/kg, about 1 mg/kg to about 5 mg/kg, about 1 mg/kg to about 4.5 mg/kg, about 1 mg/kg to about 4 mg/kg, about 1 mg/kg to about 3.5 mg/kg, about 1 mg/kg to about 3 mg/kg, about 1 mg/kg to about 2.5 mg/kg, about 1 mg/kg to about 2 mg/kg, about 1 mg/kg to about 1.5 mg/kg, about 1 mg/kg to about 20 mg/kg, about 1.5 mg/kg to about 20 mg/kg, about 2 mg/kg to about 20 mg/kg, about 2.5 mg/kg to about 20 mg/kg, about 3 mg/kg to about 20 mg/kg, about 3.5 mg/kg to about 20 mg/kg, about 4 mg/kg to about 20 mg/kg, about 4.5 mg/kg to about 20 mg/kg, about 5 mg/kg to about 20 mg/kg, about 5.5 mg/kg to about 20 mg/kg, about 6 mg/kg to about 20 mg/kg, about 6.5 mg/kg to about 20 mg/kg, about 7 mg/kg to about 20 mg/kg, about 7.5 mg/kg to about 20 mg/kg, about 8 mg/kg to about 20 mg/kg, about 8.5 mg/kg to about 20 mg/kg, about 9 mg/kg to about 20 mg/kg, about 9.5 mg/kg to about 20 mg/kg, about 10 mg/kg to about 20 mg/kg, about 11 mg/kg to about 20 mg/kg, about 12 mg/kg to about 20 mg/kg, about 13 mg/kg to about 20 mg/kg, about 14 mg/kg to about 20 mg/kg, about 15 mg/kg to about 20 mg/kg, about 16 mg/kg to about 20 mg/kg, about 17 mg/kg to about 20 mg/kg, about 18 mg/kg to about 20 mg/kg, or about 19 mg/kg to about 20 mg/kg, e.g., by one or more separate administrations, or by continuous infusion. In certain embodiments, an inhibitor of the present invention can be administered at an amount of about 5 mg/kg to about 10 mg/kg, pr about 7 mg/kg to about 9 mg/kg, e.g., about 8 mg/kg.

In certain embodiments, an agent of the present invention, e.g., an inhibitor of the SGK1 pathway (e.g., an SGK1 inhibitor) can be administered to a subject at an amount of about 0.01 mg/kg to about 10 mg/kg (see Reagan-Shaw et al., The FASEB J., Vol. 22: 659-661 (2008)). For example, and not by way of limitation, an inhibitor can be administered at an amount of about 0.01 mg/kg to about 9.5 mg/kg, about 0.01 mg/kg to about 9 mg/kg, about 0.01 mg/kg to about 8.5 mg/kg, about 0.01 mg/kg to about 8 mg/kg, about 0.01 mg/kg to about 7.5 mg/kg, about 0.01 mg/kg to about 7 mg/kg, about 0.01 mg/kg to about 6.5 mg/kg, about 0.01 mg/kg to about 6 mg/kg, about 0.01 mg/kg to about 5.5 mg/kg, about 0.01 mg/kg to about 5 mg/kg, about 0.01 mg/kg to about 4.5 mg/kg, about 0.01 mg/kg to about 4 mg/kg, about 0.01 mg/kg to about 3.5 mg/kg, about 0.01 mg/kg to about 3 mg/kg, about 0.01 mg/kg to about 2.5 mg/kg, about 0.01 mg/kg to about 2 mg/kg, about 0.01 mg/kg to about 1.5 mg/kg, about 0.01 mg/kg to about 1 mg/kg, about 0.01 mg/kg to about 0.5 mg/kg, about 0.01 mg/kg to about 0.1 mg/kg, about 0.1 mg/kg to about 10 mg/kg, about 0.5 mg/kg to about 10 mg/kg, about 1 mg/kg to about 10 mg/kg, about 1.5 mg/kg to about 10 mg/kg, about 2 mg/kg to about 10 mg/kg, about 2.5 mg/kg to about 10 mg/kg, about 3 mg/kg to about 10 mg/kg, about 3.5 mg/kg to about 10 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg, e.g., by one or more separate administrations, or by continuous infusion. In certain embodiments, an inhibitor of the present invention can be administered at an amount of about 1 mg/kg to about 8 mg/kg, or about 2 mg/kg to about 6 mg/kg, e.g., about 4 mg/kg.

In certain embodiments, the inhibitors of the present invention can be administered to a subject at least: twice every day, once every day, once every two days, once every three days, once every four days, once every five days, once every six days, once a week, once every two weeks, once every three weeks, once every month, once every two months, once every three months, once every six months or once every year. In certain embodiments, the inhibitors of the present invention can be administered one or more times per day. For example, and not by way of limitation, the inhibitors of the present invention can be administered once, twice, three, four, five or more times a day. In certain embodiments, the inhibitors of the present invention can be administered to a subject at least once a week, two times a week, three times a week, four times a week, five times a week, six times a week, or seven times a week.

In certain embodiments, the agent is administered to a subject in need thereof as described herein, or contacted to a cell as described herein, in an amount such that the combined effect of the PI3K inhibitor and the PDK1 and/or SGK1 inhibitor is greater than the additive effect of the independent inhibitors. For example, according to the methods of the present application, the agent can be administered in an amount effective to decrease tumor volume, wherein the effect of said agent is greater than the additive independent effects of a PI3K inhibitor and a PDK1 and/or SGK1 inhibitor on the reduction of tumor volume.

5.5 Kits

In certain embodiments, the present invention provides for kits. In certain embodiments, a kit can comprise (i) a container, such as a vial, that includes a pharmaceutical formulation comprising (ii) an inhibitor of the PI3K/Akt pathway (e.g., a PI3K inhibitor) in a pharmaceutically acceptable carrier, and (iii) an inhinitor of PDK1 activity, and/or the SGK1 pathway, in a pharmaceutically acceptable carrier.

In certain embodiments, a kit can comprise one or more agent that can (i) decrease the activity of mTORC1; (ii) decrease the activity PI3K and decrease the activity of PDK1 and/or SGK1; and/or (iii) reduce or inhibit cancer cell and/or tumor cell growth.

In certain embodiments, the kit of the present invention can comprise an agent that inhibits the PI3K/AKT pathway such as, but not limited to, BYL719 (Apelisib), BAY80-6946 (Copanlisib), CH5132799, GDC-0941 (Pictilisib), A66, PIK 90, HS-173, MLN1117, GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, MK2206 and combinations thereof.

In certain embodiments, the kit of the present invention can comprise an agent that inhibits PDK1 activity, such as, but not limited to, GSK2334470, BX-912, BX-795, BAG 956, OSU 03012, PHT-427, and combinations thereof.

In certain embodiments, the kit of the present invention can comprise an agent that inhibits the SGK1 pathway, such as, but not limited to, GSK650394, SI113, and combinations thereof.

In certain embodiments, a kit of the present invention comprises a PI3K inhibitor, PDK1 inhibitor, and/or SGK1 inhibitor in a pharmaceutically acceptable carrier.

In certain embodiments, the kit can further include instructions, such as a product insert or label, directing the user to utilize the pharmaceutical formulation for treating cancer in a subject, e.g., in a subject that has a gain-of-function mutation in the PI3K/AKT pathway.

In certain non-limiting embodiments, the kit can comprise means of detecting one or more gain-of-function mutation in the PI3K/AKT pathway, as set forth above. Said means may comprise, for example but not by way of limitation, one or more primer or primer pair for amplification of nucleic acid and subsequent detection of a mutation described above, as embodied in nucleic acid of a subject; one or more nucleic acid probe for detection of a mutation described above, as embodied in nucleic acid of a subject; and/or an antibody, antibody fragment, or single-chain antibody for detection of a protein form of a mutation described above. Said kit may optionally further comprise a product insert or label disclosing that cancer in a subject having a gain-of-function mutation in the PI3K/AKT pathway may be treated with a PI3K inhibitor and a PDK1 and/or DGK1 inhibitor.

6. EXAMPLES

The presently disclosed subject matter will be better understood by reference to the following Example, which is provided as exemplary of the invention, and not by way of limitation.

6.1 Example 1

Targeting of PDK1 renders sensitivity to PI3Kα inhibitors and uncovers a mechanism of SGK1-dependent regulation of mTORC1

Summary

PIK3CA, the gene encoding the alpha isoform of PI3K (PI3Kα), is frequently mutated in breast cancer, providing the rationale for the development of inhibitors that selectively target this isoform. Despite the promising clinical activity of these agents, a proportion of PIK3CA-mutant patients remain insensitive to PI3Kα blockade. We have previously reported that residual mTORC1 activity upon treatment with PI3Kα inhibitors limits sensitivity to these agents in breast cancer. However, the underlying mechanisms that mediate this phenotype are not fully understood. Here, we show that in resistant cells, SGK1 can activate mTORC1 via phosphorylation of TSC2 in a process that requires PDK1. Targeting either PDK1 or SGK1 can restore the antitumoral effect of PI3Kα inhibitors in resistant breast cancer cells.

Introduction

The PI3K pathway integrates many extracellular stimuli, triggering the phosphorylation of key downstream effectors such as AKT and the mammalian Target of Rapamycin Complex 1 and 2 (mTORC1 and 2). This signaling cascade is essential for regulating cell size, proliferation, survival, and metabolism. Activation of PI3K results in the synthesis of the second messenger phosphatidylinositol-(3,4,5)-triphosphate (PIP3) at the plasma membrane, which in turn promotes the recruitment of the pleckstrin homology (PH) domain-containing proteins PDK1 and AKT. The physical proximity at the plasma membrane allows PDK1, a constitutively active kinase, to phosphorylate AKT at the activation loop (T308). A second phosphorylation in the hydrophobic motif (S473) is then carried out by mTORC2 to fully activate AKT. Once active, AKT is able to phosphorylate a variety of substrates including antiapoptotic and cell cycle related proteins or transcription factors. Moreover, AKT predominantly mediates the crosstalk between the PI3K pathway and mTORC1.

Activating mutations in PIK3CA, the gene that encodes for the α isoform of the p110 catalytic subunit of PI3K (PI3Kα), loss of function of phosphatase and tensin homolog (PTEN), the phosphatase that modulates levels of PIP2, and overexpression of membrane-bound receptor tyrosine kinases result in hyperactivation of the PI3K/AKT/mTOR pathway. These events are common in breast cancer and provide the rationale for the development of inhibitors targeting the different nodes of the PI3K pathway.

PI3Kα specific inhibitors are currently showing promising results in patients with tumors bearing activating mutations in PIK3CA. However, despite these encouraging results, some patients treated with these agents remain insensitive. Understanding the molecular mechanisms by which these tumors bypass the pharmacological inactivation of PI3Kα is crucial for the identification of patients that are more likely to respond to these inhibitors and for testing therapeutic options to prevent or delay the emergence of drug resistance.

We have previously reported that the activation status of mTORC1 upon PI3Kα blockade is a determinant of drug sensitivity in PIK3CA-mutant tumors. Despite full inhibition of PI3K/AKT, the presence of residual mTORC1 activity is sufficient to weaken the antitumor activity of PI3Kα inhibition. Resistant tumors are re-sensitized by co-treatment with the mTORC1 allosteric inhibitor everolimus, underscoring the causative role of mTORC1 in limiting the effects of PI3Kα blockade.

In this work, we elucidated the molecular pathway that allows mTORC1 to retain activity in the presence of PI3K and AKT inactivation. These results uncover new aspects of the biology of the PI3K signaling upon pharmacological inhibition and offer novel therapeutic approaches for the clinical setting.

Results

Identification of PDK as a Candidate Kinase Responsible for Resistance to PI3Kα Inhibition Aiming to identify possible kinases or phosphatases responsible for the sustained AKT independent mTORC1 activity in cells resistant to PI3Kα inhibition, we performed an arrayed siRNA screening using a library targeting the genes encoding for the 710 kinases and 298 phosphatases of the human genome. This approach allows measurement of individual wells for cell viability and S6 ribosomal protein phosphorylation, a bona fide read-out of mTORC1 activity, in the presence of BY719, a PI3Kα-specific inhibitor.

Figure 1B:
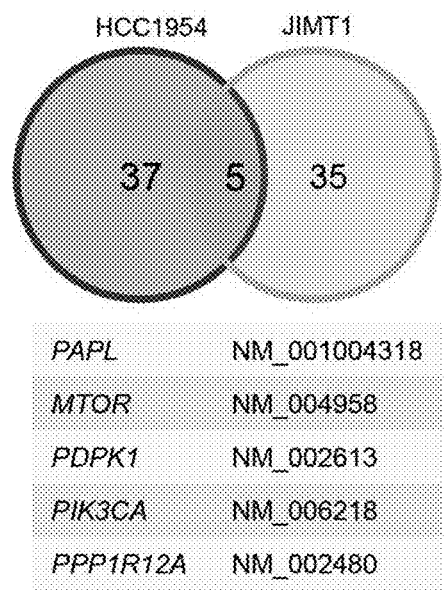
Figure 1C:
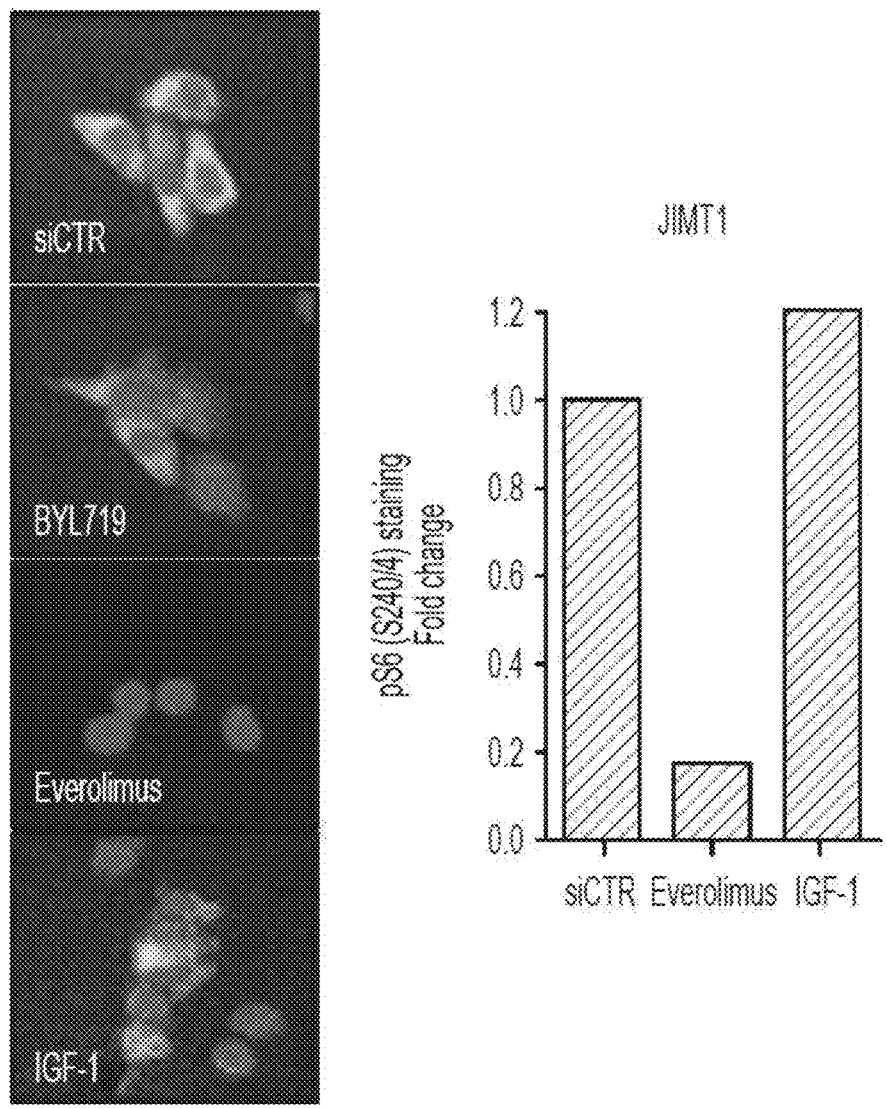
Figure 1D:
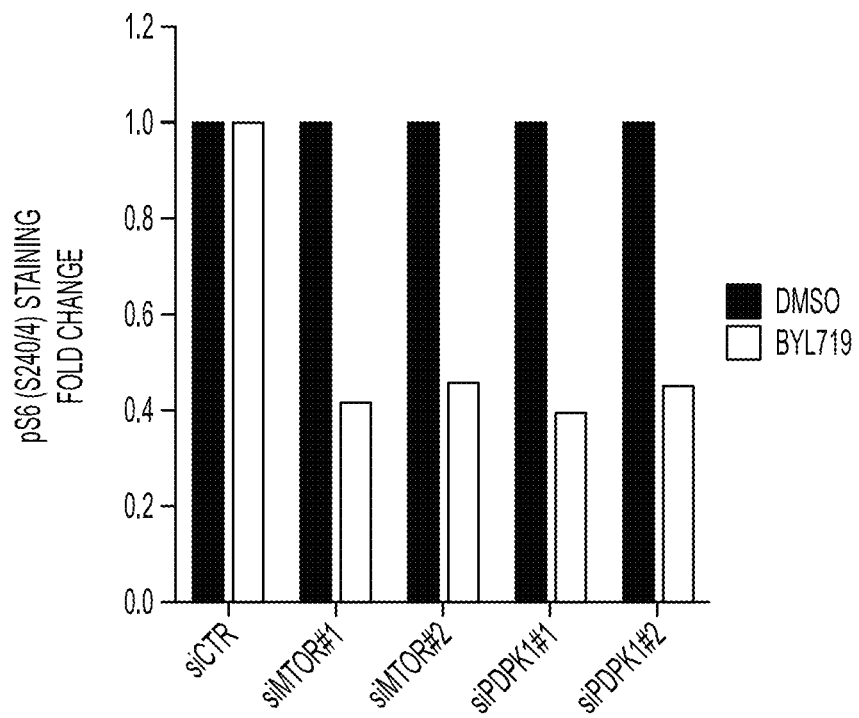
Figure 1E:
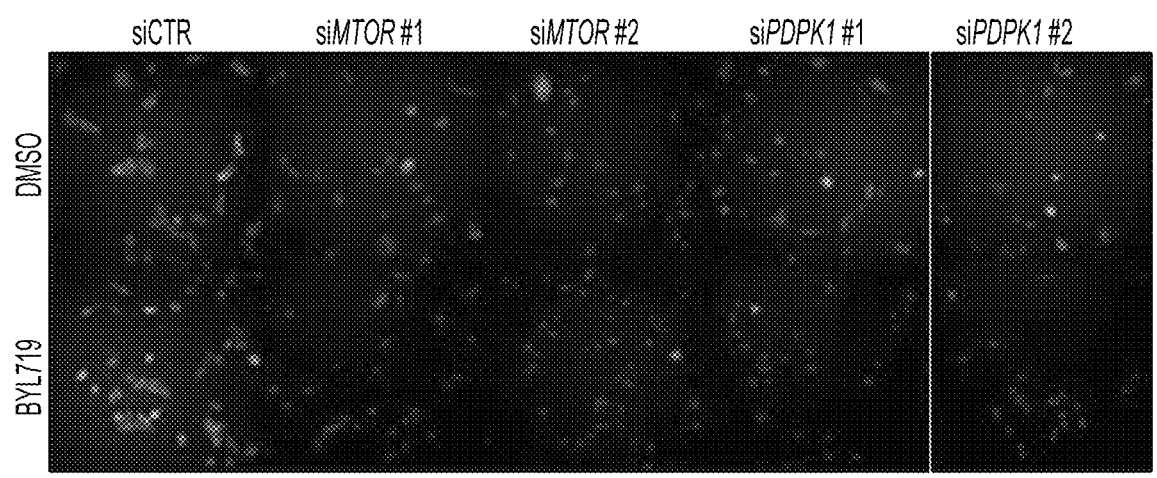

The screen design is shown in FIG. 1A. Three different siRNAs targeting each gene of the kinome/phosphatome and negative (scrambled siRNA) and positive (siPLK1) controls were transfected in JIMT1 and HCC1954 cell lines, both of which are PIK3CA-mutant and insensitive to BYL719. After treatment with BYL719 over 6 days, cell viability was quantified using both Alamar Blue and nuclear count. We found that knockdown of 37 genes in HCC1954 and 35 genes in JIMT1 sensitized cells to BYL719 (FIG. 1B). Among these genes, five were found in common in both cell lines: mTOR, PDPK1, PIK3CA, PPP1R12A, and PAPL (FIG. 1B). These findings were validated with a second targeted screening using the two most active siRNAs against these five genes, interrogating for both cell viability and phosphorylation of S6 (FIG. 1C). With this more stringent approach, we found that only knockdowns of MTOR and PDPK1, the genes encoding mTOR and PDK1, respectively, were capable of sensitizing cells to BYL719 and significantly reduce S6 phosphorylation (S240/4) in the presence of PI3Kα inhibition (FIG. 1D, E). While the ablation of mTOR confirmed our previous data (Elkabets et al., 2013), the contribution of PDK1 in maintaining the resistant phenotype was unknown.

PDK1 Inhibition Sensitizes BYL719-Resistant Cells In Vitro and In Vivo

PDK1 is a kinase that belongs to the AGC kinase family, a phylogenetically related family of 60 serine-threonine kinases that includes some well-studied members such as AKT, PKC, RSK, and S6K (Pearce et al., 2010).

Figure 2A:
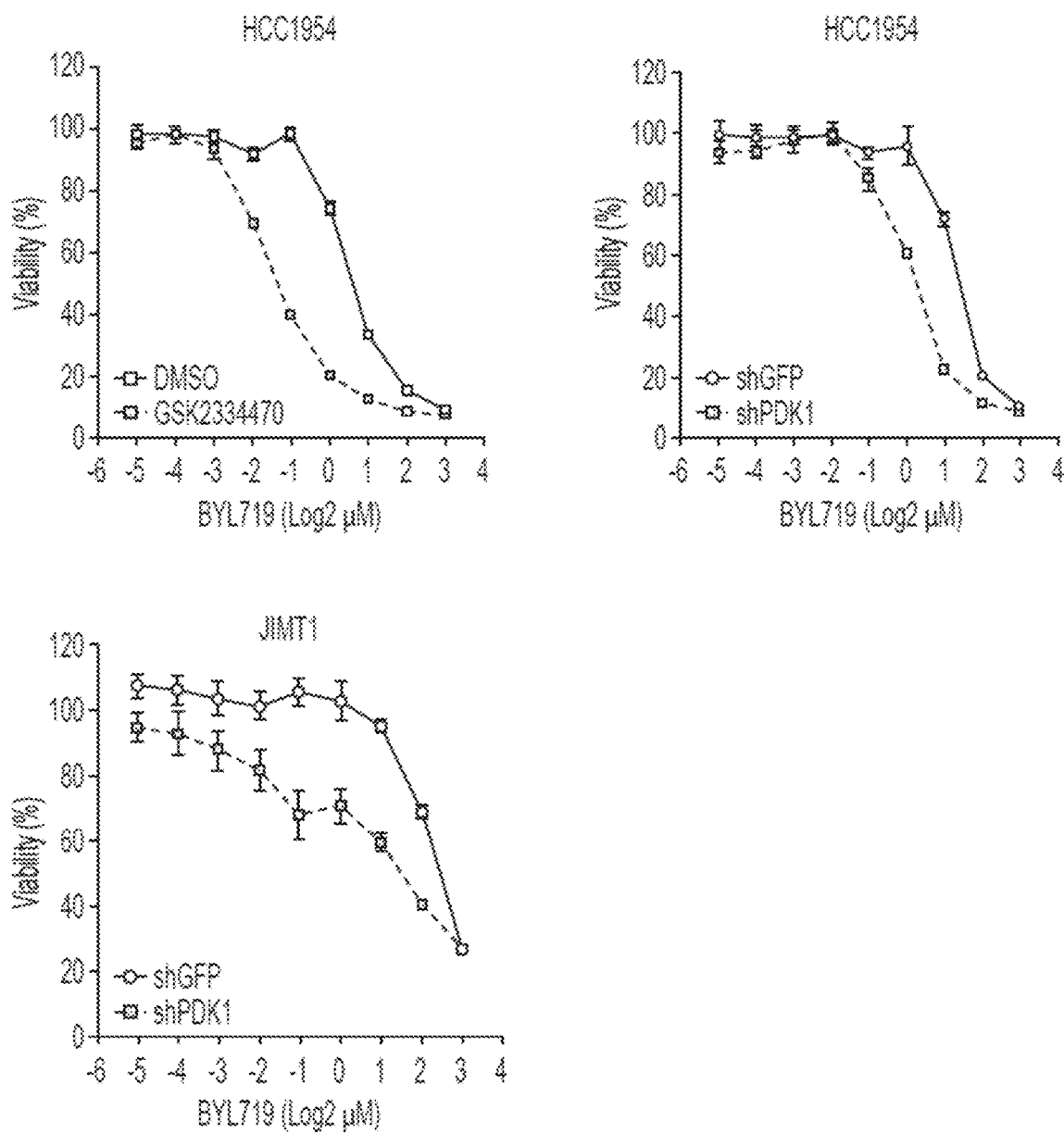
Figure 2B:
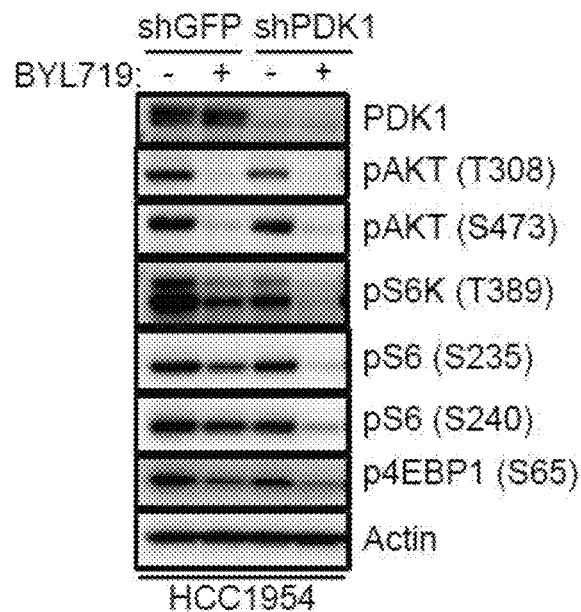
Figure 2B:
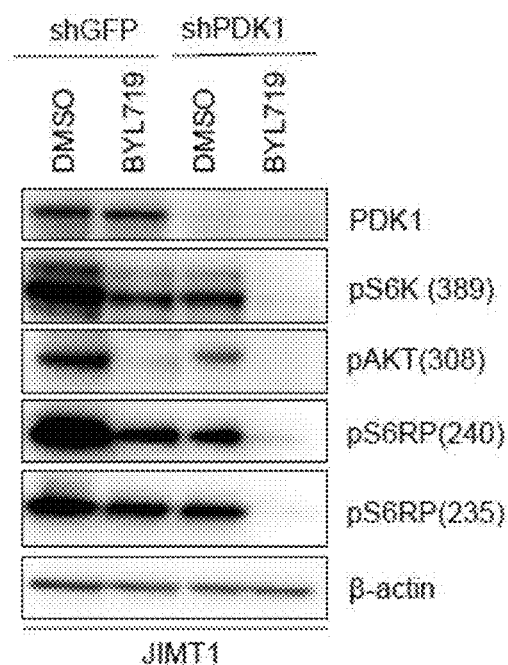
Figure 2C:
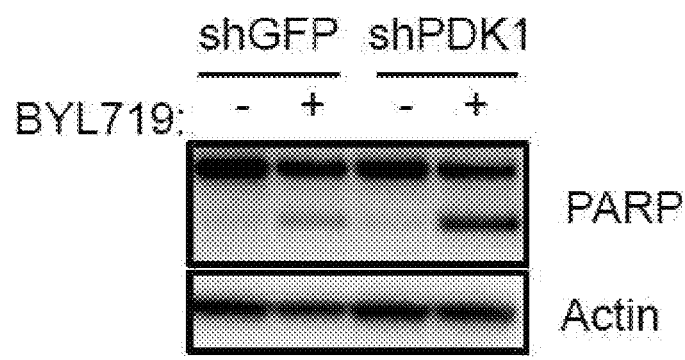
Figure 2C:
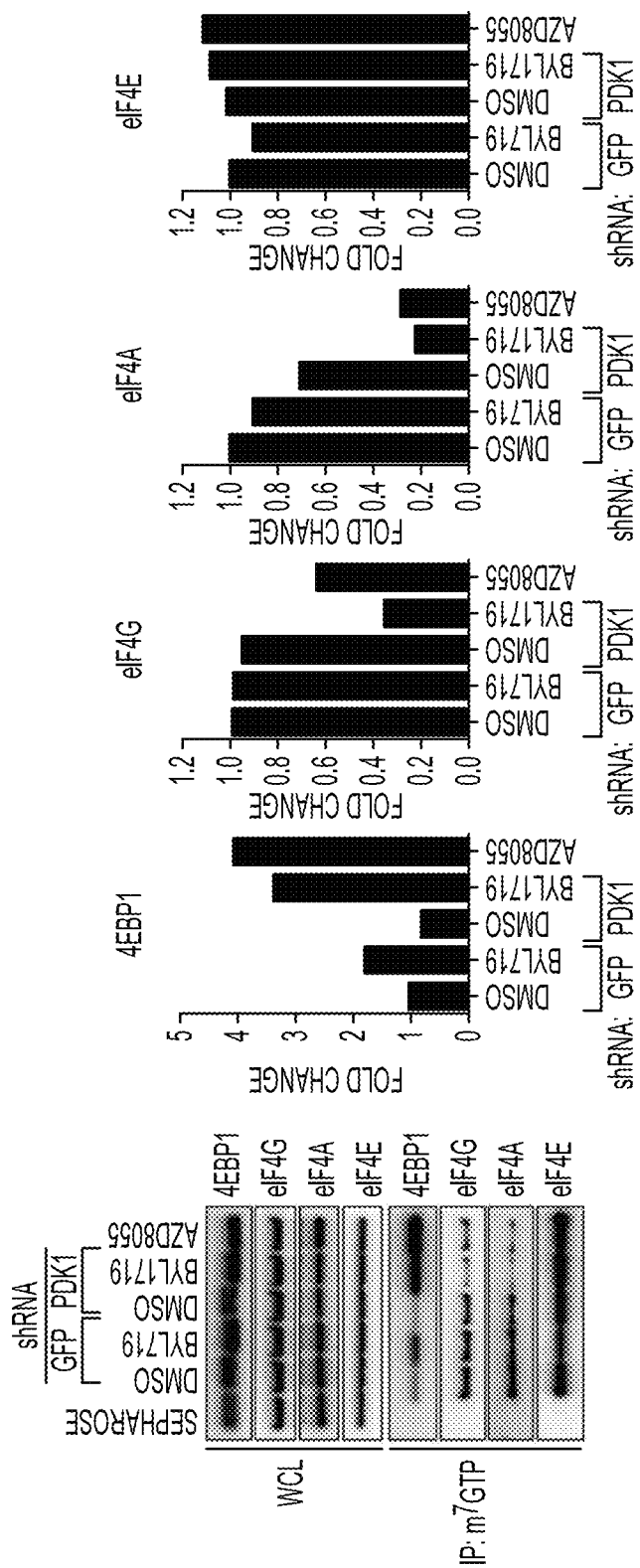
Figure 2D:
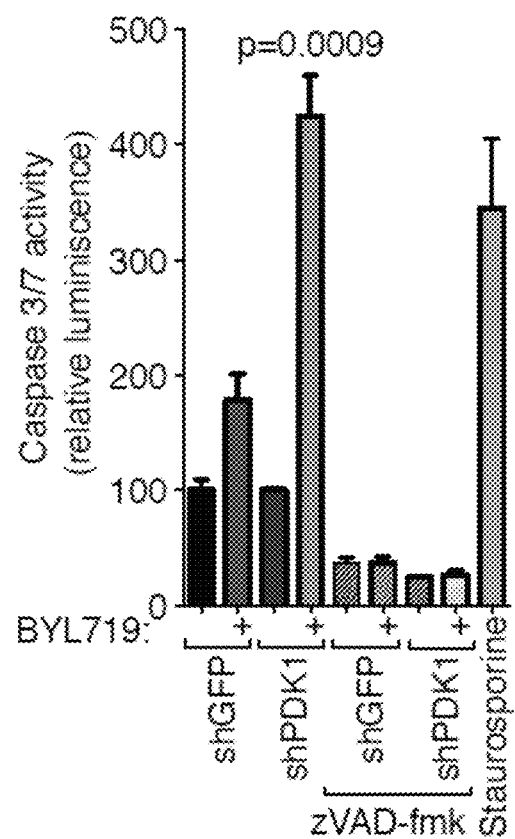

To confirm that PDK1 limits the sensitivity to PI3Kα inhibition by maintaining mTORC1 activity upon PI3Kα inhibition, we generated HCC1954 and JIMT1 cell lines stably expressing a PDK1 short hairpin RNA (shRNA). We observed that PDK1 knockdown is sufficient to decrease cell viability upon BYL719 treatment (FIG. 2A). As previously described, treatment with BYL719 alone reduced AKT phosphorylation (S473 and T308) but not downstream mTORC1 targets, (Elkabets et al., 2013). In contrast, the combination of PDK1 knockdown with BYL719 decreased the phosphorylation of the mTORC1 downstream targets p70 S6 Kinase (S6K) and translation initiation factor 4E-binding protein (4EBP1), as well as phosphorylated S6 at both S240/4 and S235/6 sites (FIG. 2B). As a result, the combination of BYL719 and PDK1 knockdown decreased cap-dependent translation (FIG. 2C), a cellular process directly regulated by mTORC1 (Silvera et al., 2010). In PDK1 knockdown cells, inhibition of PI3Kα induced an increased binding of 4EBP1 to the cap m$^7$GpppN mRNA analogue m$^7$GTP, to a similar extent as the mTOR kinase inhibitor AZD8055. On the contrary, we observed a reduction of the eukaryotic initiation factors (eIF) eIF4G and eIF4A, components of the eIF4F cap-initiation complex. As expected, eIF4E remained unchanged. In long term treatments, the combination of BYL719 and PDK1 knockdown induced PARP cleavage (FIG. 2C) and increased caspase 3/7 activity (FIG. 2D), surrogate markers of apoptotic activity.

Figure 2E:
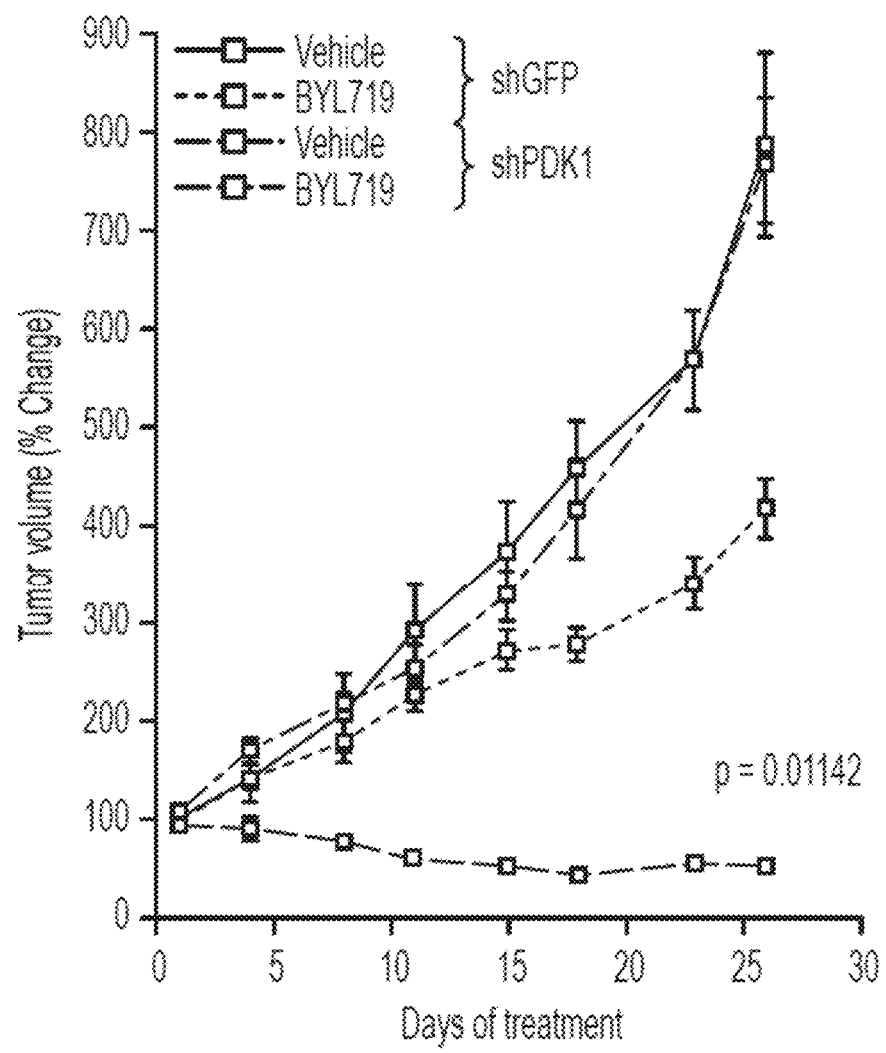
Figure 2F:
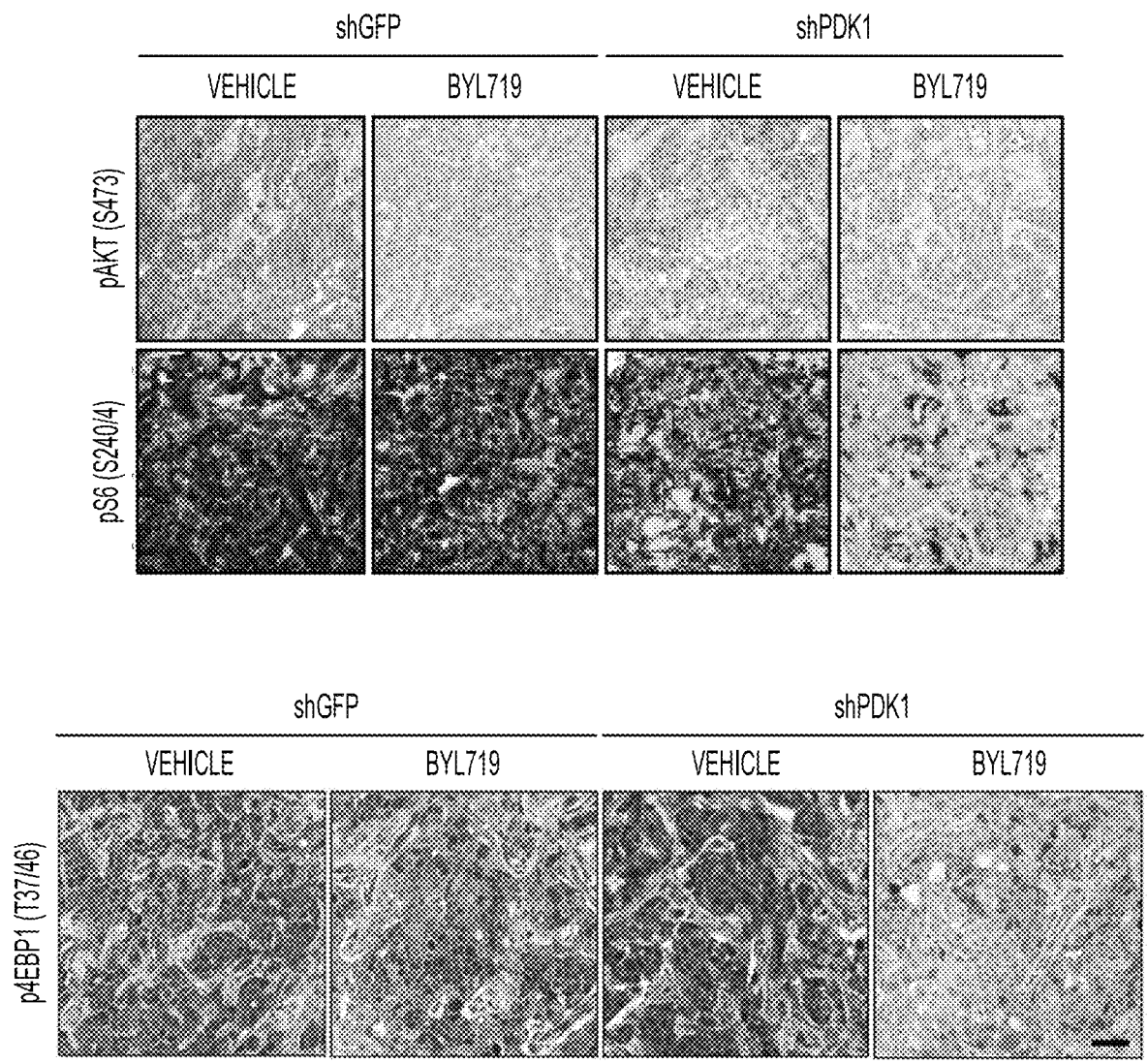

Next, we sought to test the in vivo antitumor activity of BYL719 in HCC1954 xenografts expressing either shGFP control or shPDK1. Pharmacological inhibition of PI3Kα with BYL179 resulted in a modest delay in tumor growth in shGFP xenografts but was sufficient to induce durable tumor shrinkage in tumors with ablated PDK1 (FIG. 2E). Pharmacodynamic analyses of the tumors collected at the end of the experiments showed that BYL719 treatment effectively suppressed AKT phosphorylation (S473) in both shGFP and shPDK1 tumors, whereas S6 phosphorylation (S240/4) and 4EBP1 (T37/46) was inhibited only in shPDK1 xenografts (FIG. 2F).

Figure 2G:
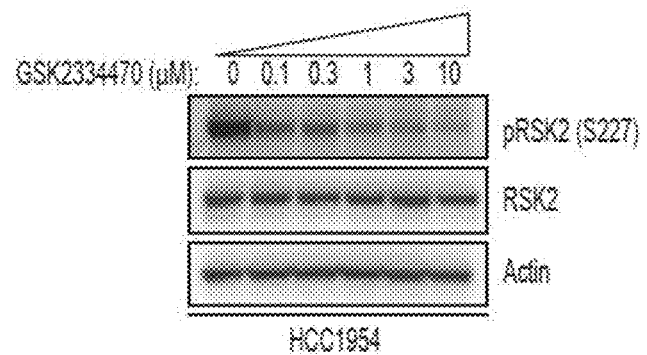
Figure 2G:
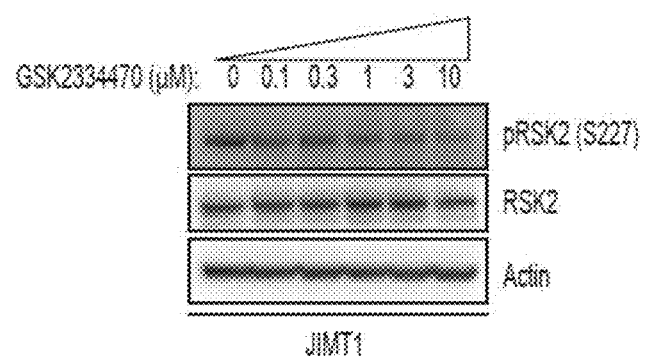
Figure 2G:
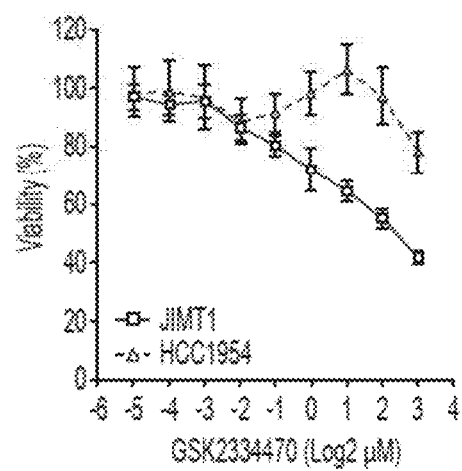
Figure 2G:
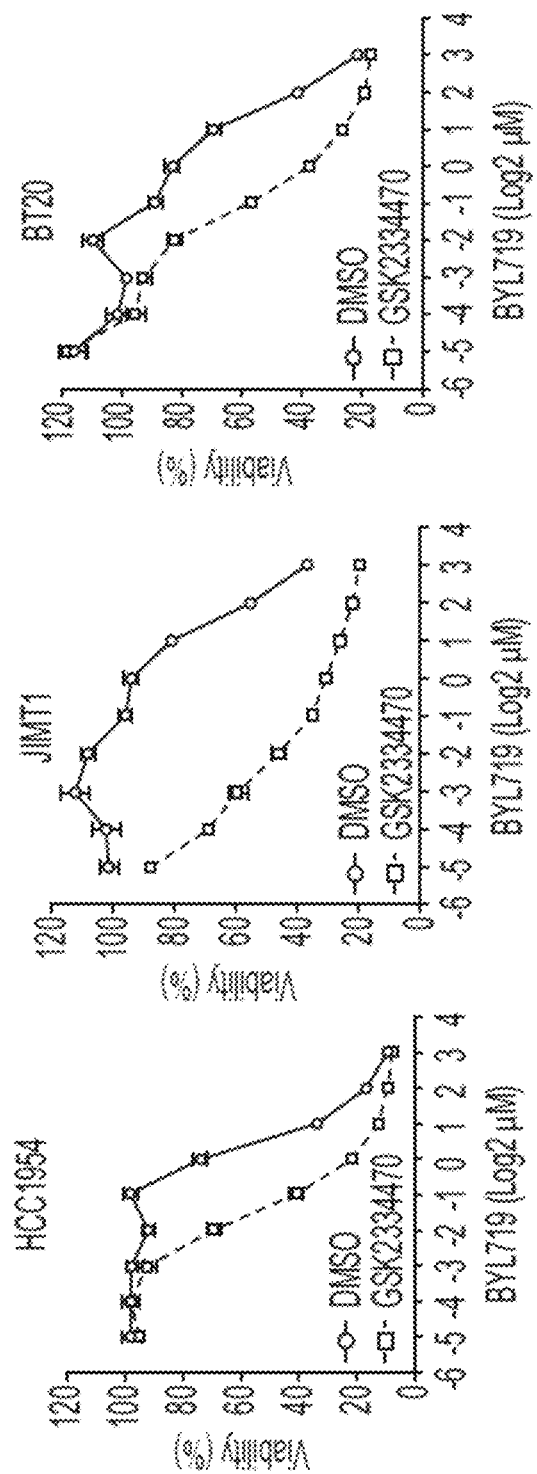
Figure 2H:
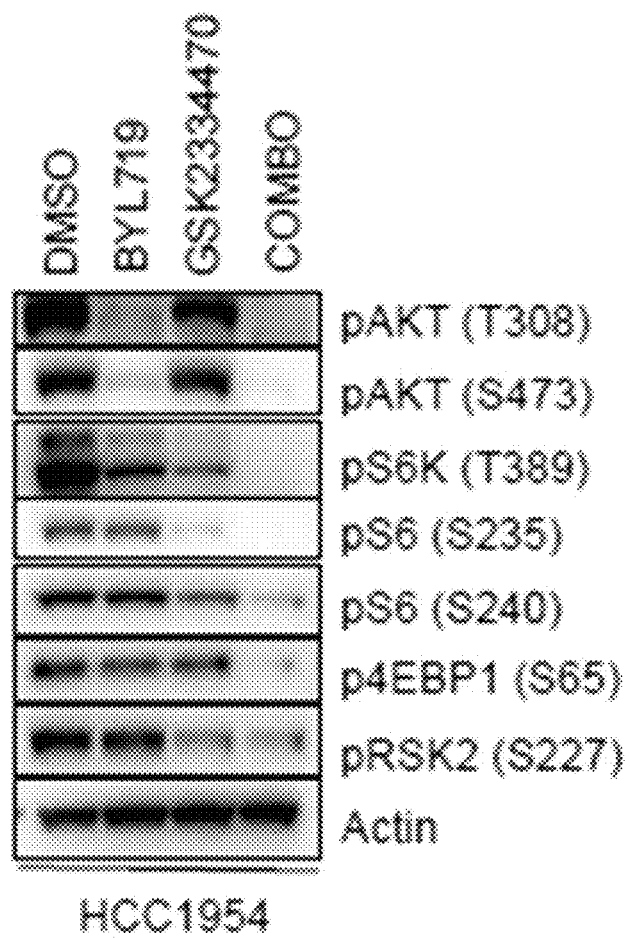
Figure 2I:
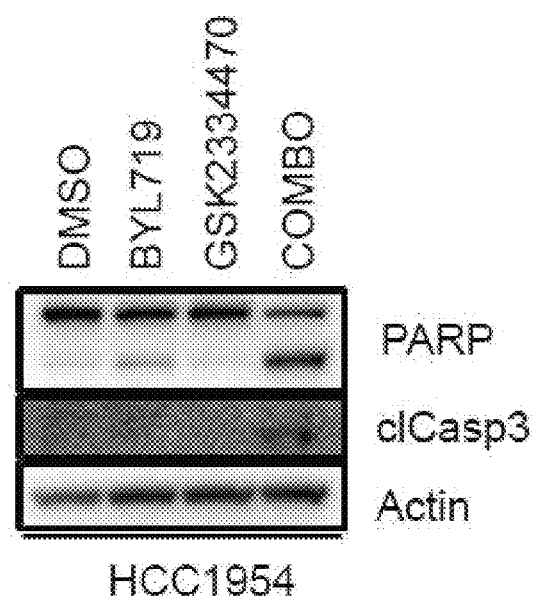
Figure 2J:
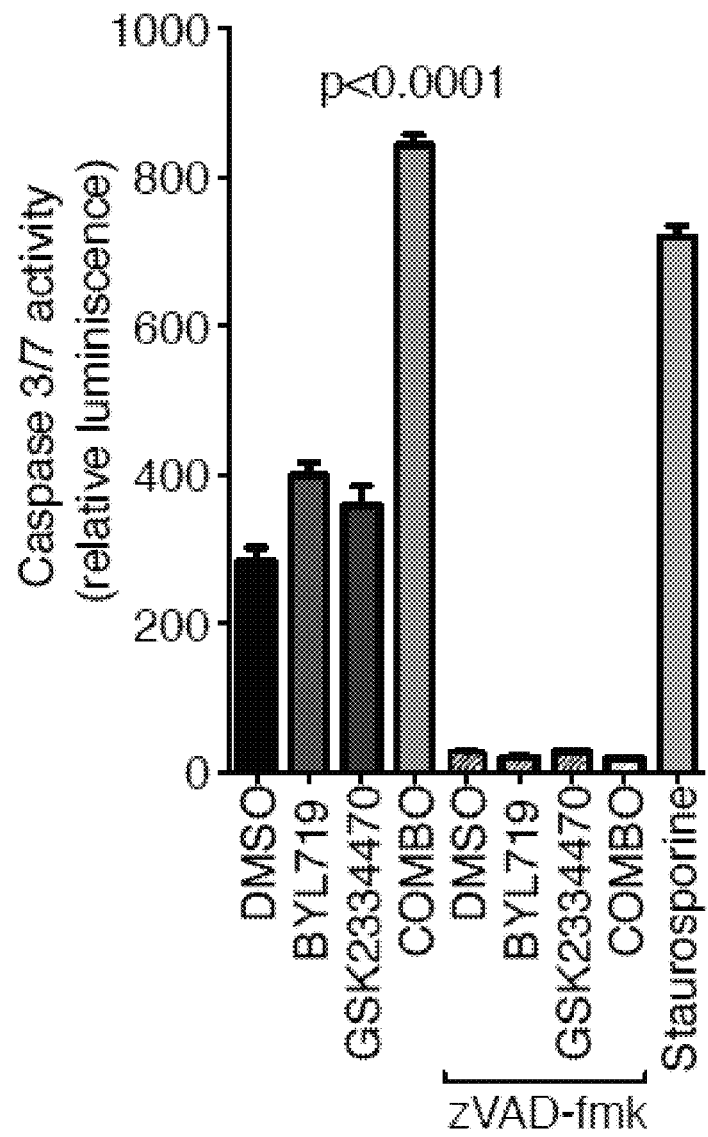
Figure 9A:
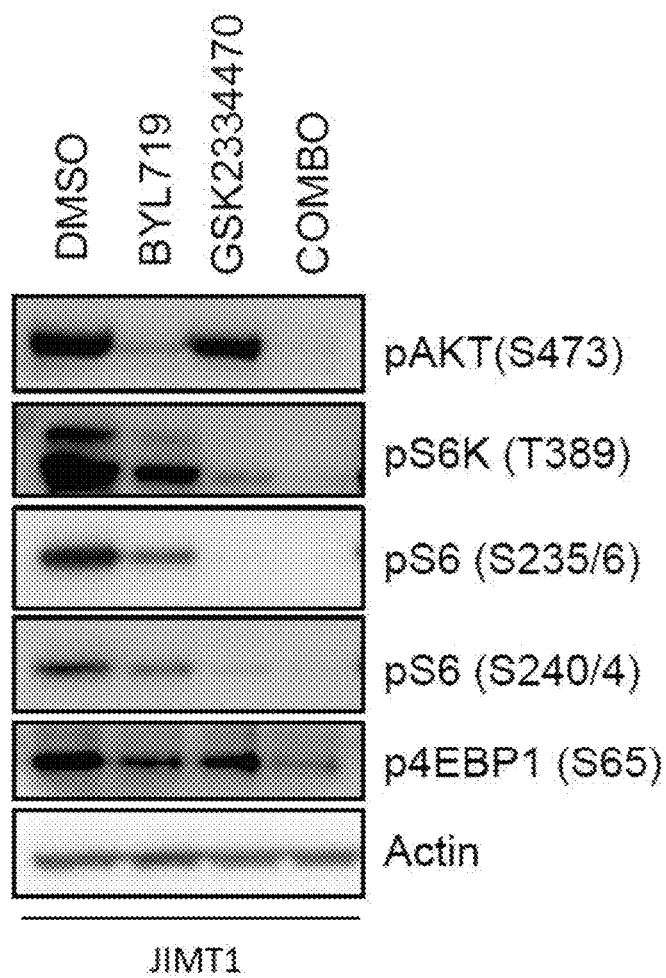
Figure 9B:
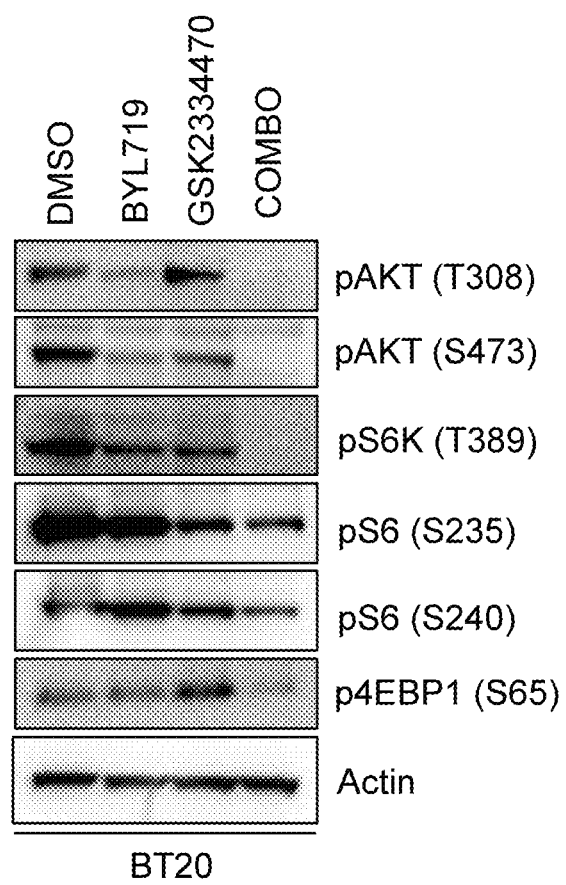
Figure 9C:
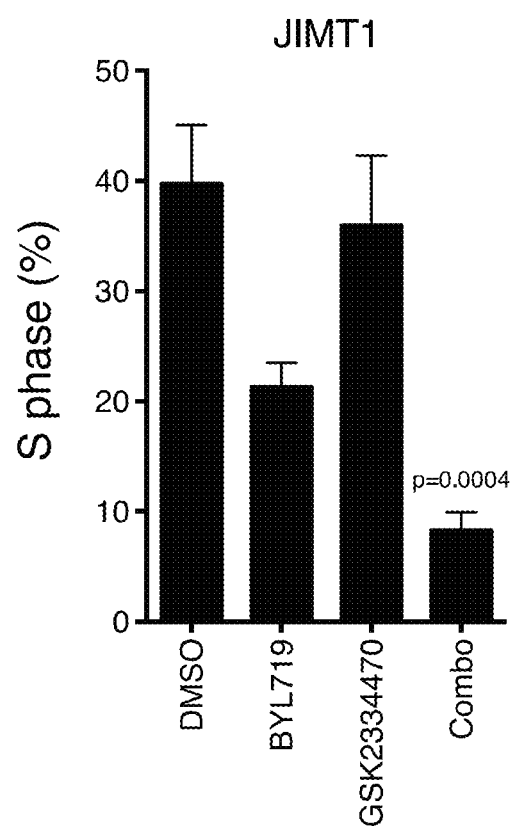
Figure 9D:
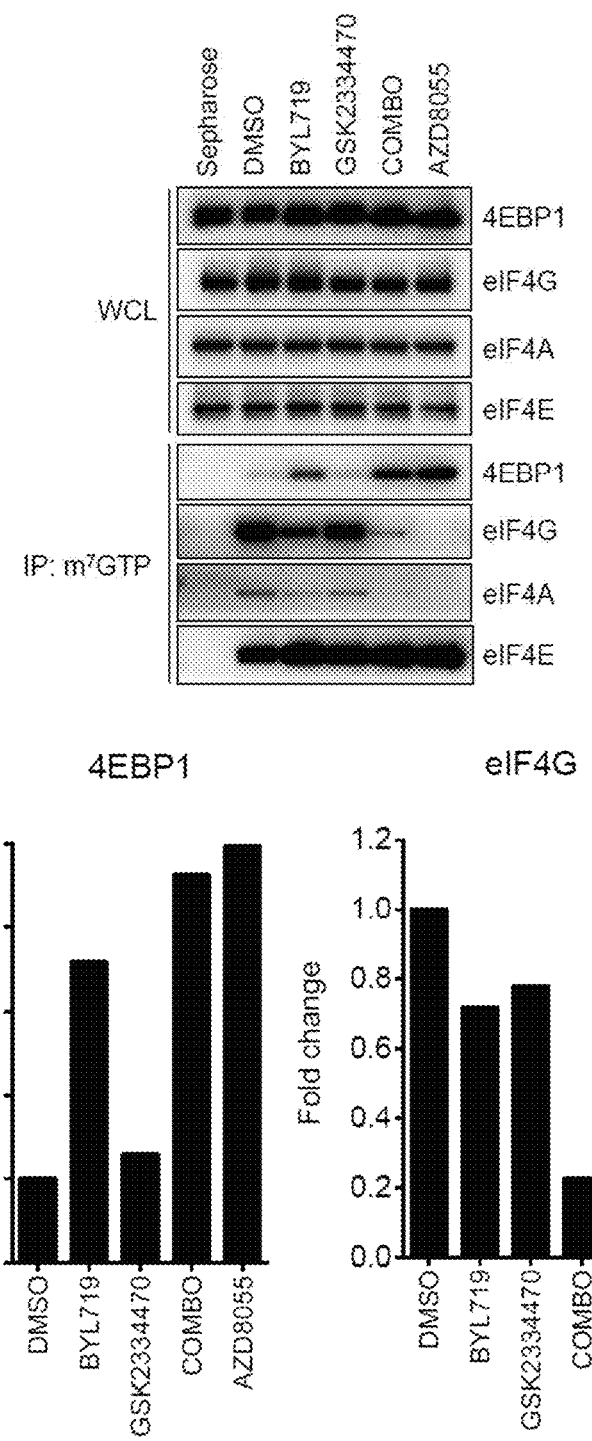
Figure 9D:
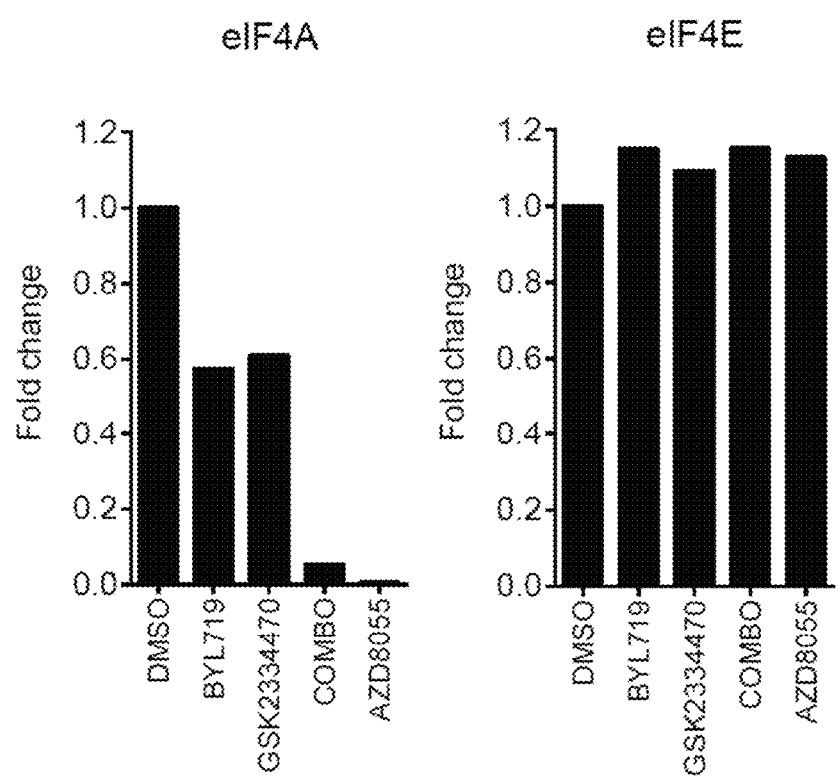

The PDK1 Inhibitor GSK2334470 Sensitizes BYL719-Resistant Cells In Vitro and In Vivo We tested the activity of BYL719 in combination with GSK2334470, a highly selective PDK1 inhibitor (Najafov et al., 2011). We determined the appropriate dose of GSK2334470 to be used in combination with PI3Kα inhibition by analyzing both phosphorylation of the PDK1 target RSK2 (S227) and cell viability upon incubation with increasing concentrations of the PDK1 inhibitor. At 1 µM, pRSK2 (S227) was appreciably reduced with no significant changes on cell viability (FIG. 2G). Despite the minimal effect on cell viability when used as a single agent, treatment with GSK2334470 was sufficient to sensitize the intrinsically resistant cell lines HCC1954, JIMT1, and the triple-negative breast cancer cell line BT20 to PI3Kα inhibition (FIG. 2G). By western blot, we observed that BYL719 effectively suppressed AKT activity but not mTORC1 signaling and only the combination of BYL719 and GSK2334470 resulted in the inhibition of mTORC1 in HCC1954 cells (FIG. 2H; FIG. 9A, B). Some residual pS6 was observed in BT20 cells, which might be attributed to the heterogeneity of the cell line or additional mechanisms that regulate S6 phosphorylation. Phosphorylation of RSK2 (S227), a surrogate of direct PDK1 phosphorylation, is inhibited when cells are treated with GSK2334470 alone or in combination, indicating a good degree of inhibition of this enzyme in vitro (FIG. 2H). PDK1 inhibition did not decrease the phosphorylation of AKT at the activation loop (T308) as a result of a compensatory mechanism involving PIP3 and mTORC2, an observation in line with previous reports (Najafov et al., 2012). Analysis of cap-dependent translation complex formation revealed an increase in 4EBP1 and a decrease in eIF4G and eIF4A in m7GTP pull downs when both drugs were combined, consistent with mTORC1 inhibition (FIG. 9D). Consistent with the knockdown experiments, the combination of BYL719 and GSK2334470 induced apoptosis in HCC1954 cells when measured by PARP cleavage (FIG. 2I) and caspase 3/7 activity (FIG. 2J).

Figure 2K:
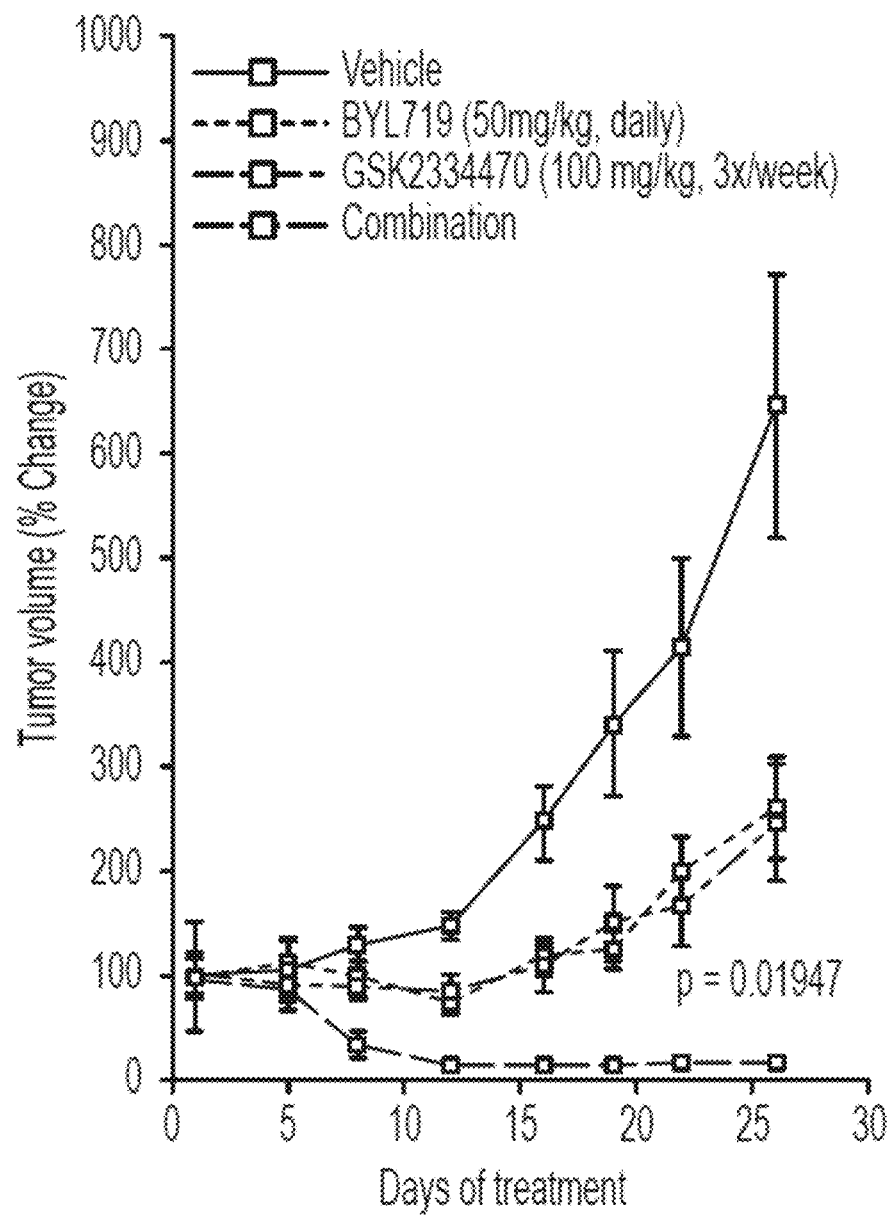
Figure 2L:
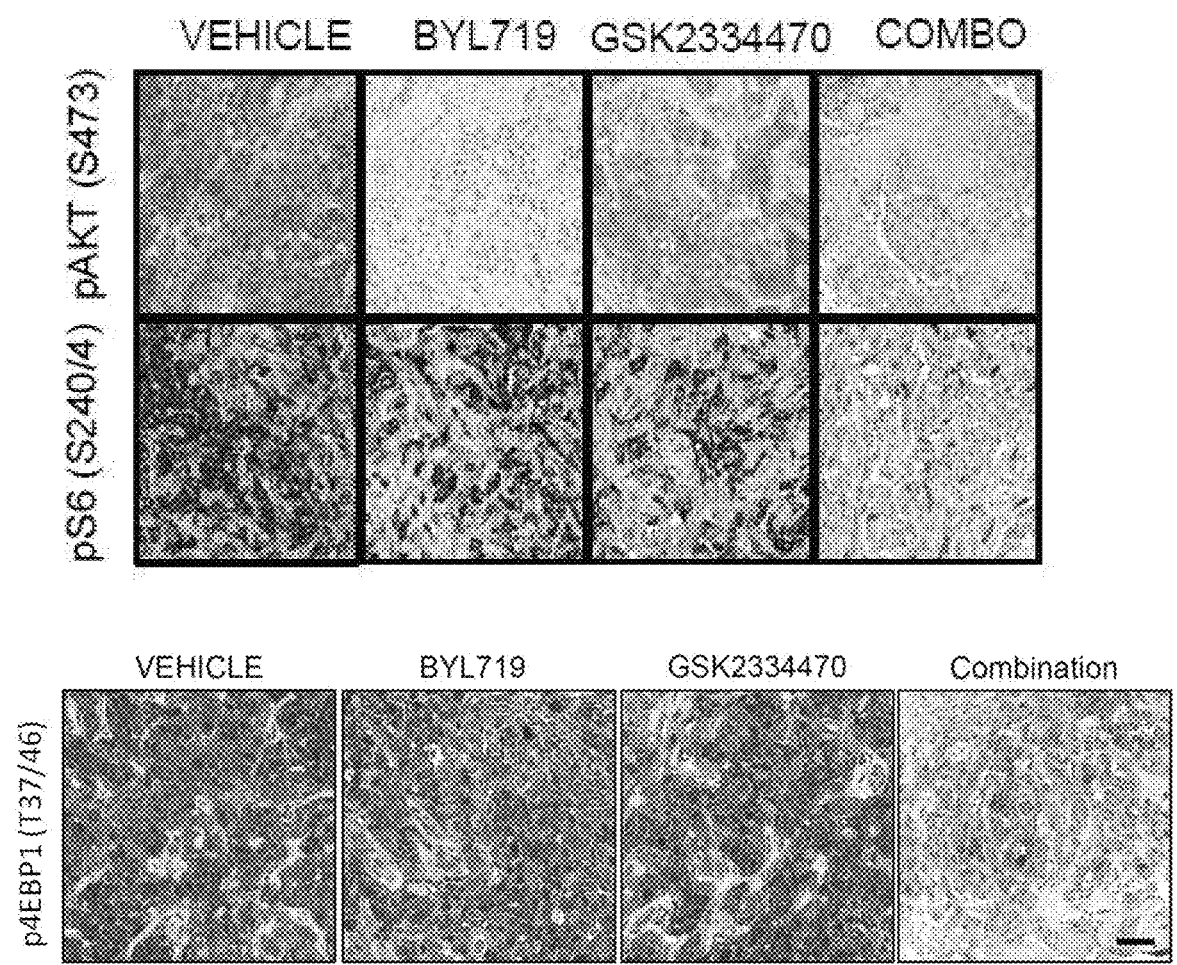
Figure 2M:
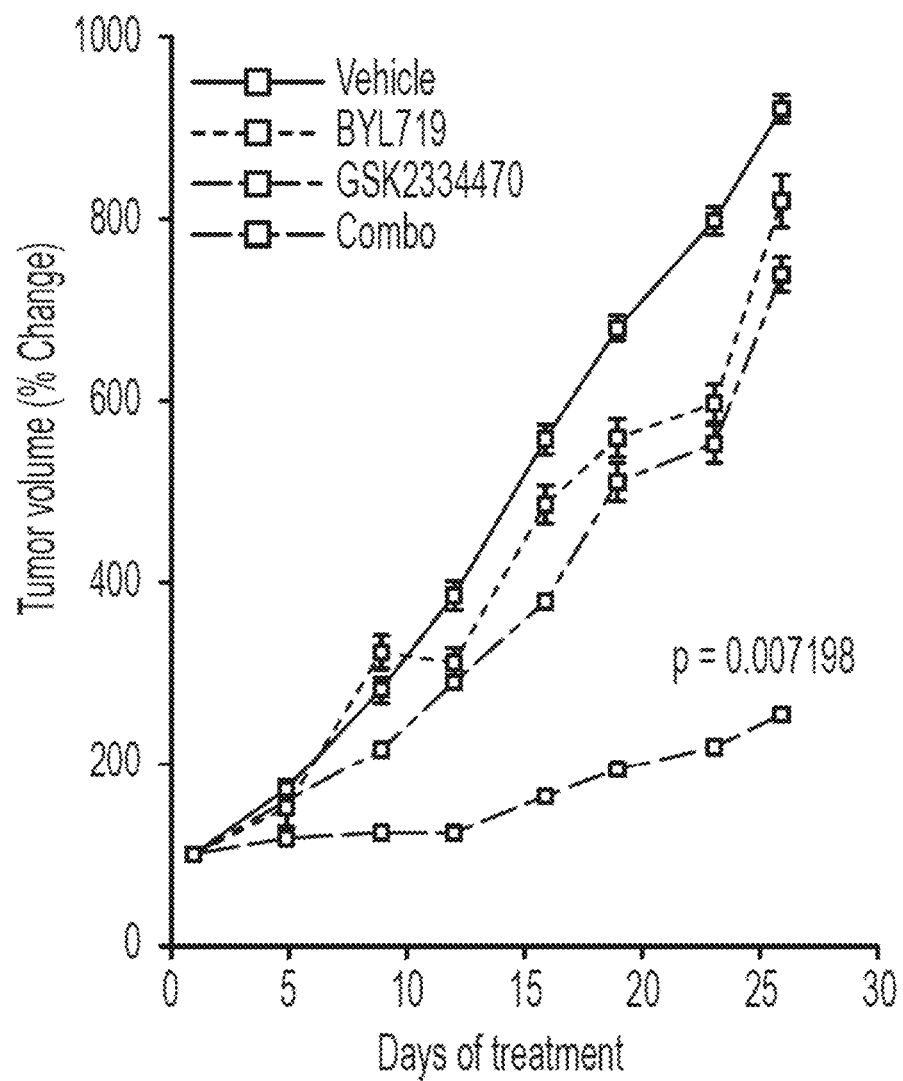
Figure 2N:
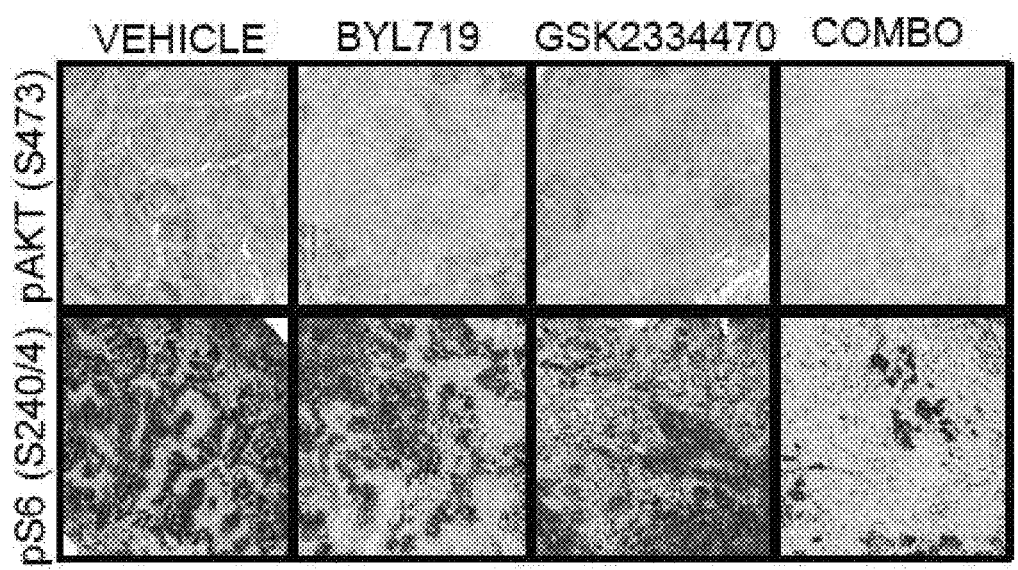

Next, we expanded our results in vivo by treating HCC1954 xenografts with BYL719, GSK2334470, or the combination of both agents. Although some antitumor activity is observed with single agent treatments, only the combination of both compounds induced durable tumor shrinkage (FIG. 2K). We measured the levels of pAKT (S473), pS6 (S240/4), and 4EBP1 (T37/46) in the tumors at the end of the experiments and observed that, while BYL719 monotherapy is sufficient to suppress pAKT, pS6 and 4EBP1 are inhibited only when both agents were used in combination (FIG. 2L). Consistent results were obtained with JIMT1 xenografts, although this cell line does not exhibit apoptosis upon drug combination but cell cycle arrest instead (FIG. 2M, 2N, and 9C). Taken together, these results indicate that PDK1 inhibition sensitizes to PI3Kα blockade via suppression of mTORC1.

The PIF-Binding Pocket of PDK1 is Required for Sustained mTORC1 Activation Upon PI3Kα Inhibition The activation of AGC kinases requires phosphorylation at two highly conserved regulatory motifs termed the hydrophobic motif (HM), at the C-terminal region, and the activation loop, in the catalytic domain. Several kinases prime AGC kinases for activation through phosphorylation at the HM. PDK1, which acts as a master regulator of this family of kinases, scaffolds at the phosphorylated HM using the PIF (PDK1-interacting Fragment) binding pocket. This interaction enables phosphorylation of the activation loop, thereby fully activating their activity.

Figure 8A:
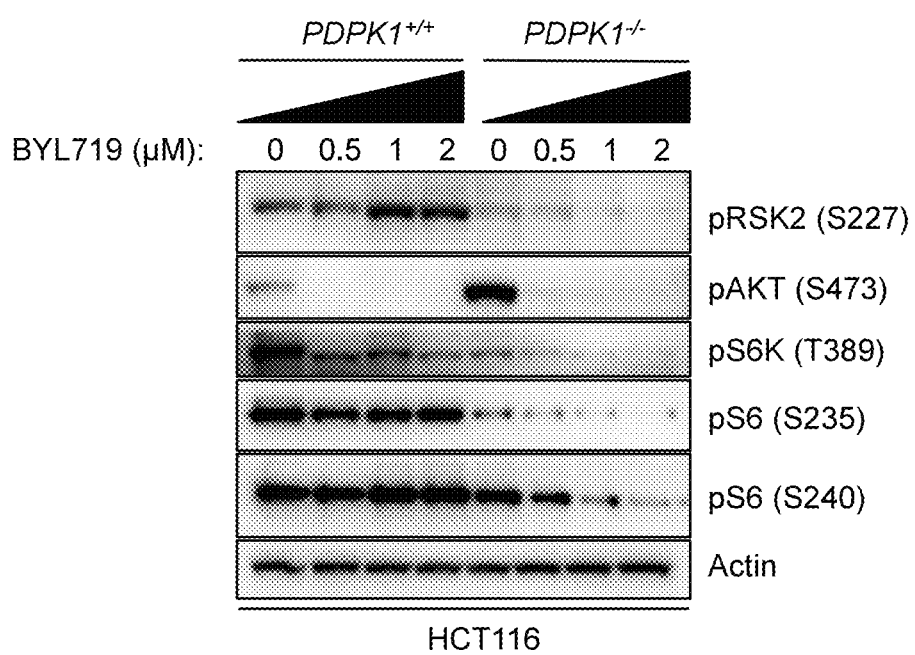

However, AKT does not require the PIF binding pocket of PDK1 but instead needs its PH domain in order to interact with PDK1 at the plasma membrane in a $PIP_3$-dependent manner (Alessi et al., 1997; Arencibia et al., 2013; Biondi et al., 2001; Collins et al., 2003; McManus et al., 2004). In order to explore the PDK1 regulatory mechanism required to sustain mTORC1 activity upon PI3Kα inhibition, we used the HCT116 parental and PDPK1-null (PDPK1$^{-/-}$) isogenic model (Ericson et al., 2010). HCT116 cells harbor the H1047R PIK3CA-activating mutation and the addition of BYL719 decreases AKT phosphorylation independently of the genetic manipulation. In parental cell lines, the addition of BYL719 does not decrease mTORC1 signaling, mimicking the phenotype observed in BYL719-resistant breast cancer cell lines. However, in PDPK1-/- cells, the addition of BYL719 inhibits mTORC1, consistent with our previous experiments (FIG. 8A).

Figure 8B:
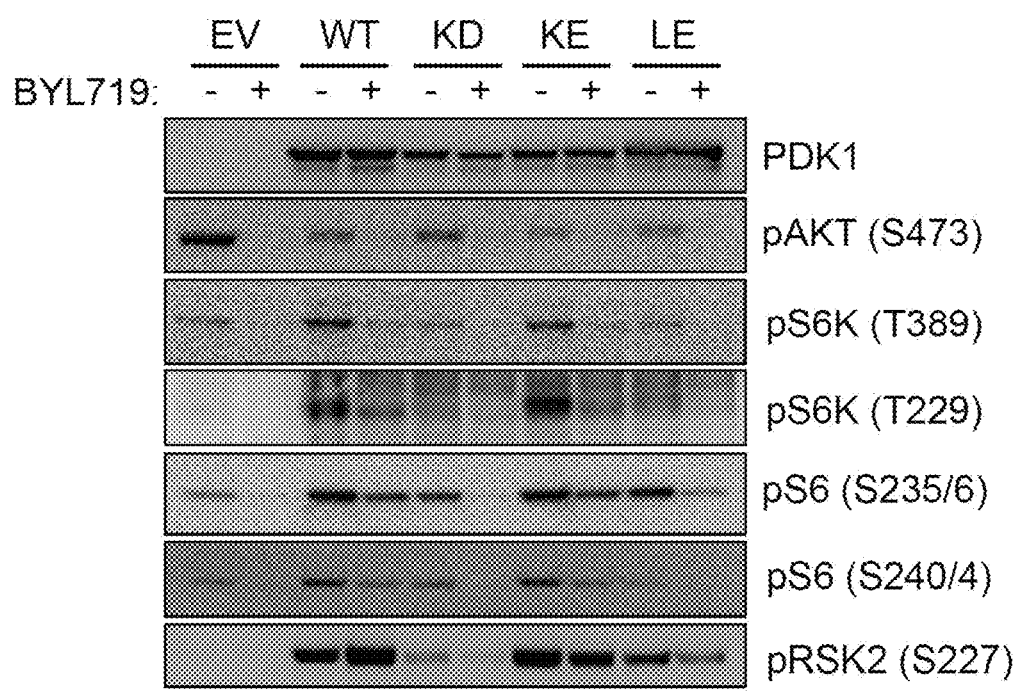
Figure 8C:
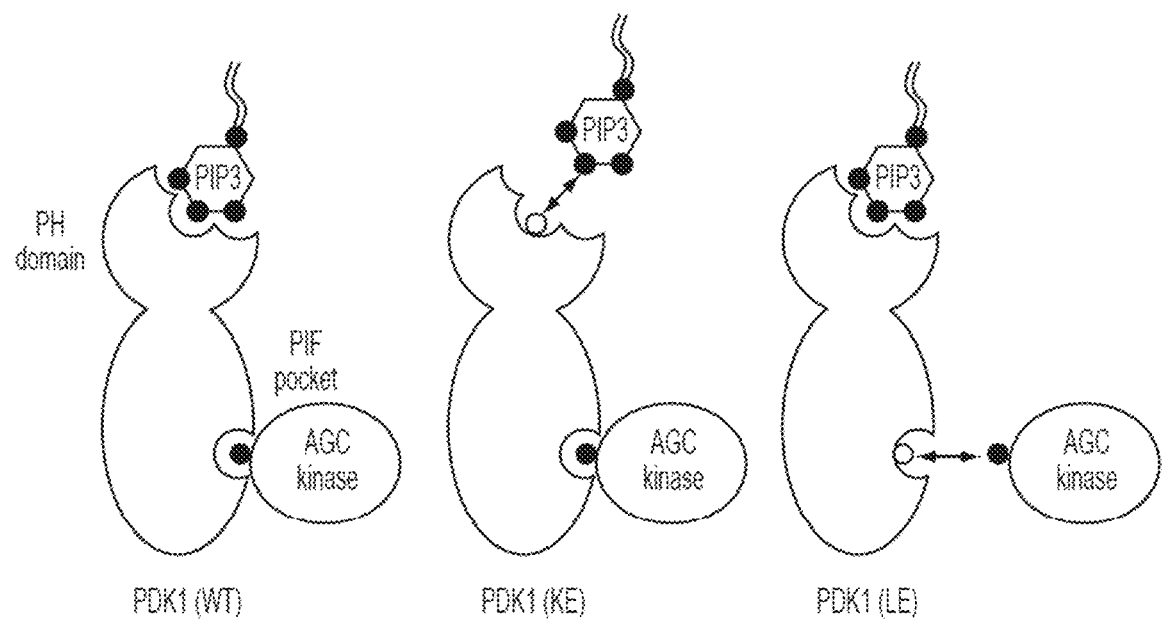

We reconstituted HCT116 PDPK1-/- cells with different PDK1 mutants and tested the contribution of each regulatory mechanism of PDK1 to mTORC1 activation. We included wild type (WT), kinase inactive K111N (KD), PIP3-binding deficient K546E (KE), and PIF pocket-deficient L155E (LE) mutants (FIG. 8C).

Reconstitution of PDK1 WT, but not the kinase inactive mutant KD, restored mTORC1 activation in the presence of BYL719. The PH domain mutant KE, which is unable to bind PIP3, was also able to restore the phenotype, suggesting that the maintenance of mTORC1 is PIP3-, and consequently, AKT-independent. On the other hand, the PIF binding pocket mutant LE was unable to rescue mTORC1 signaling (FIG. 8B). This set of experiments suggests that the kinase activity of PDK1 is required for the activation of mTORC1 in a PIF binding pocket dependent manner.

Combined Suppression of PI3Kα and PDK1 Activates FOXO-Dependent Transcription

Figure 3A:
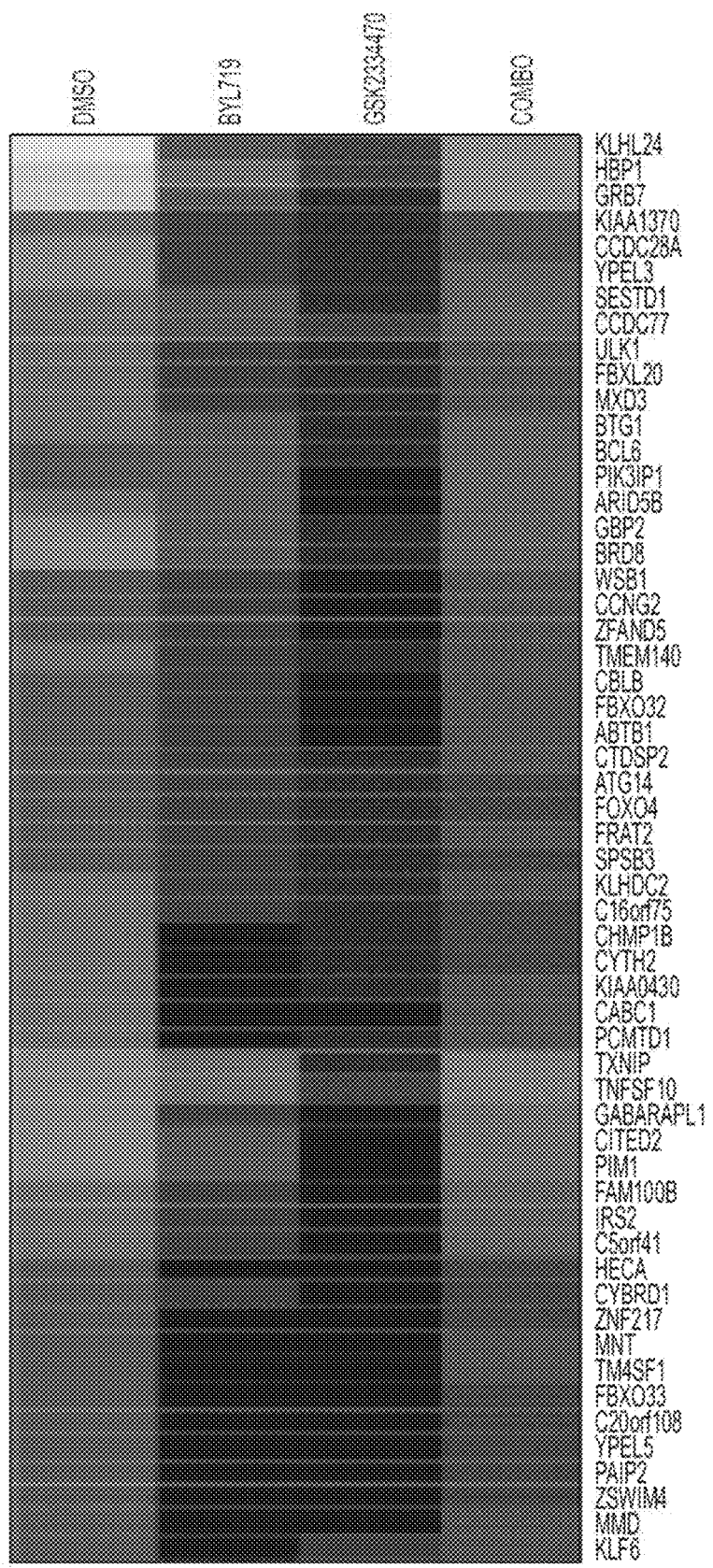
Figure 3A:
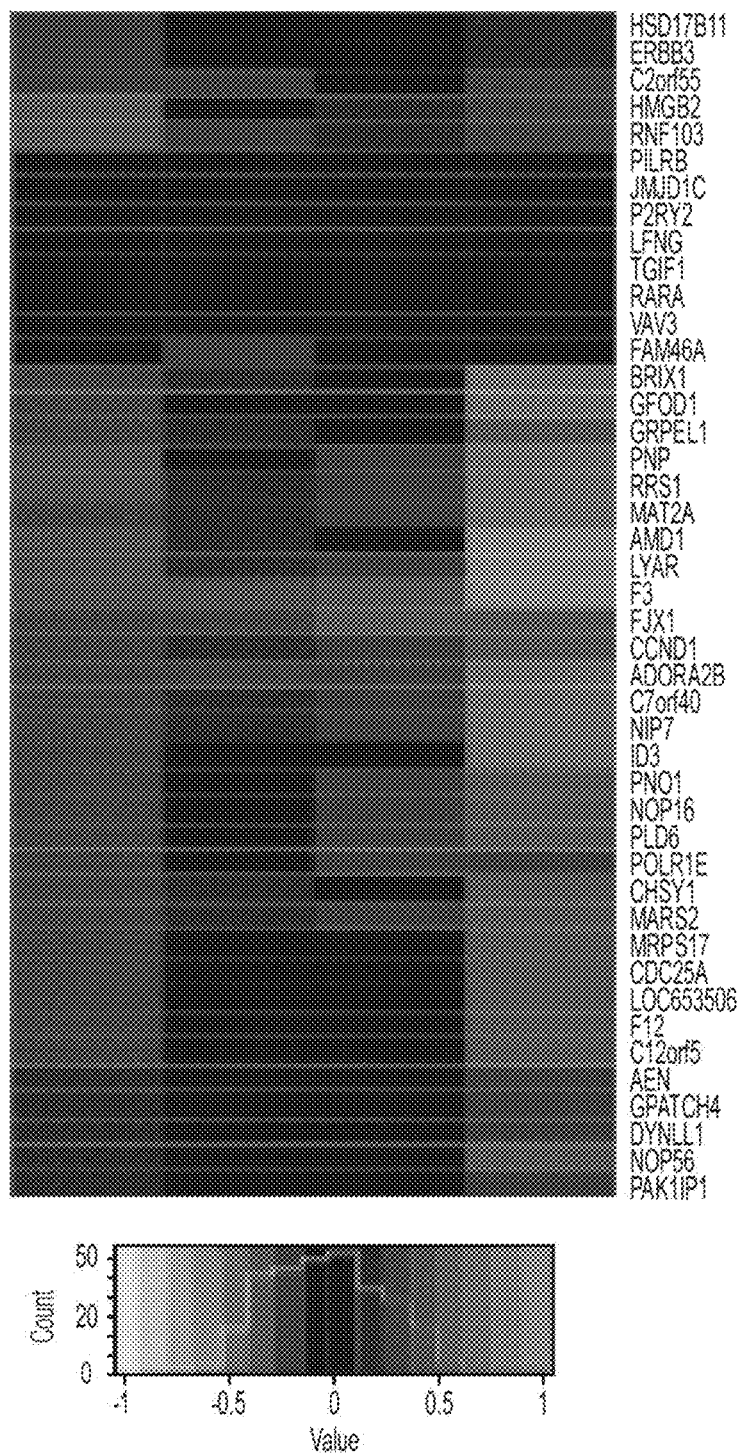
Figure 3B:
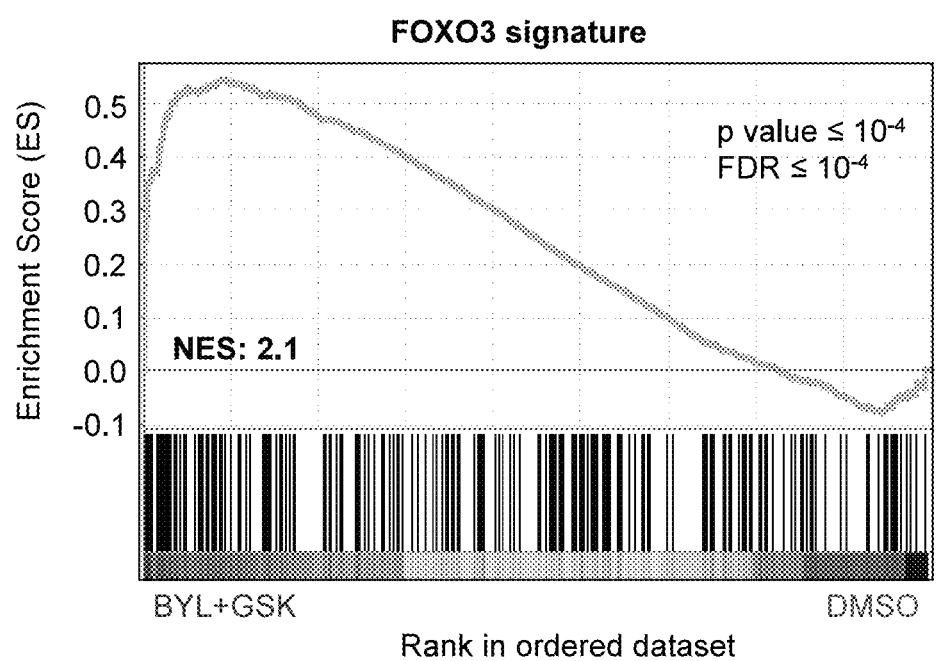
Figure 10A:
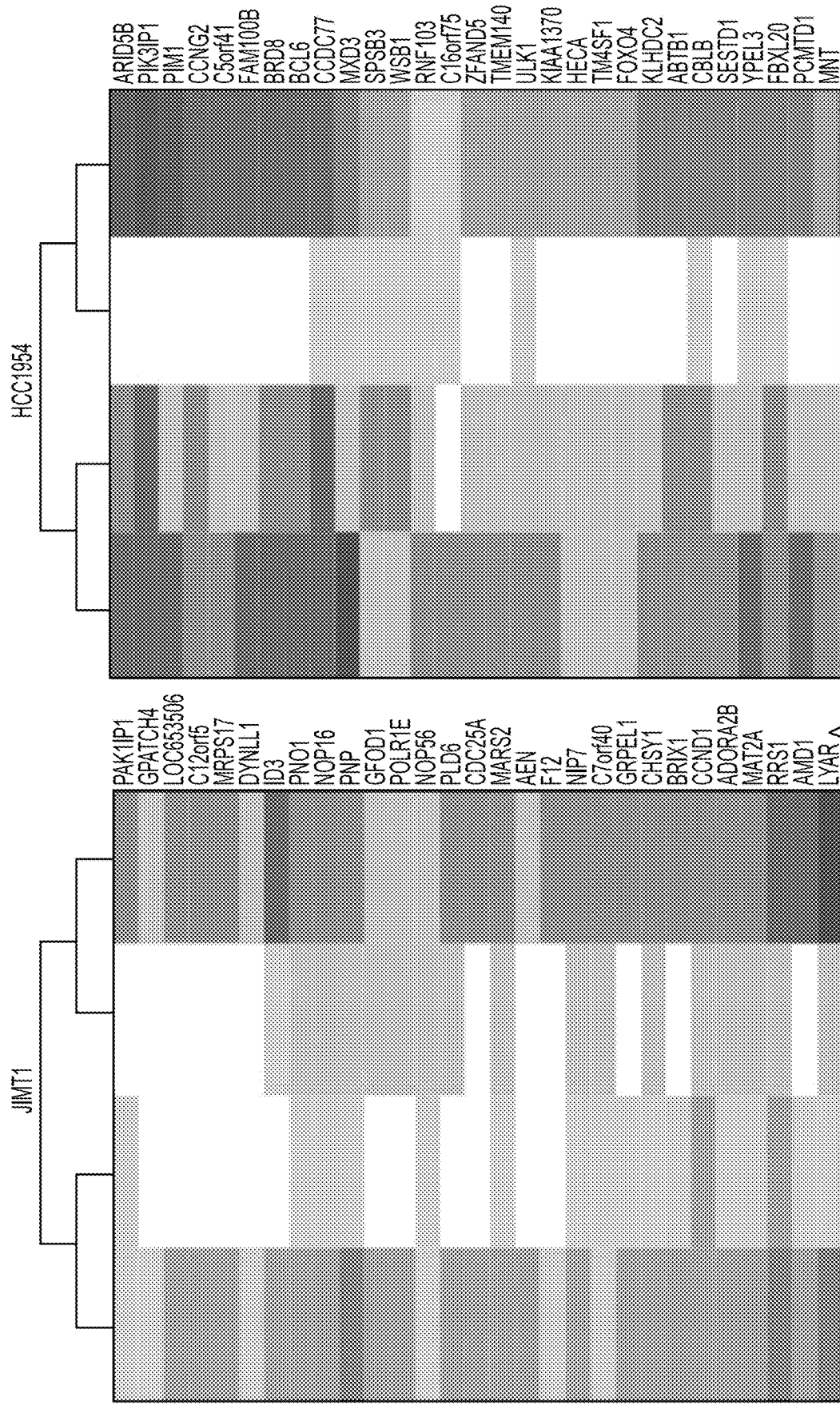
Figure 10A:
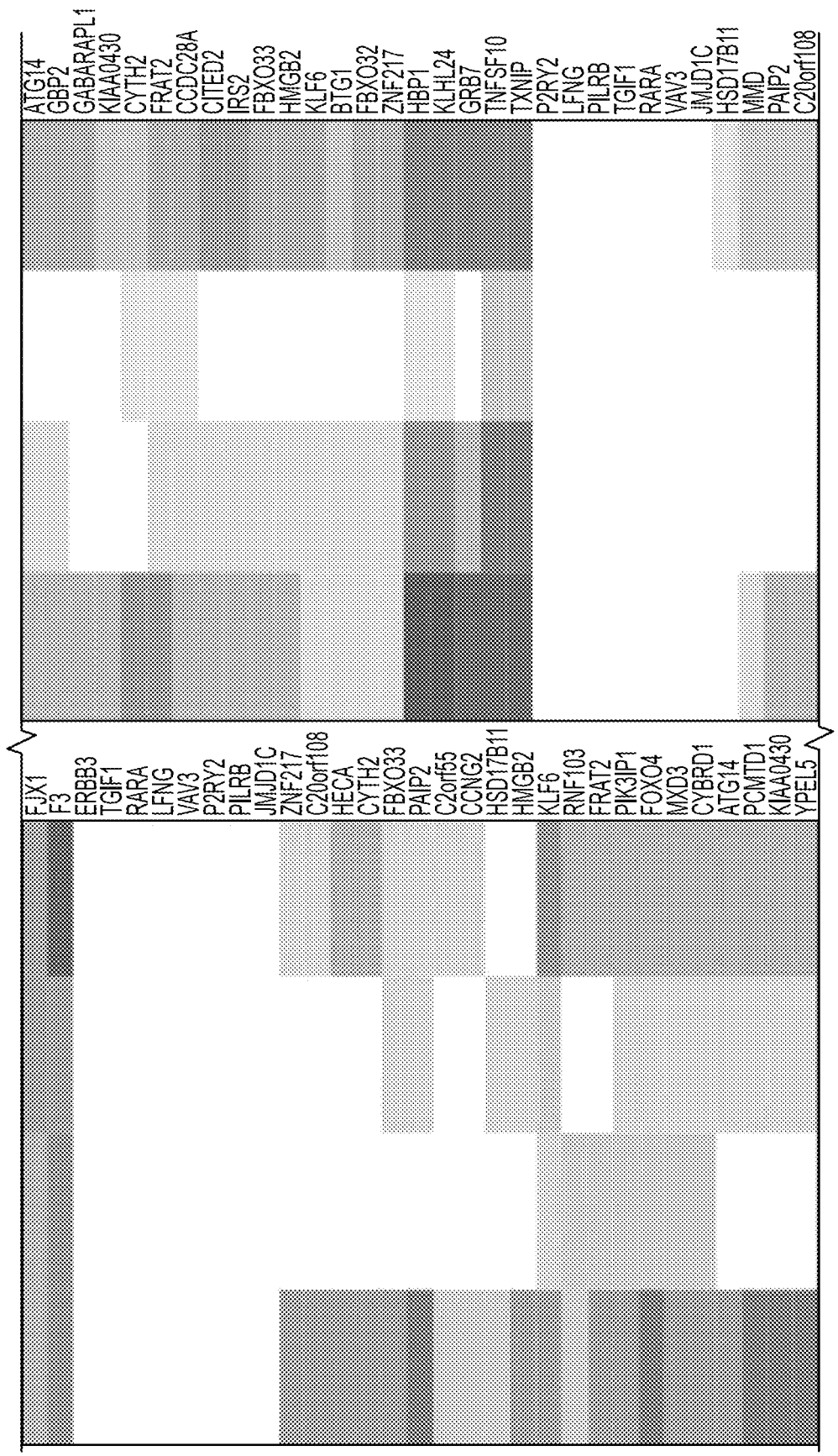
Figure 10A:
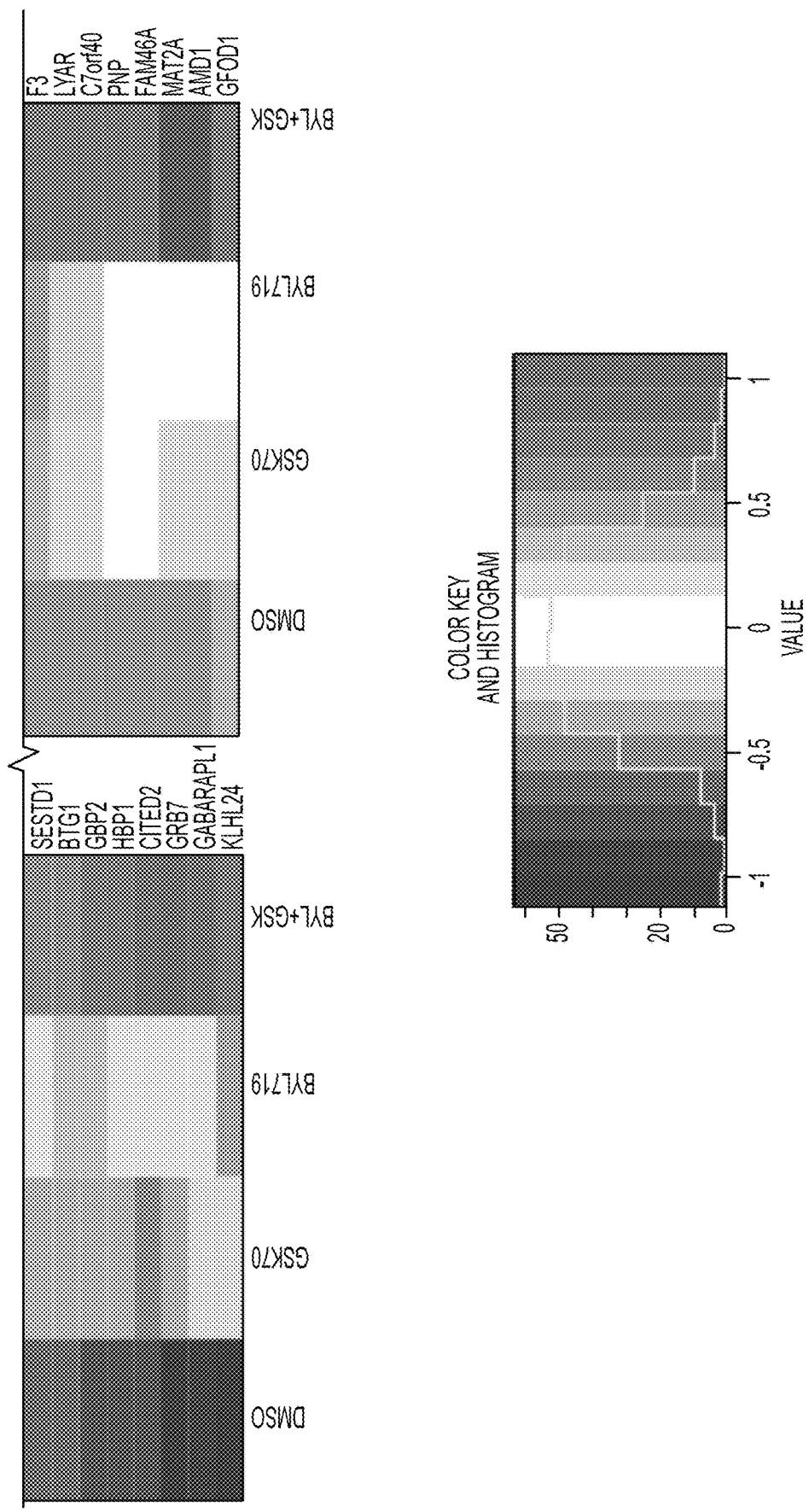
Figure 10B:
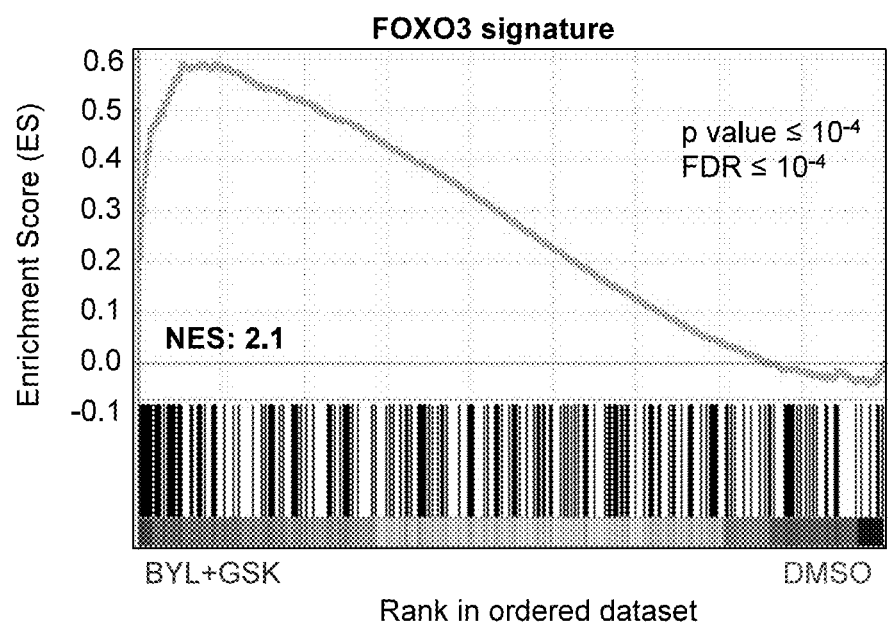

We next investigated whether mTORC1 suppression upon inhibition of both PI3Kα and PDK1 in BYL719-resistant cell lines was accompanied by specific transcriptional changes that would reveal a mechanistic explanation of the observed synergy. We performed gene expression analysis using both HCC1954 and JIMT1 cells treated with BYL719, GSK2334470, or the combination. While the differences in gene expression upon single agent treatment were modest, the combination of both drugs induced marked changes in the transcriptomic profiles when compared to the DMSO-treated control cells (FIG. 3A; FIG. 10A). Gene set enrichment analysis (GSEA) using these gene expression data showed enrichment of FOXO3 transcription factor targets in both HCC1954 and JIMT1 cells (FIG. 3B; FIG. 10B).

Figure 3C:
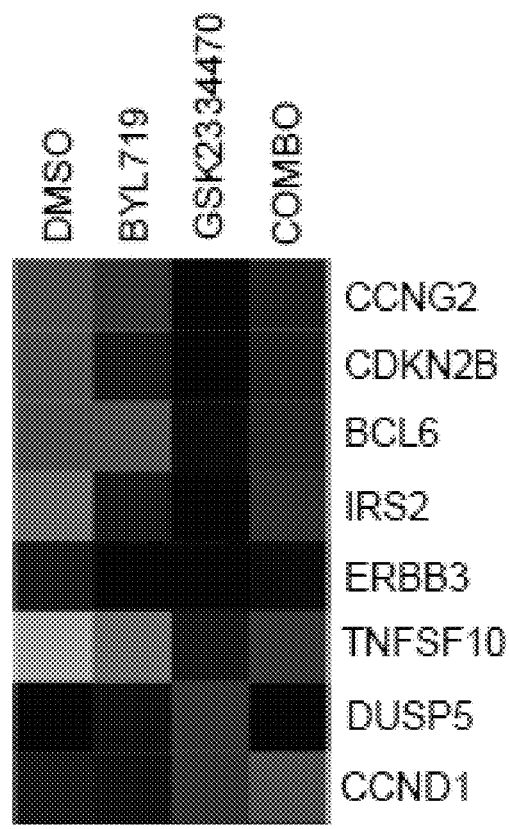
Figure 3D:
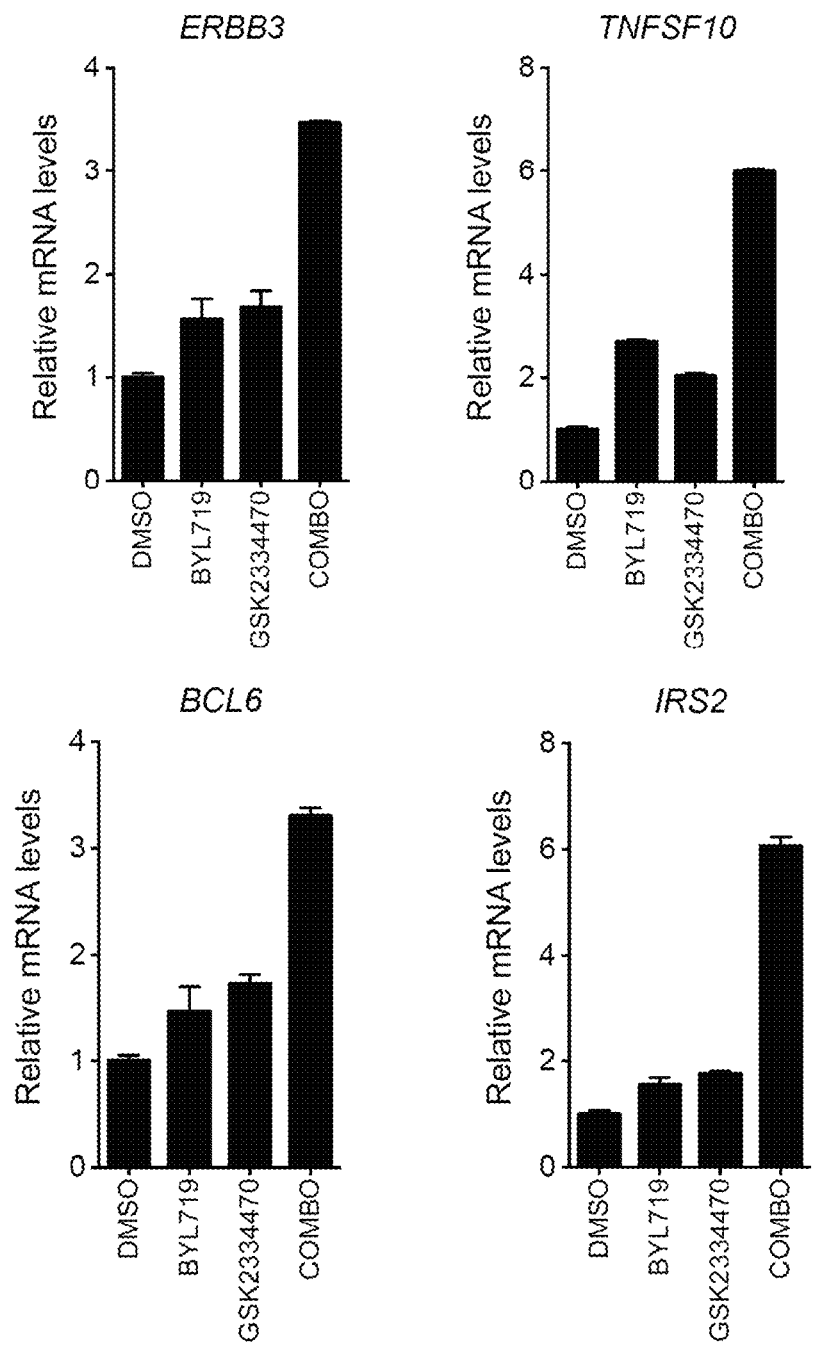
Figure 10C:
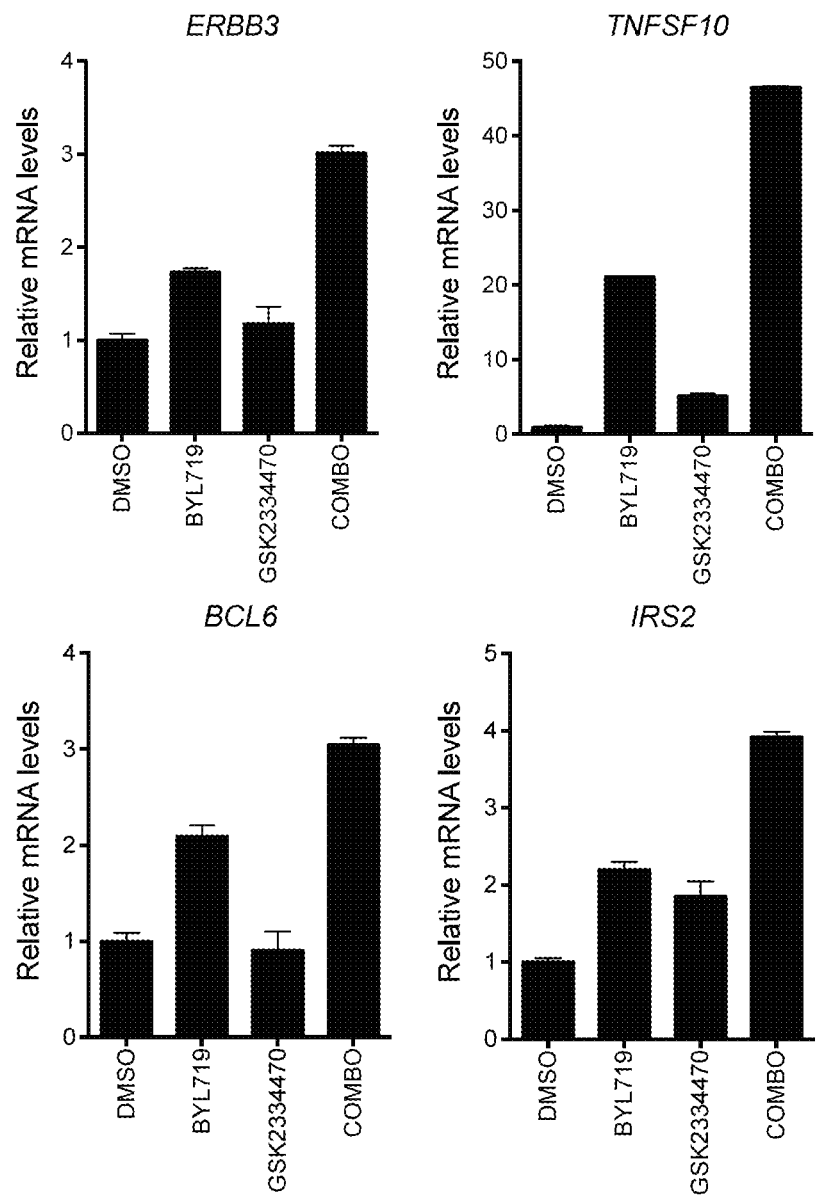

Individual genes described to be positively (CCNG2, BCL6, IRS2) or negatively (CCND1) regulated by FOXO3 (Webb and Brunet, 2014) were confirmed to be induced or repressed, respectively, upon dual PI3Kα and PDK1 blockade (FIG. 3C). These results were further validated by performing quantitative RT-PCR to measure the relative mRNA expression levels of four well-described FOXO3 targets: ERBB3, TNFSF10, BCL6, and IRS2 (Webb and Brunet, 2014) following different treatments. Significant increases in the mRNA levels of these genes only occurred when cells were treated with the combination of both BYL719 and GSK2334470 (FIG. 3D; FIG. 10C).

Figure 3E:
Figure 3F:
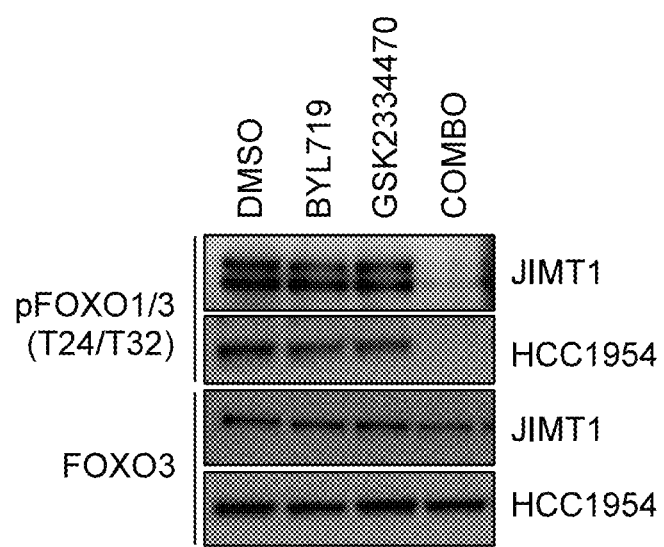
Figure 3G:
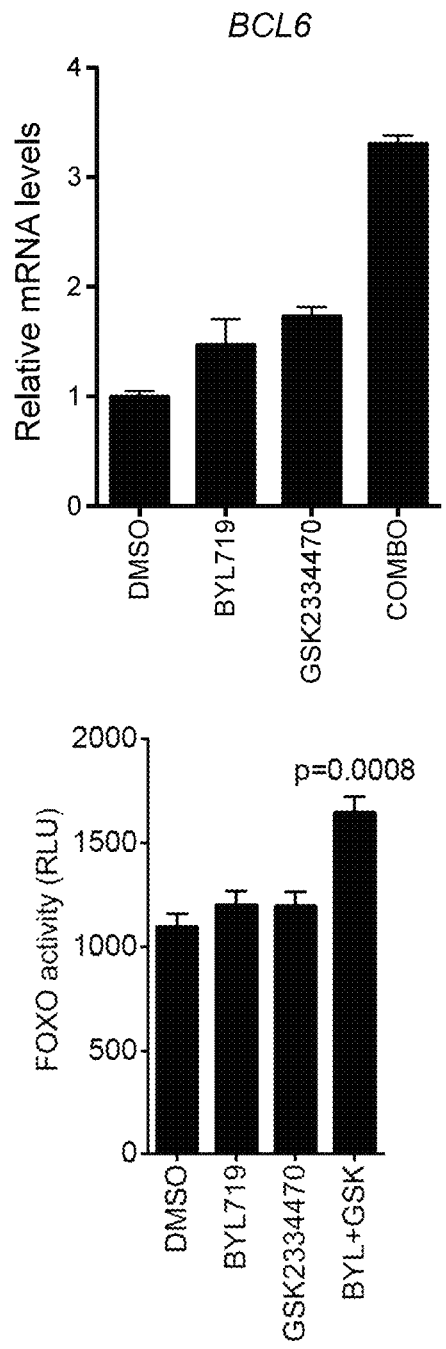
Figure 3H:
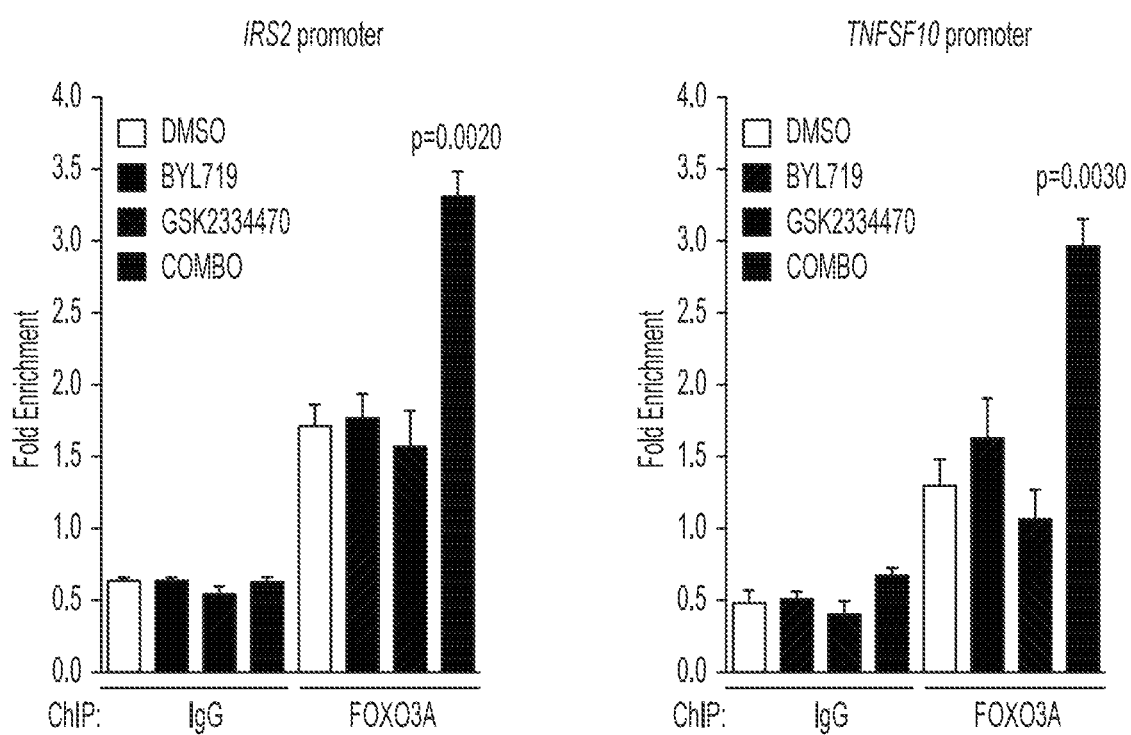
Figure 10D:
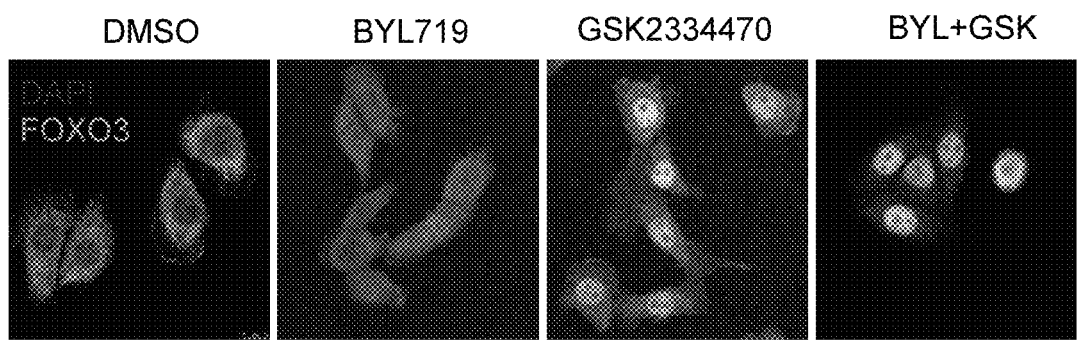
Figure 10E:
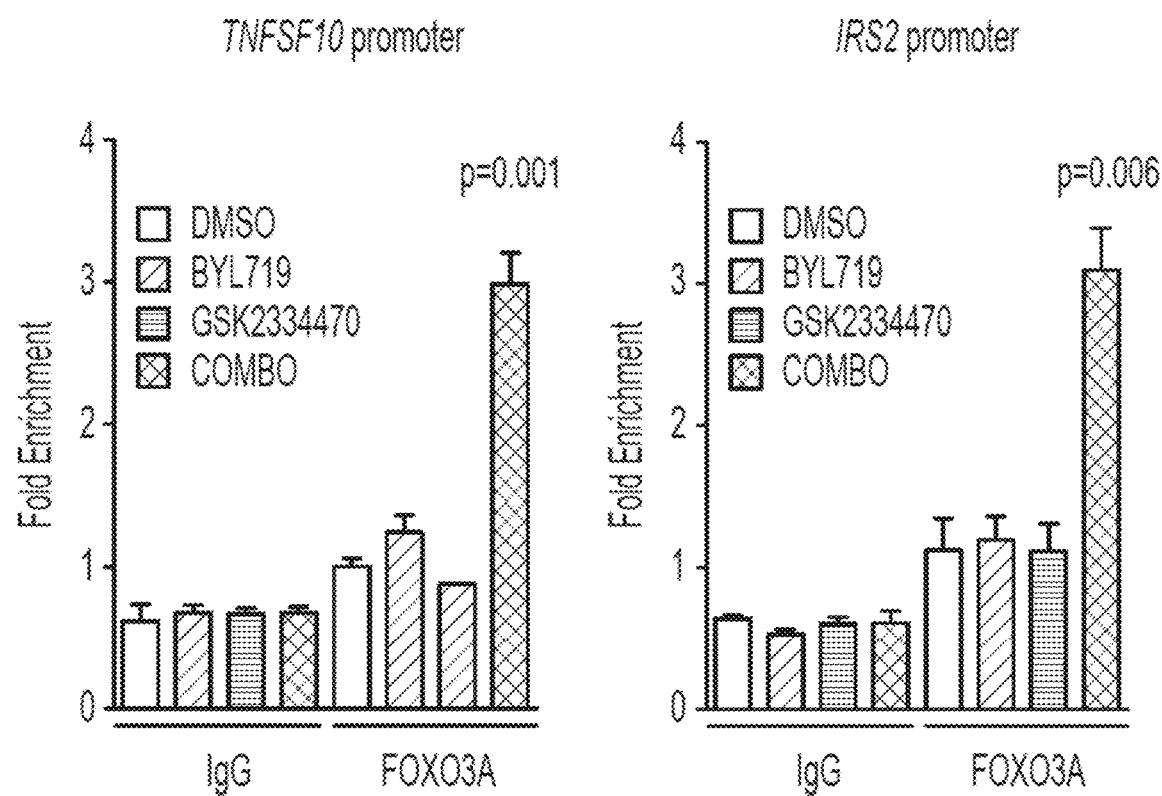

Upon growth factor stimulation, FOXO transcription factors are phosphorylated at several residues including T32 (FOXO1) and inhibited due to the interaction with the 14-3-3 proteins that prevents FOXO nuclear shuttling and gene transcription. Inhibition of these mitogenic signals (e.g. insulin) induces a rapid de-phosphorylation and nuclear translocation of FOXOs that allows expression of downstream target genes involved in apoptosis and/or cell cycle arrest (Webb and Brunet, 2014). In our cells, we found that treatment with both BYL719 and GSK234470, but not single agent, resulted in strong nuclear staining for FOXO3 (FIG. 3E; FIG. 10D). This was consistent with a decreased phosphorylation of this transcription factor at the residue T32 (FIG. 3F). Moreover, using a FOXO-luciferase reporter system we observed that only the combination of BYL719 with GSK2334470 stimulated endogenous FOXO transcriptional activity (FIG. 3G). An increased occupancy of FOXO3A at the promoters of two well-known FOXO targets, IRS2 and TNFSF10, was confirmed only when HCC1954 and JIMT1 cells were treated with BYL719 in combination with GSK234470 (FIG. 3H; FIG. 10E). These results suggest that dual PI3Kα and PDK1 inhibition induces a FOXO-dependent transcriptional activity in BYL719-resistant cells.

SGK1 is Up-Regulated in BYL719-Resistant Cell Lines

AKT has been shown to phosphorylate FOXO1 and FOXO3 at both T24 and T32 residues (Brunet et al., 1999). However, we observed that despite full inhibition of AKT by PI3Kα inhibition, FOXO3 is not efficiently primed to migrate to the nucleus and exert its transcriptional activity in cells resistant to BYL719 (FIG. 3 and FIG. 10). Since PDK1 requires downstream AGC kinases as molecular effectors (Pearce et al., 2010), we reasoned that in BYL719-resistant cells a downstream AGC kinase dependent on the PDK1 catalytic activity and docking with PIF binding pocket (FIG. 8B) regulates both FOXO1/3 phosphorylation and mTORC1 activity, independently of AKT. Serum and glucocorticoid-induced kinase (SGK) is a family of AGC serine/threonine kinases that comprises three members (SGK1, SGK2, and SGK3) highly homologous to AKT, sharing 55% identity in the kinase domain (Kobayashi and Cohen, 1999). SGK1 activation is mediated by mTORC2-dependent phosphorylation at the HM (S422) and subsequent PDK1 phosphorylation at the activation loop (T256) in a PIF binding pocket-dependent manner (Garcia-Martinez and Alessi, 2008; Pearce et al., 2010). Earlier reports have demonstrated that SGK1 is able to phosphorylate FOXO1 at residues T32 and S315 (Brunet et al., 2001). Furthermore, SGK1 has been correlated with resistance to AKT inhibition (Sommer et al., 2013). Therefore, SGK1 can play a critical role downstream of PDK1 in sustaining mTORC1 activity and inducing resistance to PI3Kα inhibition.

Figure 4A:
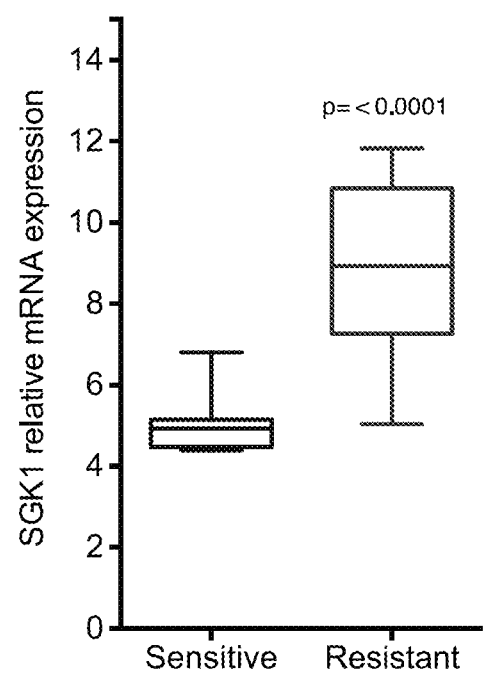
Figure 4B:
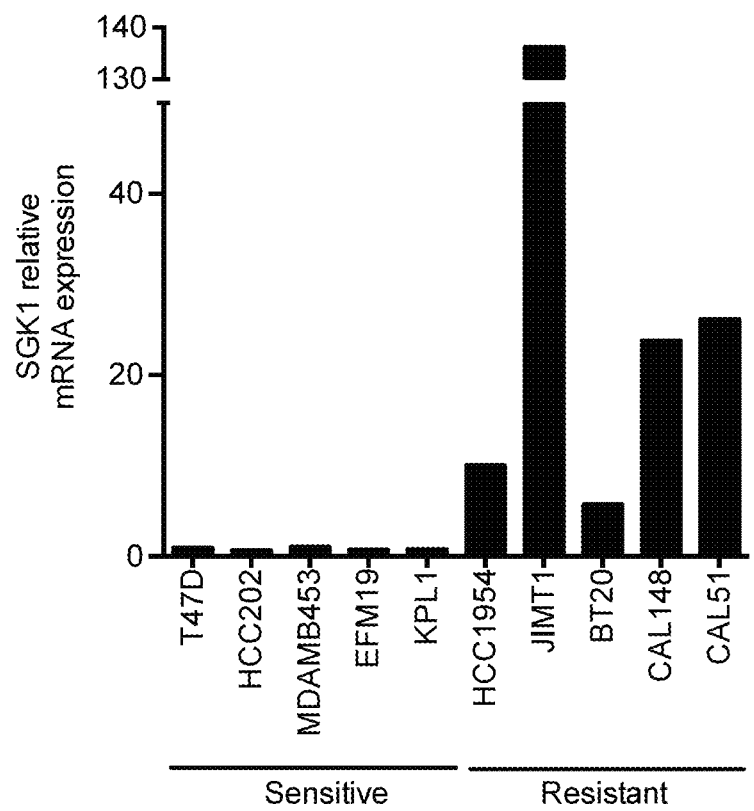
Figure 4C:
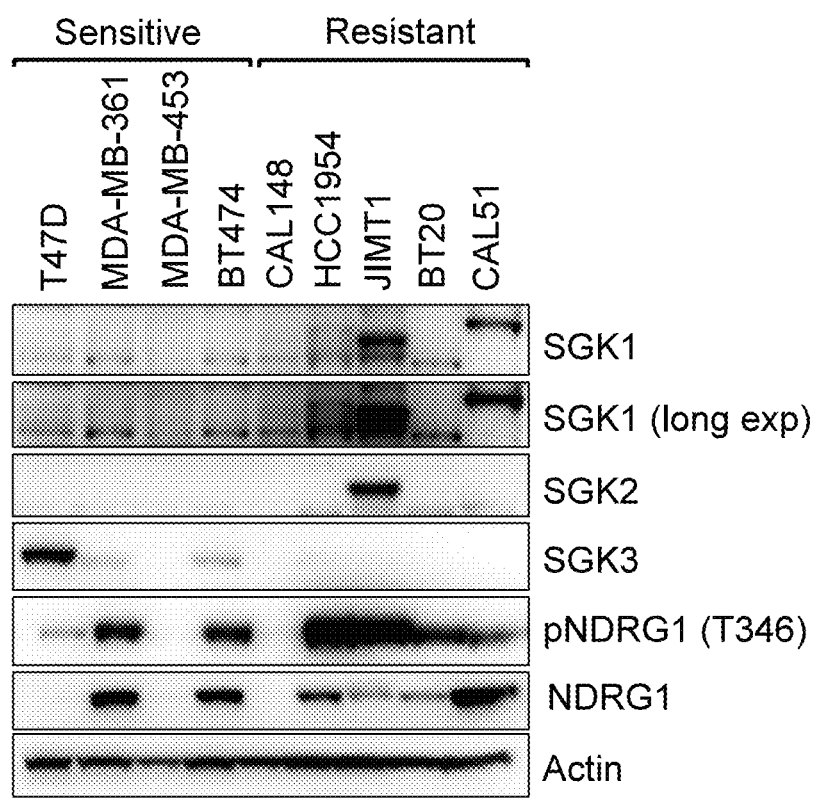
Figure 11A:
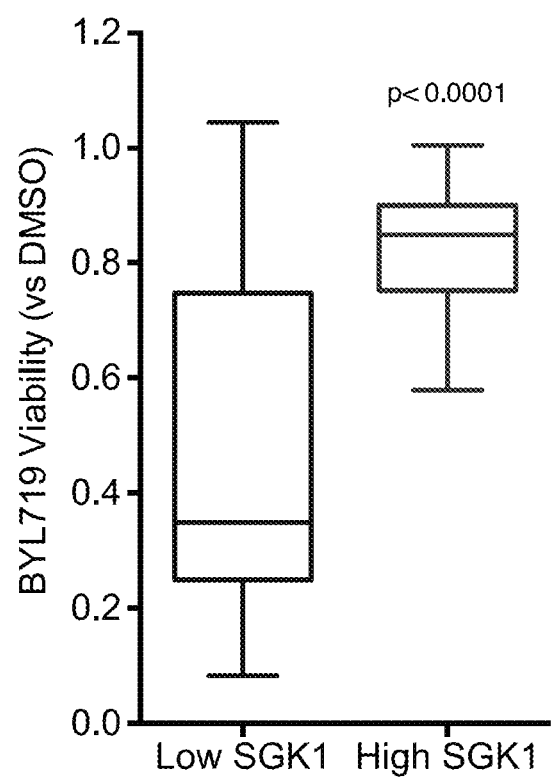
Figure 11B:
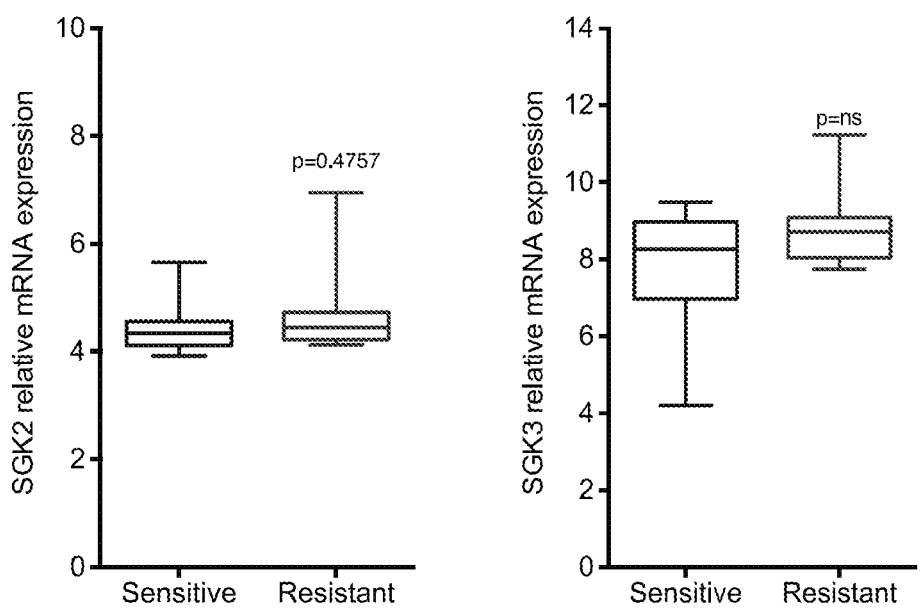
Figure 11C:
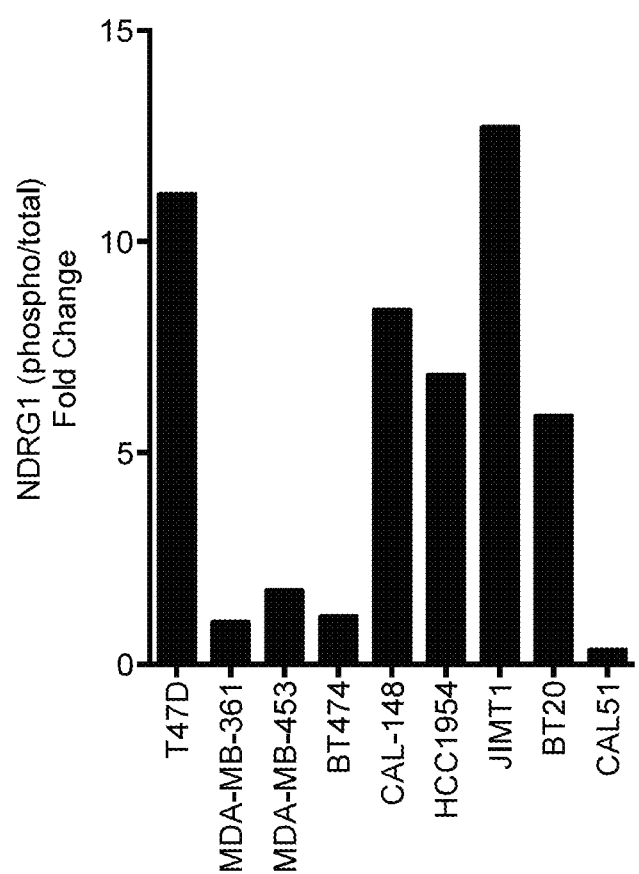

We analyzed the basal mRNA expression of 27 breast cancer cell lines, previously characterized as sensitive or resistant to BYL719 (Elkabets et al., 2013), and found that resistant cell lines have significantly higher levels of SGK1 mRNA compared to sensitive cells (FIG. 4A; FIG. 11A). This held true when only breast cancer cells harboring PIK3CA-activating mutations, which are known to be sensitive to PI3Kα inhibition (Elkabets et al., 2013), were considered in the analysis (FIGS. 4B and C). The mRNA levels of SGK2 and SGK3 were similar between sensitive and resistant cell lines (FIG. 11B), although JIMT1 cells also express high levels of SGK2. The ratio of phosphorylated N-Myc Downstream Regulated 1 (NDRG1) (T346), a a substrate of SGK1 (Murray et al., 2004), versus total NDRG1 was also higher in BYL719-resistant cells (FIG. 4C and FIG. 11C).

Figure 11D:
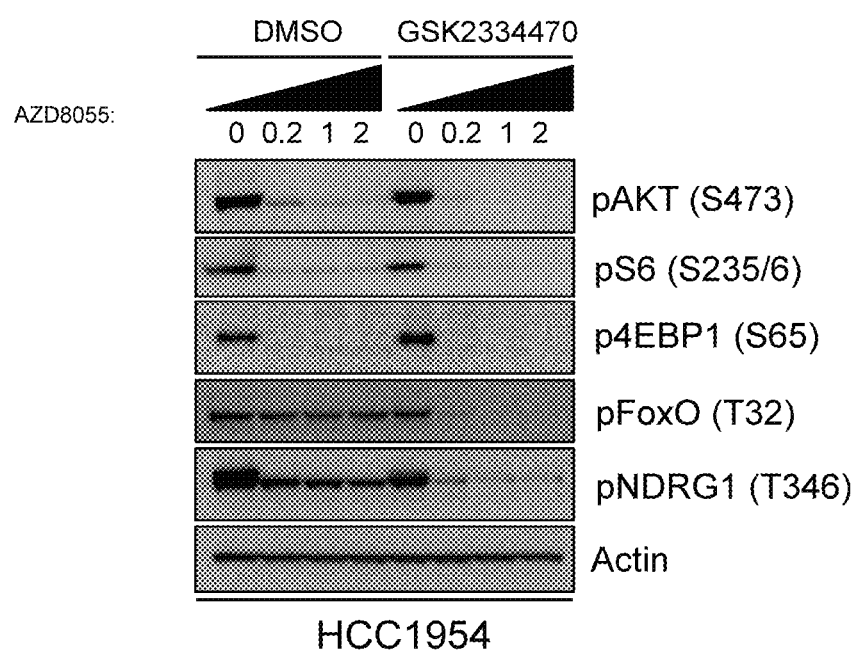
Figure 11E:
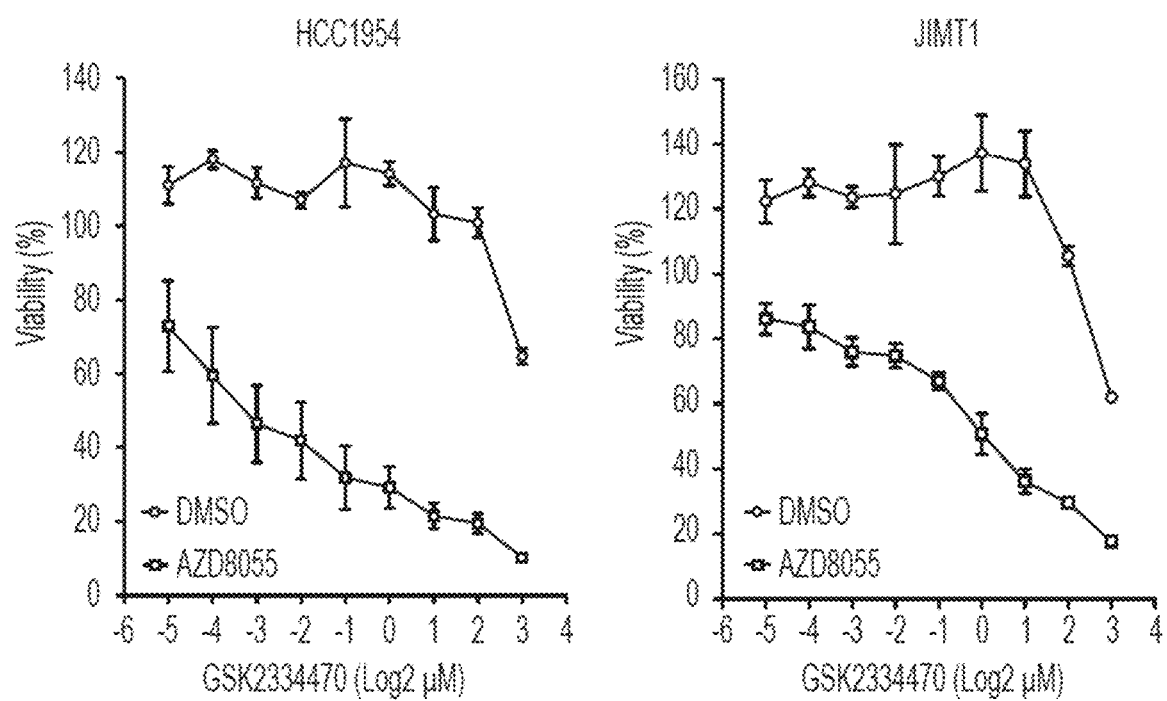
Figure 11F:
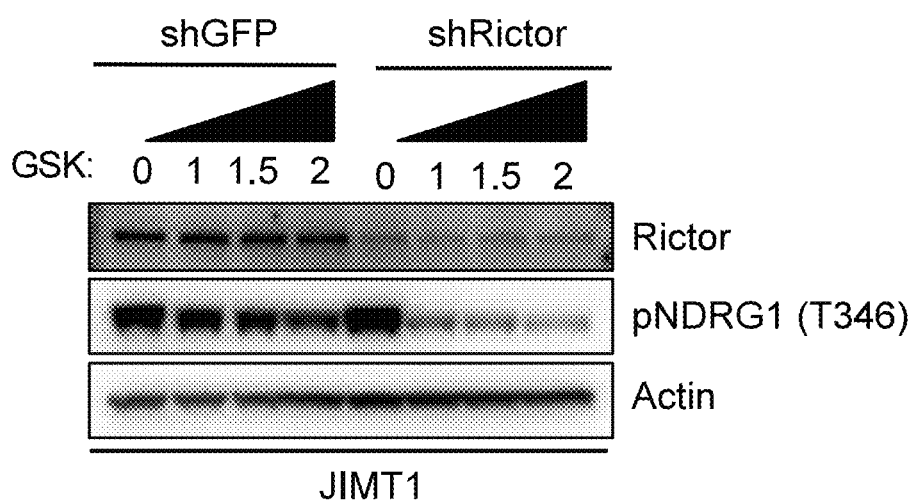
Figure 11G:
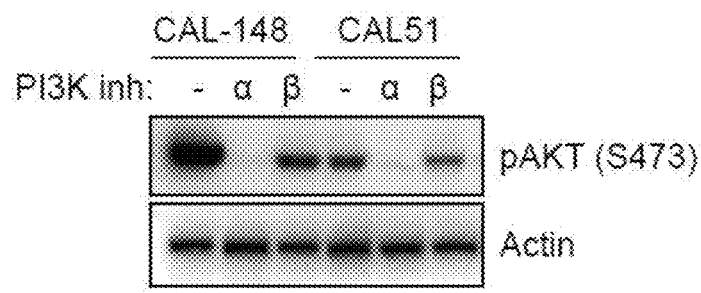
Figure 11H:
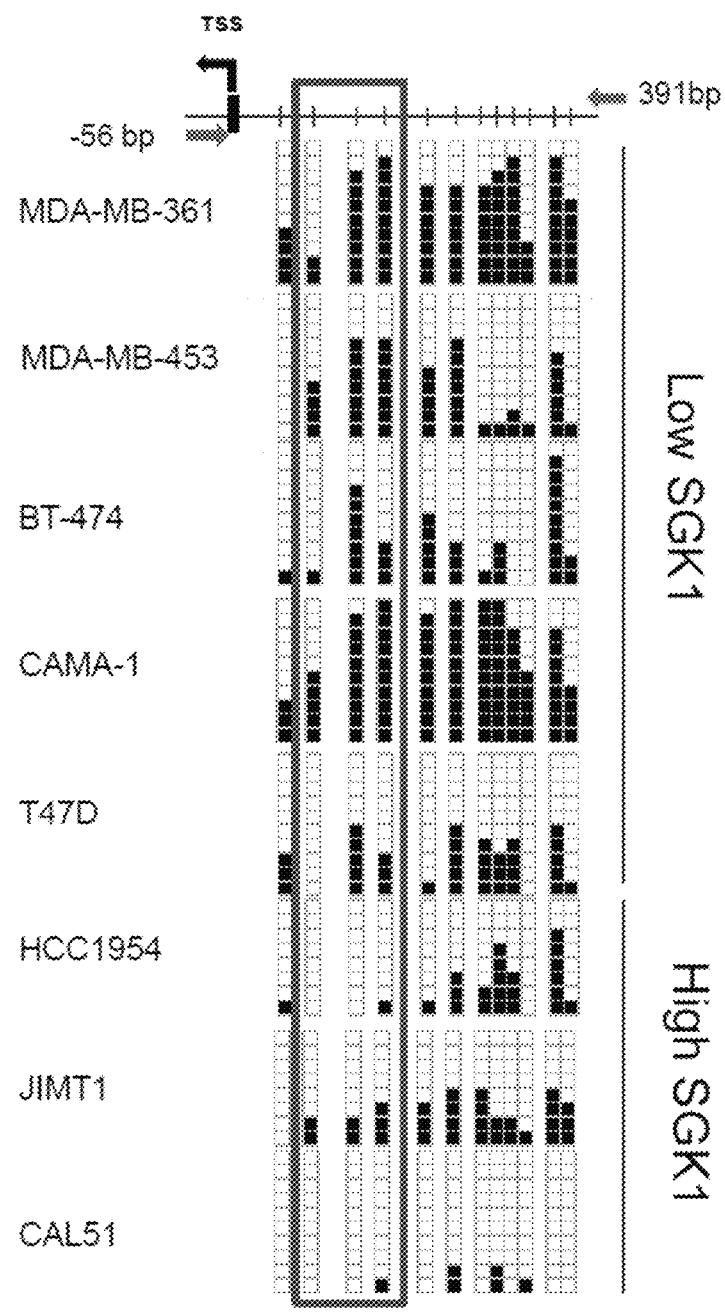

Both CAL-148 and CAL-51 cells carry mutations in PTEN (Cerami et al., 2012), their resistance to BYL719 may be due to insufficient inhibition of the PI3K/AKT pathway as a consequence of PI3Kβ activity (Juric et al., 2015). However, BYL719, but not the PI3Kβ inhibitor AZD6482, fully decreases pAKT levels in both CAL-148 and CAL-51 cells (FIG. 11G).

Figure 11I:
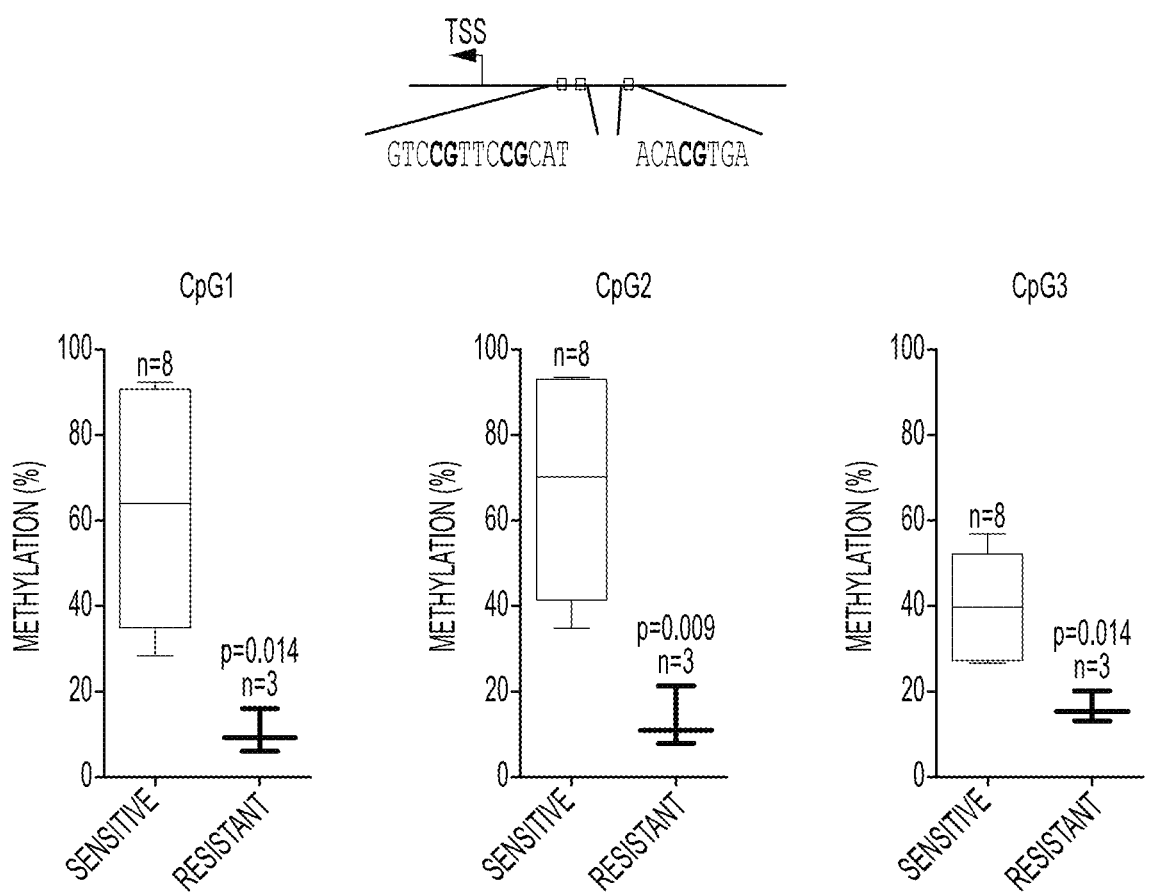
Figure 11J:
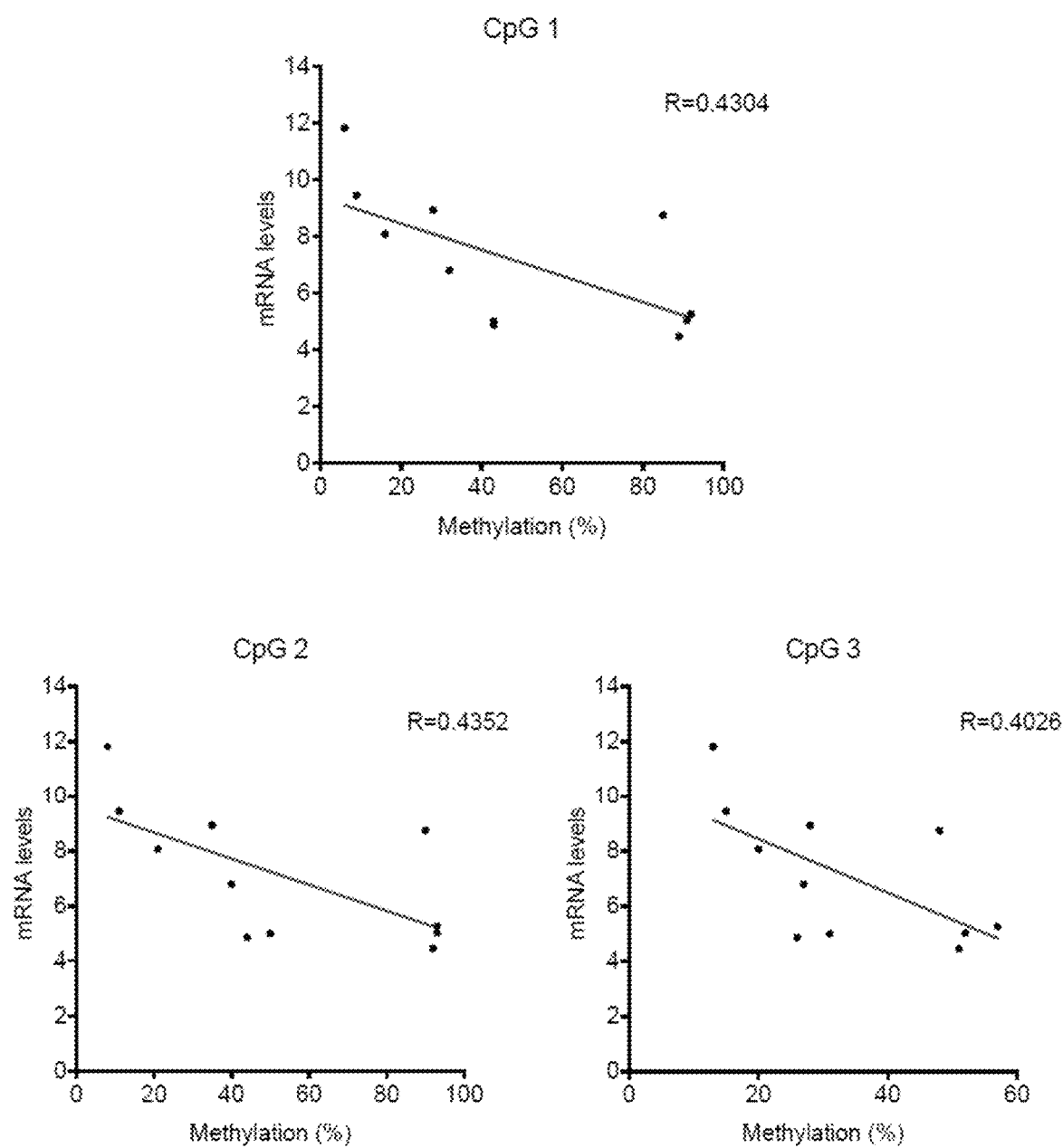
Figure 11K:
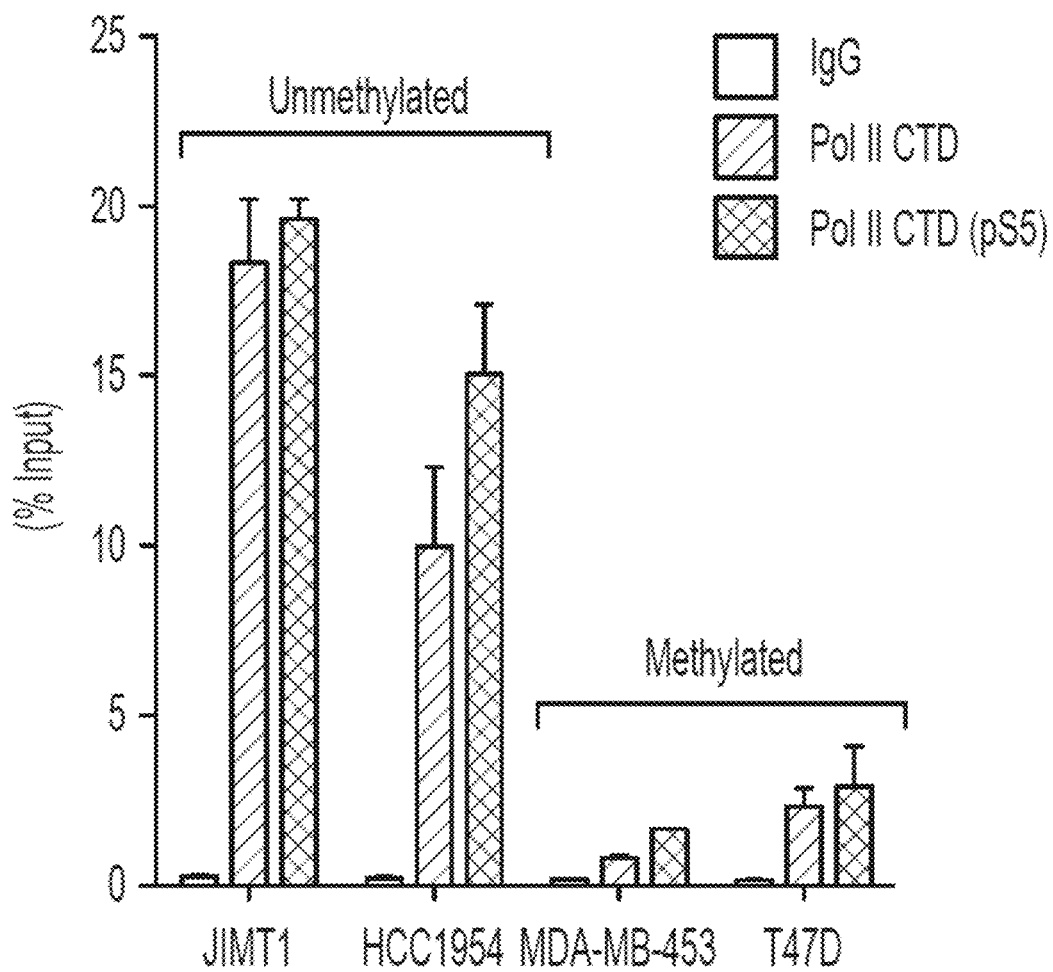
Figure 11L:
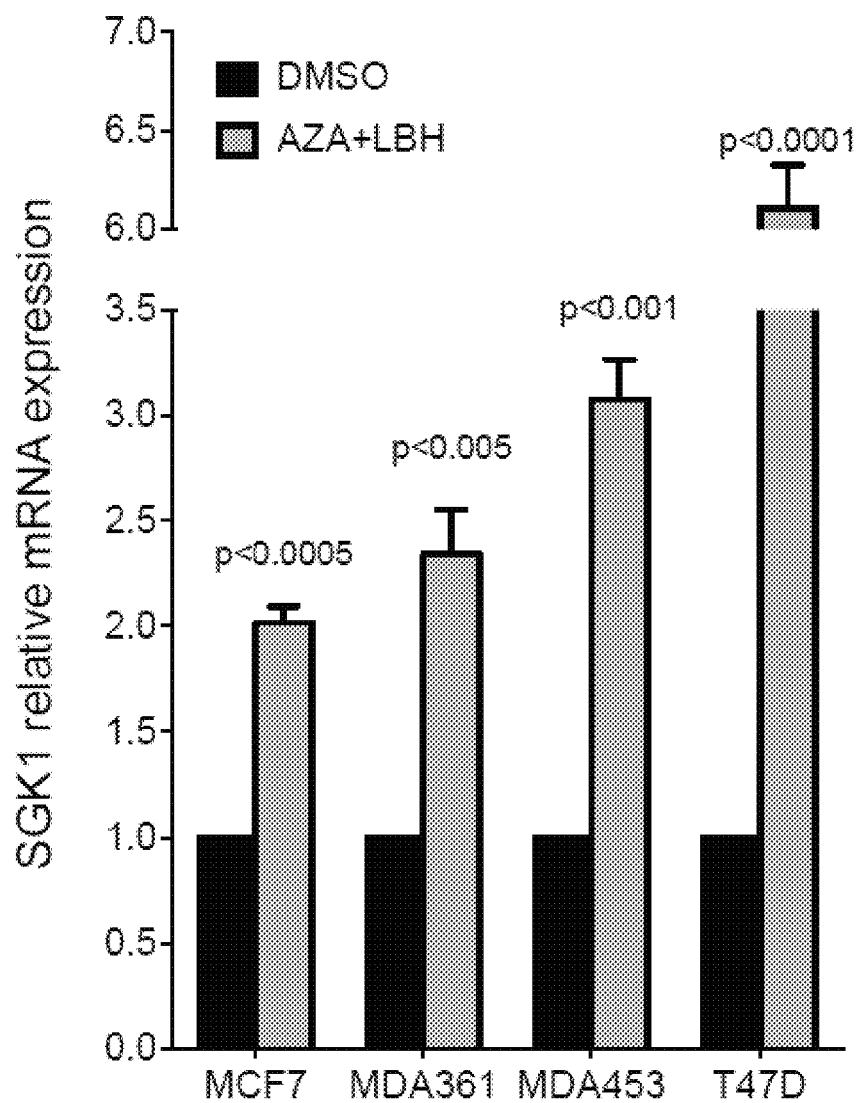

We then sought to investigate the mechanism underlying this variability in SGK1 expression. We analyzed the promoter of SGK1 and realized that in the region between −56 bp and +391 bp of the transcription start site (TSS) there are 12 CpG sites that are susceptible for DNA methylation. Using bisulphite sequencing we found that three of these CpG sites were differentially methylated between sensitive and resistant cell lines (FIG. 11E). We confirmed our results quantitatively using direct pyrosequencing in 11 cell lines (8 sensitive and 3 resistant to PI3Kα inhibition). Sensitive cell lines exhibited high levels of SGK1 promoter methylation (Mean CpG1=65%, CpG2=67%, and CpG3=40%), while resistant cell lines displayed low levels of SGK1 promoter methylation (Mean CpG1=11%, CpG2=13%, and CpG3=16%) (FIG. 11I). The degree of promoter DNA methylation inversely correlated with SGK1 mRNA levels in these cells (FIG. 11J). By ChIP-qPCR assays, we found high occupancy of RNA polymerase II (Pol II), an enzyme essential for transcription, and phosphorylated (S5) Pol II in both HCC1954 and JIMT1 cells, indicating that SGK1 transcription is active in these resistant cell lines (FIG. 11K). On the contrary, in the sensitive cell lines MDA-MB-453 and T47D we found low occupancy of both Pol II and phosphorylated Pol II (S5) in the SGK1 promoter (FIG. 11K). Treatment with the DNA demethylating agent 5-Aza-2'-deoxycytidine and the histone deacetylase inhibitor panobinostat reduced SGK1 promoter DNA methylation and increased mRNA levels of SGK1 in the four sensitive cell lines tested (FIG. 11L). Our results indicate that the differential expression of SGK1 is mediated, at least in part, by epigenetic regulation.

NDRG1 is efficiently phosphorylated by SGK1 in vitro, and it has been considered a specific substrate of this kinase in vivo (Murray et al., 2004). Nevertheless, some reports indicate that also AKT can phosphorylate NDRG1 in the absence of SGK1. As a matter of fact, cells that do not express SGK1 but have high AKT activity exhibit NDRG1 phosphorylation, which is sensitive to AKT inhibitors (Sommer et al., 2013). In our models, we observed that only cells which are sensitive to BYL719 display decreased NDRG1 phosphorylation at T346 when treated with BYL719, suggesting that AKT is responsible for the phosphorylation of NDRG1 in these cells (FIG. 4D).

Figure 4D:
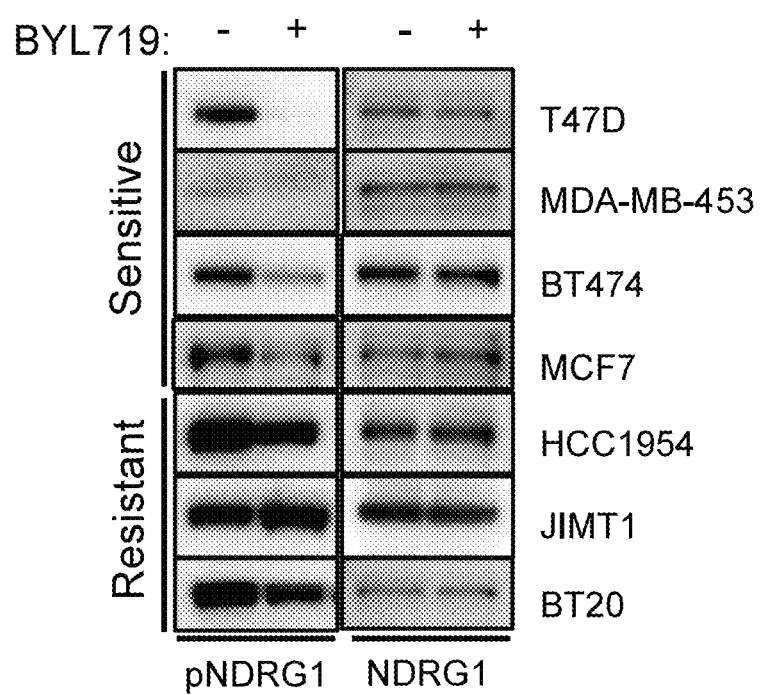
Figure 4E:
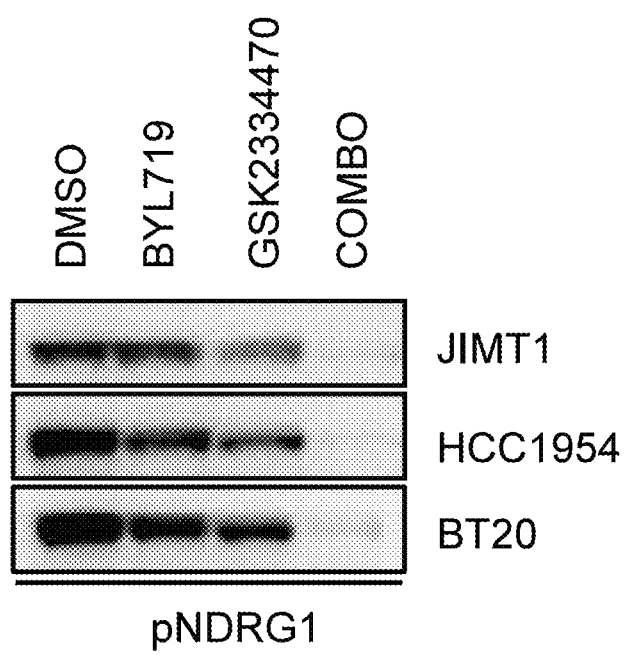

In contrast, resistant cell lines treated with BYL719 maintain NDRG1 phosphorylation, underscoring the role of SGK1 in this setting (FIG. 4D). Central to our work, the combination of BYL719 and GSK2334470 decreases the phosphorylation of NDRG1 in BYL719-resistant cell lines, confirming that the combination of both drugs effectively inhibits both SGK1 and AKT activity (FIG. 4E).

Figure 4F:
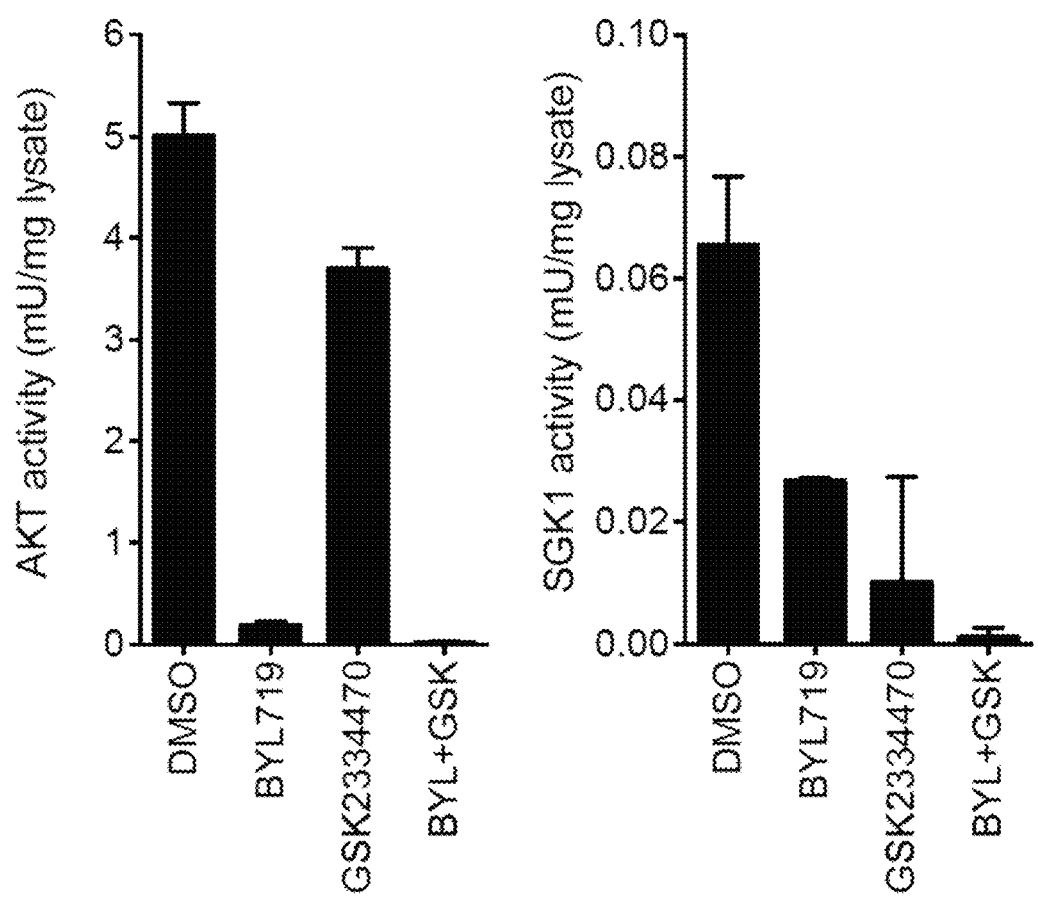

Next, we aimed to further characterize the phosphorylation events that regulate SGK1 activity upon PI3Kα and PDK1 inhibition. Endogenous SGK1 was immunoprecipitated upon different treatments and we found that GSK2334470, but not BYL719, was able to decrease the phosphorylation at both the HM (S422) and the activation loop (T256). Accordingly, the endogenous kinase activity of SGK1 was abolished only in the presence of the PDK1 inhibitor (FIG. 4F). On the other hand, immunoprecipitation of endogenous AKT revealed that upon BYL719 treatment, SGK1 kinase activity is completely abrogated. This is not the case when cells are treated with the PDK1 inhibitor GSK2334470, as AKT is still efficiently activated under these conditions (Najafov et al., 2012). This explains why NDRG1 remains phosphorylated in the absence of SGK1 kinase activity. The combination of BYL719 and GSK2334470 inhibited the kinase activity of both kinases and subsequently, the downstream target pNDRG1. This is indicative of a signaling compensation between AKT and SGK1 and that only the combination of PI3Kα and PDK1 inhibitors can simultaneously block the activity of the endogenous enzymes in resistant cells While mTORC2-mediated phosphorylation at the HM is indispensable for SGK1 kinase activity (Kobayashi and Cohen, 1999), several reports indicate that AKT remains active in the absence of HM phosphorylation, as phosphorylation at the activation loop (T308) is sufficient to partially activate the kinase (Guertin et al., 2006; Jacinto et al., 2006; Rodrik-Outmezguine et al., 2011). Treatment of HCC1954 cells with increasing concentrations of AZD8055, an mTOR catalytic inhibitor, which targets both mTOR complex 1 and 2 and completely inhibits SGK1 but not AKT, did not reduce the levels of the substrates pFOXO3 (T32) and pNDRG1 (T346). This confirmed that mTORC2 inhibition is not sufficient to abolish AKT activity in these cells (FIG. 11D).

However, addition of GSK2334470, which fully inhibits the phosphorylation of the AKT activation loop and thus its activity, resulted in a marked decrease in the phosphorylation of both FOXO3 and NDRG1. This combination phenocopied the effects observed using the PI3Kα inhibitor, resulting in decreased cell viability in both HCC1954 and JIMT1 cells (FIG. 11E). To rule out that this effect was not mediated by mTORC1 inhibition, we knocked down RICTOR, a key mTOR component, in JIMT1 cells using a shRNA. We observed that RICTOR knockdown decreased the phosphorylation of NDRG1 (T346) only in the presence of PDK1 inhibition (FIG. 11F). These results demonstrate that combined PI3Kα and PDK1 inhibition is required to fully suppress endogenous SGK1 and AKT activity in BYL719-resistant cells.

SGK1 Mediates Resistance to the PI3Kα Inhibitor BYL719

Figure 5A:
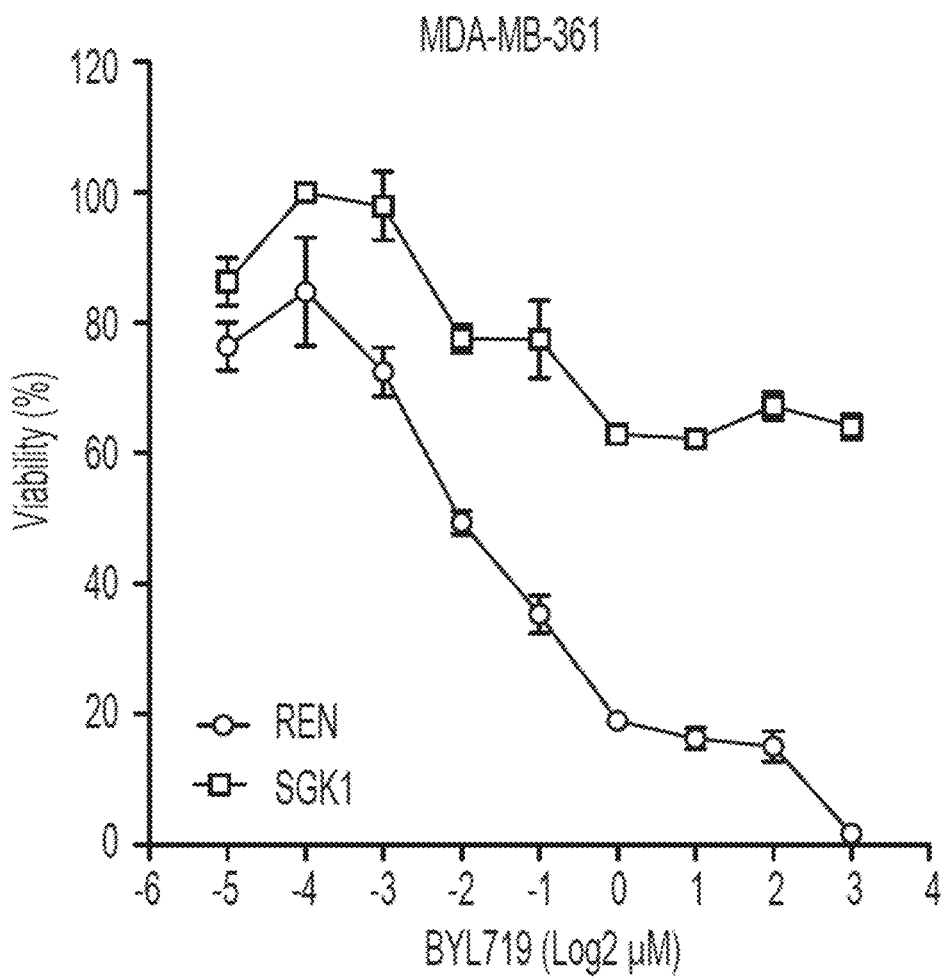
Figure 5B:
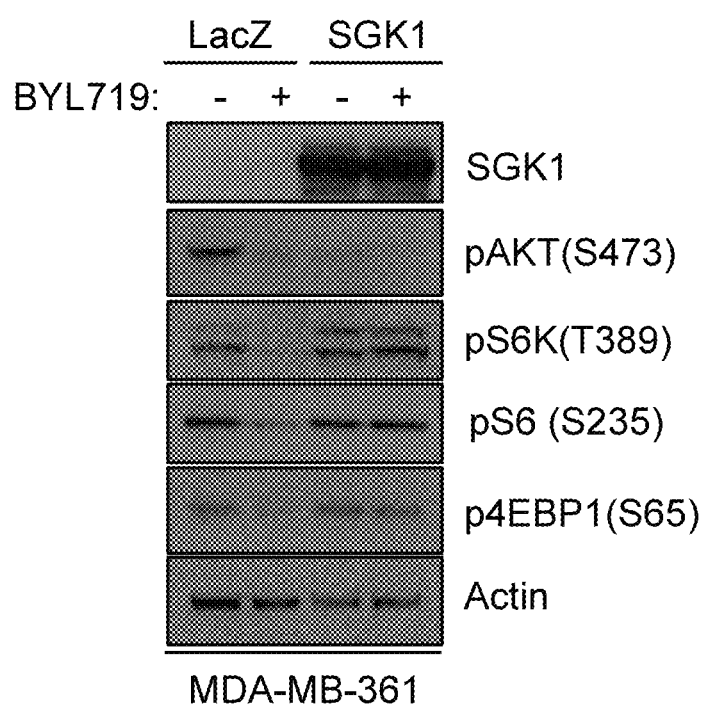

We next assessed the contribution of SGK1 in mediating resistance to PI3Kα inhibition. The overexpression of a constitutively active form of SGK1 in MDA-MB-361 cells, which are sensitive to BYL719, was sufficient to increase cell viability in the presence of BYL719 (FIG. 5A). In parental cells, PI3Kα inhibition decreased both AKT phosphorylation and mTORC1 signaling, as assessed by S6K, S6, and 4EBP1 phosphorylation. On the contrary, cells overexpressing SGK1 maintained mTORC1 signaling in the presence of the BYL719 (FIG. 5B).

Figure 5C:
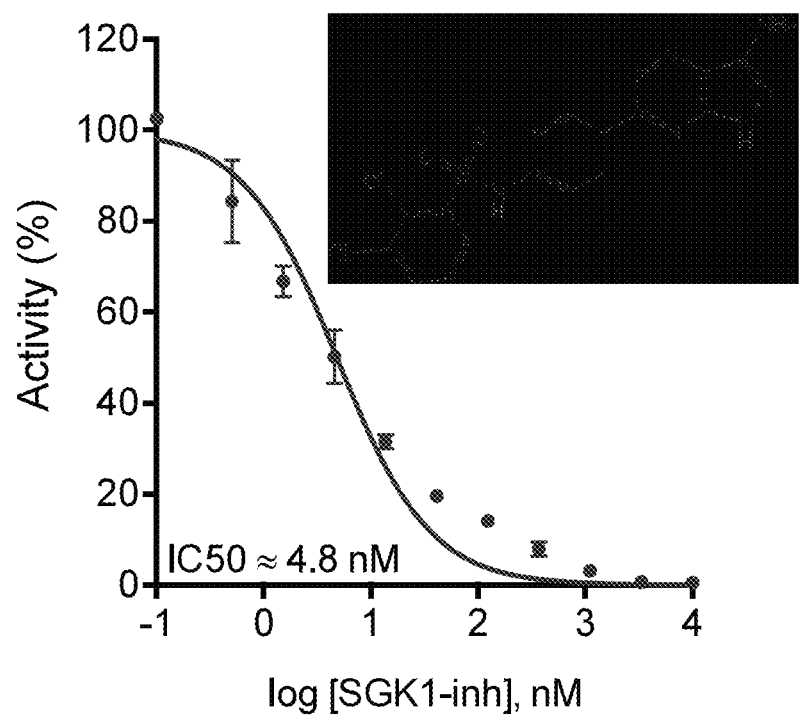
Figure 5D:
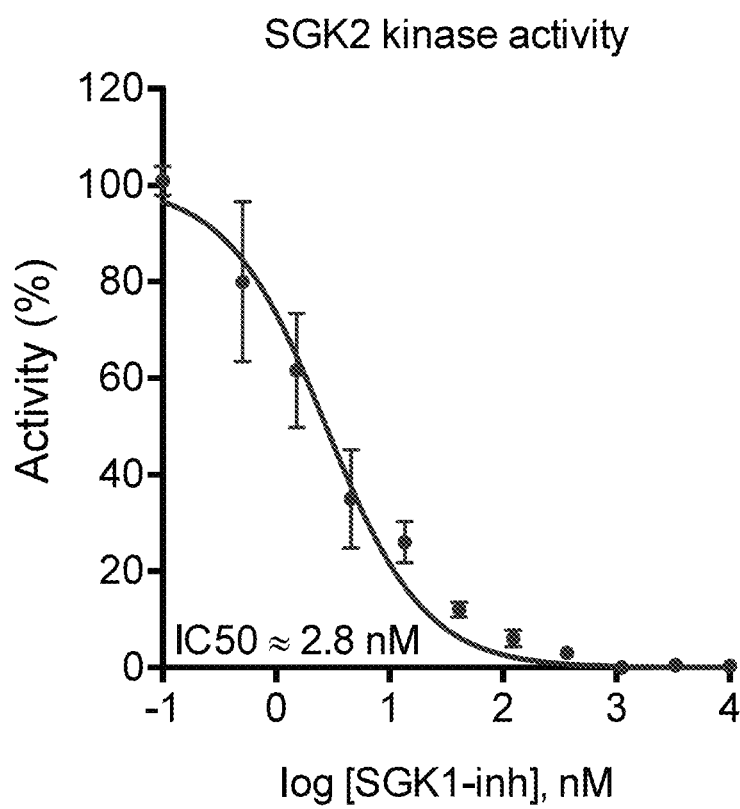
Figure 5E:
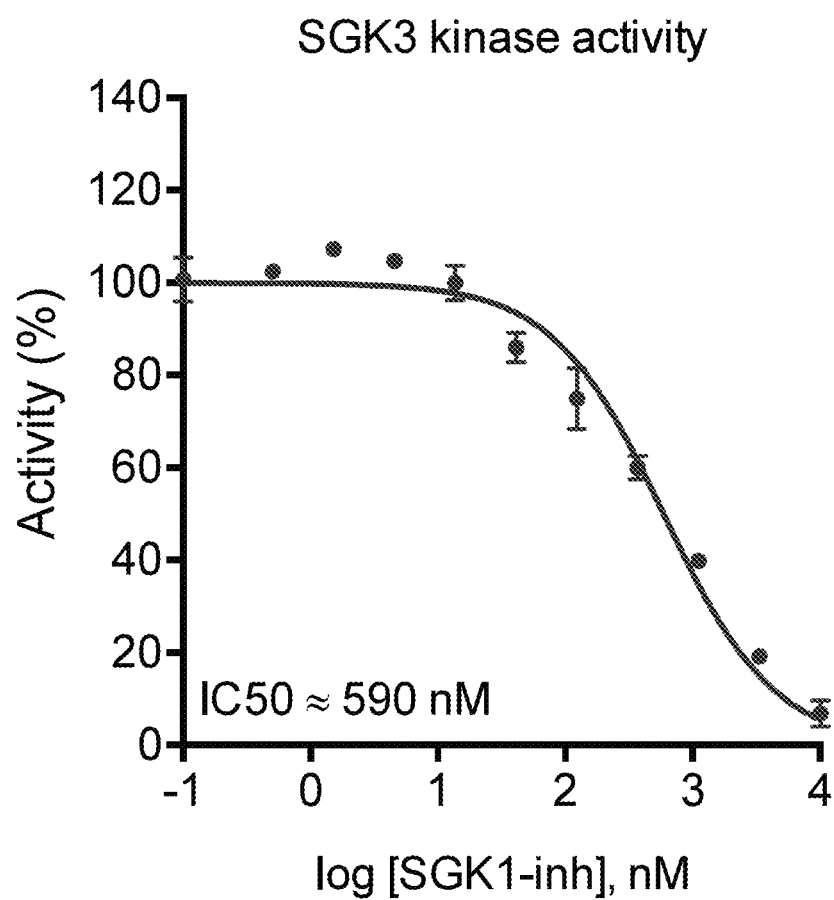
Figure 5F:
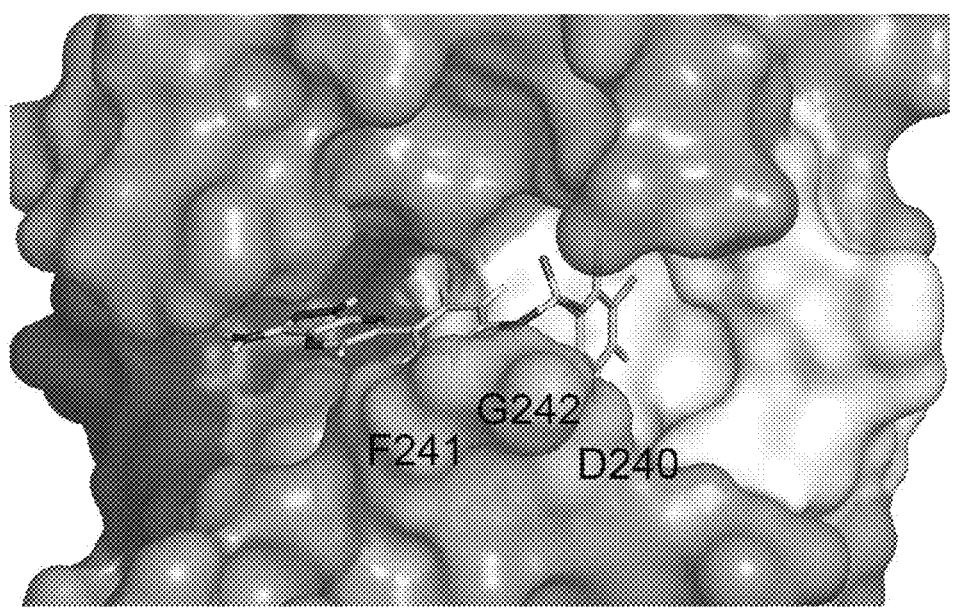
Figure 5G:
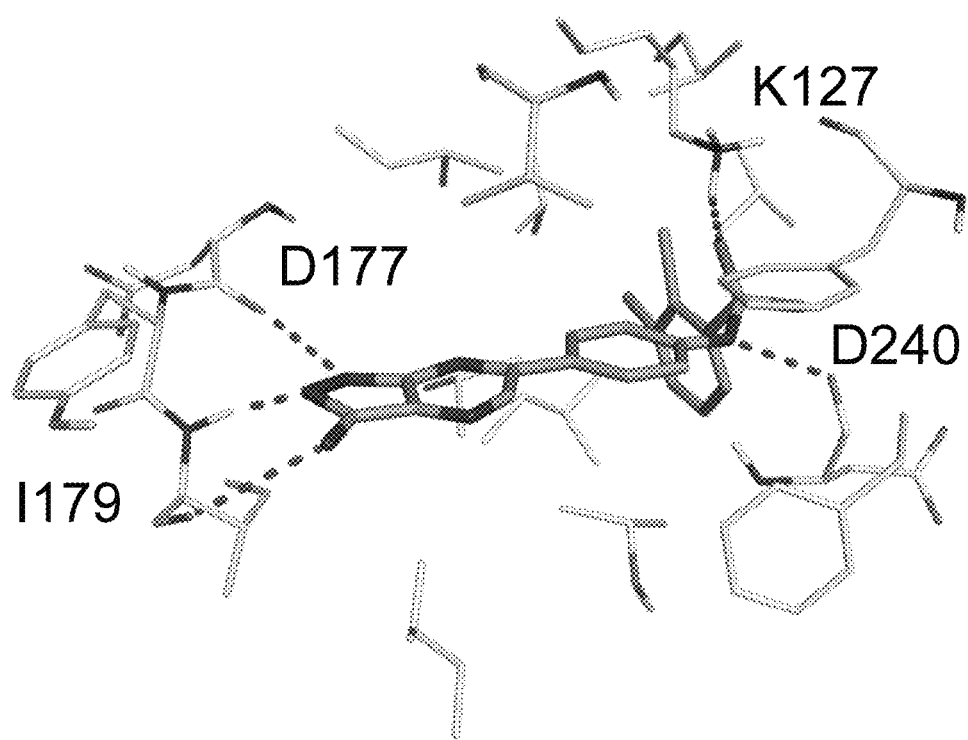
Figure 5H:
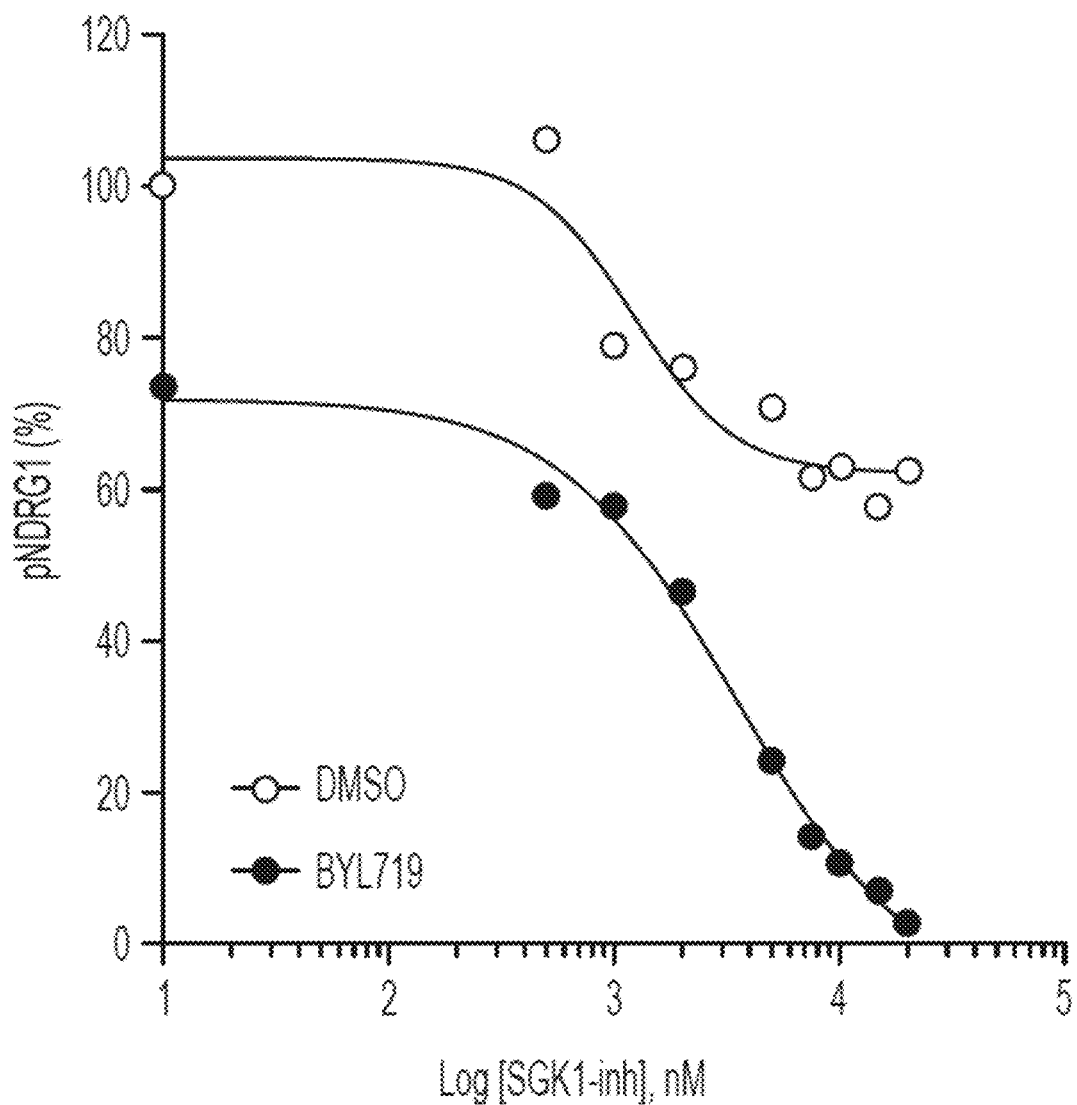

Given that genetic inactivation of SGK1 is toxic (Sommer et al., 2013), we generated doxycycline-inducible shRNA targeting SGK1. Upon SGK1 knockdown we observed decrease in cell viability that was enhanced in the presence of BYL719 (FIG. 5M). Accordingly, SGK1 knockdown decreased pNDRG1 and mTORC1 targets levels only when combined with PI3Kα inhibition. Our experiments showed that this method was potent but not durable, consistent with previous observations that suggest a short SGK1 mRNA half-life (t½~30 min) (Arteaga et al., 2007).

Figure 12A:
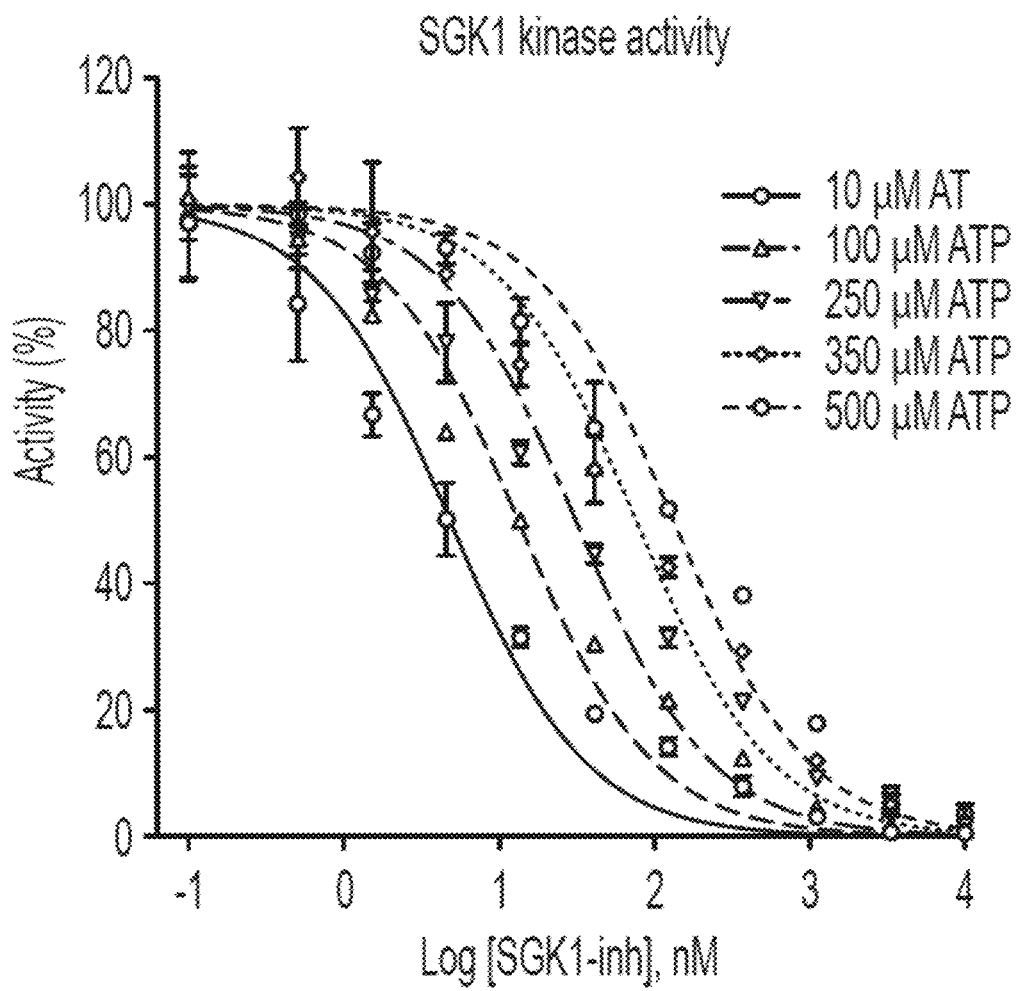
Figure 12B:
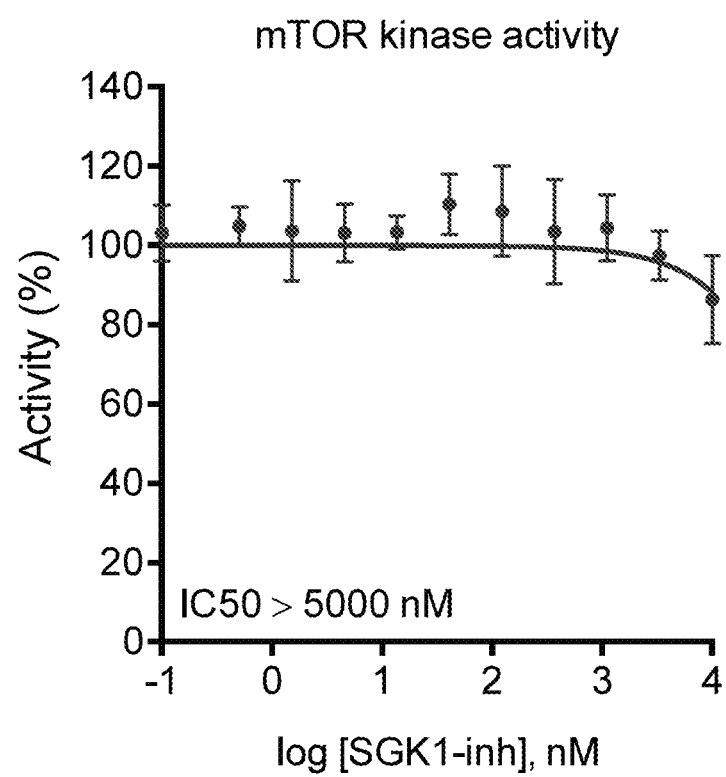
Figure 12C:
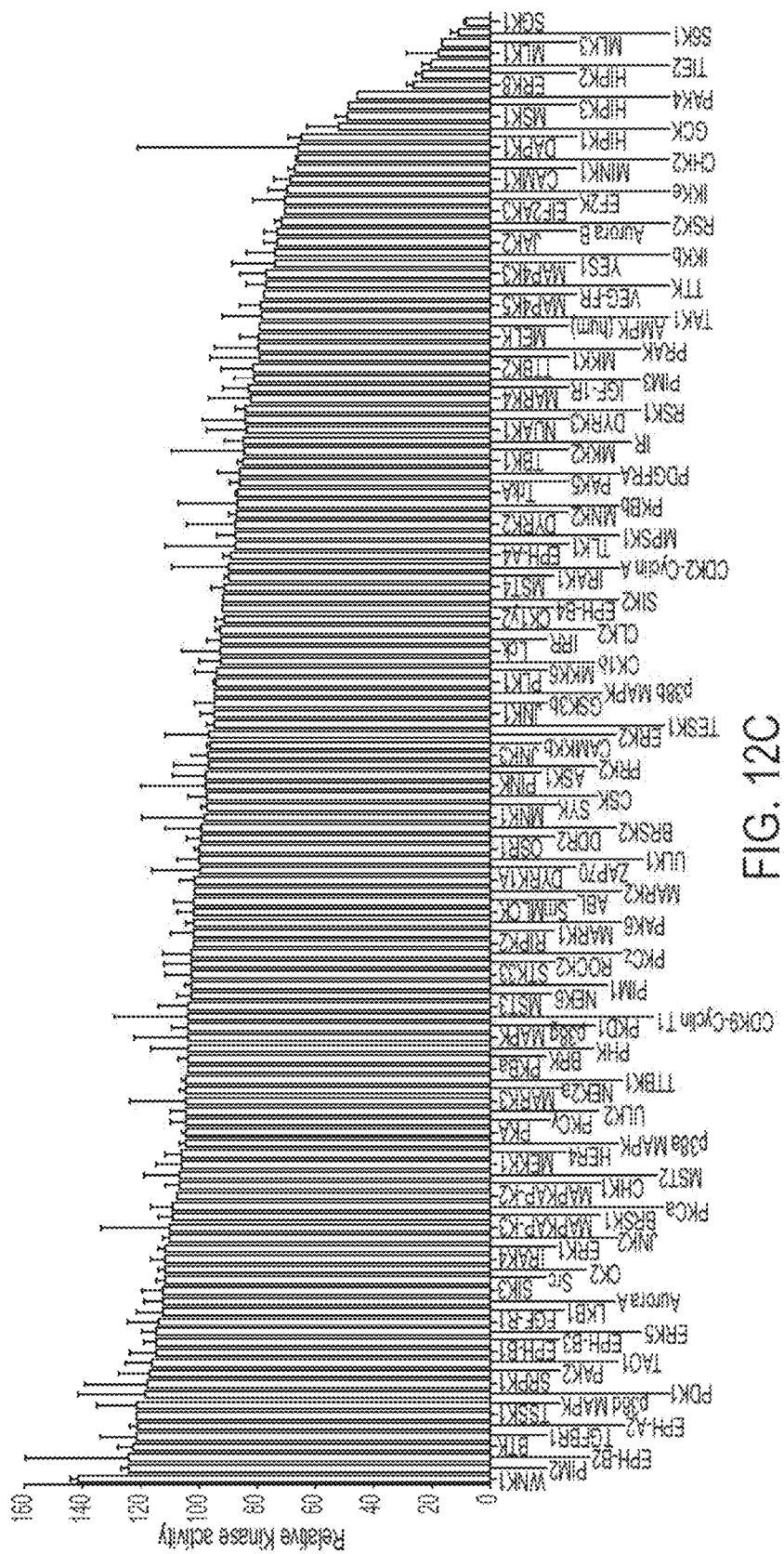

The few SGK inhibitors currently available have low activity in cellular models (data not shown). In order to overcome this problem, we characterized a recently described SGK inhibitor (SGK1-inh) that was discovered using 3D ligand-based virtual screening (Halland et al., 2015). SGK1-inh exhibited an IC50 of 4.8 nM at 10 µM ATP using recombinant SGK1 kinase assay (FIG. 5C), with appreciable activity also towards SGK2 and SGK3 (IC50 of 2.8 nM and 590 nM, respectively, FIG. 5D, E). The specificity of this compound was tested at a concentration of 1 µM (200× higher than the SGK1 inhibitory dose) against a panel of 140 human kinases. SGK1-inh showed selectivity towards SGK1 (FIG. 12C).

Figure 12D:
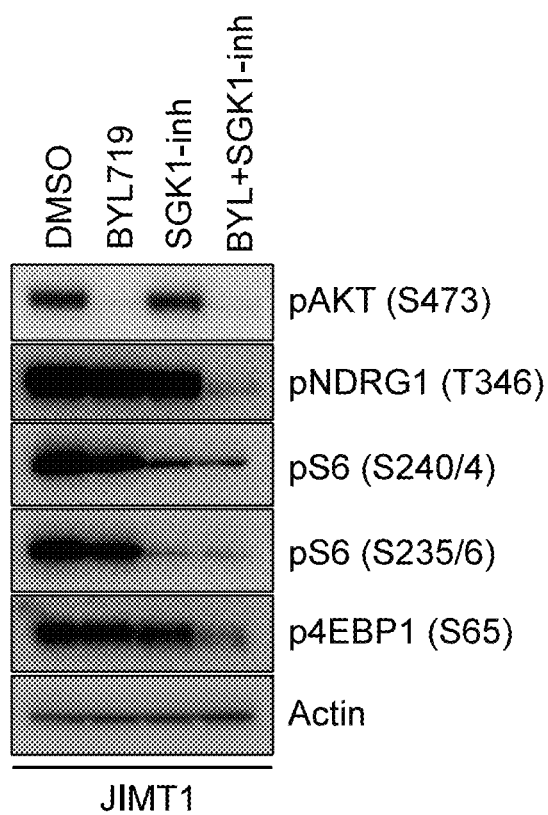
Figure 12E:
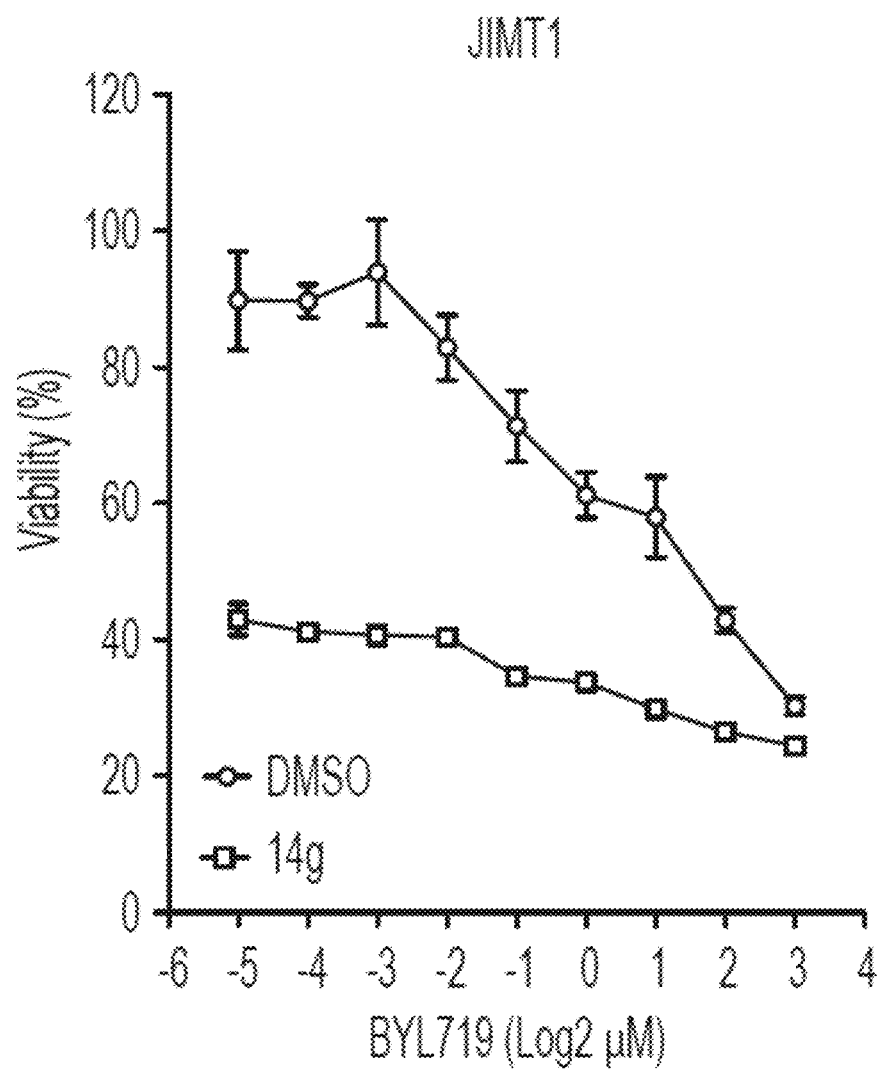
Figure 12F:
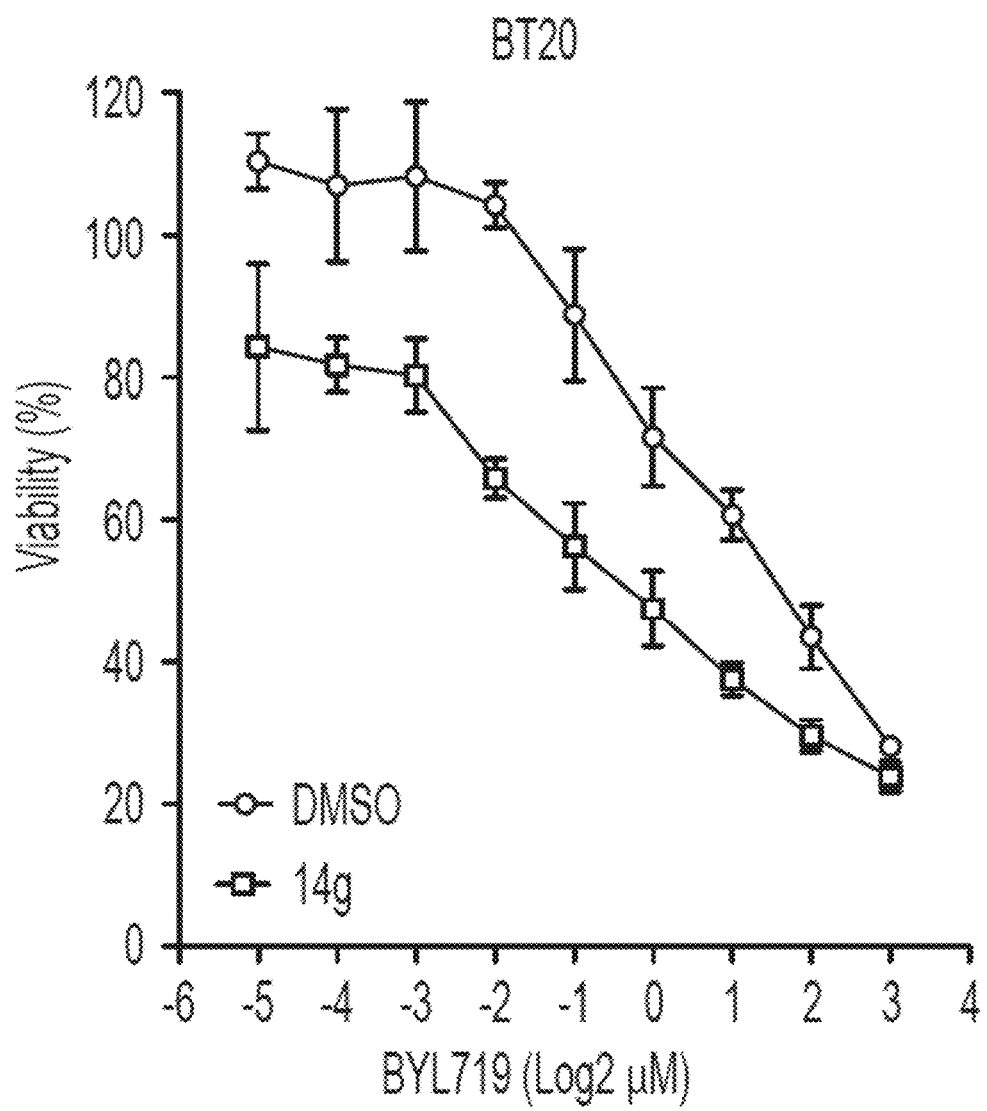
Figure 12G:
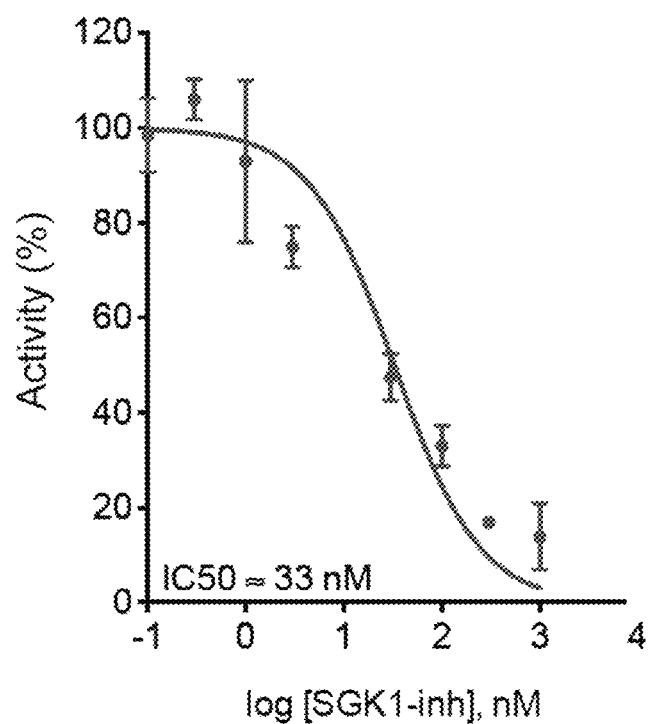
Figure 12H:
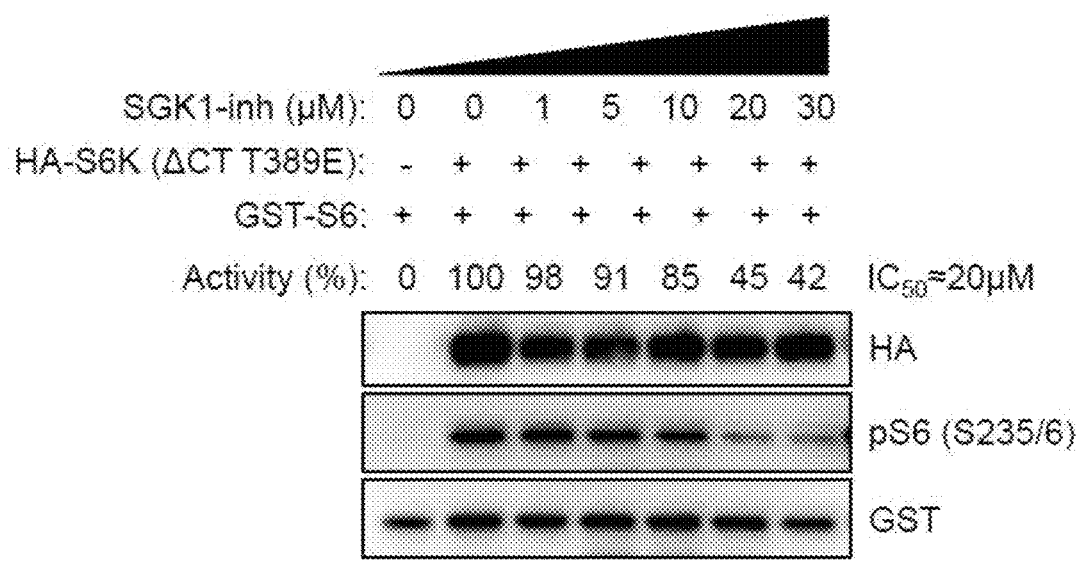
Figure 12I:
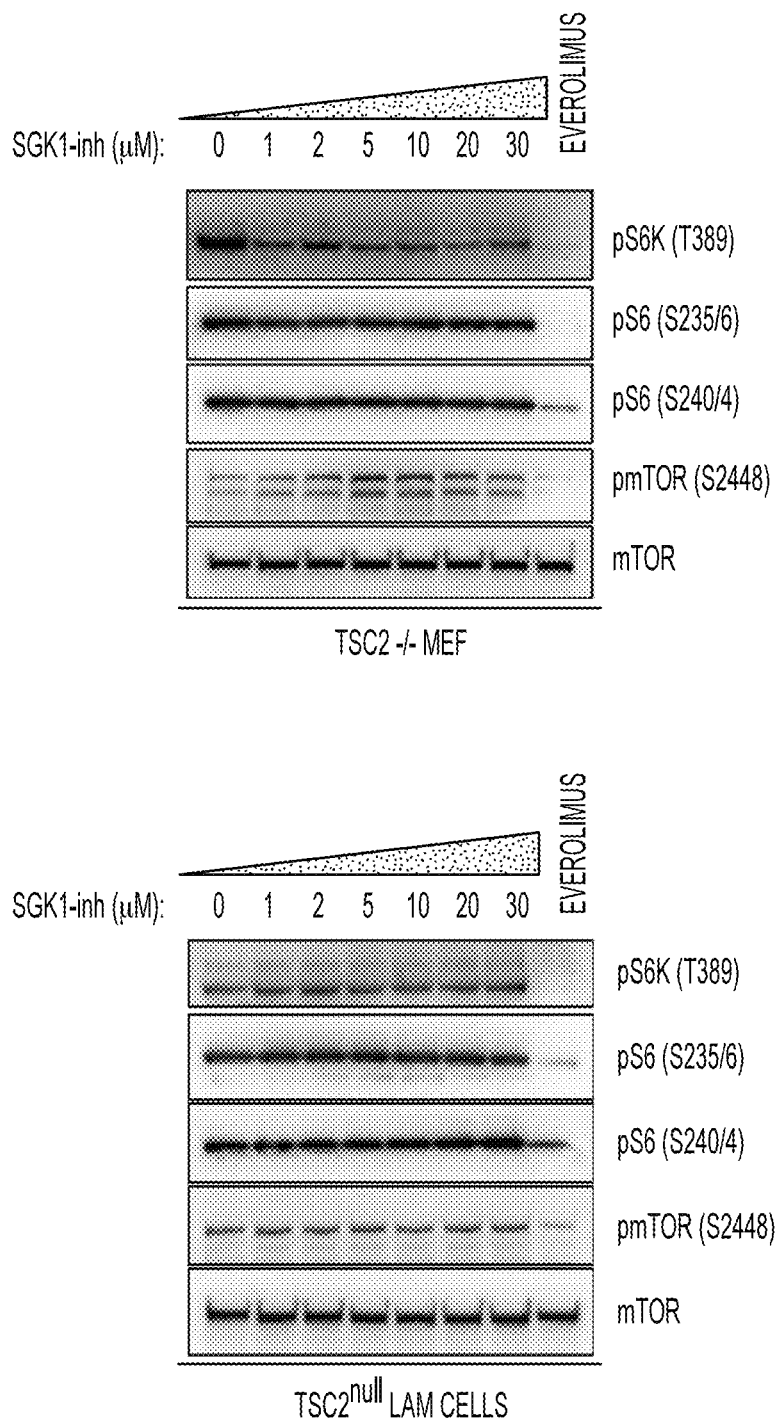

Although no activity against AKT1, PDK1, PKC or RSK was detected, we found that at this high concentration S6K was also inhibited, probably due to the high similarity of their catalytic site. Because S6K is a key downstream substrate of mTORC1, we aimed to further characterize the activity of SGK1-inh towards S6K. Recombinant in vitro kinase assay of S6K demonstrated an $IC_{50}$ of 33 nM, seven times higher that than SGK1 IC50 (FIG. 12G). At the cellular level, we performed S6K kinase assay in 293T cells overexpressing constitutively active S6K (ΔCT T389E) treated with increasing concentrations of SGK1-inh and found an $IC_{50}$ of ~20 µM (FIG. 12H). Next, using two fibroblast cell lines that lack TSC2 (derived from TSC2 KO mice and a lymphangioleiomyomatosis patient, respectively) we observed that increasing concentrations of SGK1-inh up to 30 µM were not able to reduce S6K signaling in these cellular models, as assed by the downstream S6K targets pS6 (S235/6), pS6 (S240/4), and pmTOR (S2448) (FIG. 12I). This suggests that SGK1-inh does not have activity towards S6K at concentrations below 20-30 µM. We also excluded any potential inhibition of mTORC1 by SGK1-inh testing this compound against mTOR in a recombinant kinase assay using 4EBP1 as a substrate (IC50 of >5000 nM, FIG. 12B).

Figure 13A:
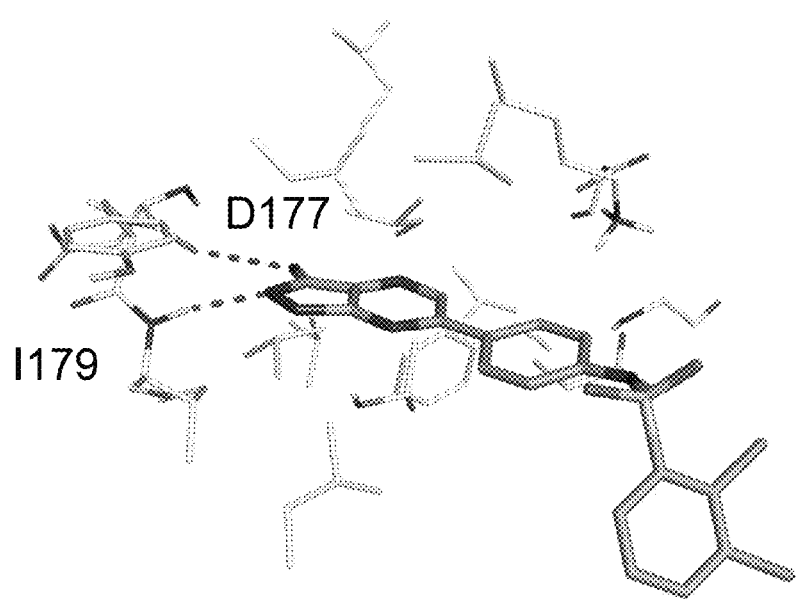
Figure 13B:
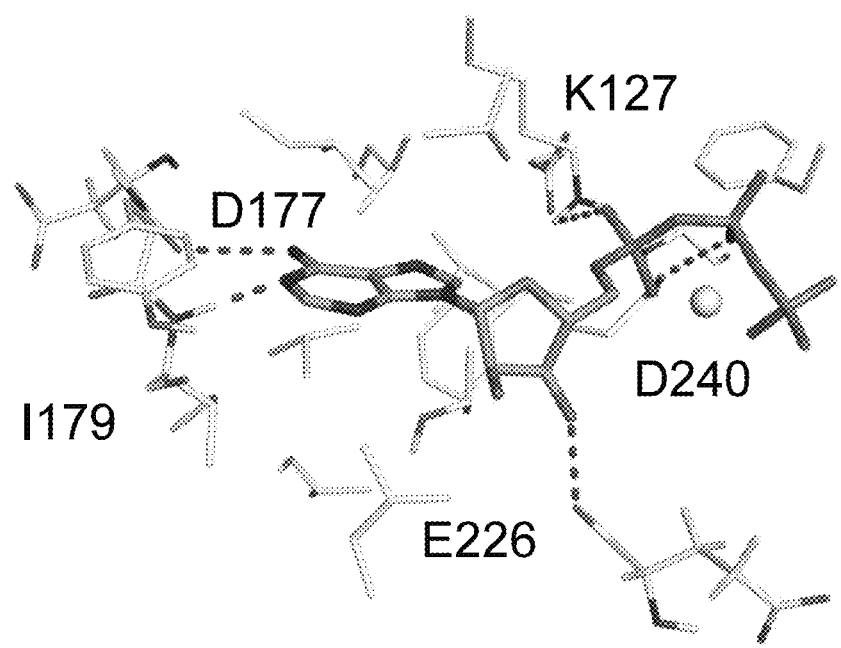
Figure 13C:
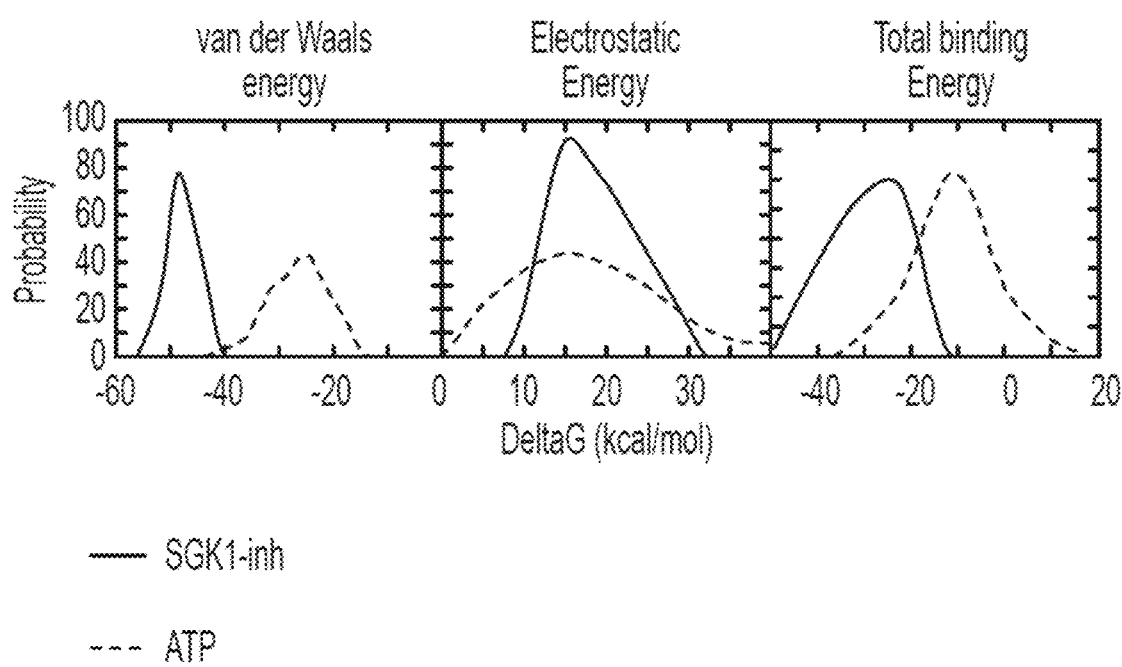
Figure 13D:
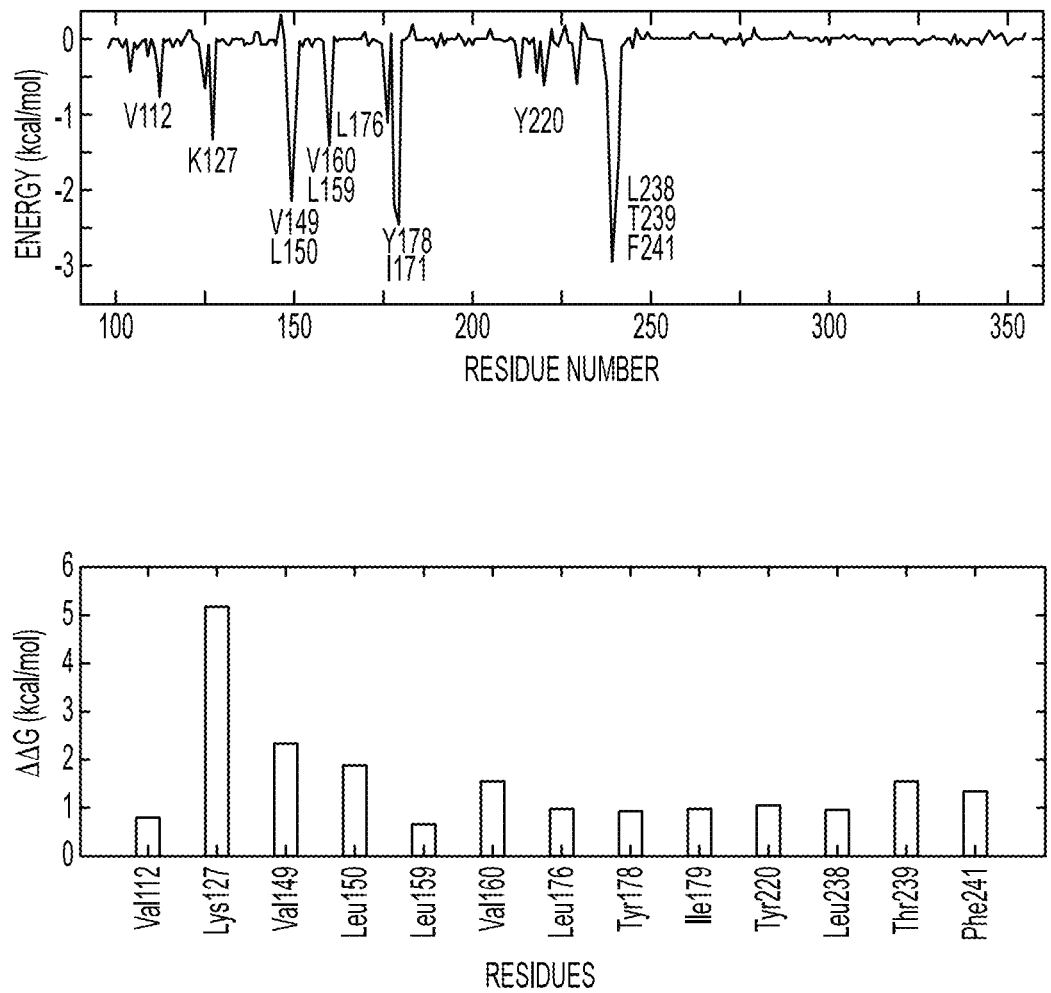

Although the chemical structure and preliminary characterization of SGK1-inh suggested that this compound acts as an ATP-competitive inhibitor, we further validated these observations with an ATP-competition assay. Consistently, we found that addition of increasing concentrations of ATP at 100 µM, 250 µM, 350 µM, and 500 µM decreased the potency of SGK1-inh in a dose-dependent manner (FIG. 12A). Our computational analyses suggest that SGK1-inh is a type II kinase inhibitor as it binds preferentially to the inactive conformation of the kinase (FIG. 5F). In fact, the docking model using the active conformation of SGK1 shows that the sulfonamide moiety points out from the pocket towards the solvent (FIG. 13A) rendering the bound state unstable. In contrast, in the inactive conformation, several hydrophobic residues mediate interactions with SGK1-inh within the allosteric DFG-out pocket (mainly by V149, L159, V154, and V160 residues, FIG. 5G). The pyrazolo(3,4-b)pyrazine head portion of SGK1-inh interacts with the key residues D177 and I179, similar to the interactions of the adenine moiety of ATP (FIG. 5G; FIG. 13B). The energetics of SGK1-SGK1-inh binding are more favorable than SGK1-ATP, as assessed by binding free energy calculations. The electrostatic components of these interactions are similar between ATP and SGK1-inh and the majority of the binding energy arises from more favorable packing (van der Waals interactions) made between SGK1-inh and the kinase (FIG. 13C). Next, we analyzed the energetic contribution of each individual residue of SGK1 by decomposing the binding free energies. Most of the favorable interactions that take place between SGK1 and SGK1-inh are with amino acids found within the SGK1 active site (FIG. 13D). In silico alanine scanning of the key residues resulted in substantial loss of binding free energies of hydrophobic residues and K127 and confirmed the importance of these amino acids in the protein-ligand interactions (FIG. 13D).

Given our in vitro and docking results, we moved forward to cell-based experiments. In our models, we estimated that the appropriate concentration of SGK1-inh to inhibit endogenous SGK1 is 10 µM, based on the ability to inhibit NDRG1 phosphorylation in the presence of BYL719 (FIG. 5H). This relatively high concentration (still lower than the concentration needed to affect S6K activity) may be explained by the fact that these sulfonamide derivatives exhibit poor permeability ($133 \times 10^{-7}$ cm/s in $CaCO_2$ cells permeability assays) (Halland et al., 2015)

Figure 5I:
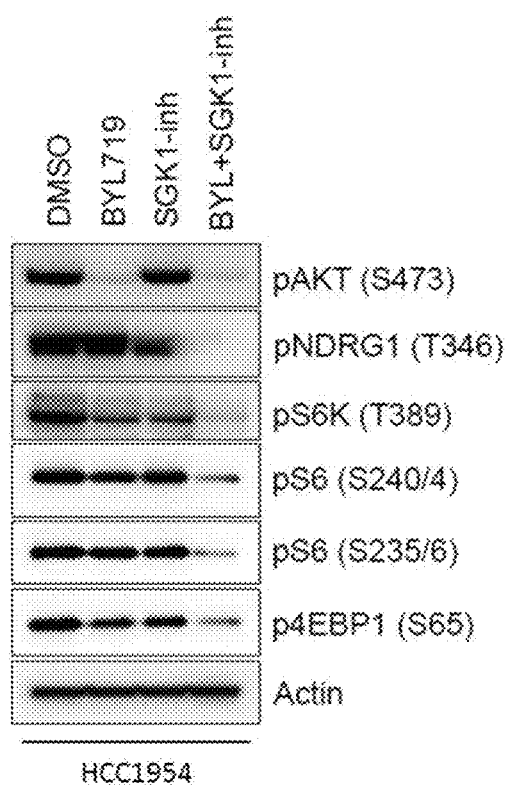
Figure 5J:
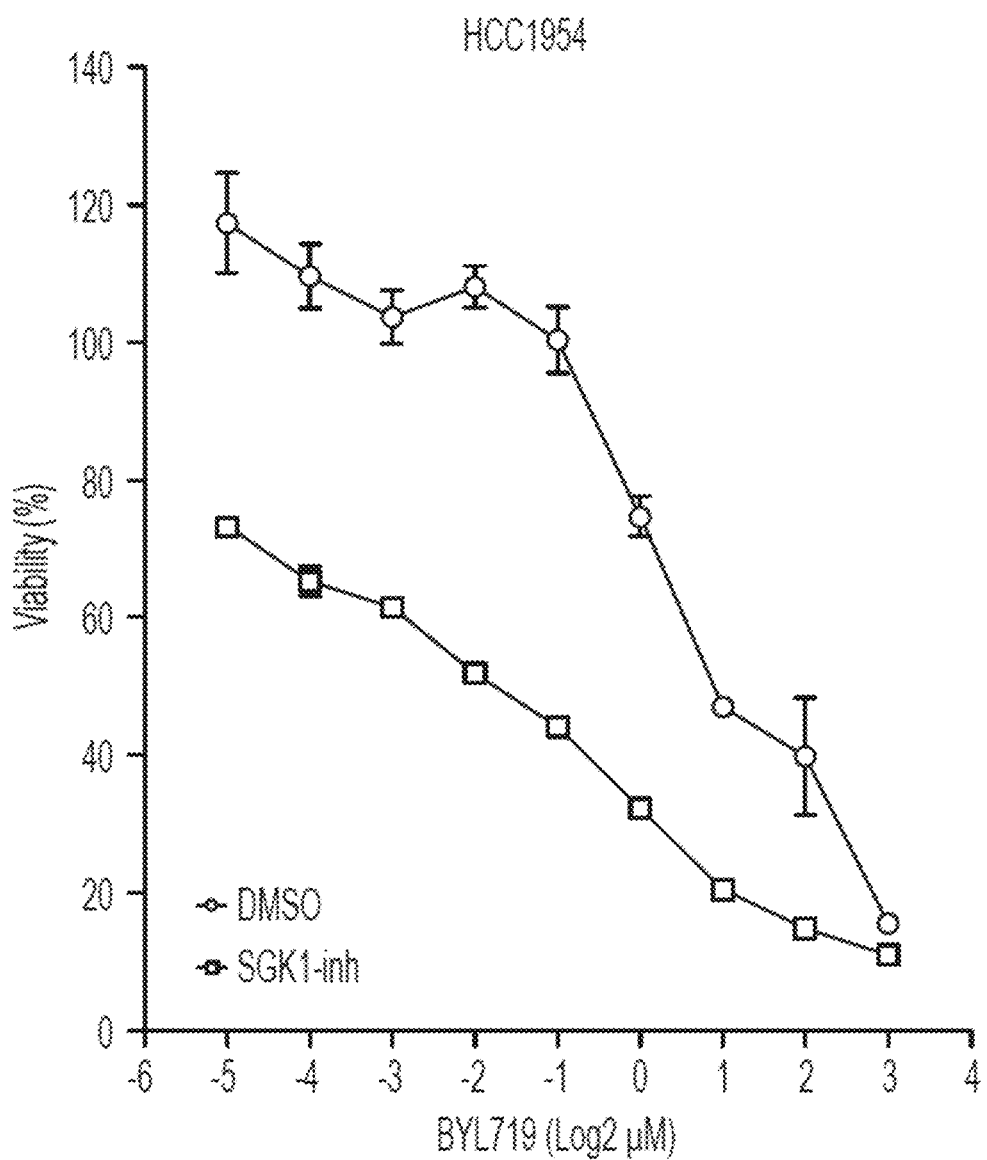
Figure 12J:
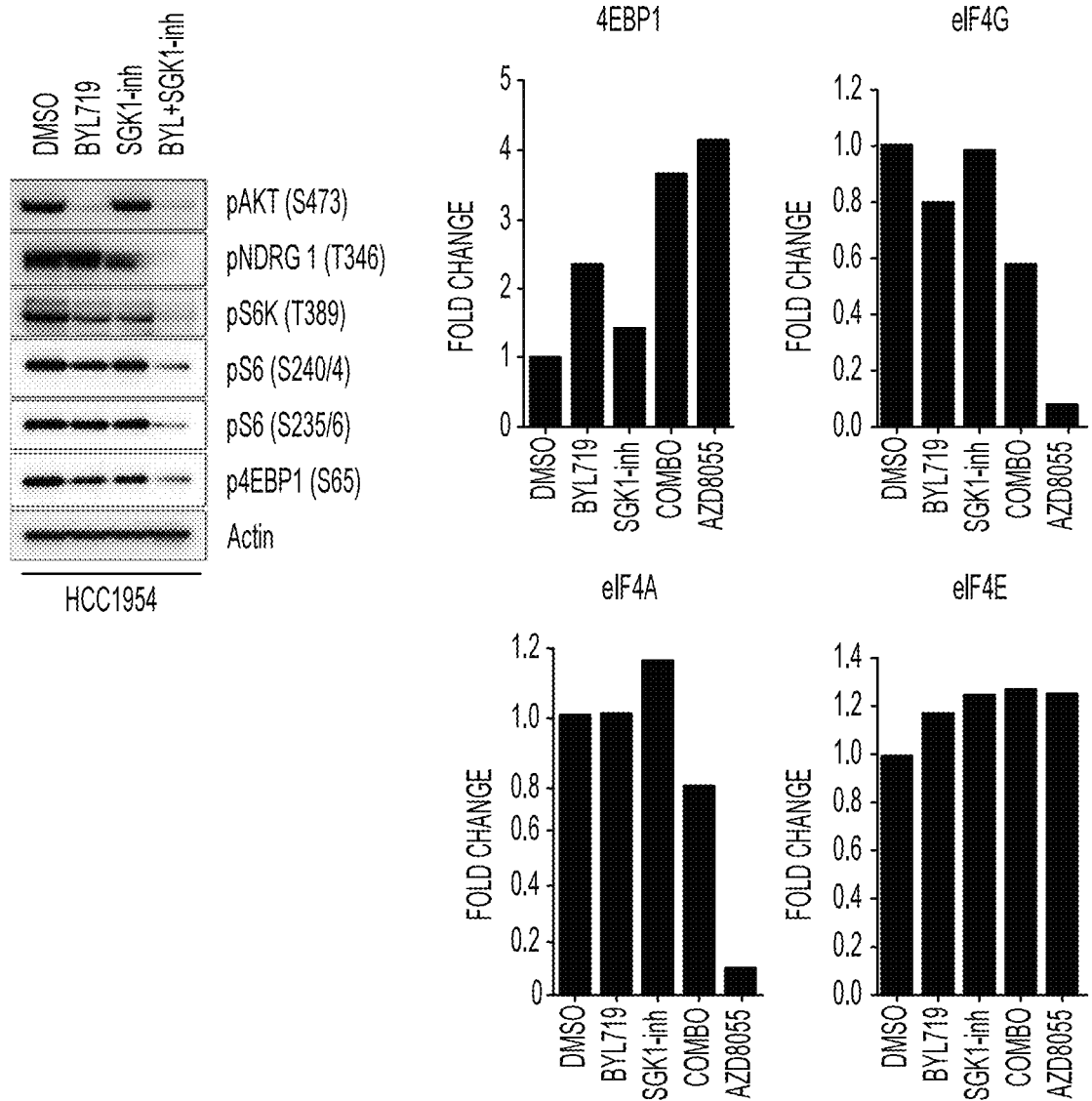
Figure 12K:
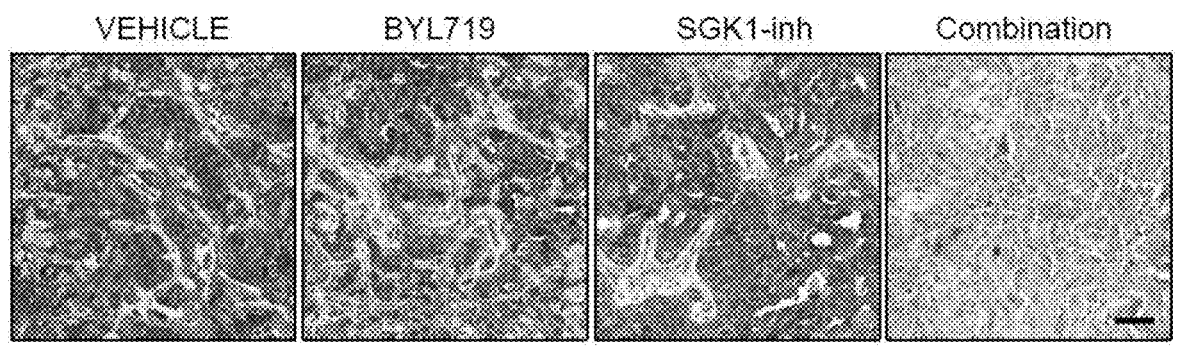

Treatment of HCC1954 and JIMT1 cells with the combination of BYL719 and SGK1-inh not only abrogated pNDRG1 (T346) but also mTORC1 signaling (FIG. 5I; FIG. 12D). It should be noted that SGK1-inh alone has some activity towards S6K signaling. However, in combination with BYL719, the phosphorylation of 4EBP1 is inhibited, which indicates that SGK1 acts on mTORC1 signaling in the absence of AKT. Using m7GTP pull downs we also found that combined PI3Kα and SGK1 inhibition induces a decreased cap-dependent translation as seen by the increased 4EBP1 and decreased eIF4A and eIF4G binding to the m7GTP beads (FIG. 12J). This translated to superior inhibition of cell viability of BYL719-resistant cell lines HCC1954, JIMT1, and BT20 treated with the combination of BYL719 and SGK1-inh (FIG. 5J; FIG. 12E, F). Our results support that in high SGK1-expressing cells, both AKT and SGK kinases need to be inhibited simultaneously in order to block mTORC1 and proliferation.

Figure 5K:
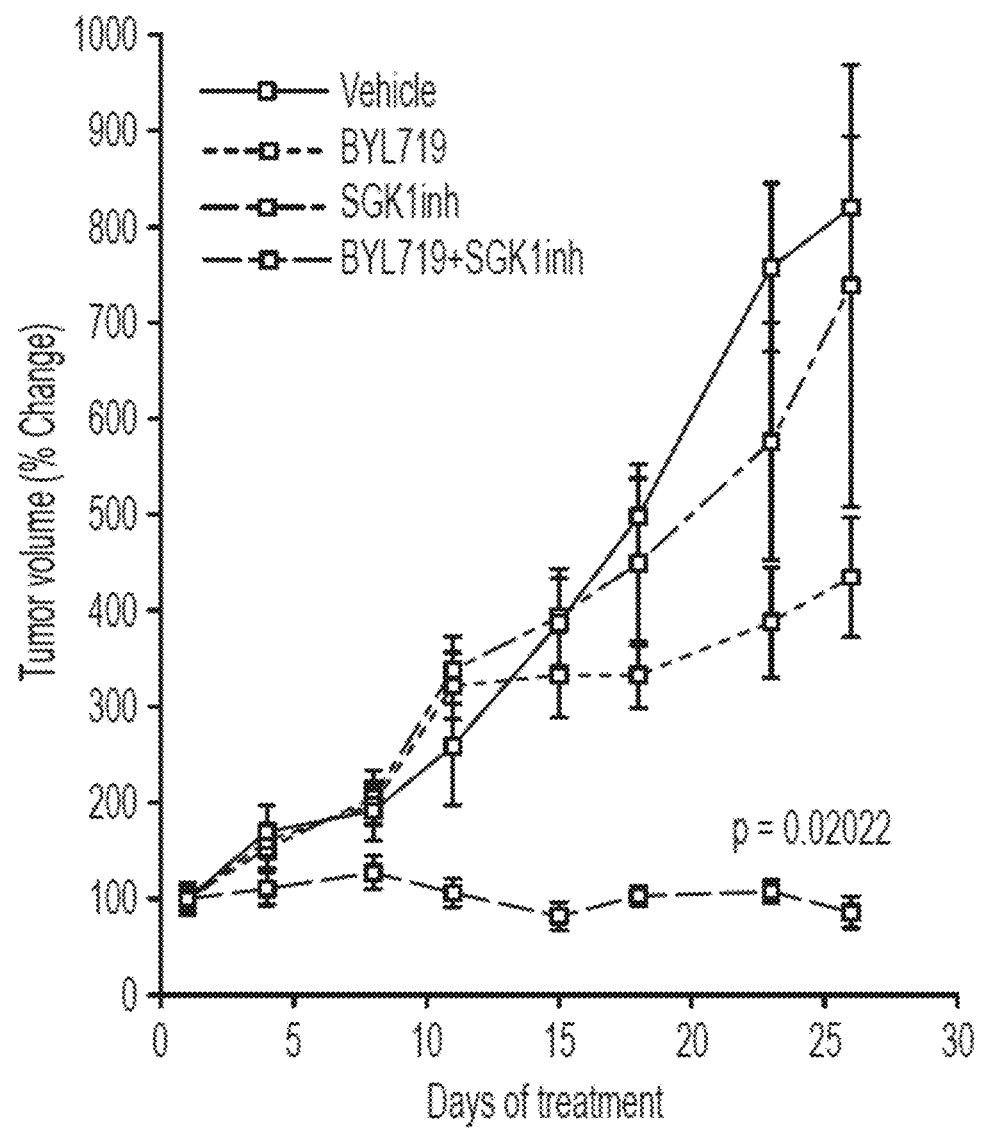

We then assessed the potential antitumor activity of SGK1-inh in HCC1954-derived xenografts treated with BYL719, SGK1-inh, and the combination of both agents. We observed that only the combination of BYL719 and SGK1-inh reduced tumor burden in this model (FIG. 5K). Contrary to the observations seen in the in vitro experiments, pS6 (S240/4) remained elevated in tumors treated with SGK1-inh alone for a prolonged period of time (26 days).

Figure 5L:
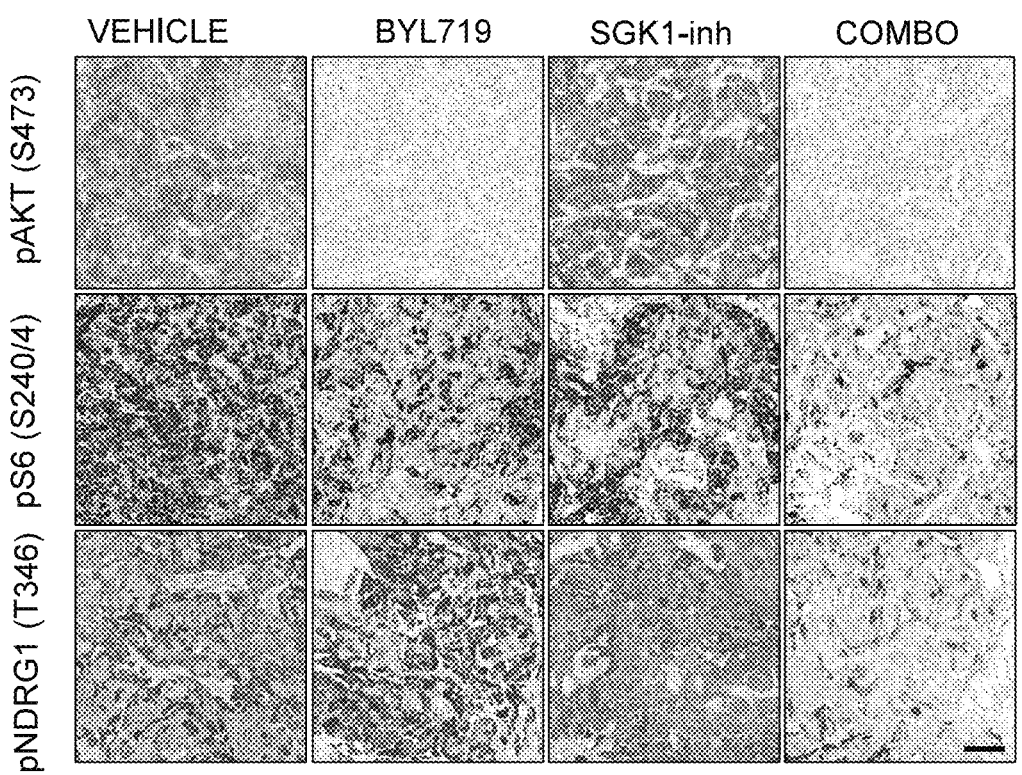
Figure 5M:
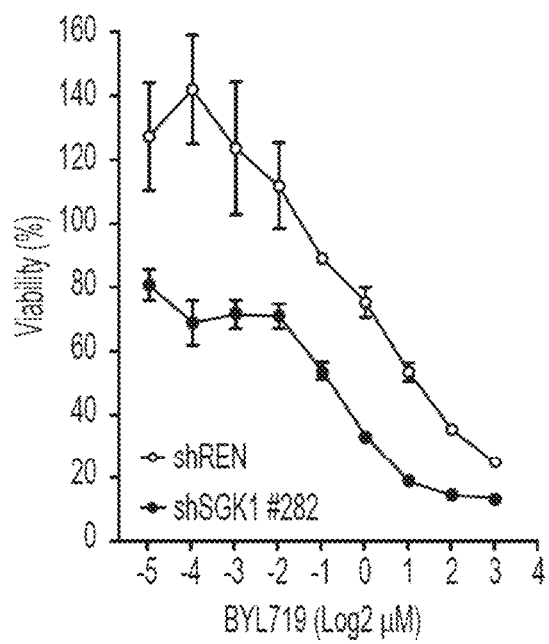
Figure 5M:
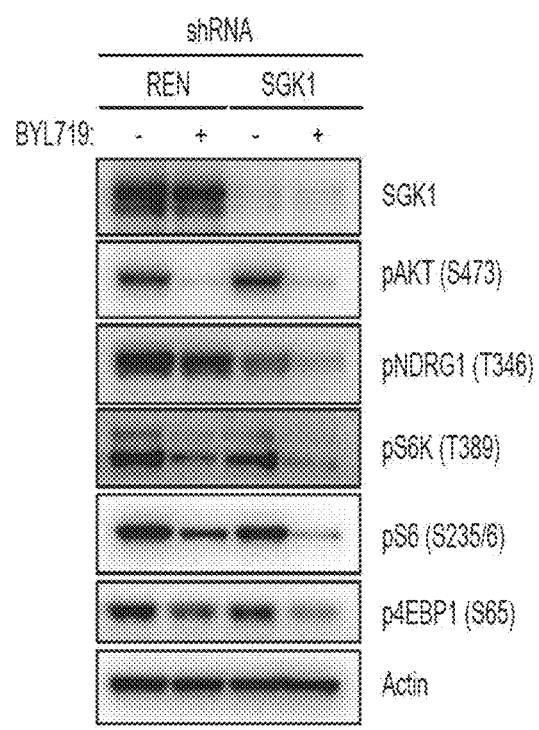

Additionally, pS6 (S240/4) levels only decreased in tumors treated with the combination of BYL719 and SGK1-inh (FIG. 5L, K). Similarly, only the combination of both agents decreased the phosphorylation of NDRG1 at T346.

These results show that targeting SGK1 pharmacologically is feasible, and demonstrate that dual inhibition of AKT and SGK1 is required to achieve full suppression of mTORC1 and proliferation.

SGK1 Interacts with and Phosphorylates TSC2

Due to its similarity with AKT, we reasoned that SGK1 could modulate mTORC1 activity by interacting with a component of the TSC/RHEB/mTORC1 axis.

Figure 6A:
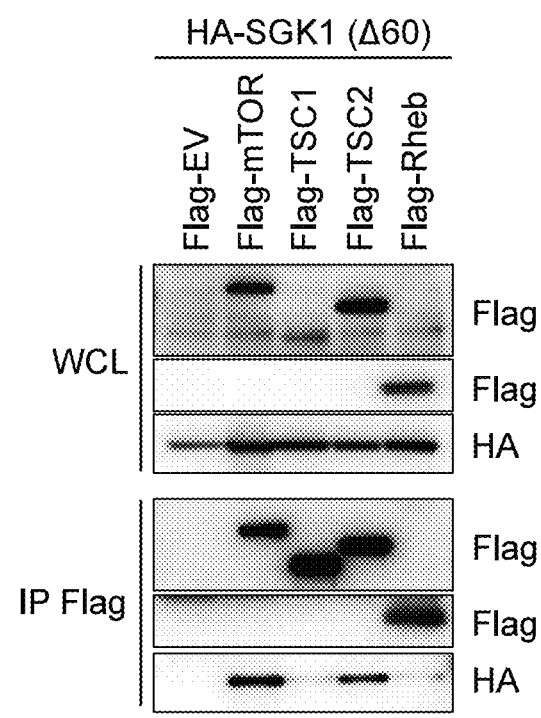
Figure 6B:
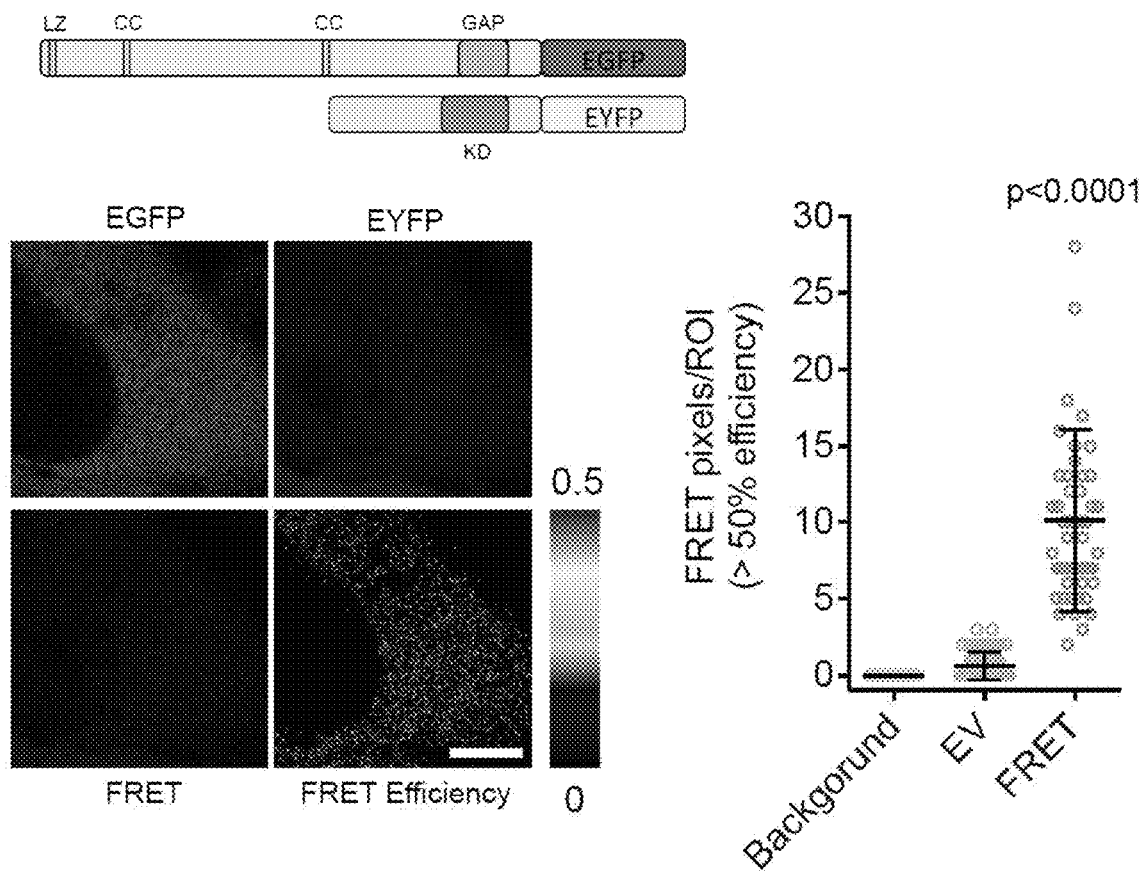
Figure 14A:
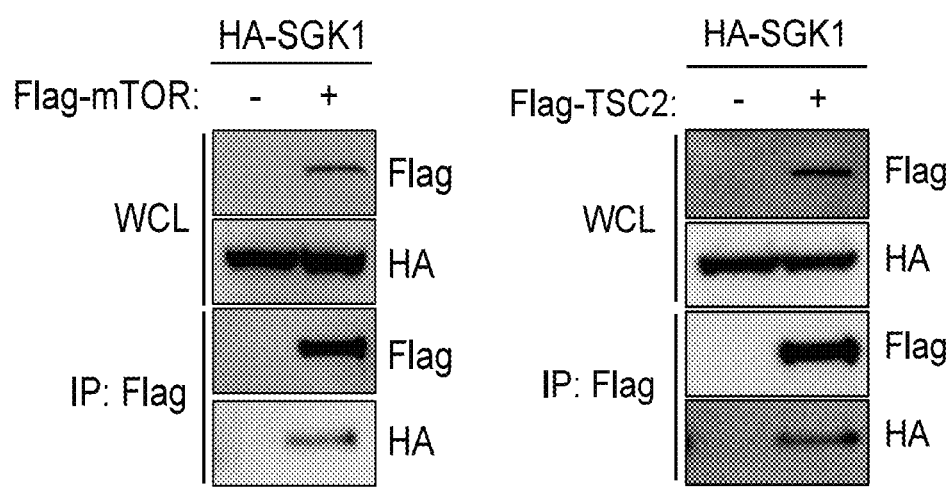

Immunoprecipitation of recombinant Flag-tagged TSC1, TSC2, RHEB, and mTOR in 293T cells revealed that SGK1 physically interacts with both mTOR and TSC2 proteins (FIG. 6A, FIG. 14A). While the interaction between SGK1 and mTOR has previously been described, as mTORC2 is responsible for the HM phosphorylation of SGK1 (Garcia-Martinez and Alessi, 2008), to our knowledge this is the first report showing an interaction between SGK1 and TSC2. This result was corroborated in a cell-live context by performing fluorescence resonance energy transfer (FRET) experiments using EGFP-tagged TSC2 and EYFP-tagged SGK1 in HeLa cells. Excitation of the donor (EGFP) molecule led to emission from the acceptor molecule (EYFP), demonstrating the in vivo direct interaction of these proteins, as assessed by FRET efficiency calculation (FIG. 6B).

Figure 6C:
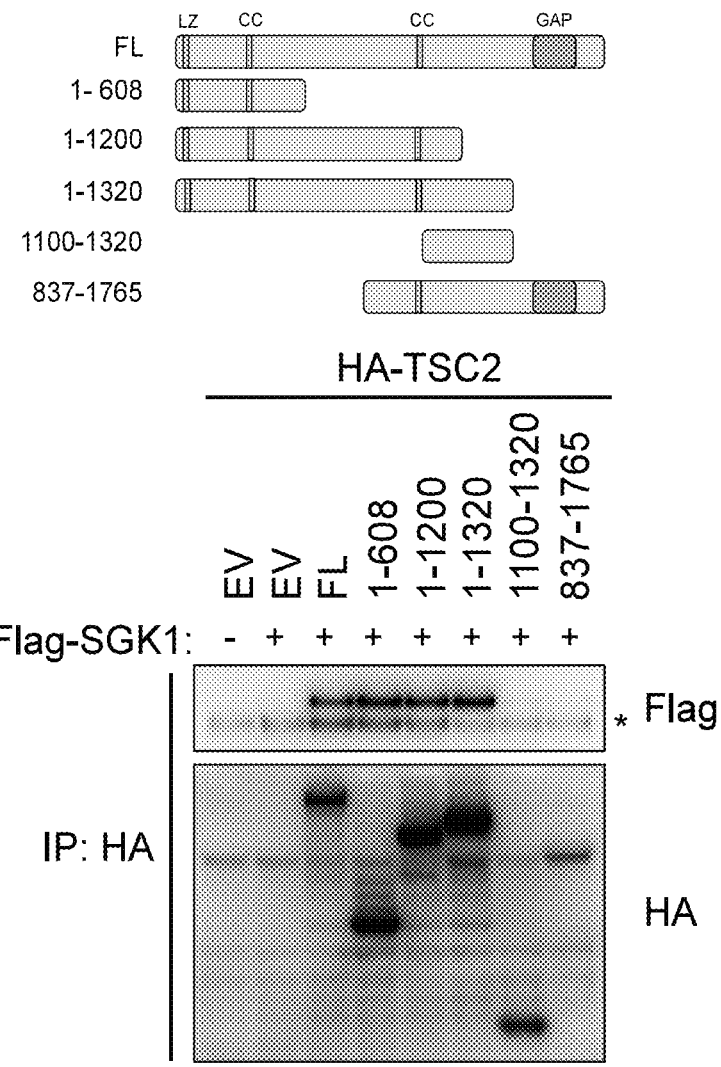
Figure 6D:
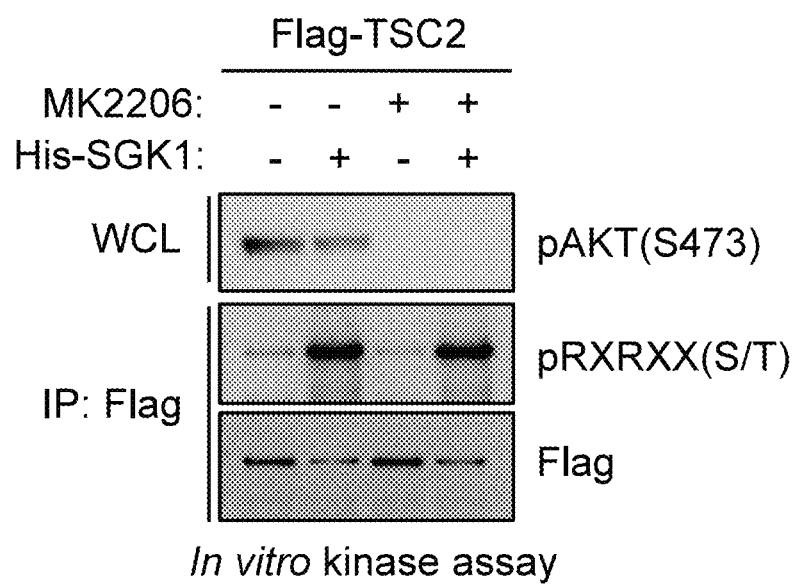
Figure 6E:
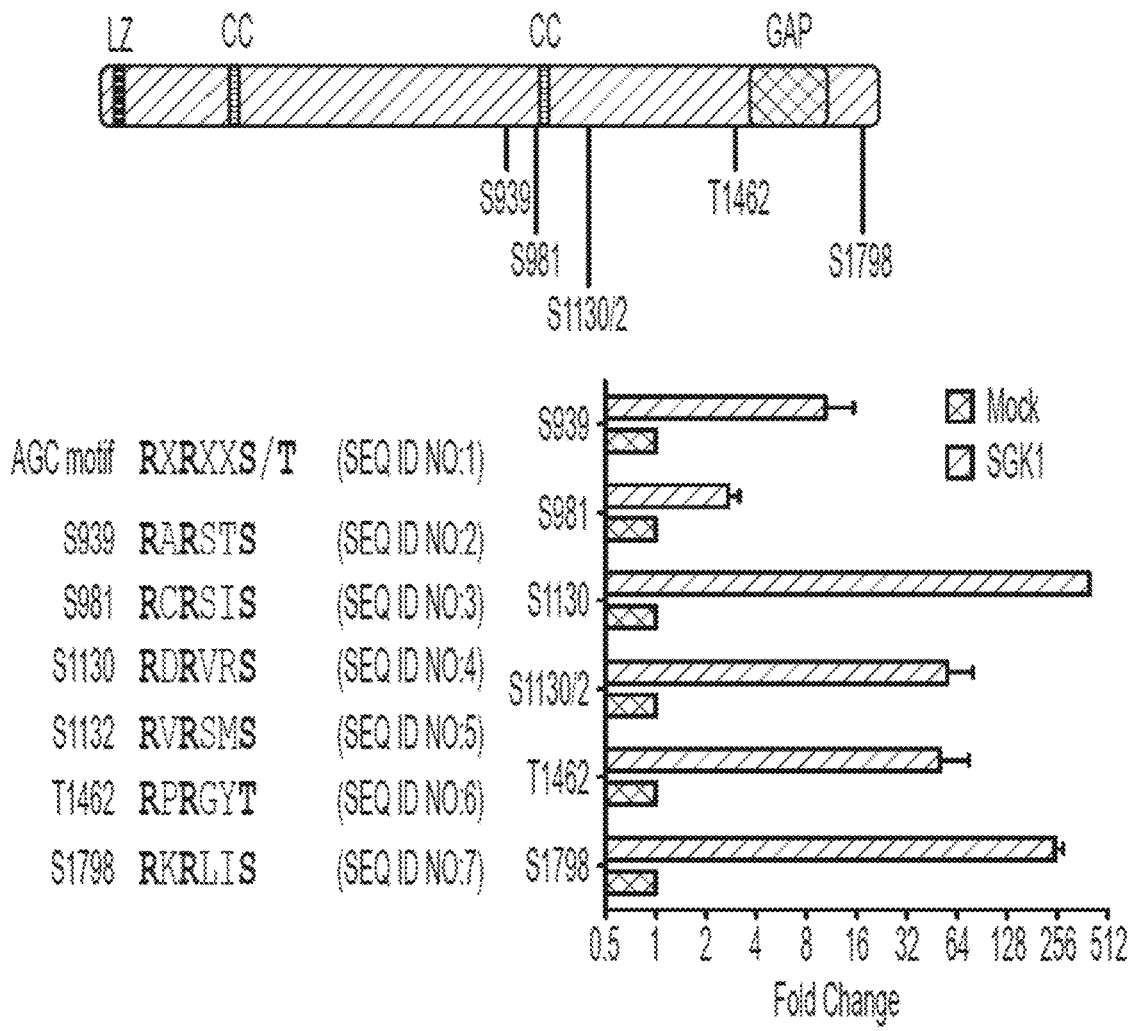
Figure 6F:
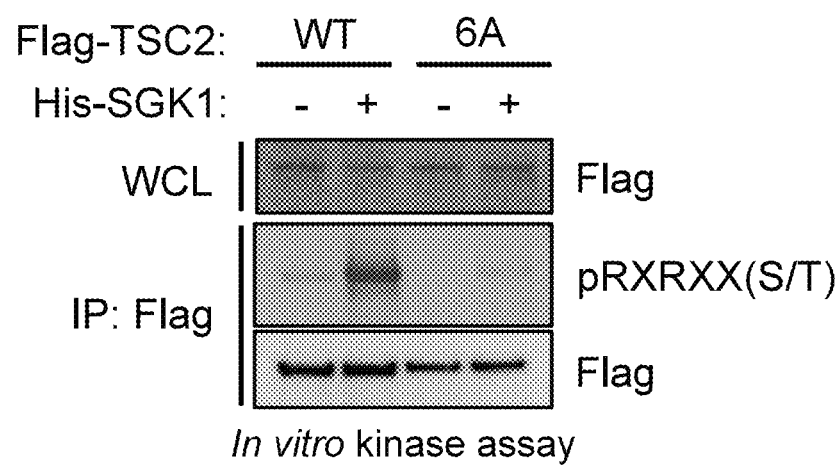
Figure 6G:
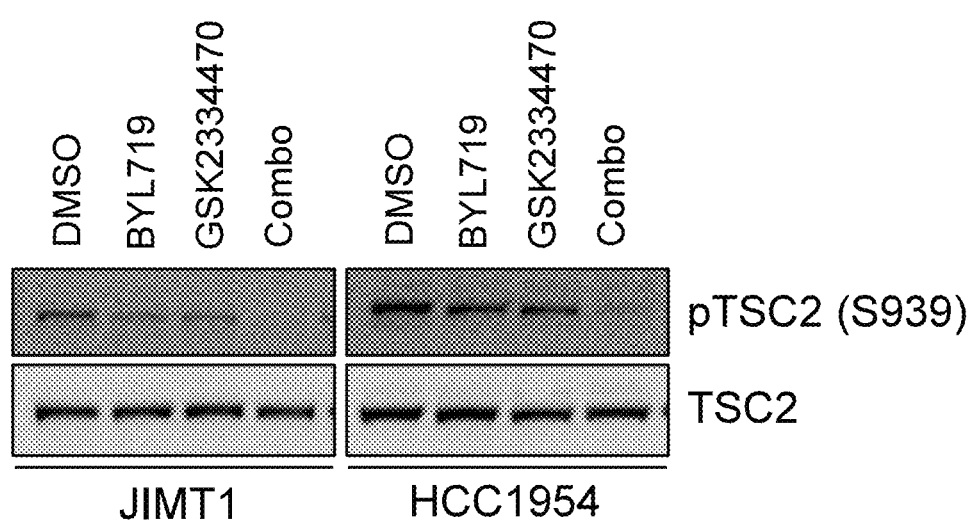
Figure 6H:
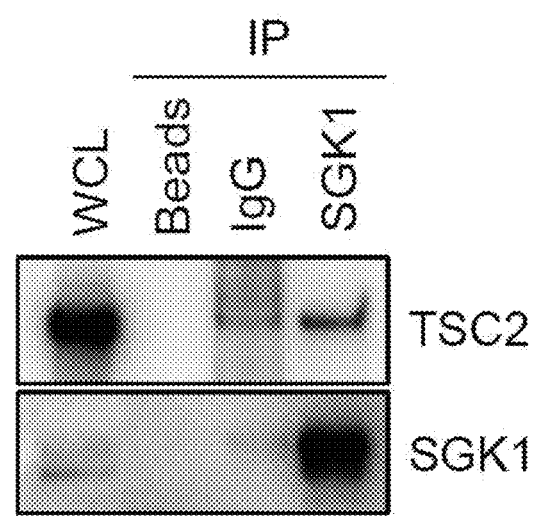
Figure 6I:
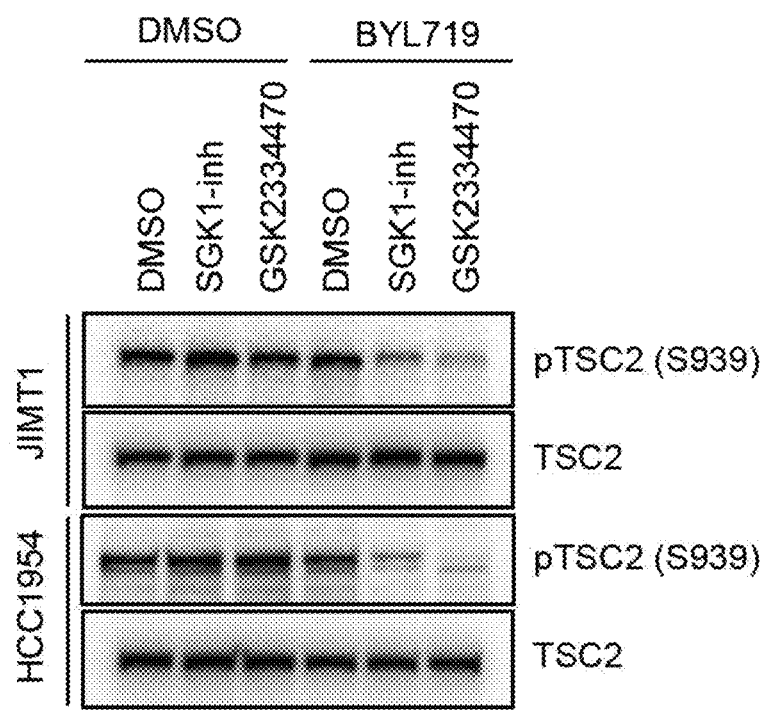
Figure 7:
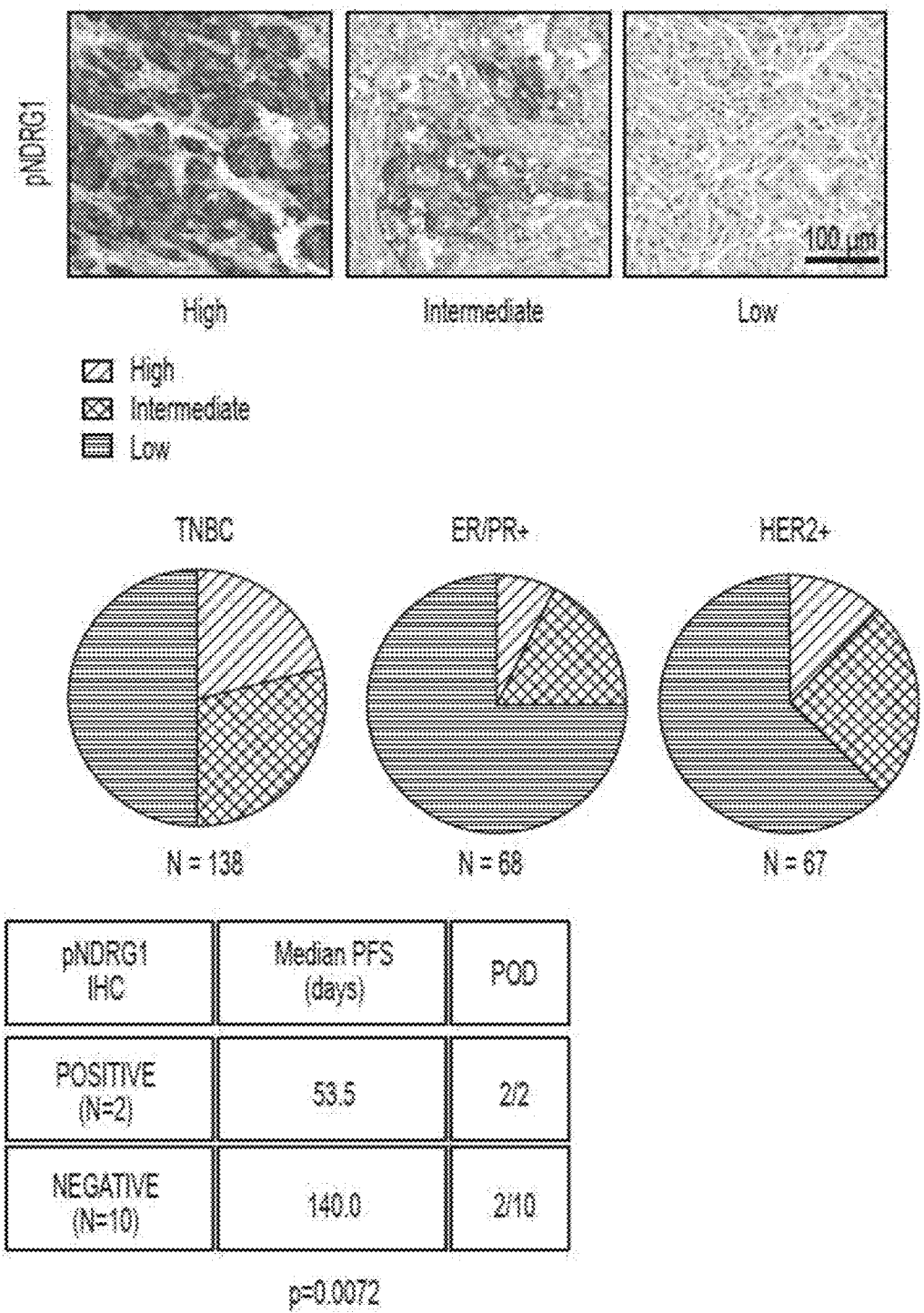

We further confirmed the interaction between endogenous SGK1 and TSC2 by co-immunoprecipitation (FIG. 6H). Moreover, we determined the proportion of endogenous SGK1 that is associated with the TSC complex by performing sucrose gradient experiments in JIMT1 lysates. The TSC complex fractionated at high-density fractions (fraction 5), as assessed by the presence of the three components TSC1, TSC2, and TBC1D7 (FIG. 14E) (Dibble et al., 2012). Although most of SGK1 fractionated at low molarity fractions, approximately 20% of the kinase eluted at similar fractions as the TSC complex. Considering SGK1 as a monomer (or maybe a dimer (Zhao et al., 2007)), only the association with a larger complex such as the TSC complex can explain the elution at these high sucrose gradients.

Co-immunoprecipitation assays using five different fragments of TSC2 demonstrated that SGK1 binds its N-terminal region, found between amino acids 1-608 (FIG. 6C). This region of TSC2 contains a Leucine Zipper (LZ) domain important for protein-protein interactions and is also required for the interaction with TSC1 (Li et al., 2004). In our immunoprecipitation assays, TSC2 mutants that lack this region of the protein are unable to bind SGK1 (FIG. 6C).

SGK1 has high similarity to AKT in the kinase domain and thus shares many substrates that contain the AGC-kinase consensus motif RXRXX(S/T) (SEQ ID NO: 1), where R is Arginine, X is any amino acid, and (S/T) is a phosphorylatable Serine or Threonine (Alessi et al., 2009). The use of a degenerated phospho-specific motif antibody allows detection of these phosphosites and has previously been shown to be a reliable surrogate for phospho-TSC2 detection (Manning et al., 2002).

In our model, we observed that co-expression of SGK1 with TSC2 increased the phosphorylation of RXRXX(S/T) (SEQ ID NO: 1) motifs in. When we analyzed the TSC2 protein sequence searching for identifiable RXRXX(S/T) (SEQ ID NO: 1) motifs, we found seven putative sites of phosphorylation: S939, S981, T993, S1130, S1132, T1462, and S1798. All these sites were conserved across lower species, including mouse, rat, cattle, chicken, frog, and zebra fish (FIG. 14B, F). To systematically test the ability of SGK1 to phosphorylate these residues, we established an in vitro kinase assay using recombinant active SGK1 and TSC2 as a substrate, immunoprecipitated from 293T cells expressing Flag-TSC2. In order to deplete endogenous phosphorylation of TSC2, we pre-treated cells with the AKT inhibitor MK2206. The addition of recombinant SGK1 kinase increased the phosphorylation of the RXRXX(S/T) (SEQ ID NO: 1) sites of TSC2 independent of the AKT activity (FIG. 6D). Using mass spectrometry to identify the phosphorylation status of the aforementioned residues in our in vitro kinase assay, we found increased phosphorylation in all these sites, except at T993 (FIG. 6E). Mutation of these six sites into the non-phosphorylatable amino acid alanine (TSC2 6A) completely abrogated the ability of SGK1 to phosphorylate TSC2 in vitro (FIG. 6F).

Figure 14C:
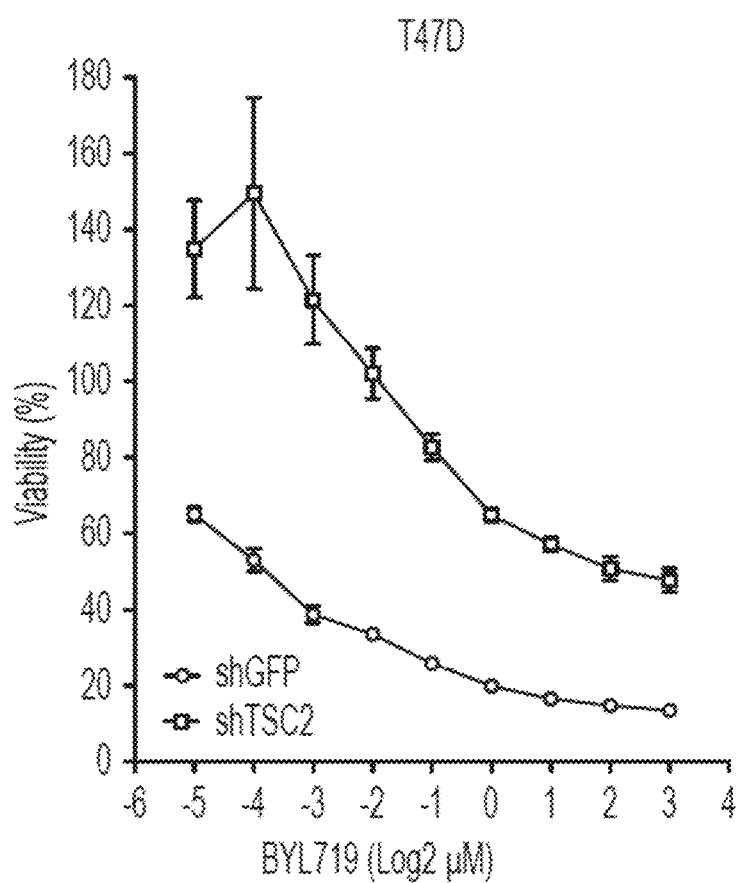
Figure 14D:
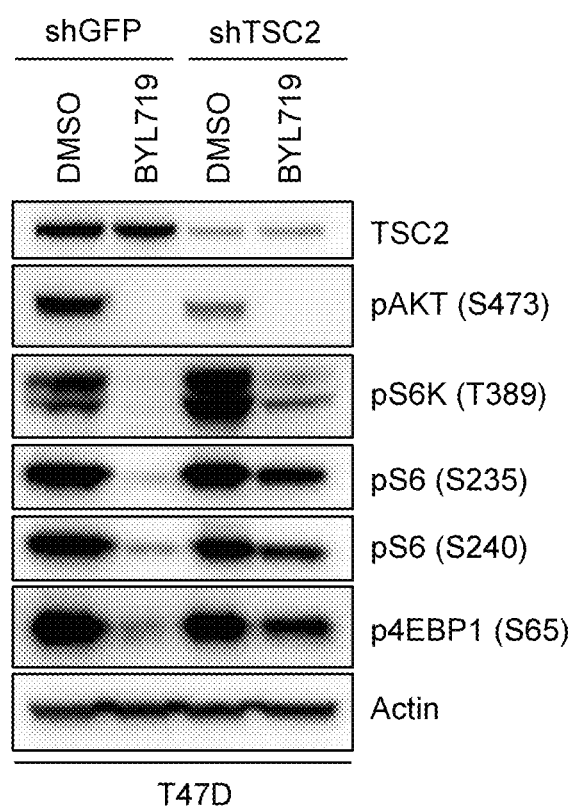
Figure 14E:
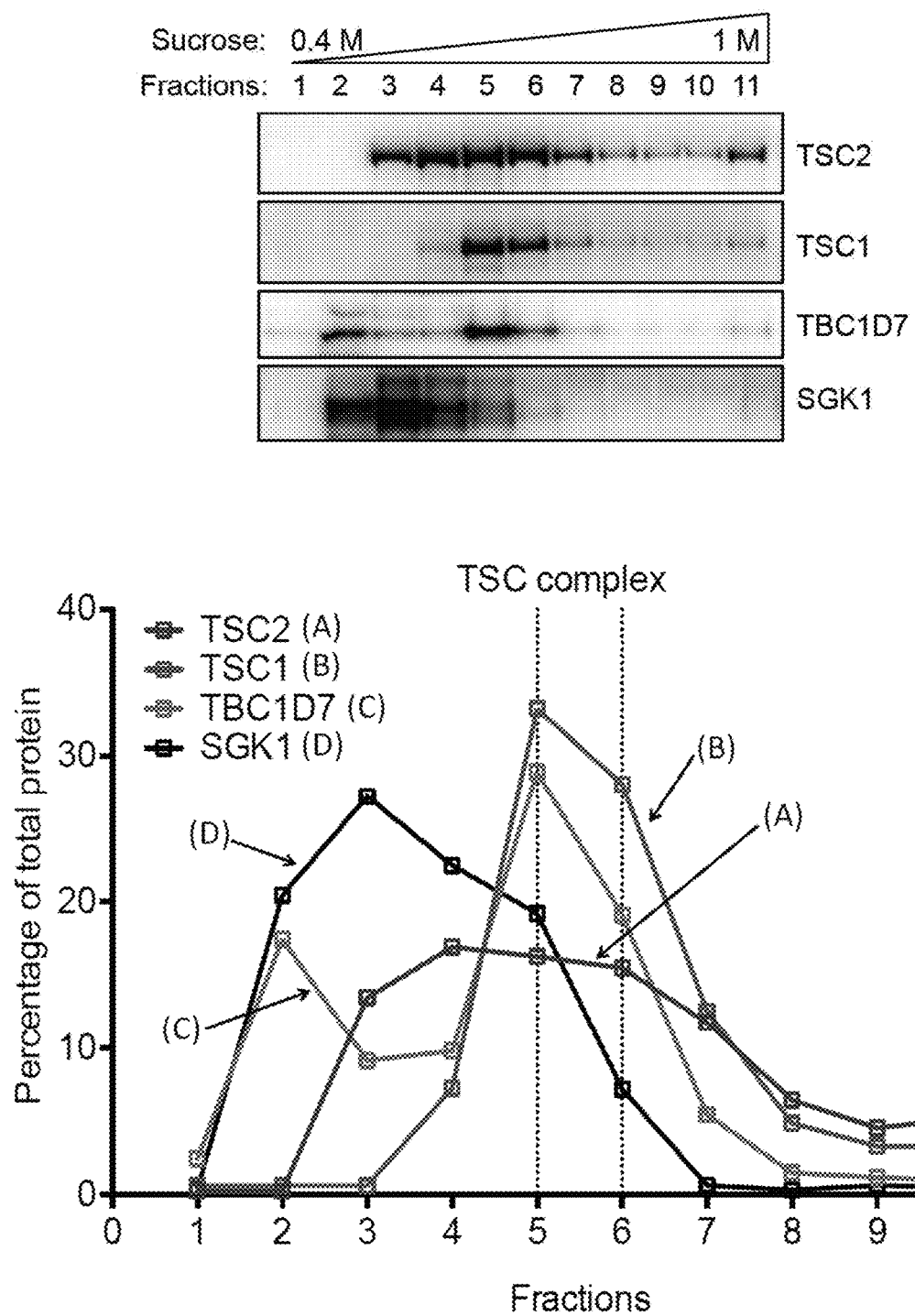

SGK1 and AKT share the capability to phosphorylate five of these six sites in TSC2. It is well accepted that phosphorylation of these residues by AKT inhibits the GAP activity of TSC2, which increases the downstream RHEB-GTP loading and mTORC1 signaling (Inoki et al., 2003a; Inoki et al., 2002; Menon et al., 2014). We then wanted to test whether the SGK1-mediated phosphorylation of TSC2 is sufficient to activate downstream mTORC1 signaling. We transfected HeLa cells with TSC2 wild type, TSC2 6A, and the phosphomimetic mutant TSC2 6E in which the six phosphorylation sites have been mutated to the positively charged amino acid glutamate, mimicking the phosphorylation state. We observed that the low level of mTORC1 activity (measured by basal phosphorylation of S6K and 4EBP1) induced in serum-starved HeLa cells can be restored with the TSC2 6E mutant but not with the TSC2 6A mutant (FIG. 14C). The phosphorylation and inhibition of TSC2 phenocopies the loss of expression of the protein itself, as demonstrated by the induction of mTORC1 activity and consequent resistance to BYL719 in the T47D BYL719-sensitive cell line depleted of TSC2 (FIG. 14C, D).

To confirm that our biochemical findings are consistent with the proposed mechanism of resistance to BYL719, we treated HCC1954 and JIMT1 cells with BYL719, GSK2334470, SGK1-inh and the combination of these agents and found that the phosphorylation of endogenous TSC2 decreases only upon dual PI3Kα and PDK1 or SGK1 suppression (FIG. 6G, I).These results demonstrate that SGK1 can sustain mTORC1 activity in BYL719-resistant cells by phosphorylating and inhibiting the mTORC1 negative regulator TSC2.

Figure 14F:
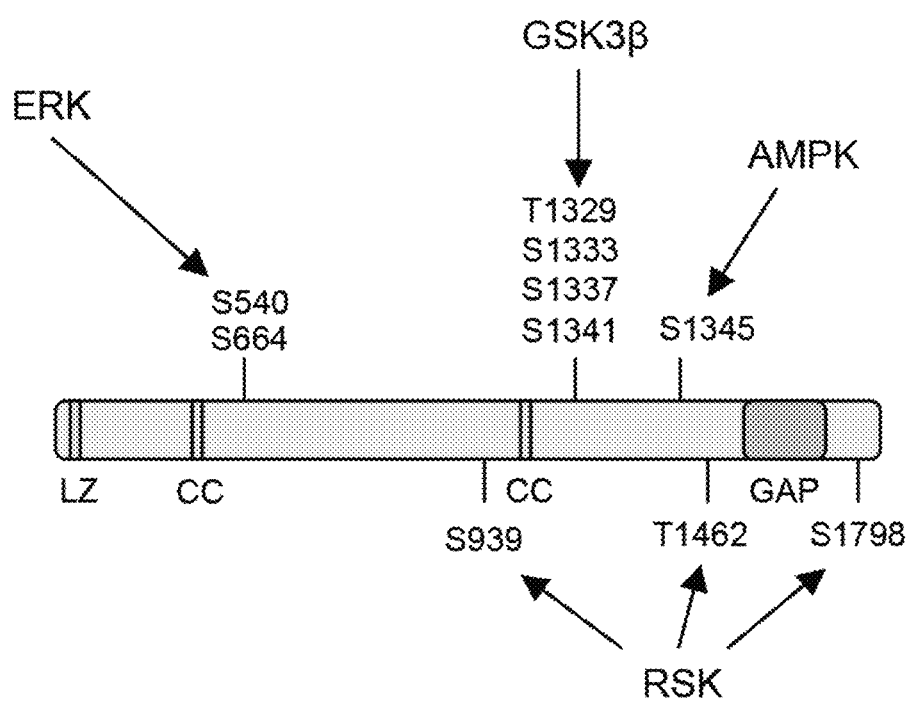
Figure 14G:
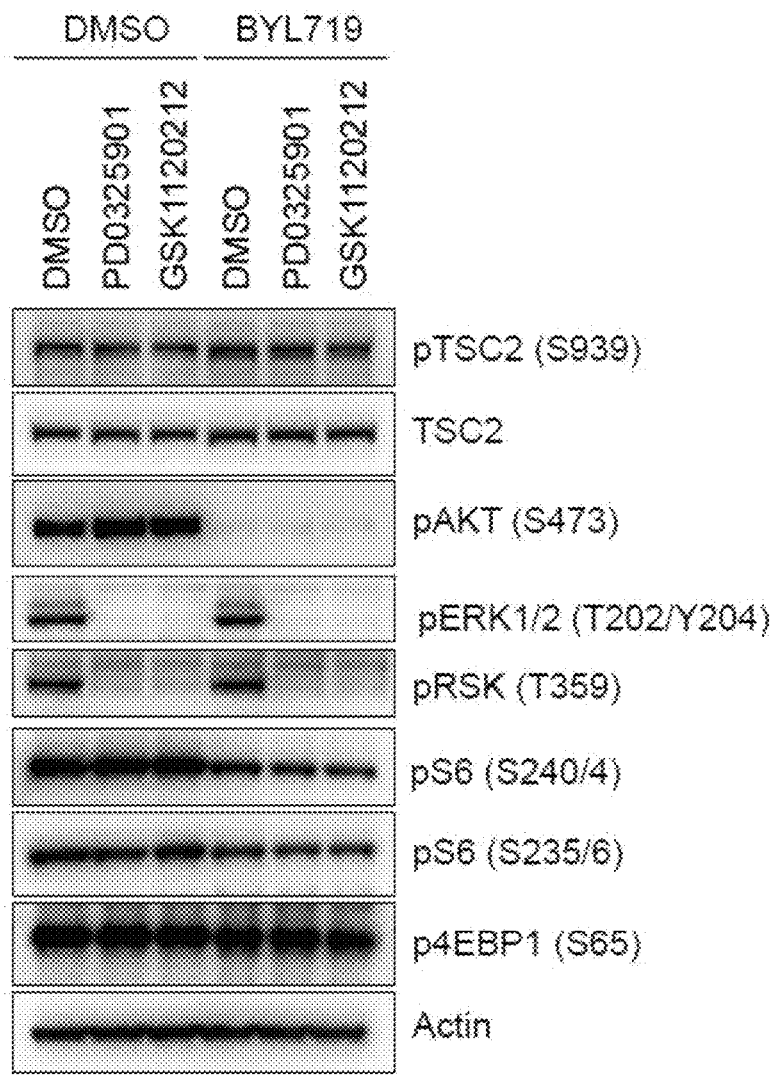
Figure 14H:
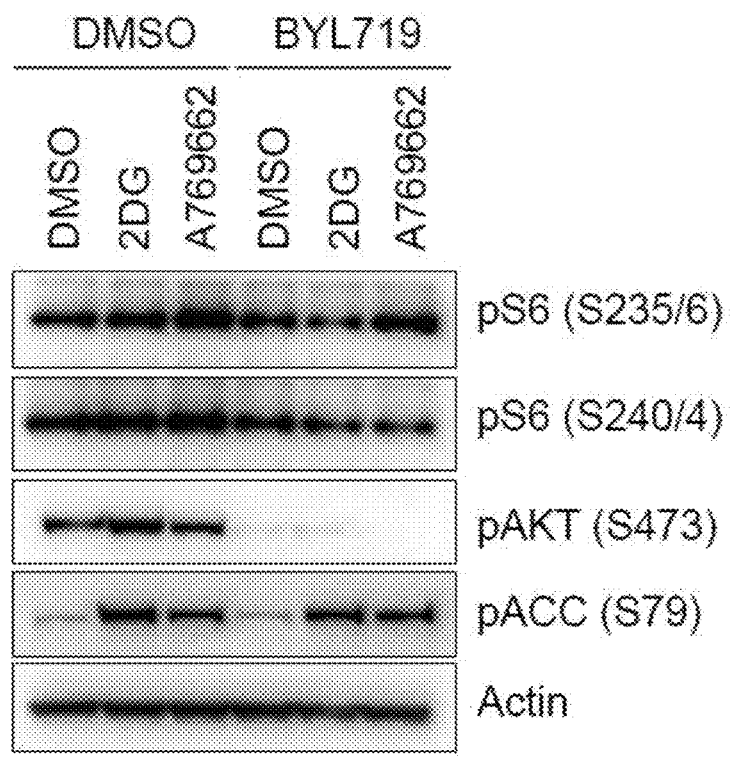
Figure 14I:
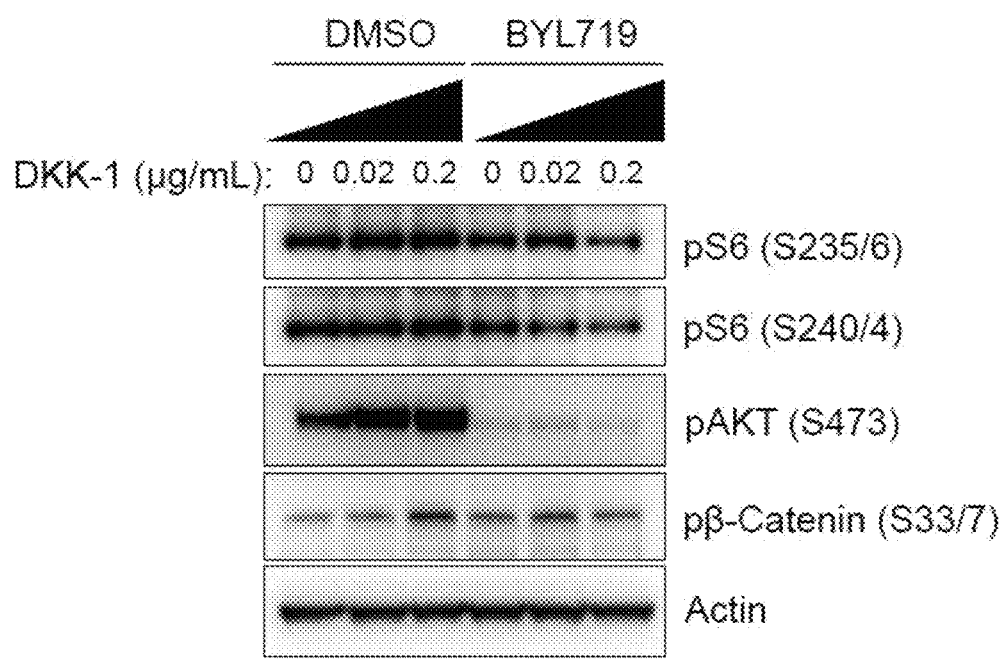

Then, we asked whether kinases other than AKT or SGK1 are involved in the phosphorylation of TSC2 and sustained activation of mTORC1 upon PI3Kα inhibition (FIG. 14F). Extracellular Signal-regulated Kinase (ERK) and the downstream AGC kinase RSK phosphorylate TSC2, activating downstream mTORC1 effectors (Ma et al., 2005; Roux et al., 2004). However, we did not detect changes in TSC2 phosphorylation at S939 (or mTORC1 downstream signaling) when HCC1954 cells were treated with the MEK inhibitors PD0325901 and GSK1120212 and downstream ERK and RSK were fully inhibited (FIG. 14G). AMP-dependent protein kinase (AMPK), which is activated in conditions of energy stress, phosphorylates TSC2 at S1345 and induces the inhibition of mTORC1 (Inoki et al., 2003b). Treatment of HCC1954 cells with the stress-inducing agent 2-deoxyglucose (2DG) and the AMPK activator A769662 were unable to rescue the sustained phosphorylation of S6 in this resistant model (FIG. 14H). In line with the AMPK regulation of mTORC1 signaling, GSK3 kinase has also been reported to phosphorylate TSC2 using the AMPK-specific site S1345 as a priming event, in a process downstream of WNT signaling (Inoki et al., 2006). However, incubation of HCC1954 cells with the recombinant WNT antagonist DKK-1 did not reduce the sustained S6 phosphorylation (FIG. 14I).

Altogether, these results suggest that in our resistant models SGK1 is the main kinase involved in the phosphorylation of TSC2 and sustained mTORC1 activation.

SGK1 Expression in Breast Cancer Patients

In order to establish the importance of our findings in patients, we assessed the expression of SGK1 mRNA levels in the TCGA breast cancer patient cohort. In these patients, we found that about 10% of cases harbor upregulation of SGK1 mRNA.

Figure 4G:
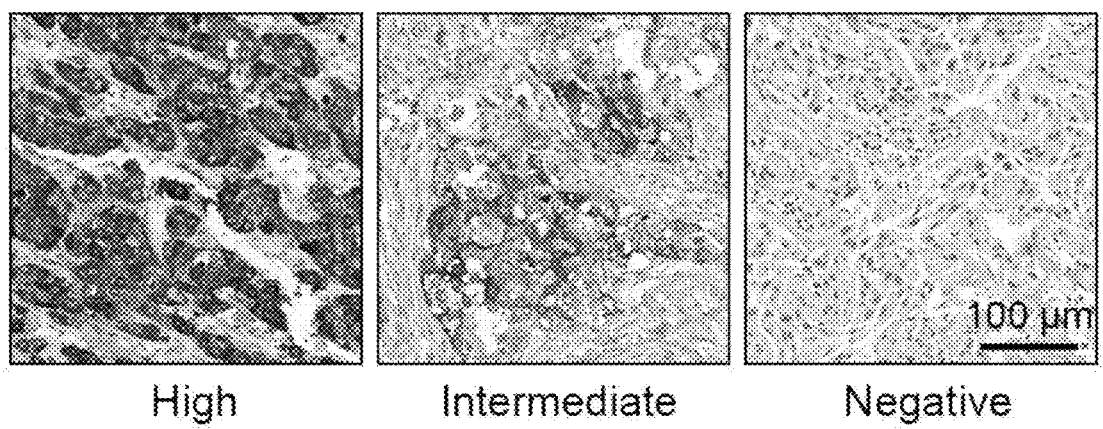
Figure 4G:
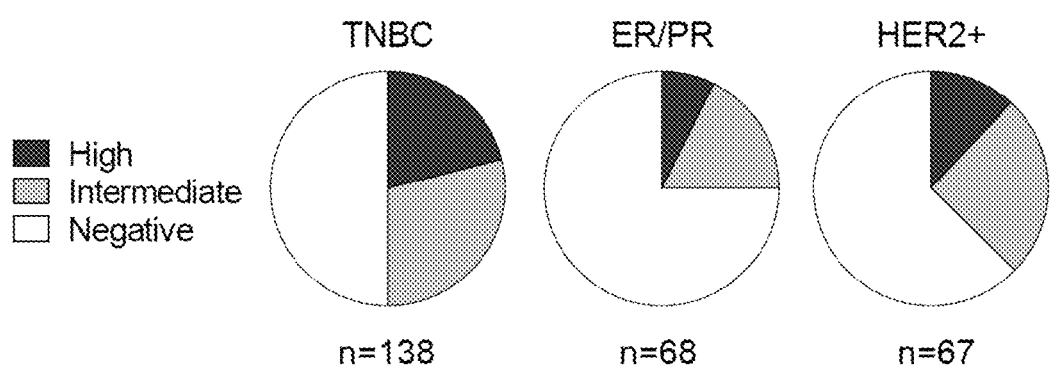
Figure 4I:
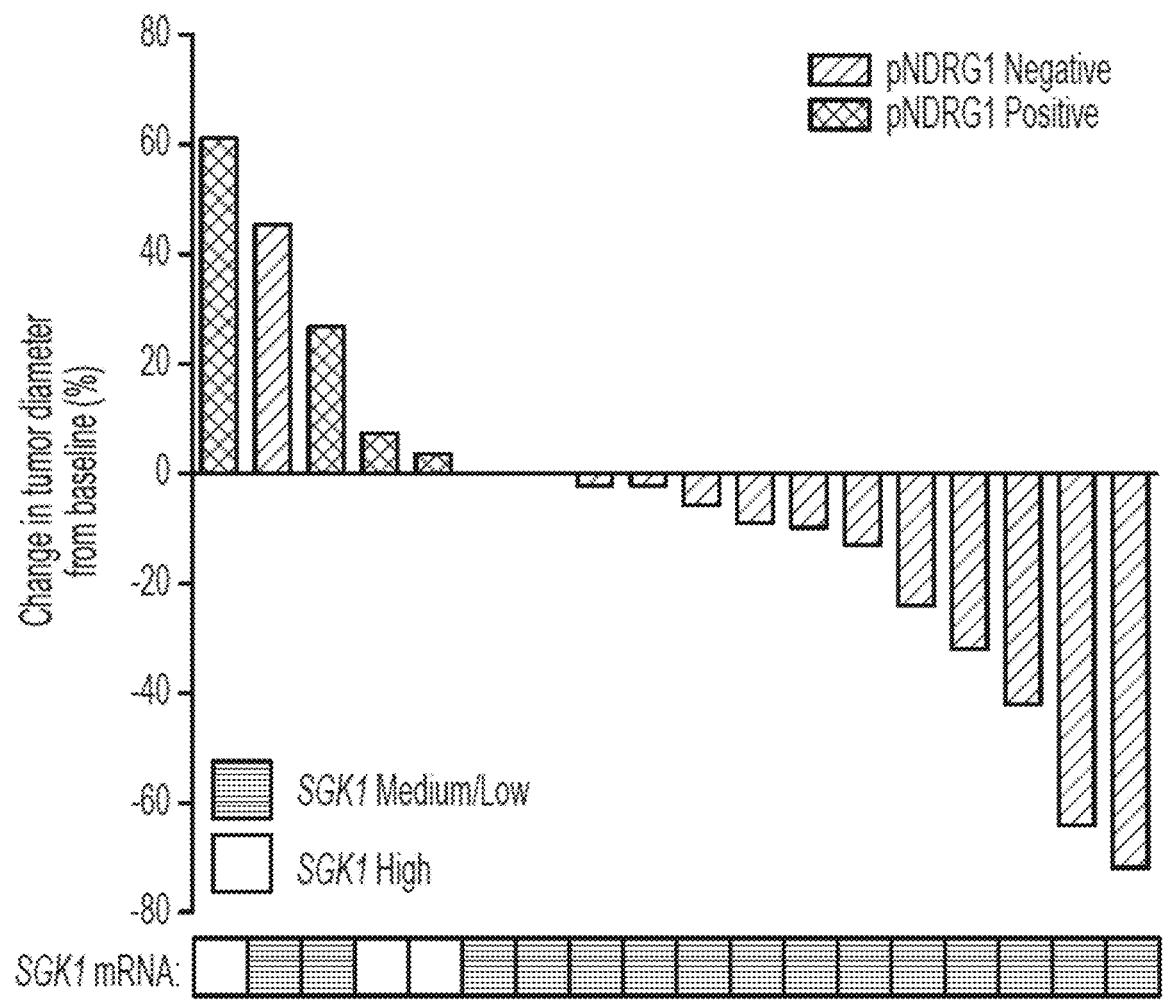

Given the lack of reliable results obtained with commercially available antibodies against SGK1, we analyzed expression of pNDRG1 (T346) in 273 breast invasive carcinomas, comprised of 138 triple-negative breast cancer (TNBC), 68 ER/PR receptor-positive, and 67 HER2-positive breast cancer patients. High pNDRG1 staining was found in TNBC (21%) and HER2-positive tumors (12%) (FIG. 4G), a finding in line with the percentage of breast cancer samples expressing high levels of SGK1 in the TCGA cohort (Ciriello et al., 2015).

We then explored whether SGK1 and pNDRG1 expression correlate with clinical outcome to PI3Kα inhibition by analyzing PIK3CA-mutant breast cancer samples from 18 patients treated with BYL719 in combination with an aromatase inhibitor (NCT01870505). Three of these tumors expressed high levels of SGK1 mRNA while the remaining 15 had medium/low levels of SGK1 mRNA. The three patients with tumors exhibiting high SGK1 expression, which also stained positive for pNDRG1, did not respond to therapy (FIG. 4H, I). Two patients with tumors expressing medium/low levels of SGK1 stained positive for pNDRG1 and rapidly progressed. On the contrary, in the group of patients with pNDRG1-negative tumors, three had partial responses and eight had stable disease by RECIST criteria (Therasse et al., 2000). This was in agreement with the longer time to disease progression of this subset of patients when compared to the SGK1-high/pNDRG1-positive cohort (FIG. 4H, I). Although suggestive of a role of SGK1 in mediating intrinsic resistance to PI3Kα inhibitors, these results should be validated in larger cohorts of patients.

Discussion

Figure 15:
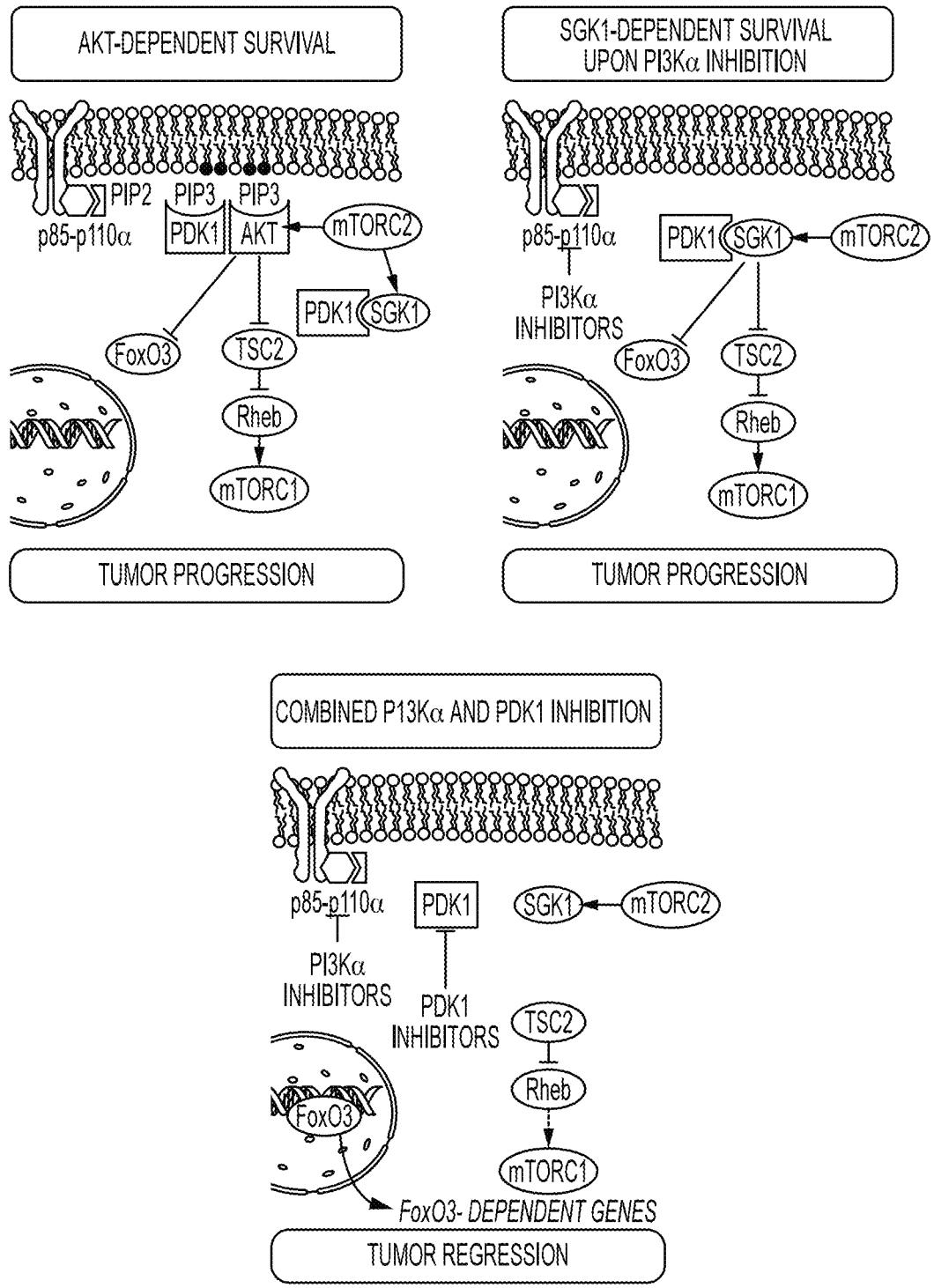

In this work, we show that inhibition of the constitutively active kinase PDK1 overcomes resistance to PI3Kα inhibitors in PIK3CA-mutant breast cancer cells insensitive to these agents. We discovered that in the presence of low levels of PIP3 and full suppression of AKT as a result of PI3Kα inhibition, SGK1 contributes to the maintenance of residual mTORC1 activity and cell survival through direct phosphorylation and inhibition of TSC2. Suppression of either PDK1 or SGK1 sensitizes resistant cells to the antitumor activity of PI3Kα blockade, underscoring the causative role of this signaling pathway in inducing the resistance phenotype (FIG. 15).

The combination of PI3Kα and PDK1 inhibitors may be of great interest in cases where resistance is driven by alternative AGC kinases such as S6K, RSK, PKC, or others (Elkabets et al., 2015; Elkabets et al., 2013; Serra et al., 2013).

Summarizing our current knowledge, resistance to PI3Kα inhibitors in PIK3CA-mutant malignancies may occur either as a result of PI3K-dependent or -independent mechanisms. An example of PI3K-dependent acquired resistance mechanism has recently been shown by the observation that loss of PTEN results in activation of PI3K p110β and therefore forfeiting PI3Kα signaling (Juric et al., 2015). Similarly, reactivation of PI3K p110β signaling has also been revealed to be a mechanism of adaptive resistance in PI3Kα-driven cells (Costa et al., 2015). In terms of PI3K-independent mechanisms, we now propose that mTORC1 sustained activity is, at least in part, mediated by PDK1-SGK1 signaling. In this context, AKT activity would be dispensable for cell survival, in accordance with previous reports showing that AKT activity is not always required for the downstream PI3K signaling (Gasser et al., 2014; Vasudevan et al., 2009).

The role of SGK1 in mediating mTORC1 activation upon PI3Kα inhibition can be explained by the differential regulation of AKT and SGK1 upon pharmacological stress. Although both kinases share the same upstream regulators, mTORC2 and PDK1, AKT contains a PH domain that is required for the PI3K-dependent plasma membrane translocation and subsequent activation. In contrast, SGK1 does not require plasma membrane localization, which could partially explain why it remains active in the absence of PIP3. In our resistant cell lines treated with PI3Kα inhibitor, we observe a substantial but incomplete decrease in SGK1 activity. This can be partially explained by the fact that PIP3 controls mTORC2 (Gan et al., 2011), in a mechanism that seems to require mSIN1 (Liu et al., 2015). However, other PIP3-independent pools of mTORC2 that are not regulated by growth factors (Frias et al., 2006) might be responsible for residual SGK1 activity. While PDK1 is a constitutively active kinase and can be present in both the cytoplasm and membrane (upon PIP3 synthesis), the subcellular localization of mTORC2 is ambiguous (Cybulski and Hall, 2009). Therefore, it is plausible that different pools of mTORC2 can be found within the cell.

Pharmacological inhibition of PDK1 has been reported to have a profound effect on the activity of several AGC kinases such as RSK, S6K, PKC, and SGK (Najafov et al., 2011). However, in order to achieve the same inhibitory effects on AKT, higher doses of PDK1 inhibitors must be used. This is explained by the fact that AKT can be efficiently activated by PDK1 through PIP3-independent and PIF binding pocket-dependent mechanisms, leading to resistance to PDK1 inhibitors (Najafov et al., 2012). In our experiments using endogenous immunoprecipitated SGK1 and AKT1, we show that this is indeed the case in our model. In the presence of BYL719, SGK1 but not AKT remains active; conversely, upon GSK2334470 treatment, SGK1 but not AKT is fully inhibited. Single activity of any of these kinases seems to be sufficient to propagate downstream pro-survival signaling through mTORC1 activation and FOXO3 repression. This is also confirmed by the fact that the combination of both agents efficiently inhibits FOXO3 and mTORC1, inducing antitumor effects in cancer cells. In this setting, rather than inhibition of AKT, NDRG1 phosphorylation (substrate of both AKT and SGK1) should be used as readout of pathway inhibition (Kobayashi et al., 1999).

Some evidence also suggests that SGK3 may play an important role in the oncogenicity of PI3K-driven cells. Our results indicate that this is not the case in intrinsic resistance to PI3K pathway inhibitors since low levels of SGK1, but not SGK2 or SGK3, are correlated with sensitivity to BYL719 (FIG. 4) and AKT inhibitors (Sommer et al., 2013). Moreover, SGK3 is a direct downstream target of class III phosphoinositide 3-kinase and is indirectly inactivated upon class I PI3K inhibitor treatment (Bago et al., 2014), so it is an unlikely mediator of intrinsic resistance.

In summary, our findings show that SGK1 mediates resistance to PI3Kα inhibitors through the activation of mTORC1, which can be reverted by PDK1 blockade. This study highlights the importance of understanding the underlying mechanisms of protein kinase regulation in order to uncover critical nodes for pharmacological intervention and improve the therapeutic options for oncogene-driven cancers.

Methods

Plasmids and Site-Directed Mutagenesis

The Myc-tagged constructs pCCL-PDK1 WT, KD (K111N), K465E, and L155E were a gift from Dr. Primo and Dr. Gagliardi (University of Turin). pLPCX-HA-SGK1 (Δ60) was obtained from Dr. Conzen (The University of Chicago) and was used as a template to subclone the cDNA and generate pdEYFP-SGK1(Δ60) and pLenti7.3-V5-SGK1 (Δ60,S422D). The kinase-inactive K127A and constitutively active S422D mutant were generated using PCR-based site-directed mutagenesis.

Plasmids expressing Flag-tagged mTOR (26603), TSC1 (8995), TSC2 (8996), and RHEB (15888) were obtained from Addgene. pcDNA3-Flag-TSC2 WT and 5A (S939A, S981A, S1130A, S1132A, T1462A) were a gift from Dr. Manning and were used as a template for the generation of pcDNA3-Flag-TSC2 6A (5A, S1798A) and pcDNA3-Flag-TSC2 6E, respectively. Plasmids encoding for the TSC2 truncation mutants were provided by Dr. Xiong (University of North Carolina at Chapel Hill) and pEGFP-TSC2 was from Dr. Krymskaya (University of Pennsylvania). PDPK1 targeting shRNA pLKO-based vector used in this study was TRCN0000039782, although other clones were also tested. RICTOR-targeting shRNA plasmid was from Addgene (1853).

LT3GEPIR vector is a mirE-based and doxycycline-inducible shRNA that has previously described (Fellmann et al., 2013) and was used as a backbone to generate different SGK1 targeting vectors as described in the paper. Briefly, this all-in-one vector contains the puromycin resistance and the reverse transactivator (rtTA3) under the control of the constitutive phosphoglycerate kinase (PGK) promoter. The shRNA and the fluorescent marker GFP are expressed under the control of the Tet-responsive element promoter (T3G). Control shRNA was a hairpin designed against the Renilla reniformis luciferase. SGK1 shRNA was chosen experimentally based on five different hairpins. The sequence targeting the exon 5 provided the most robust results.

The sequences for the hairpins used in this study were:

```
REN shRNA:
                                            (SEQ ID NO: 40)
5'-TGCTGTTGACAGTGAGCGCAGGAATTATAATGCTTATCTATAGTGAA
GCCACAGATGTATAGATAAGCATTATAATTCCTATGCCTACTGCCTCGG
A-3'

SGK1#282 shRNA:
                                            (SEQ ID NO: 41)
5'-TGCTGTTGACAGTGAGCGCAGAAGTGTTCTATGCAGTCAATAGTGAA
GCCACAGATGTATTGACTGCATAGAACACTTCTTTGCCTACTGCCTCGG
A-3'

#357:
                                            (SEQ ID NO: 42)
5'-TGCTGTTGACAGTGAGCGAGGAGCGGAATGTTCTGTTGAATAGTGAA
GCCACAGATGTATTCAACAGAACATTCCGCTCCGTGCCTACTGCCTCGG
A-3'
```

Oligonucleotides were obtained from Sigma, annealed, and cloned between the EcoRI and XhoI sites of the LT3GEPIR vector. All constructs were validated by Sanger sequencing.

Cells and Lentiviral Production

All cell lines were obtained from ATCC except for JIMT1 (AddexBio), used at low passages, and maintained at 37° C. in a 5% CO2 atmosphere in the recommended culture media. HCT116 PDPK1−/− and +/+ cells were a gift from Dr. Mills (MD Anderson) and were originally generated by Dr. Vogelstein's laboratory (Johns Hopkins University) (Ericson et al., 2010).

For lentiviral production, 293T cells were seeded in 10-cm plates, transfected with pCMVVSVG, pCMV-dR8.2, and the plasmid of interest using FuGene HD (Promega). Viruses were collected 72 h post-transfection, filtered through a 0.45 μm filter (Millipore), and recipient cells were infected twice using viral supernatants supplemented with 8 μg/μL of polybrene (Sigma).

Transduced cells were selected using puromycin (2 μg/mL) or Fluorescence Activated Cell Sorting (FACS) for the pCCL and pLenti7.3 vectors, which contain EGFP as a selectable marker.

Reagents, Cell Viability and Apoptosis

BYL719 and MK2206 were obtained from the Stand Up to Cancer (SU2C). GSK2334470 and Staurosporine were purchased at Selleckchem. SGK1-inh was a gift from M. Nazare and N. Halland. All drugs were dissolved in DMSO for in vitro experiments.

Cell viability was measures using the MTT assay. Briefly, 5000 cells were seeded in 96 well plates, treated for 6 days, and assayed using 0,25% MTT (Sigma) and 50 mM sodium succinate (Sigma) solutions during 3 h. Formazan crystals were dissolved with DMSO and absorbance was measured at 570 nm of wavelength.

For Caspase 3/7 activity, the Caspase-Glo® 3/7 Assay kit from Promega was used following manufacturer's instructions. The caspase inhibitor zVAD-fmk was used to inhibit apoptosis in cells and was also obtained from Promega.

Immunoblot, Immunoprecipitation, and Kinase Assay

For western blot analysis proteins were extracted in RIPA buffer supplemented with protease and phosphatase inhibitors (Roche). Protein lysates were separated using SDS-PAGE gels and transferred to a PVDF membrane. Then, membranes were probed using specific antibodies. PDK1, pAKT (S473), pAKT (T308), pS6K (T389), pS6 (S240/4), pS6 (235/6), p4EBP1 (S65), PARP, Actin, pRSK (S227), cleaved Caspase 3, pFOXO1/3 (T24/T32), SGK1, SGK2, SGK3, pNDRG1 (T346), NDRG1, Flag, HA, and phospho-RXRXX(S/T) (SEQ ID NO: 1) were from Cell Signaling Technology (CST).

For SGK1 HM and activation loop phosphorylation detection we used pS6K (T389) antibody (9205) and pPKC (pan) (γT514) (9379) from CST, respectively, as previously reported (Garcia-Martinez and Alessi, 2008).

For S6K T229 phosphorylation detection we used pPKC (pan) (γT514) (9379) from CST, as previously reported (Garcia-Martinez and Alessi, 2008). The SGK1 and AKT antibodies for endogenous immunoprecipitation were raised in sheep by the Division of Signal Transduction Therapy (DSTT) at the University of Dundee and affinity-purified against the indicated antigens: anti-AKT1 (S695B, third bleed; raised against residues 466-480 of human Akt1: RPHFPQFSYSASGTA), anti-SGK1 antibody (S062D, third bleed, raised against recombinant SGK1 protein (DU35257). For endogenous co-immunoprecipitation of SGK1 and TSC2, we employed the S062D sheep antibody in 10 mg of JIMT1 lysate and TSC2 was recognized using the CST rabbit antibody with a secondary conformational specific antibody (Clean Blot from Thermo).

For immunoprecipitation assays, 293T cells were transiently transfected with appropriate plasmids and 24 h post-transfection cells were washed in cold PBS, and lysed using NP-40 buffer (150 mM NaCl, 10 mM Tris pH=8, 1% NP-40, 10% glycerol). Lysates were rotated at 4° C. for four hours with EZview™ Red ANTI-FLAG® M2 or ANTI-HA agarose beads (Sigma) and washed three times using NP-40 buffer. For in vitro kinase assay, immunoprecipitated Flag-TSC2 was used as a substrate in a reaction with recombinant His-SGK1 ($\Delta$60) (MRC-PPU Reagents) and ATP (Signalchem) in kinase assay buffer containing 25 mM MOPS pH 7.2, 12.5 mM $\beta$-glycerolphosphate, 25 mM MgCl2, 5 mM EGTA, 2 mM EDTA and 0.25 mM DTT at 30° C. for 30 minutes.

In vitro kinase activity of endogenous SGK1 and AKT was assayed by measuring [$\gamma$-32P] ATP incorporation into Crosstide substrate peptide [GRPRTSSFAEGKK] (SEQ ID NO: 43). SGK1 and AKT were immunoprecipitated from HCC1954 cell line 4 hr after treatment. Immunoprecipitates were washed once with lysis buffer containing 500 mM NaCl, once with lysis buffer, and twice with Buffer A (50 mM Tris pH 7.5, 0.1 mM EGTA). Reactions were carried out in 40 µL total volume containing 0.1 mM [$\gamma$-32P] ATP (400-1000 cpm/pmol), 10 mM magnesium acetate, and 30 µM Crosstide peptide. Reactions were terminated by adding 10 µL 0.1 mM EDTA. 40 µL of the reaction mix was spotted on P81 paper, which was immediately immersed into 50 mM ortophosphoric acid and washed several times. Papers were rinsed in acetone and air dried. Radioactivity was quantified by Cerenkov counting. One unit of enzyme activity was defined as the amount of enzyme that catalyzes incorporation of 1 nmol of [$\gamma$-32P] ATP into the substrate over one minute.

m7GTP Pull Downs 2 million cells were seeded in 10 cm plates and treated accordingly 12 hr after seeding. Lysates were prepared using m7GTP pull down buffer (50 mM Hepes, pH 7.4, 75 mM NaCl, 10 mM MgCl2, 1 mM DTT, 8 mM EGTA, 10 mM $\beta$-glycerophosphate, 0.5 mM Na3VO4, 0.5% Triton X-100) supplemented with protease and phosphatase inhibitors. Lysates were centrifuged at 13000 rpm for 10 min and supernatants were rotated for 2 h at 4° C. with 7-methyl-GTP-Sepharose or control Sepharose beads (Jena Bioscience). Beads were washed three times with m$^7$GTP pull down buffer, resuspended in Laemmli buffer, and associated proteins were detected by Western blot.

Mass Spectrometry

Kinase assay reactions were performed in biological triplicates and resolved using SDS polyacrylamide gel electrophoresis, stained with SimplyBlue SafeStain (Life Technologies, Thermo Fisher Scientific), and the band corresponding to Flag-TSC2 was excised, and digested with trypsin as described by (Shevchenko et al., 2006). The tryptic peptides were resuspended in buffer A containing 3% formic acid and analyzed by microcapillary liquid chromatography with tandem mass spectrometry using a NanoAcquity LC (Waters) with a 100 µm-inner-diameter×10 cm-length C18 column (1.7 µm BEH130, Waters) configured with a 180 µm×2 cm trap column coupled to a Q-Exactive mass spectrometer (Thermo Fisher Scientific) scanning 380-1800 m/z at 70,000 resolution with AGC set at 3×10$^6$. Peptides were eluted with a linear gradient of 2-30% acetonitrile (0.1% formic acid) in water over 90 min at a flow rate of 300 nL/min. Key parameters for the data dependent MS were top 10 DDA, AGC 5e4, and ms/ms resolution of 17,000. Data were analyzed using MaxQuant (Max Planck Institute of Biochemistry, Germany; version 1.5.1.0) at default settings with a few modifications. The default was used for first search tolerance and main search tolerance: 20 ppm and 6 ppm, respectively. MaxQuant was set up to search the reference human proteome database. Maxquant performed the search using trypsin digestion with up to 2 missed cleavages. Peptide, Site and Protein FDR were all set to 1% with a minimum of 1 peptide needed for identification but 2 peptides needed to calculate a protein ratio. LFQ quantitation was confirmed by manual integration of the MS1 data for the phosphorylation sites of interest. Raw data as well as original MaxQuant results files can be provided upon request.

Microarray, qPCR, and ChIP-qPCR

RNA was isolated from cells using the QIAGEN RNeasy kit. For microarray analysis, biotinylated cRNA was prepared according to the standard Illumina protocol. After fragmentation, cRNA was hybridized with Illumina GX HT12 Human Array. Slides were washed and stained in the Illumina instrument following manufactured protocol. Slides were scanned using Illumina Bead Array Reader. Data were analyzed using GenomeStudio software. No normalization and background correction are performed first, then quantile normalization and background correction are done.

For mRNA expression analysis, cDNA was prepared using the Bio-Rad cDNA synthesis kit. cDNA was amplified by quantitative PCR using SYBR Select Master Mix (Applied Biosystems) in the ViiA 7 Real-Time PCR system. All reactions were carried out in triplicate.

Primers used for mRNA expression were:

```
ERBB3:
                                     (SEQ ID NO: 44)
    Fw-CTGATCACCGGCCTCAAT;

(SEQ ID NO: 45)
    Rv-GGAAGACATTGAGCTTCTCTGG

IRS2:
                                     (SEQ ID NO: 46)
    Fw-TTCTTGTCCCACCACTTGAA;

(SEQ ID NO: 47)
    Rv-CTGACATGTGACATCCTGGTG

TNFSF10:
                                     (SEQ ID NO: 48)
    Fw-CCTCAGAGAGTAGCAGCTCACA;

(SEQ ID NO: 49)
    Rv-CAGAGCCTTTTCATTCTTGGA

BCL6:
                                     (SEQ ID NO: 50)
    Fw-CTGCAGATGGAGCATGTTGT;

(SEQ ID NO: 51)
    Rv-TCTTCACGAGGAGGCTTGAT

Actin:
                                     (SEQ ID NO: 52)
    Fw-CGTCTTCCCCTCCATCGT;

(SEQ ID NO: 53)
    Rv-GAAGGTGTGGTGCCAGATTT
```

ChIP assays were performed as described previously (Toska et al., 2012). Briefly, cells were treated with 1% formaldehyde for 15 min at room temperature and quenched with ice-cold 125 nM glycine for 5 min. Lysed cells were sonicated on ice to yield 200-800 bp DNA fragments. Chromatin was incubated overnight at 4° C. with 2 µg of anti-FOXO3A antibody (Santa Cruz Biotechnology;

sc-11351) or nonspecific IgG. Immunocomplexes were precipitated by incubation overnight with protein G-conjugated beads. Immunoprecipitates were washed and crosslinks were reversed by heating to 65° C. for 6 hours and then treated with proteinase K for 1 h at 55° C. Chromatin was purified using QiaQuick PCR clean-up columns.

ChIP primers used in this study were:

```
Control:
                                   (SEQ ID NO: 54)
Fw-CAGCTCAGTGCTGTTGGTGG (SEQ ID NO: 55)
Rv-ACCATCCAACCCTGGAGATC IRS2 promoter:
                                   (SEQ ID NO: 56)
Fw-GACAATCAAAGTCCTTCCCAAA;

(SEQ ID NO: 57)
Rv-CCTTTTGACCTGTGCTGTTGT

TNFSF10 promoter:
                                   (SEQ ID NO: 58)
Fw-AAAGAAAATCCCTCCCCTCTT;

(SEQ ID NO: 59)
Rv-CACTCACCTCAAGCCCATTT

SGK1 promoter:
                                   (SEQ ID NO: 60)
Fw-GGGAGGGAGAGGTCAGGAAT;

(SEQ ID NO: 61)
Rv-TCGCTTGTTACCTCCTCACG
```

Animal Studies and IHC

Animals were maintained and treated in accordance with Institutional Guidelines of Memorial Sloan Kettering Cancer Center (Protocol number 12-10-019). $5 \times 10^6$ cells in 1:1 PBS/Matrigel (Corning) were injected subcutaneously into six-week-old female athymic Foxn1$^{nu}$ nude mice.

When tumors reached a volume of ~150 mm$^3$ mice were randomized, treated, and tumors were measured twice a week during a month. At least 10 tumors per group were used in all the studies. Treatments were as follows: BYL719 (25 mg/kg in 0.5% carboxymethylcellulose (Sigma), daily p.o.); GSK2334470 (100 mg/kg in 10% of 1:1 Kolliphor® EL/EtOH (Sigma), three times/week, i.p.); SGK1-inh (50 mg/kg in 40% of 3:1 Glycofurol/Kolliphor® RH 40 mixture (Sigma) in 0.9% saline, daily p.o.). Tumors were harvested at the end of the experiment three hours after the last dosage, fixed in 4% formaldehyde in PBS, and paraffin-embedded. IHC was performed on a Ventana Discovery XT processor platform using standard protocols and the following antibodies from Cell Signaling Technology: pAKT(S473) (4060),1:70; pS6 (S240/4) (5364),1:500; pNDRG1 (T346) (5482), 1:200. Primary staining was followed by 60 minutes incubation with biotinylated goat anti-rabbit IgG (Vector labs) 1:200. Blocker D, Streptavidin-HRP and DAB detection kit (Ventana Medical Systems) were used according to the manufacturer instructions.

Docking and Molecular Dynamics Simulations

The structure of SGK1 kinase is only available in its inactive form, with missing structural information such as the coordinates of the αC helix. We constructed the 3D structures of SGK1 kinase both in its active and inactive forms using comparative modeling methods based on homology. The templates used were the available crystal structure of SGK1 kinase in the inactive state (pdb: 2R5T) (Zhao et al., 2007), high-resolution crystal structure of the kinase domain of AKT (55% homology) in its active (pdb: 1O6K) (Yang et al., 2002a) and inactive (pdb: 1GZN) (Yang et al., 2002b) states. The program Modeller (version 9.12) (Sali and Blundell, 1993) was used for the generation of homology models. Several models were generated and the models with the best physicochemical properties were further refined using all atom molecular dynamics (MD) simulations.

The 3D structures of SGK1-inh and ATP were built using the Maestro module and minimized using the Macromodel module, employing the OPLS-2005 force field, in the program Schrodinger 9.0. The minimized SGK1 inhibitor and ATP were docked into the binding pockets of SGK1 kinase models with Glide (Friesner et al., 2004) using standard docking protocols (Kannan et al., 2015). Refinement of the docked models of SGK1-inhibitor and SGK1-ATP complexes were carried out using MD simulations under the Sander module of the program Amber14. The partial charges and force field parameters for SGK1 inhibitor and ATP were generated using the Antechamber module in Amber. All atom versions of the Amber 03 force field (ff03) (Duan et al., 2003) and the general Amber force field (GAFF) (Wang et al., 2004) were used for the protein and the inhibitors respectively. All the simulations were carried out at 300 K using standard protocols (Kannan et al., 2015). Three independent MD simulations (assigning different initial velocities) were carried out on each equilibrated SGK1-ATP and SGK1-inhibitor structure for 100 ns each, with conformations saved every 10 ps. Simulation trajectories were visualized using VMD (Humphrey et al., 1996) and figures were generated using Pymol.

The binding free energies (enthalpic components), energy decompositions (to identify "hot spot" residues) and computational alanine scans (of the "hot spot" residues) were calculated using the MMPBSA (Molecular Mechanics Poisson-Boltzmann Surface Area) methodology (Kannan et al., 2015).

DNA Methylation Quantification

For DNA methylation analyses, bisulfite conversion of 500 ng of genomic DNA was performed using the EZ DNA Methylation Gold kit (Zymo Research, Orange, Calif., USA) following the manufacturer's indications. For bisulfite sequencing, specific primers were designed to amplify the annotated promoter region using the MethylExpress program (Applied Biosystems) (Fw-AATTTTAGAATTTG-GAAGAGGA (SEQ ID NO: 62) and Rv-ACAACCT-TAAATTAAACCCAAA (SEQ ID NO: 63)), and a minimum of eight single clones was interrogated for each cell line. In order to quantify the absolute levels of DNA methylation on CpG sites in the proximity of the transcription start site of SGK1 we carried out pyrosequencing on bisulfite-treated DNA using specific primers designed with the PyroMark Assay Design Software (Qiagen, version 2.0.01.15) (Fw-GAGGGAGAGGTTAGGAATGT (SEQ ID NO: 64), Rv-CCCTCCCTTCRCTTATTACCTCCTCAC (SEQ ID NO: 65), and Seq-TTTTGAAGTAATTTTT-GAGAATATT (SEQ ID NO: 66)). Pyrosequencing reactions and quantification of DNA methylation values were performed in a PyroMark Q96 System version 2.0.6 (Qiagen) including appropriate controls. As previously described, SGK1 DNA methylation levels were categorized into three groups. DNA methylation values in the first group (<33%) were defined as low DNA methylation, and high DNA methylation was assigned to values on the two top groups (>33%).

FRET

For FRET experiments, HeLa cells were seeded in chambered coverglass and transfected with 0.5 µg of EGFP Donor plasmid, 0.5 µg of EYFP Acceptor plasmid, or both constructs. 16 h posttransfection cells were imaged with a Leica TCS SP8 microscope using the established parameters for Donor (Ex: 458 nm laser at 15%; Em: 466-501 nm) and Acceptor (Ex: 528 nm laser at 3%; Em: 555-600 nm).

FRET efficiency was calculated using the following equation as described in (van Rheenen et al., 2004):

$$E_{FRET} = \frac{FRET - EGFP \times \beta - EYFP \times (\gamma - \alpha \times \beta)}{EYFP \times (1 - \beta \times \delta)}$$

Where FRET, EGFP and EYFP refers to the FRET, Donor and Acceptor channels respectively. The corrections factors were $\alpha=0.01$; $\beta=0.37$; $\gamma=0.31$; $\delta=0.02$, where $\alpha$ corrects for acceptor cross-excitation crosstalk ($\alpha$=Donor/Acceptor), $\beta$ corrects for donor crosstalk ($\beta$=FRET/Donor), $\gamma$ corrects for acceptor cross-excitation ($\gamma$=FRET/Acceptor), and $\delta$ corrects for FRET crosstalk ($\delta$=Donor/FRET). Mock-transfected cells were used to calculate the background threshold level (background intensity mean+4 Standard deviation).

RNAi Screening

The synthetic lethal RNAi screening was carried out at the High-Throughput Screening Core Facility of MSKCC. The kinome and phosphatome Ambion Silencer Select v4.0 libraries were purchased from Life Technologies and contain 2130 unique siRNAs targeting each of the 710 human kinase genes and 894 unique siRNAs targeting each of the 298 human phosphatase genes. Diluted siRNA were transferred into assay plates at a final concentration of 50 nM. As a reference, we used Silencer Select Negative Control #1 siRNA (4390843) as a negative control and PLK1 siRNA (s449) as the positive control.

JIMT1 and HCC1954 cells were seeded and were reverse transfected using Dharmafect-1 at 0.05 µL/well. Next, cells were treated with DMSO or BYL719 1 µM and 7 days after transfection, cell viability was assessed using Alamar blue and Nuclei Count using Hoechst staining and quantified using LEADseeker (GE Healthcare) and INCA2000 (GE Healthcare), respectively.

For the hit nomination, the BDA method was used as previously described (Bhinder and Djaballah, 2012). Briefly, this method comprises 5 steps to analyze and score active siRNA duplexes and genes: (1) active duplex identification, (2) active gene identification, (3) off-targeteffects filtering, (4) re-scoring, and (5) biological classifications. To identify modulators of BYL719 resistance, active genes were nominated from the active siRNA duplexes using a hit rate per gene (H score) of ≥60. H score is defined as follows:

$$H\ score = \frac{number\ of\ active\ siRNA\ duplex}{total\ number\ of\ siRNA\ duplexes} \times 100$$

Using this approach, 5 genes were identified and the two most active duplexes of each gene were purchased and screened for cell viability and pS6 staining in the presence of BYL719 1 µM. siRNA were from Ambion: PIK3CA (s10520, s10522), MTOR (s602, s603), PDPK1 (s10274, s10275), PAPL (s52890, s52892), and PP1R12A (s935, s937). Confirmation screening was carried out as described above. For pS6 (S240/4) staining, cells were reversetransfected and after 72 hr, they were treated for 4 hr with BYL719 at 1 µM. Next, cells were fixed with 4% Paraformaldehyde in PBS and stained using pS6 (S240/4) antibody from Cell Signaling (2215), followed by Alexa Fluor 488 secondary antibody. Fluorescence was quantified using INCA2000 (GE Healthcare). Final nomination was performed using the H score described above and genes that sensitized cells to BYL719 and decreased pS6 (S240/4) were selected.

Patient Samples

The MSKCC Institutional Review Board approved the study. Pre-treatment FFPE blocks from patients treated with the PI3Kα inhibitor BYL719 enrolled in the clinical trial NCT01870505 conducted at MSKCC were used for IHC. Informed consent was obtained from all subjects.

TMA and Patients

Formalin-fixed paraffin-embedded (FFPE) tissue blocks from primary invasive breast carcinomas were used to construct the TMA reported in this study. A certified pathologist (E.B.) microscopically examined hematoxylin and eosin-stained sections of all the tumors and selected representative areas, excluding foci of ductal carcinoma in situ and tumor necrosis. All carcinomas were represented in the TMAs in triplicate 0.6-mm cores. An Automatic Tissue MicroArrayer (ATA-27, Beecher Instruments Inc) was used to construct TMAs from a total of 273 breast invasive carcinomas. This comprised clinically and pathologically confirmed triple-negative breast cancer patients, ER/PR receptor-positive breast cancer patients, and HER2-positive cancer patients. Tumor were considered ER/PR receptor-positive if >10% of neoplastic cells showed nuclear positivity. Cases with HER-2 staining intensity of 3+ were considered positive, whereas those with 2+ staining intensity of HER2 were further evaluated by ERBB2 FISH using the PathVision HER2 probe Kit (Abbott Laboratories), and scored as positive if the HER2/Cep17 ratio was 2.2 or greater. 5-µm thick TMA sections were stained for pNDRG1 (T346) following the protocol described above. Based on the observed staining across the different samples, cases were scored as High expression when pNDRG1 staining intensity of 2+ was found >20% of the neoplastic cells. Intermediate staining represented tumors that had 1+ staining intensity in >10% of the neoplastic cells.

For the study of patients treated with the PI3Kα inhibitor BYL719, pre-treatment biopsy FFPE blocks from patients enrolled in the clinical trial NCT01870505 conducted at MSKCC were used for IHC as described above. For the selection of the patients, PIK3CA and other tumor genomic drivers were analyzed using MSK-IMPACT (Cheng et al., 2015). Only patients that did not exhibit toxicity during the trial, harbored hot-spot mutations in PIK3CA, and did not harbor mutations in PTEN or KRAS (known to cause resistance to PI3Kα inhibitors) were selected for the biomarker study. SGK1 mRNA levels were determined using next-generation sequencing (NGS) and the expression results were presented as raw Reads Per Kilobase of transcript per Million mapped reads (RPKM). Mean and standard deviation (SD) was calculated across all the samples with available NGS data and overexpression of SGK1 was called for the samples with mRNA levels greater than mean+1SD. For 6 samples, RNA quality and quantity was not optimal for NGS. In these cases, SGK1 mRNA levels were determined using RT-qPCR as described above. RNA from low expressing (T47D) and high expressing (HCC1954) cell lines were used as positive control and absolute mRNA levels were quantified.

Primers used for the detection of SGK1 were:

```
Fw:
                                    (SEQ ID NO: 67)
GACAGGACTGTGGACTGGTG;

Rv:
                                    (SEQ ID NO: 68)
TTTCAGCTGTGTTTCGGCTA.
```

The MSKCC Institutional Review Board approved the study and informed consent was obtained from all subjects.

Accession Numbers

The microarray data has been deposited in the Gene Expression Omnibus database. Accession number: GSE69189.

REFERENCES

1. Alessi, D. R., James, S. R., Downes, C. P., Holmes, A. B., Gaffney, P. R., Reese, C. B., and Cohen, P. (1997). Characterization of a 3-phosphoinositide-dependent protein kinase which phosphorylates and activates protein kinase Balpha. Curr Biol 7, 261-269.
2. Alessi, D. R., Pearce, L. R., and Garcia-Martinez, J. M. (2009). New insights into mTOR signaling: mTORC2 and beyond. Sci Signal 2, pe27.
3. Arencibia, J. M., Pastor-Flores, D., Bauer, A. F., Schulze, J. O., and Biondi, R. M. (2013). AGC protein kinases: from structural mechanism of regulation to allosteric drug development for the treatment of human diseases. Biochim Biophys Acta 1834, 1302-1321.
4. Arteaga, M. F., Alvarez de la Rosa, D., Alvarez, J. A., and Canessa, C. M. (2007). Multiple translational isoforms give functional specificity to serum- and glucocorticoid-induced kinase 1. Molecular biology of the cell 18, 2072-2080.
5. Biondi, R. M., Kieloch, A., Currie, R. A., Deak, M., and Alessi, D. R. (2001). The PIF-binding pocket in PDK1 is essential for activation of S6K and SGK, but not PKB. EMBO J 20, 4380-4390.
6. Bhinder, B., and Djaballah, H. (2012). A simple method for analyzing actives in random RNAi screens: introducing the "H Score" for hit nomination & gene prioritization. Comb Chem High Throughput Screen 15, 686-704.
7. Brunet, A., Bonni, A., Zigmond, M. J., Lin, M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell 96, 857-868.
8. Brunet, A., Bonni, A., Zigmond, M. J., Lin, M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell 96, 857-868.
9. Brunet, A., Park, J., Tran, H., Hu, L. S., Hemmings, B. A., and Greenberg, M. E. (2001). Protein kinase SGK mediates survival signals by phosphorylating the forkhead transcription factor FKHRL1 (FOXO3a). Mol Cell Biol 21, 952-965.
10. Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer Discov 2, 401-404.
11. Cheng, D. T., Mitchell, T. N., Zehir, A., Shah, R. H., Benayed, R., Syed, A., Chandramohan, R., Liu, Z. Y., Won, H. H., Scott, S. N., et al. (2015). Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. J Mol Diagn 17, 251-264.
12. Ciriello, G., Gatza, M. L., Beck, A. H., Wilkerson, M. D., Rhie, S. K., Pastore, A., Zhang, H., McLellan, M., Yau, C., Kandoth, C., et al. (2015). Comprehensive Molecular Portraits of Invasive Lobular Breast Cancer. Cell 163, 506-519.
13. Collins, B. J., Deak, M., Arthur, J. S., Armit, L. J., and Alessi, D. R. (2003). In vivo role of the PIF-binding docking site of PDK1 defined by knock-in mutation. EMBO J 22, 4202-4211
14. Costa, C., Ebi, H., Martini, M., Beausoleil, S. A., Faber, A. C., Jakubik, C. T., Huang, A., Wang, Y., Nishtala, M., Hall, B., et al. (2015). Measurement of PIP3 levels reveals an unexpected role for p110beta in early adaptive responses to p110alpha-specific inhibitors in luminal breast cancer. Cancer Cell 27, 97-108.
15. Currie, R. A., Walker, K. S., Gray, A., Deak, M., Casamayor, A., Downes, C. P., Cohen, P., Alessi, D. R., and Lucocq, J. (1999). Role of phosphatidylinositol 3,4,5-trisphosphate in regulating the activity and localization of 3-phosphoinositide-dependent protein kinase-1. The Biochem J 337 (Pt 3), 575-583.
16. Cybulski, N., and Hall, M. N. (2009). TOR complex 2: a signaling pathway of its own. Trends Biochem Sci 34, 620-627.
17. Dibble, C. C., Elis, W., Menon, S., Qin, W., Klekota, J., Asara, J. M., Finan, P. M., Kwiatkowski, D. J., Murphy, L. O., and Manning, B. D. (2012). TBC1D7 is a third subunit of the TSC1-TSC2 complex upstream of mTORC1. Mol Cell 47, 535-546.
18. Duan, Y., Wu, C., Chowdhury, S., Lee, M. C., Xiong, G., Zhang, W., Yang, R., Cieplak, P., Luo, R., Lee, T., et al. (2003). A point-charge force field for molecular mechanics simulations of proteins based on condensed-¬-phase quantum mechanical calculations. Journal of computational chemistry 24, 1999-2012.
19. Elkabets, M., Vora, S., Juric, D., Morse, N., Mino-Kenudson, M., Muranen, T., Tao, J., Campos, A. B., Rodon, J., Ibrahim, Y. H., et al. (2013). mTORC1 inhibition is required for sensitivity to PI3K p110alpha inhibitors in PIK3CA-mutant breast cancer. Sci Transl Med 5, 196ra199.
20. Engelman, J. A. (2009). Targeting PI3K signalling in cancer: opportunities, challenges and limitations. Nat Rev Cancer 9, 550-562.
21. Ericson, K., Gan, C., Cheong, I., Rago, C., Samuels, Y., Velculescu, V. E., Kinzler, K. W., Huso, D. L., Vogelstein, B., and Papadopoulos, N. (2010). Genetic inactivation of AKT1, AKT2, and PDPK1 in human colorectal cancer cells clarifies their roles in tumor growth regulation. Proc Natl Acad of Sci USA 107, 2598-2603.
22. Fellmann, C., Hoffmann, T., Sridhar, V., Hopfgartner, B., Muhar, M., Roth, M., Lai, D. Y., Barbosa, I. A., Kwon, J. S., Guan, Y., et al. (2013). An optimized microRNA backbone for effective single-¬-copy RNAi. Cell reports 5, 1704-1713.
23. Frias, M. A., Thoreen, C. C., Jaffe, J. D., Schroder, W., Sculley, T., Carr, S. A., and Sabatini, D. M. (2006). mSin1 is necessary for Akt/PKB phosphorylation, and its isoforms define three distinct mTORC2s. Curr Biol 16, 1865-1870.

24. Friesner, R. A., Banks, J. L., Murphy, R. B., Halgren, T. A., Klicic, J. J., Mainz, D. T., Repasky, M. P., Knoll, E. H., Shelley, M., Perry, J. K., et al. (2004). Glide: a new approach for rapid, accurate docking and scoring. 1. Method and assessment of docking accuracy. Journal of medicinal chemistry 47, 1739-1749.

25. Fruman, D. A., and Rommel, C. (2014). PI3K and cancer: lessons, challenges and opportunities. Nat Rev Drug Discov 13, 140-156.

26. Gan, X., Wang, J., Su, B., and Wu, D. (2011). Evidence for direct activation of mTORC2 kinase activity by phosphatidylinositol 3,4,5-trisphosphate. J Biol Chem 286, 10998-11002.

27. Garcia-Martinez, J. M., and Alessi, D. R. (2008). mTOR complex 2 (mTORC2) controls hydrophobic motif phosphorylation and activation of serum- and glucocorticoid-induced protein kinase 1 (SGK1). Biochem J 416, 375-385.

28. Gasser, J. A., Inuzuka, H., Lau, A. W., Wei, W., Beroukhim, R., and Toker, A. (2014). SGK3 mediates INPP4B-dependent PI3K signaling in breast cancer. Mol Cell 56, 595-607.

29. Guertin, D. A., Stevens, D. M., Thoreen, C. C., Burds, A. A., Kalaany, N. Y., Moffat, J., Brown, M., Fitzgerald, K. J., and Sabatini, D. M. (2006). Ablation in mice of the mTORC components raptor, rictor, or mLST8 reveals that mTORC2 is required for signaling to Akt-FOXO and PKCalpha, but not S6K1. Dev Cell 11, 859-871.

30. Halland, N., Schmidt, F., Weiss, T., Saas, J., Li, Z., Czech, J., Dreyer, M., Hofmeister, A., Mertsch, K., Dietz, U., et al. (2015). Discovery of N44-(1H-Pyrazolo[3,4-b]pyrazin-6-yl)-phenyl]-sulfonamides as Highly Active and Selective SGK1 Inhibitors. ACS Med Chem Lett 6, 73-78.

31. Humphrey, W., Dalke, A., and Schulten, K. (1996). VMD: visual molecular dynamics. Journal of molecular graphics 14, 33-38, 27-38.

32. Inoki, K., Li, Y., Xu, T., and Guan, K. L. (2003a). Rheb GTPase is a direct target of TSC2 GAP activity and regulates mTOR signaling. Genes Dev 17, 1829-1834.

33. Inoki, K., Li, Y., Zhu, T., Wu, J., and Guan, K. L. (2002). TSC2 is phosphorylated and inhibited by Akt and suppresses mTOR signalling. Nat Cell Biol 4, 648-657.

34. Inoki, K., Ouyang, H., Zhu, T., Lindvall, C., Wang, Y., Zhang, X., Yang, Q., Bennett, C., Harada, Y., Stankunas, K., et al. (2006). TSC2 integrates Wnt and energy signals via a coordinated phosphorylation by AMPK and GSK3 to regulate cell growth. Cell 126, 955-968.

35. Inoki, K., Zhu, T., and Guan, K. L. (2003b). TSC2 mediates cellular energy response to control cell growth and survival. Cell 115, 577-590.

36. Jacinto, E., Facchinetti, V., Liu, D., Soto, N., Wei, S., Jung, S. Y., Huang, Q., Qin, J., and Su, B. (2006). SIN1/MIP1 maintains rictor-mTOR complex integrity and regulates Akt phosphorylation and substrate specificity. Cell 127, 125-137.

37. Juric, D., Castel, P., Griffith, M., Griffith, O. L., Won, H. H., Ellis, H., Ebbesen, S. H., Ainscough, B. J., Ramu, A., Iyer, G., et al. (2015). Convergent loss of PTEN leads to clinical resistance to a PI(3)Kalpha inhibitor. Nature 518, 240-244.

38. Juric, D., Krop, I., Ramanathan, R. K., Xiao, J., Sanabria, S., Wilson, T. R., Choi, Y., Parmar, H., Hsu, J., Baselga, J., and Von Hoff, D. D. (2013). GDC-0032, a beta isoform-sparing PI3K inhibitor: Results of a first-in-human phase Ia dose escalation study. Cancer Res 73, LB-64.

39. Juric, D., Rodon, J., Gonzalez-Angulo, A. M., Burris, H. A., Bendell, J., Berlin, J. D., Middleton, M. R., Bootle, D., Boehm, M., Schmitt, A., et al. (2012). BYL719, a next generation PI3K alpha specific inhibitor: Preliminary safety, PK, and efficacy results from the first-in-human study. Cancer Res 72, CT-01.

40. Kannan, S., Poulsen, A., Yang, H. Y., Ho, M., Ang, S. H., Eldwin, T. S., Jeyaraj, D. A., Chennamaneni, L. R., Liu, B., Hill, J., et al. (2015). Probing the binding mechanism of Mnk inhibitors by docking and molecular dynamics simulations. Biochemistry 54, 32-46.

41. Kobayashi, T., and Cohen, P. (1999). Activation of serum- and glucocorticoid-regulated protein kinase by agonists that activate phosphatidylinositide 3-kinase is mediated by 3-phosphoinositide-dependent protein kinase-1 (PDK1) and PDK2. Biochem J 339 (Pt 2), 319-328.

42. Kobayashi, T., Deak, M., Morrice, N., and Cohen, P. (1999). Characterization of the structure and regulation of two novel isoforms of serum- and glucocorticoid-induced protein kinase. Biochem J 344 Pt 1, 189-197.

43. Li, Y., Corradetti, M. N., Inoki, K., and Guan, K. L. (2004). TSC2: filling the GAP in the mTOR signaling pathway. Trends Biochem Sci 29, 32-38.

44. Liu, P., Gan, W., Chin, Y. R., Ogura, K., Guo, J., Zhang, J., Wang, B., Blenis, J., Cantley, L. C., Toker, A., et al. (2015). PtdIns(3,4,5)P3-Dependent Activation of the mTORC2 Kinase Complex. Cancer Discov 5, 1194-1209.

45. Ma, L., Chen, Z., Erdjument-Bromage, H., Tempst, P., and Pandolfi, P. P. (2005). Phosphorylation and functional inactivation of TSC2 by Erk implications for tuberous sclerosis and cancer pathogenesis. Cell 121, 179-193.

46. Manning, B. D., and Cantley, L. C. (2007). AKT/PKB signaling: navigating downstream. Cell 129, 1261-1274.

47. Manning, B. D., Tee, A. R., Logsdon, M. N., Blenis, J., and Cantley, L. C. (2002). Identification of the tuberous sclerosis complex-2 tumor suppressor gene product tuberin as a target of the phosphoinositide 3-kinase/akt pathway. Mol Cell 10, 151-162.

48. McManus, E. J., Collins, B. J., Ashby, P. R., Prescott, A. R., Murray-Tait, V., Armit, L. J., Arthur, J. S., and Alessi, D. R. (2004). The in vivo role of PtdIns(3,4,5)P3 binding to PDK1 PH domain defined by knockin mutation. EMBO J 23, 2071-2082.

49. Menon, S., Dibble, C. C., Talbott, G., Hoxhaj, G., Valvezan, A. J., Takahashi, H., Cantley, L. C., and Manning, B. D. (2014). Spatial control of the TSC complex integrates insulin and nutrient regulation of mTORC1 at the lysosome. Cell 156, 771-785.

50. Murray, J. T., Campbell, D. G., Morrice, N., Auld, G. C., Shpiro, N., Marquez, R., Peggie, M., Bain, J., Bloomberg, G. B., Grahammer, F., et al. (2004). Exploitation of KESTREL to identify NDRG family members as physiological substrates for SGK1 and GSK3. Biochem J 384, 477-488.

51. Najafov, A., Shpiro, N., and Alessi, D. R. (2012). Akt is efficiently activated by PIF-pocket-and PtdIns(3,4,5)P3-dependent mechanisms leading to resistance to PDK1 inhibitors. Biochem J 448, 285-295.

52. Najafov, A., Sommer, E. M., Axten, J. M., Deyoung, M. P., and Alessi, D. R. (2011). Characterization of GSK2334470, a novel and highly specific inhibitor of PDK1. Biochem J 433, 357-369.

53. Pearce, L. R., Komander, D., and Alessi, D. R. (2010). The nuts and bolts of AGC protein kinases. Nat Rev Mol Cell Biol 11, 9-22.

54. Potter, C. J., Pedraza, L. G., and Xu, T. (2002). Akt regulates growth by directly phosphorylating Tsc2. Nat Cell Biol 4, 658-665.
55. Rodrik-Outmezguine, V. S., Chandarlapaty, S., Pagano, N. C., Poulikakos, P. I., Scaltriti, M., Moskatel, E., Baselga, J., Guichard, S., and Rosen, N. (2011). mTOR kinase inhibition causes feedback-dependent biphasic regulation of AKT signaling. Cancer Discov 1, 248-259.
56. Roux, P. P., Ballif, B. A., Anjum, R., Gygi, S. P., and Blenis, J. (2004). Tumor-promoting phorbol esters and activated Ras inactivate the tuberous sclerosis tumor suppressor complex via p90 ribosomal S6 kinase. Proc Natl Acad of Sci USA 101, 13489-13494.
57. Sali, A., and Blundell, T. L. (1993). Comparative protein modelling by satisfaction of spatial restraints. Journal of molecular biology 234, 779-815.
58. Sancak, Y., Thoreen, C. C., Peterson, T. R., Lindquist, R. A., Kang, S. A., Spooner, E., Carr, S. A., and Sabatini, D. M. (2007). PRAS40 is an insulin-regulated inhibitor of the mTORC1 protein kinase. Mol Cell 25, 903-915.
59. Sarbassov, D. D., Guertin, D. A., Ali, S. M., and Sabatini, D. M. (2005). Phosphorylation and regulation of Akt/PKB by the rictor-mTOR complex. Science 307, 1098-1101.
60. Shevchenko, A., Tomas, H., Havlis, J., Olsen, J. V., and Mann, M. (2006). In-gel digestion for mass spectrometric characterization of proteins and proteomes. Nature protocols 1, 2856-2860.
61. Silvera, D., Formenti, S. C., and Schneider, R. J. (2010). Translational control in cancer. Nat Rev Cancer 10, 254-266.
62. Sommer, E. M., Dry, H., Cross, D., Guichard, S., Davies, B. R., and Alessi, D. R. (2013). Elevated SGK1 predicts resistance of breast cancer cells to Akt inhibitors. Biochem J 452, 499-508.
63. Therasse, P., Arbuck, S. G., Eisenhauer, E. A., Wanders, J., Kaplan, R. S., Rubinstein, L., Verweij, J., Van Glabbeke, M., van Oosterom, A. T., Christian, M. C., and Gwyther, S. G. (2000). New guidelines to evaluate the response to treatment in solid tumors. European Organization for Research and Treatment of Cancer, National Cancer Institute of the United States, National Cancer Institute of Canada. J Natl Cancer Inst 92, 205-216.
64. Thorpe, L. M., Yuzugullu, H., and Zhao, J. J. (2015). PI3K in cancer: divergent roles of isoforms, modes of activation and therapeutic targeting. Nat Rev Cancer 15, 7-24.
65. Toska, E., Campbell, H. A., Shandilya, J., Goodfellow, S. J., Shore, P., Medler, K. F., and Roberts, S. G. (2012). Repression of transcription by WT1-BASP1 requires the myristoylation of BASP1 and the PIP2-dependent recruitment of histone deacetylase. Cell reports 2, 462-469. van Rheenen, J., Langeslag, M., and Jalink, K. (2004). Correcting confocal acquisition to optimize imaging of fluorescence resonance energy transfer by sensitized emission. Biophysical journal 86, 2517-2529.
66. Vasudevan, K. M., Barbie, D. A., Davies, M. A., Rabinovsky, R., McNear, C. J., Kim, J. J., Hennessy, B. T., Tseng, H., Pochanard, P., Kim, S. Y., et al. (2009). AKT-independent signaling downstream of oncogenic PIK3CA mutations in human cancer. Cancer Cell 16, 21-32.
67. Wang, J., Wolf, R. M., Caldwell, J. W., Kollman, P. A., and Case, D. A. (2004). Development and testing of a general amber force field. Journal of computational chemistry 25, 1157-1174. Webb, A. E., and Brunet, A. (2014). FOXO transcription factors: key regulators of cellular quality control. Trends in biochemical sciences 39, 159-169.
68. Webb, A. E., and Brunet, A. (2014). FOXO transcription factors: key regulators of cellular quality control. Trends Biochem Sci 39, 159-169.
69. Yang, J., Cron, P., Good, V. M., Thompson, V., Hemmings, B. A., and Barford, D. (2002a). Crystal structure of an activated Akt/protein kinase B ternary complex with GSK3-peptide and AMP-PNP. Nature structural biology 9, 940-944.
70. Yang, J., Cron, P., Thompson, V., Good, V. M., Hess, D., Hemmings, B. A., and Barford, D. (2002b). Molecular mechanism for the regulation of protein kinase B/Akt by hydrophobic motif phosphorylation. Molecular cell 9, 1227-1240.
71. Zhao, B., Lehr, R., Smallwood, A. M., Ho, T. F., Maley, K., Randall, T., Head, M. S., Koretke, K. K., and Schnackenberg, C. G. (2007). Crystal structure of the kinase domain of serum and glucocorticoid-regulated kinase 1 in complex with AMP PNP. Protein Sci 16, 2761-2769.

Although the presently disclosed subject matter and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, and composition of matter, means, methods and steps described in the specification. As one of ordinary skill in the art will readily appreciate from the invention of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the inventions of which are incorporated herein by reference in their entireties for all purposes.

What is claimed is:

1. A method of treating a FOXO3-associated cancer in a subject who is resistant to a phosphoinositide 3-kinase (PI3K) inhibitor monotherapy, comprising:
   (a) sensitizing the subject to the PI3K inhibitor, wherein the sensitizing comprises administering to the subject an effective amount of a 3-phosphoinositide dependent protein kinase-1 (PDK1) inhibitor, a serine/threonine-protein kinase (SGK1) inhibitor, or a combination thereof; and
   (b) administering to the subject an effective amount of the PI3K inhibitor, wherein the PI3K inhibitor is BYL719 (apelisib), the PDK1 inhibitor is GSK2334470 or a nucleic acid that specifically binds to a nucleic acid encoding PDK1 and reduces PDK1 activity and/or expression, and the SGK1 inhibitor is a nucleic acid that specifically binds to a nucleic acid encoding SGK1 and reduces SGK1 activity and/or expression or a small molecule comprising a pyrazolo(3,4-b)pyrazine head.

2. The method of claim 1, wherein the sensitizing comprises administering to the subject the effective amount of the PDK1 inhibitor.

3. The method of claim 1, wherein the sensitizing comprises administering to the subject the effective amount of the SGK1 inhibitor.

4. The method of claim 1, wherein the nucleic acid that specifically binds to a nucleic acid encoding PDK1 and reduces PDK1 activity and/or expression comprises a micro RNA (miRNA) molecule, an interfering RNA (RNAi) molecule, an shRNA molecule, an antisense RNA molecule, a catalytic RNA molecule, and/or a catalytic DNA molecule.

5. The method of claim 1, wherein the nucleic acid that specifically binds to a nucleic acid encoding SGK1 and reduces SGK1 activity and/or expression comprises a micro RNA (miRNA) molecule, an interfering RNA (RNAi) molecule, an shRNA molecule, an antisense RNA molecule, a catalytic RNA molecule, and/or a catalytic DNA molecule.

6. The method of claim 1, wherein the subject has a gain-of-function mutation in the PI3K/AKT pathway.

7. The method of claim 6, wherein the gain-of-function mutation in the PI3K/AKT pathway is an activating mutation in PIK3CA gene or p110α encoded by a PIK3CA gene.

8. The method of claim 7, wherein the activating mutation comprises a mutation at amino acid 88, 143, 345, 420, 542, 545, and/or 1047 of p110α.

9. The method of claim 8, wherein the mutation in p110α is selected from the group consisting of R88Q, N345K, E542K, E545K, E545Q, H1047L, H1047Q, H1047R, C420R, I143V, and combinations thereof.

* * * * *